(12) United States Patent
Faustman

(10) Patent No.: US 10,906,982 B2
(45) Date of Patent: Feb. 2, 2021

(54) ANTAGONISTIC ANTI-TUMOR NECROSIS FACTOR RECEPTOR 2 ANTIBODIES

(71) Applicant: The General Hospital Corporation, Boston, MA (US)

(72) Inventor: Denise L. Faustman, Boston, MA (US)

(73) Assignee: The General Hospital Corporation, Boston, MA (US)

(*) Notice: Subject to any disclaimer, the term of this patent is extended or adjusted under 35 U.S.C. 154(b) by 276 days.

(21) Appl. No.: 15/573,747

(22) PCT Filed: May 13, 2016

(86) PCT No.: PCT/US2016/032547
§ 371 (c)(1),
(2) Date: Nov. 13, 2017

(87) PCT Pub. No.: WO2016/187068
PCT Pub. Date: Nov. 24, 2016

(65) Prior Publication Data
US 2018/0194850 A1 Jul. 12, 2018

Related U.S. Application Data

(60) Provisional application No. 62/276,073, filed on Jan. 7, 2016, provisional application No. 62/162,449, filed on May 15, 2015.

(51) Int. Cl.
*C07K 16/28* (2006.01)
*A61K 39/395* (2006.01)
(Continued)

(52) U.S. Cl.
CPC ........ *C07K 16/2878* (2013.01); *A61K 39/395* (2013.01); *A61K 38/00* (2013.01);
(Continued)

(58) Field of Classification Search
None
See application file for complete search history.

(56) References Cited

U.S. PATENT DOCUMENTS 4,309,418 A 1/1982 Green
4,457,916 A 7/1984 Hayashi et al.
(Continued)

FOREIGN PATENT DOCUMENTS

EP 0612529 A2 8/1994
EP 2295588 A1 3/2011
(Continued)

OTHER PUBLICATIONS

MacCallum et al., Antibody-antigen interactions: Contact analysis and binding siite topography, J. Mol. Biol 262:732-745, 1996.*
(Continued)

*Primary Examiner* — Claire Kaufman
(74) *Attorney, Agent, or Firm* — Clark & Elbing LLP

(57) ABSTRACT

Antagonistic TNFR superfamily polypeptides, such as antibodies and antigen-binding fragments thereof, and the use of these polypeptides to inhibit the proliferation of regulatory T cells (T-regs). For example, antibodies of the invention include antagonistic TNFR2 antibodies and antigen-binding fragments thereof, and can be used to suppress the T-reg-mediated deactivation of tumor reactive T-lymphocytes, as well as to treat a wide variety of cancers and infectious diseases.

16 Claims, 44 Drawing Sheets
Specification includes a Sequence Listing.

(51) Int. Cl.
   *A61K 38/00* (2006.01)
   *A61K 39/00* (2006.01)
(52) U.S. Cl.
   CPC .. *A61K 2039/572* (2013.01); *A61K 2039/585* (2013.01); *C07K 2317/34* (2013.01); *C07K 2317/54* (2013.01); *C07K 2317/565* (2013.01); *C07K 2317/567* (2013.01); *C07K 2317/73* (2013.01); *C07K 2317/732* (2013.01); *C07K 2317/76* (2013.01); *C07K 2317/92* (2013.01)

(56) References Cited

U.S. PATENT DOCUMENTS

| | | |
|---|---|---|
| 4,495,282 A | 1/1985 | Ohnishi et al. |
| 4,677,063 A | 6/1987 | Mark et al. |
| 4,677,064 A | 6/1987 | Mark et al. |
| 4,681,760 A | 7/1987 | Fathman |
| 4,791,101 A | 12/1988 | Adolf |
| 4,816,567 A | 3/1989 | Cabilly et al. |
| 4,879,226 A | 11/1989 | Wallace et al. |
| 4,963,354 A | 10/1990 | Shepard et al. |
| 4,985,241 A | 1/1991 | Zimmerman et al. |
| 5,002,876 A | 3/1991 | Sreekrishna et al. |
| 5,059,530 A | 10/1991 | Oshima et al. |
| 5,139,481 A | 8/1992 | Faustman et al. |
| 5,215,743 A | 6/1993 | Singh et al. |
| 5,283,058 A | 2/1994 | Faustman |
| 5,288,852 A | 2/1994 | Yamada et al. |
| 5,370,870 A | 12/1994 | Wong |
| 5,487,984 A | 1/1996 | Allet et al. |
| 5,538,854 A | 7/1996 | Faustman |
| 5,560,908 A | 10/1996 | Satoh et al. |
| 5,593,698 A | 1/1997 | Weiner et al. |
| 5,783,216 A | 7/1998 | Faustman |
| 5,821,337 A | 10/1998 | Carter et al. |
| 5,843,425 A | 12/1998 | Sachs et al. |
| 5,843,452 A | 12/1998 | Wiedmann et al. |
| 5,874,306 A | 2/1999 | Beattie et al. |
| 5,919,452 A | 7/1999 | Le et al. |
| 5,939,532 A | 8/1999 | Nakamura et al. |
| 6,046,031 A | 4/2000 | Ni et al. |
| 6,056,952 A | 5/2000 | Rosenberg |
| 6,159,461 A | 12/2000 | Besmer et al. |
| 6,165,737 A | 12/2000 | Wang et al. |
| 6,177,076 B1 | 1/2001 | Lattime et al. |
| 6,284,879 B1 | 9/2001 | Faustman |
| 6,414,218 B1 | 7/2002 | Faustman et al. |
| 6,420,139 B1 | 7/2002 | Classen |
| 6,491,908 B1 | 12/2002 | Rosenberg |
| 6,599,710 B1 | 7/2003 | Faustman |
| 6,617,171 B2 | 9/2003 | Faustman et al. |
| 6,660,487 B2 | 12/2003 | Faustman |
| 6,709,833 B2 | 3/2004 | Fukui et al. |
| 6,773,705 B1 | 8/2004 | Faustman et al. |
| 6,844,011 B1 | 1/2005 | Faustman |
| 6,866,843 B2 | 3/2005 | Habener et al. |
| 6,923,959 B2 | 8/2005 | Habener et al. |
| 6,984,380 B1 | 1/2006 | Faustman |
| 7,015,037 B1 | 3/2006 | Furcht et al. |
| 7,438,902 B2 | 10/2008 | Habener et al. |
| 7,485,293 B1 | 2/2009 | Faustman |
| 7,510,877 B2 | 3/2009 | Yilmaz et al. |
| 7,537,756 B2 | 5/2009 | Habener et al. |
| 7,582,313 B2 | 9/2009 | Faustman |
| 7,628,988 B2 | 12/2009 | Faustman |
| 8,173,129 B2 | 5/2012 | Faustman |
| 8,314,213 B2 | 11/2012 | Bernett et al. |
| 9,676,862 B2* | 6/2017 | Ellmark ............... A61K 9/0019 |
| 9,821,010 B2 | 11/2017 | Faustman |
| 2002/0106689 A1 | 8/2002 | Faustman et al. |
| 2002/0123472 A1 | 9/2002 | Faustman |
| 2002/0187548 A1 | 12/2002 | Keller et al. |
| 2003/0005469 A1 | 1/2003 | Faustman et al. |
| 2003/0031657 A1 | 2/2003 | Habener et al. |
| 2004/0028658 A1 | 2/2004 | Faustman |
| 2004/0031066 A9 | 2/2004 | Faustman et al. |
| 2004/0229785 A1 | 11/2004 | Faustman |
| 2005/0043514 A1 | 2/2005 | Fukui et al. |
| 2005/0158288 A1 | 7/2005 | Faustman |
| 2005/0158302 A1 | 7/2005 | Faustman et al. |
| 2005/0244386 A1 | 11/2005 | Habener et al. |
| 2006/0062769 A1 | 3/2006 | Habener et al. |
| 2007/0116688 A1 | 5/2007 | Faustman |
| 2008/0102054 A1 | 5/2008 | Faustman |
| 2008/0175830 A1 | 7/2008 | Steinman et al. |
| 2009/0028877 A1 | 1/2009 | Iida et al. |
| 2010/0068177 A1 | 3/2010 | Faustman |
| 2010/0298232 A1 | 11/2010 | Liu |
| 2011/0236374 A1 | 9/2011 | Shitara et al. |
| 2012/0066777 A1 | 3/2012 | Kawamura et al. |
| 2012/0115739 A1 | 5/2012 | Schmittling et al. |
| 2012/0196919 A1 | 8/2012 | Brown et al. |
| 2013/0064831 A1 | 3/2013 | Humphrey |
| 2014/0096274 A1 | 4/2014 | Quax et al. |
| 2014/0121123 A1 | 5/2014 | Wang et al. |
| 2015/0366909 A1 | 12/2015 | Faustman |
| 2019/0202925 A1* | 7/2019 | Thompson ......... C07K 16/2878 |

FOREIGN PATENT DOCUMENTS

| | | |
|---|---|---|
| WO | WO-92/04033 A1 | 3/1992 |
| WO | WO-93/02690 A1 | 2/1993 |
| WO | WO-94/09137 A1 | 4/1994 |
| WO | WO-95/24914 A1 | 9/1995 |
| WO | WO-95/25533 A1 | 9/1995 |
| WO | WO-97/08328 A1 | 3/1997 |
| WO | WO-97/13844 A1 | 4/1997 |
| WO | WO-97/21802 A1 | 6/1997 |
| WO | WO-99/53953 A2 | 10/1999 |
| WO | WO-99/59632 A1 | 11/1999 |
| WO | WO-00/53209 A1 | 9/2000 |
| WO | WO-01/44472 A1 | 6/2001 |
| WO | WO-01/91793 A1 | 12/2001 |
| WO | WO-02/26819 A2 | 4/2002 |
| WO | WO-2004/003164 A2 | 1/2004 |
| WO | WO-2005/042727 A2 | 5/2005 |
| WO | WO-2006/109044 A2 | 10/2006 |
| WO | WO-2008/157394 A2 | 12/2008 |
| WO | WO-2010/124259 A1 | 10/2010 |
| WO | WO-2012/122464 A1 | 9/2012 |
| WO | WO-2014/124134 A1 | 8/2014 |
| WO | WO-2015/145360 A1 | 10/2015 |
| WO | WO-2016/187068 A1 | 11/2016 |
| WO | WO-2017/040312 A1 | 3/2017 |
| WO | WO-2017/083525 A1 | 5/2017 |

OTHER PUBLICATIONS

MacCallum et al., Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Blol. Chem. 276:36687-94, 2001.*
Chen et al.Enhancement and destruction of antibody function by somatic mutation: unequal occurrence is controlled by V gene combinatorial associations EMBO J., 14 (12): 2784-2794, 1995.*
Parsons, J.A., Peptide Hormones (University Press:Baltimre), pp. 1-7, 1976.*
Ji et al., "Cutting Edge: The Natural Ligand for Glucocorticoid-Induced TNF Receptor-Related Protein Abrogates Regulatory T Cell Suppression," J Immunol. 172(10):5823-7 (2004).
Chen et al., "The phenotypic and functional consequences of tumour necrosis factor receptor type 2 expression on CD4(+) FoxP3(+) regulatory T cells," Immunology. 133(4):426-33 (2011).
International Preliminary Report on Patentability for International Application No. PCT/US2017/032513, dated Nov. 22, 2018 (8 pages).
Santee et al., "Human tumor necrosis factor receptor p75/80 (CD120b) gene structure and promoter characterization," J Biol Chem. 271(35):21151-9 (1996).
Extended European Search Report for European Application No. 18199457.5, dated May 2, 2019 (7 pages).

(56) References Cited

OTHER PUBLICATIONS

International Search Report and Written Opinion for International Application No. PCT/US18/59779, dated Apr. 18, 2019 (19 pages).
Al-Awqati et al., "Stem cells in the kidney," Kidney Int. 61(2):387-95 (2002).
Aldrich et al., "Positive selection of self- and alloreactive CD8+ T cells in Tap-1 mutant mice," Proc Natl Acad Sci USA. 91(14):6525-8 (1994).
Alison et al., "Hepatocytes from non-hepatic adult stem cells," Nature. 406(6793):257 (2000).
Allen et al., "Effect of bacillus Calmette-Guerin vaccination on new-onset Type 1 Diabetes," Diabetes Care. 22(10):1703-1707 (1999).
Altomonte et al., "Serum levels of interleukin-1b, tumour necrosis factor-a and interleukin-2 in rheumatoid arthritis. Correlation with disease activity," Clin Rheumatol. 11(2):202-205 (1992).
Anderson et al., "Can stem cells cross lineage boundaries?" Nat Med. 7(4):393-5 (2001).
Anderson et al., "Studies on the cytophilic properties of human beta2 microglobulin," J Immunol. 114(3):997-1000 (1975).
Anderson et al., "The NOD mouse: a model of immune dysregulation," Annu Rev Immunol. 23:447-485 (2005).
Aranda et al., "Analysis of intestinal lymphocytes in mouse colitis mediated by transfer of CD4+, CD45RBhigh T Cells to SCID recipients," J Immunol. 158(7):3464-3473 (1997).
Aristarkhov et al., "E2-C, a cyclin-selective ubiquitin carrier protein required for the destruction of mitotic cyclins," Proc Natl Acad Sci USA. 93(9):4294-9 (1996).
Ashton-Rickardt et al., "Evidence for a differential avidity model of T Cell selection in the thymus," Cell. 76(4):651-63 (1994).
Ashton-Rickardt et al., "Peptide contributes to the specificity of positive selection of CD8+ T Cells in the thymus," Cell. 73(5):1041-9 (1993).
Atkinson et al., "The NOD mouse model of Type 1 Diabetes: As good as it gets?" Nat Med. 5(6):601-604 (1999).
Baeuerle et al., "NF-kappaB: Ten years after," Cell. 87(1):13-20 (1996).
Baeza et al., "Pancreatic regenerating gene overexpression in the nonobese diabetic mouse during active diabetogenesis," Diabetes. 45(1):67-70 (1996) (5 pages).
Baeza et al., "Reg protein: a potential beta-cell-specific growth factor?" Diabetes Metab. 22(4):229-234 (1996).
Baeza et al., "Specific reg II gene overexpression in the non-obese diabetic mouse pancreas during active diabetogenesis," FEBS Letters. 416(3):364-8 (1997).
Baik et al., "BCG vaccine prevents insulitis in low dose streptozotocin-induced diabetic mice," Diabetes Res Clin Pract. 46(2):91-97 (1999).
Baldwin, "The NF-$_{kappa}$B and I$_{kappa}$B proteins: new discoveries and insights," Ann Rev Immunol. 14:649-683 (1996).
Ban et al., "Selective death of autoreactive T Cells in human diabetes by TNF or TNF receptor 2 agonism," Proc Natl Acad Sci USA. 105(36):13644-13649 (2008).
Barres, "A new role for glia: generation of neurons!" Cell. 97(6):667-70 (1999).
Baxter et al., "Mycobacteria precipitate an SLE-like syndrome in diabetes-prone NOD mice," Immunology. 83(2):227-231 (1994).
Beers et al. Disorders of Carbohydrate Metabolism: Diabetes Mellitus. *The Merck Manual of Diagnosis and Therapy, 17th Ed.* Merck Research Laboratories, 165-171, 1999.
Beg et al., "An essential role for NF-kappaB in preventing TNF-alpha-induced cell death," Science. 274(5288):782-784 (1996).
Bendelac et al., "Syngeneic transfer of autoimmune diabetes from diabetic NOD mice to healthy neonates. Requirement for both L3T4+ and Lyt-2+ T Cells," J Exp Med. 166(4):823-832 (1987).
Benkler et al., "Parkinson's disease, autoimmunity, and olfaction," Int J Neurosci. 119(12):2133-43 (2009) (Abstract only) (1 page).
Bercovici et al., "Systemic administration of agonist peptide blocks the progression of spontaneous CD8-mediated autoimmune diabetes in transgenic mice without bystander damage," J Immunol. 165(1):202-10 (2000).

Bernabeu et al., "Beta2 -microglobulin from serum associates with MHC class I antigens on the surface of cultured cells," Nature. 308:642-645 (1984) (Abstract only) (2 pages).
Bill et al., "Use of soluble MHC class II/peptide multimers to detect antigen-specific T cells in human disease," Arthritis Res. 4:261-265 (2002).
Bjornson et al., "Turning brain into blood: A hematopoietic fate adopted by adult neural stem cells in vivo," Science. 283(5401):534-537 (1999).
Bleumink et al., "Etanercept-induced subacute cutaneous lupus erythematosus" Rheumatology. 40:1317-1319 (2001).
Boches et al., "Role for the adenosine triphosphate-dependent proteolytic pathway in reticulocyte maturation," Science. 215:978-980 (1982).
Brayer et al., "Alleles from chromosomes 1 and 3 of NOD mice combine to influence Sjögren's syndrome-like autoimmune exocrinopathy," J. Rheumatol. 27(8):1896-1904 (2000).
Brazelton et al., "From marrow to brain: expression of neuronal phenotypes in adult mice," Science. 290:1775-1779 (2000).
Brod et al., "Ingested interferon alpha suppresses Type I diabetes in non-obese diabetic mice," Diabetologia. 41:1227-1232 (1998).
Brod et al., "New clinical trial in newly diagnosed type 1 diabetes," <http://www.diabetesstation.org/articles/brod.htm>, retrieved Jun. 19, 2001 (2 pages).
Brodbeck et al., "Genetic determination of nephrogenesis: the Pax/Eya/Six gene network," Pediatr Nephrol. 19(3):249-255 (2004) (Abstract Only).
Brás et al., "Diabetes-prone NOD mice are resistant to mycobacterium avium and the infection prevents autoimmune disease," Immunology. 89:20-25 (1996).
Bunting et al., "Enforced P-glycoprotein pump function in murine bone marrow cells results in expansion of side population stem cells in vitro and repopulating cells in vivo," Blood. 96(3):902-909 (2000).
Burnham et al., "Oral BCG vaccine in Crohn's disease," Gut. 20:229-233 (1979).
Caetano et al., "Effect of methotrexate (MTX) on Nad(P)+ dehydrogenases of HeLa cells: malic enzyme, 2-oxoglutarate and isocitrate dehydrogenases," Cell Biochem Funct. 15(4):259-264 (1997).
Cairns et al., "New onset systemic lupus erythematosus in a patient receiving etanercept for rheumatoid arthritis," Ann Rheum Dis. 61(11):1031-2 (2002).
Cavallo et al., "BCG vaccine with and without nicotinamide in recent onset IDDM: a multicenter randomized trial," Second Congress of the Immunology of Diabetes Society. 18, A063 (1996).
Cebrián et al., "MHC-I expression renders catecholaminergic neurons susceptible to T-cell-mediated degeneration," Nat Commun. 5:3633 (2014) (Abstract only) (1 page).
Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials." Arthritis Rheum. 43(11):2383-90 (2000).
Chatenoud et al., "CD3 antibody-induced dominant self tolerance in overtly diabetic NOD mice," J Immunol. 158(6):2947-2954 (1997).
Choi et al., "Prevention of Encephalomyocarditis virus-induced diabetes by live recombinant Mycobacterium bovis Bacillus Calmette-Guérin in susceptible mice," Diabetes. 49:1459-1467 (2000).
Chopra et al. "Exogenous TNFR2 activation protects from acute GvHD via host T reg cell expansion", J Exp Med 213(9):1881-1900 (2016) (21 pages).
Christen et al., "A dual role for TNF-alpha in type 1 diabetes: islet-specific expression abrogates the ongoing autoimmune process when induced late but not early during pathogenesis," J Immunol. 166(12):7023-32 (2001).
Cole et al., "Two ParaHox genes, SpLox and SpCdx, interact to partition the posterior endoderm in the formation of a functional gut," Development. 136(4):541-549 (2009).
Colucci et al., "Programmed cell death in the pathogenesis of murine IDDM: resistance to apoptosis induced in lymphocytes by cyclophosphamide," J Autoimmunity 9:271-276 (1996).

(56) References Cited

OTHER PUBLICATIONS

Communication pursuant to Article 94(3) EPC for European Patent Application No. 14189654.8, dated Oct. 19, 2016 (5 pages).
Communication pursuant to Rules 70(2) and 70a(2) EPC for European Application No. 14748807.6, dated Aug. 2, 2016 (1 page).
Corbett et al., "Nitric oxide mediates cytokine-induced inhibition of insulin secretion by human islets of Langerhans," Proc Natl Acad Sci USA. 90(5):1731-1735 (1993).
Coux et al., "Enzymes catalyzing ubiquitination and proteolytic processing of the p105 precursor of nuclear factor kappaB1," J Biol Chem. 273(15):8820-8828 (1998).
Couzin, "Diabetes studies conflict on power of spleen cells," Science. 311:1694 (2006).
Creasey et al., "Biological effects of recombinant human tumor necrosis factor and its novel muteins on tumor and normal cell lines," Cancer Res. 47(1):145-9 (1987).
D'Andrea, "Add Alzheimer's disease to the list of autoimmune diseases," Med Hypotheses. 64(3):458-63 (2005) (Abstract only) (2 pages).
Darzynkiewicz et al., "Use of flow and laser scanning cytometry to study mechanisms regulating cell cycle and controlling cell death," Clinics in Laboratory Medicine. 21(4):857-873 (2001).
Dear et al., "The Hox11 gene is essential for cell survival during spleen development," Development. 121:2909-2915 (1995).
Declaration of Dr. Denise Faustman from U.S. Appl. No. 10/358,644, dated on May 2009 (4 pages).
Declaration of Dr. Denise Faustman from U.S. Appl. No. 10/775,487, dated on Jun. 14, 2007 (13 pages).
Declaration of Dr. Denise Faustman from U.S. Appl. No. 10/851,983, dated on Jul. 3, 2007 (7 pages).
Diaw et al., "Structural and affinity studies of IgM polyreactive natural autoantibodies," J Immunol. 158(2):968-76 (1997).
Dieguez-Acuna et al., "Characterization of mouse spleen cells by subtractive proteomics," Mol Cell Proteomics. 4(10):1459-1470 (2005).
Dieguez-Acuña et al., "Proteomics identifies multipotent and low oncogenic risk stem cells of the spleen," Int J Biochem Cell Biol. 42(10):1651-1660 (2009) (10 pages).
Dilts et al., "Autoimmune diabetes: The involvement of benign and malignant autoimmunity," J Autoimmun. 12:229-232 (1999).
Dinarello, "Interleukin-1, Interleukin-1 receptors and Interleukin-1 receptor antagonist," Intern Rev Immunol. 16:457-499 (1998).
Driscoll et al., "The proteasome (multicatalytic protease) is a component of the 1500-kDa proteolytic complex which degrades ubiquitin-conjugated proteins," J Biol Chem. 265(9):4789-4792 (1990).
Durand et al., "Mesenchymal lineage potentials of aorta-gonad-mesonephros stromal clones," Heamatologica. 91(9):1172-1179 (2006).
Eglitis et al., "Hematopoietic cells differentiate into both microglia and macroglia in the brains of adult mice," Proc Natl Acad Sci USA. 94:4080-4085 (1997).
Elliott et al., "Effect of Bacille Calmette-Guérin vaccination on C-Peptide secretion in children newly diagnosed with IDDM," Diabetes Care. 21(10):1691-1693 (1998).
Enayati et al., "Association of anti-tumor necrosis factor therapy with the development of multiple sclerosis," J Clin Gastroenterol. 39(4): 303-6 (2005) (Abstract only).
Engleman et al., "Treatment of NZB/NZW F1 hybrid mice with Mycobacterium bovis strain BCG or type II interferon preparations accelerates autoimmune disease," Arthritis Rheum. 24(11):1396-1402 (1981).
EPO Communication Enclosing Supplementary European Search Report for EP Application No. 03762242.0, dated Jun. 8, 2009 (8 pages).
EPO Communication for International Application No. PCT/US2014/015101, dated Oct. 15, 2015 (2 pages).
EPO Communication pursuant to 94(3) for European Application No. 12005556.1, dated Jul. 2, 2015 (7 pages).
EPO Communication pursuant to Article 94(3) and Rule 71(1) EPC for European Application No. 00914899.0, dated Mar. 6, 2015 (3 pages).
EPO Communication pursuant to Article 94(3) EPC for European Application No. 00914899.0, dated May 25, 2012 (9 pages).
EPO Communication Pursuant to Article 94(3) EPC issued in European Patent Application No. 03762242.0, dated Dec. 1, 2011 (4 pages).
EPO Communication Pursuant to Article 94(3) EPC issued in European Patent Application No. 03762242.0, dated Oct. 30, 2009 (2 pages).
EPO Communication Pursuant to Article 94(3) EPC issued in European Patent Application No. 04817543.4, dated Jan. 22, 2010 (5 pages).
EPO Communication Pursuant to Article 94(3) EPC issued in European Patent Application No. 11008889.5, dated Mar. 19, 2014 (4 pages).
EPO Communication Pursuant to Article 94(3) EPC issued in European Patent Application No. 11008889.5, dated Mar. 4, 2013 (4 pages).
EPO Communication Pursuant to Article 94(3) EPC issued in European Patent Application No. 11008889.5, dated Oct. 27, 2014 (5 pages).
EPO Communication pursuant to Rule 69 EPC for European Application No. 12005556.1, dated Oct. 7, 2014 (2 pages).
EPO Communication under Rule 71(3) EPC for European Application No. 00914899.0, dated Jun. 23, 2015 (6 pages).
EPO Invitation pursuant to Article 94(3) and Rule 71(1) EPC for European Application No. 00914899.0, dated Jun. 2, 2014 (4 pages).
EPO Summons to attend oral proceedings pursuant to Rule 115(1) EPC for European Application No. 00914899.0, dated Nov. 12, 2014 (6 pages).
EPO Summons to attend oral proceedings pursuant to Rule 115(1) EPC for European Application No. 12005556.1, dated Dec. 18, 2015 (4 pages).
Examination Report issued in Australian Patent Application No. 2003247840, dated Jan. 31, 2008 (4 pages).
Examiner's Report for Canadian Application No. 2,543,745, dated Jul. 15, 2011 (4 pages).
Extended European Search Report for European Application No. 12005556.1, dated Sep. 2, 2014 (8 pages).
Extended European Search Report for European Application No. 14748807.6, dated Jul. 15, 2016 (10 pages).
Extended European Search Report for European Patent Application No. 11008889.5, dated Apr. 12, 2012 (10 pages).
Extended European Search Report issued in European Application No. 14189654.8, dated Feb. 16, 2015 (7 pages).
Eytan et al., "ATP-dependent incorporation of 20S protease into the 26S complex that degrades proteins conjugated to ubiquitin," Proc Natl Acad Sci USA. 86:7751-7755 (1989).
Fan et al., "Generation of p50 subunit of NF-kappaB by processing of p105 through an ATP-dependent pathway," Nature. 354:395-398 (1991).
Faustman et al., "Abnormal T-lymphocyte subsets in Type I Diabetes," Diabetes. 38:1462-1468 (1989).
Faustman et al., "Linkage of faulty major histocompatibility complex class I to autoimmune diabetes," Science. 254:1756-1761 (1991).
Faustman et al., "Murine pancreatic beta-Cells express H-2K and H-2D but not Ia antigens," J Exp Med. 151:1563-1568 (1980).
Faustman et al., "Prevention of xenograft rejection by masking donor HLA class I antigens," Science. 252:1700-1702 (1991).
Faustman et al., "Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).
Faustman et al., "T-lymphocyte changes linked to autoantibodies. Association of insulin autoantibodies with CD4+CD45R+ lymphocyte subpopulation in prediabetic subjects," Diabetes. 40:590-597 (1991).
Faustman et al., "TNF receptor 2 pathway: drug target for autoimmune diseases," Nat Rev Drug Discov. 9(6):482-93 (2010).

(56) References Cited

OTHER PUBLICATIONS

Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).
Feldmann et al., "Role of cytokines in rheumatoid arthritis," Annu Rev Immunol. 14:397-440 (1996) (abstract only).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11:Abstract 578 (2002).
Fischer et al., "A TNF receptor 2 selective agonist rescues human neurons from oxidative stress-induced cell death," PloS One. 6(11):e27621 (2011) (11 pages).
Fischer et al., "An improved flow cytometric assay for the determination of cytotoxic T lymphocyte activity," J Immunol Methods. 259:159-169 (2002).
Foulis, "C.L. Oakley lecture (1987). The pathogenesis of beta cell destruction in Type I (insulin-dependent) diabetes mellitus," J Pathol. 152(3):141-148 (1987).
Fu et al., "Antigen processing and autoimmunity: Evaluation of mRNA abundance and function of HLA-Linked genes," Ann NY Acad Sci. 842:138-155 (1998).
Fu et al., "Defective major histocompatibility complex class I expression on lymphoid cells in autoimmunity," J Clin Invest. 91:2301-2307 (1993).
Fukada et al., "Two signals are necessary for cell proliferation induced by a cytokine receptor gp130: Involvement of STAT3 in anti-apoptosis," Immunity. 5:449-460 (1996).
Gage et al., "Multipotent progenitor cells in the adult dentate gyrus," J Neurobiol. 36:249-266 (1998).
Gage, "Mammalian neural stem cells," Science. 287:1433-1438 (2000).
Galaria et al., "Leukocytoclastic vasculitis due to etanercept," J Rheumatol. 27(8):2041-4 (2000) (Abstract only).
Ganoth et al., "A multicomponent system that degrades proteins conjugated to ubiquitin. Resolution of factors and evidence for ATP-dependent complex formation," J Biol Chem. 263(25):12412-12419 (1988).
Gaur et al., "Induction of islet allotolerance in nonhuman primates," Ann NY Acad Sci. 958:199-203 (2002).
Gazda et al., "Diabetes results from a late change in the autoimmune response of NOD mice," J Autoimmun. 10:261-270 (1997).
Gazda et al., "Regulation of autoimmune diabetes: characteristics of non-islet-antigen specific therapies," Immunol Cell Biol. 74: 401-407 (1996).
Genestier et al., "Immunosuppressive properties of methotrexate: Apoptosis and clonal deletion of activated peripheral T Cells," J Clin Invest. 102(2):322-328 (1998).
Gerich et al., "Advances in diabetes for the millenium: Understanding insulin resistance," MedGenMed. 6(3 Suppl):11 (2004) (9 pages).
Ghosh et al., "Activation in vitro of NF-kappaB by phosphorylation of its inhibitor IkappaB," Nature. 344:678-682 (1990).
Glas et al., "The CD8+ T Cell repertoire in beta2-microglobulin-deficient mice is biased towards reactivity against self-major histocompatibility class I," J Exp Med. 179(2):661-672 (1994).
Goldberg, "Functions of the proteasome: The lysis at the end of the tunnel," Science. 268:522-523 (1995).
Goldberg, "The mechanism and functions of ATP-dependent proteases in bacterial and animal cells," Eur J Biochem. 203:9-23 (1992).
Gottlieb et al., "Cell acidification in apoptosis: Granulocyte colony-stimulating factor delays programmed cell death in neutrophils by up-regulating the vacuolar $H^+$-ATPase," Proc Natl Acad Sci USA. 92:5965-5968 (1995).
Graves et al., "Lack of association between early childhood immunizations and beta-Cell autoimmunity," Diabetes Care 22:1694-1697 (1999).
Grewal et al., "Local expression of transgene encoded TNFalpha in islets prevents autoimmune diabetes in nonobese diabetic (NOD) mice by preventing the development of auto-reactive islet-specific T Cells," J Exp Med. 184:1963-1974 (1996).
Grilli et al., "Neuroprotection by aspirin and sodium salicylate through blockade of NF-kappaB activation," Science. 274:1383-1385 (1996).
Gronostajski et al., "The ATP dependence of the degradation of short- and long-lived proteins in growing fibroblasts," J Biol Chem. 260(6):3344-3349 (1985).
Gueckel et al., "Mutations in the yeast proteasome beta-Type subunit Pre3 uncover position-dependent effects on proteasomal peptidase activity and in vivo function," J Biol Chem. 273(31):19443-19452 (1998).
Gupta, "Molecular steps of tumor necrosis factor receptor-mediated apoptosis," Curr Mol Med. 1(3):317-324 (2001).
Haas et al., "Pathways of ubiquitin conjugation," FASEB J. 11:1257-1268 (1997).
Hao et al., "Effect of mycophenolate mofetil on islet allografting to chemically induced or spontaneously diabetic animals," Transplant Proc. 24(6): 2843-2844 (1992).
Harada et al., "Prevention of overt diabetes and insulitis in NOD mice by a single BCG vaccination," Diabetes Res Clin Pract. 8:85-89 (1990).
Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).
Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).
Hayashi et al., "NOD mice are defective in proteasome production and activation of NF-kappaB," Mol Cell Biol. 19(12):8646-8659 (1999).
Hershko et al., "The ubiquitin system for protein degradation," Annu Rev Biochem. 61: 761-807 (1992).
Hester et al., "Studies on the cytophilic properties of human beta2-microglobulin. II. The role of histocompatibility antigens," Scand J Immunol. 9(2):125-134 (1979).
Hoffmann et al. "Large-scale in vitro expansion of polyclonal human CD4(+)CD25high regulatory T cells," Blood. 104(3):895-903 (2004).
Horsfall et al., "Characterization and specificity of B-cell responses in lupus induced by Mycobacterium bovis in NOD/Lt mice," Immunology 95:8-17 (1998).
Horwitz et al., "Recombinant bacillus Calmette-Guérin (BCG) vaccines expressing the Mycobacterium tuberculosis 30-kDa major secretory protein induce greater protective immunity against tuberculosis than conventional BCG vaccines in a highly susceptible animal model," Proc Natl Acad Sci USA. 97(35):13853-13858 (2000).
Hostikka et al., "The mouse Hoxc11 gene: genomic structure and expression pattern," Mech Dev. 70(1-2):133-145 (1998) (Abstract Only).
Hsu et al., "TRADD-TRAF2 and TRADD-FADD interactions define two distinct TNF receptor 1 signal transduction pathways," Cell. 84:299-308 (1996).
Humphreys-Beher et al., "New concepts for the development of autoimmune exocrinopathy derived from studies with the NOD mouse model," Arch Oral Biol. 44(Suppl 1):S21-S25 (1999) (Abstract Only) (2 pages).
Hyafil et al., "Dissociation and exchange of the beta2-micoglobulin subunit of HLA-A and HLA-B antigens," Proc Natl Acad Sci USA. 76(11):5834-5838 (1979).
Hymowitz et al., "Toward small-molecule agonists of TNF receptors," Nat Chem Biol. 1(7):353-354 (2005).
International Preliminary Report on Patentability for International Application No. PCT/US2014/015101, dated Aug. 11, 2015 (9 pages).
International Preliminary Report on Patentability for International Application No. PCT/US2016/032547, dated Nov. 21, 2017 (16 pages).

(56) References Cited

OTHER PUBLICATIONS

International Search Report and Written Opinion for International Application No. PCT/US16/32547, dated Aug. 31, 2016 (24 pages).
International Search Report and Written Opinion for International Application No. PCT/US17/32513, dated Oct. 25, 2017 (17 pages).
International Search Report and Written Opinion for International Patent Application No. PCT/US14/15101, dated Jun. 24, 2014 (14 pages).
International Search Report for International Application No. PCT/US00/06239 dated Jul. 31, 2000 (2 pages).
International Search Report for International Application No. PCT/US2004/037998, dated Feb. 28, 2008 (2 pages).
International Search Report for International Patent Application No. PCT/US03/20578, dated Apr. 27, 2004 (1 page).
International Search Report for International Patent Application No. PCT/US03/36531, dated Jul. 14, 2004 (1 page).
Jackson et al., "Hematopoietic potential of stem cells isolated from murine skeletal muscle," Proc Natl Acad Sci USA. 96(25):14482-14486 (1999).
Jacob et al., "Monoclonal anti-tumor necrosis factor antibody renders non-obese diabetic mice hypersensitive to irradiation and enhances insulitis development," Int Immunol. 4(5):611-614 (1992).
Jacob et al., "Prevention of diabetes in nonobese diabetic mice by tumor necrosis factor (TNF): Similarities between TNF-alpha and interleukin 1," Proc Natl Acad Sci USA. 87:968-972 (1990).
Jacob et al., "Tumour necrosis factor-alpha in murine autoimmune 'lupus' nephritis," Nature. 331:356-358 (1988).
Jakubowski et al., "Phase I trial of intramuscularly administered tumor necrosis factor in patients with advanced cancer," J Clin Oncol. 7(3):298-303 (1989).
Jarrett et al., "Anti-tumor necrosis factor-alpha therapy-induced vasculitis: case series," J Rheumatol. 30(10):2287-91 (2003) (Abstract only).
Jiang et al., "Pluripotency of mesenchymal stem cells derived from adult marrow," Nature. 418:41-49 (2002).
Johansson et al., "Identification of a neural stem cell in the adult mammalian central nervous system," Cell. 96:25-34 (1999).
Juang et al., "Beneficial influence of glycemic control upon the growth and function of transplanted islets," Diabetes 43:1334-1339 (1994).
Kaijzel et al., "Functional analysis of a human tumor necrosis factor alpha (TNF-alpha) promoter polymorphism related to joint damage in rheumatoid arthritis," Mol Med. 4:724-733 (1998).
Kanzler et al., "Hox11 acts cell autonomously in spleen development and its absence results in altered cell fate of mesenchymal spleen precursors," Devel Biol. 234:231-243 (2001).
Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).
Kawasaki et al., "Prevention of type 1 diabetes: from the view point of beta cell damage," Diabetes Res Clin Pract. 66:S27-S32 (2004).
Kieran et al., "The DNA binding subunit of NF-kappaB is identical to factor KBF1 and homologous to the rel oncogene product," Cell. 62:1007-1018 (1990).
Klingensmith et al., "Vaccination with BCG at diagnosis does not alter the course of IDDM," Diabetes 57th Annual Meeting and Scientific Sessions, Jun. 21-24, Boston MA. 40(Suppl1):193A, 0744 (1997) (3 pages) (Abstract Only).
Klinkhoff, "Biological agents for rheumatoid arthritis: targeting both physical function and structural damage," Drugs. 64(12):1267-83 (2004) (Abstract only).
Koarada et al., "B Cells lacking RP105, A novel B cell antigen, in systemic lupus erythematosus," Arthritis & Rheumatism. 42(12):2593-2600 (1999).
Kodama et al., "Islet regeneration during the reversal of autoimmune diabetes in NOD mice," Science. 302:1223-1227 (2003).
Kodama et al., "Regenerative medicine: A radical reappraisal of the spleen," Trends Mol Med. 11(6):271-276 (2005).
Kodama et al., "The therapeutic potential of tumor necrosis factor for autoimmune disease: A mechanistically based hypothesis," Cell Mol Life Sci. 62:1850-1862 (2005).
Kopp et al., "Inhibition of NF-kappaB by sodium salicylate and aspirin," Science. 265:956-959 (1994).
Kouskoff et al., "Organ-specific disease provoked by systemic autoimmunity," Cell. 87(5):811-822 (1996) (Abstract Only).
Koyama et al., "Hox11 genes establish synovial joint organization and phylogenetic characteristics in developing mouse zeugopod skeletal elements," Development. 137(22): 3795-800 (2010) (Abstract Only).
Krause et al., "Multi-organ, multi-lineage engraftment by a single bone marrow-derived stem cell," Cell. 105:369-377 (2001).
Kretschmer et al., "Strong antigenic selection shaping the immunoglobulin heavy chain repertoire of B-1a lymphocytes in lambda 2(315) transgenic mice," Eur J Immunol. 32(8):2317-27 (2002).
Kuehnle et al., "The therapeutic potential of stem cells from adults," BMJ. 325:372-376 (2002).
Kwon et al., "Evidence for involvement of the proteasome complex (26S) and NFkappaB in IL-1 beta-induced nitric oxide and prostaglandin production by rat islets and RINm5F Cells" Diabetes. 47:583-591 (1998).
Kwon et al., "Interleukin-1beta-induced nitric oxide synthase expression by rat pancreatic beta-cells: Evidence for the involvement of nuclear factor kappaB in the signaling mechanism," Endocrinology. 136(11):4790-4795 (1995).
Laakko et al., "Versatility of merocyanine 540 for the flow cytometric detection of apoptosis in human and murine cells," J Immunol Methods. 261:129-139 (2002).
Lahav-Baratz et al., "Reversible phosphorylation controls the activity of cyclosome-associated cyclin-ubiquitin ligase," Proc Natl Acad Sci USA. 92:9303-9307 (1995).
Lakey et al., "BCG immunotherapy prevents recurrence of diabetes in islet grafts transplanted into spontaneously diabetic NOD mice," Transplantation. 57(8):1213-1217 (1994).
Lammert et al., "Induction of pancreatic differentiation by signals from blood vessels," Science. 294:564-567 (2001).
Lanza et al., "Transplantation of encapsulated canine islets into spontaneously diabetic BB/Wor rats without immunosuppression," Endocrinology. 131(2):637-642 (1992).
Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).
Lawrence et al., "Differential hepatocyte toxicity of recombinant Apo2L/TRAIL versions," Nat Med. 7(4):383-385 (2001).
Lewis et al., "Integrins regulate the apoptotic response to DNA damage through modulation of p53," Proc Natl Acad Sci USA. 99(6):3627-3632 (2002).
Li et al., "Abnormal class I assembly and peptide presentation in the nonobese diabetic mouse," Proc Natl Acad Sci USA. 91:11128-11132 (1994).
Li et al., "Reduced expression of peptide-loaded HLA class I molecules on multiple sclerosis lymphocytes," Ann Neurol. 38:147-154 (1995).
Li et al., "Use of Donor beta2-Microglobulin-Deficient Transgenic Mouse Liver Cells for Isografts, Allografts, and Xenografts," Transplantation. 55(4):940-6 (1993).
Lipsky et al., "Infliximab and methotrexate in the treatment of rheumatoid arthritis," N Eng J Med. 343:1594-1602 (2000).
Ljunggren et al., "MHC class I expression and CD8+ T cell development in TAP1/beta2-microglobulin double mutant mice," Int Immunol. 7(6):975-984 (1995).
Loetscher et al., "Human tumor necrosis factor alpha (TNF alpha) mutants with exclusive specificity for the 55-kDa or 75-kDa TNF receptors," J Biol Chem. 268(35):26350-26357 (1993).
Macchi et al., "Impaired apoptosis in mitogen-stimulated lymphocytes of patients with multiple sclerosis," NeuroReport. 10(25):399-402 (1999).
Mak et al., "Signaling for survival and apoptosis in the immune system," Arthritis Res. 4(Suppl 3):S243-S252 (2002).

(56) References Cited

OTHER PUBLICATIONS

Markiewicz et al., "Long-term T cell memory requires the surface expression of self-peptide/major histocompatibility complex molecules," Proc Natl Sci USA. 95:3065-3070 (1998).
Markmann et al., "Indefinite survival of MHC class I-deficient murine pancreatic islet allografts," Transplantation. 54(6):1085-1089 (1992).
Marriott, "TNF-alpha antagonists: Monoclonal antibodies, soluble receptors, thalidomide and other novel approaches," Expert Opin Invest Drugs. 6(8):1105-1108 (1997).
Matsumoto et al., "Liver organogenesis promoted by endothelial cells prior to vascular function," Science. 294:559-563 (2001).
Mayer-Proschel et al., "Isolation of lineage-restricted neuronal precursors from multipotent neuroepithelial stem cells," Neuron. 19:773-785 (1997).
McGuire et al., "An enzyme related to the high molecular weight multicatalytic proteinase, macropain, participates in a ubiquitin-mediated, ATP-stimulated proteolytic pathway in soluble extracts of BHK 21/C13 fibroblasts," Biochim Biophys Acta. 967:195-203 (1988).
McInerney et al., "Prevention of insulitis and diabetes onset by treatment with complete Freund's adjuvant in NOD mice," Diabetes. 40:715-725 (1991).
McKay, "Mammalian deconstruction for stem cell reconstruction," Nat Med. 6(7):747-748 (2000).
Mercurio et al., "p105 and p98 precursor proteins play an active role in NF-Kappa B-mediated signal transduction," Genes Dev. 7:705-718 (1993).
Mestas et al., "Of mice and not men: Differences between mouse and human immunology," J Immunol. 172:2731-2738 (2004).
Mezey et al., "Turning blood into brain: Cells bearing neuronal antigens generated in vivo from bone marrow," Science. 290:1779-1782 (2000).
Miller et al., "Both the Lyt-2+ and L3T4+ T cell subsets are required for the transfer of diabetes in nonobese diabetic mice," J Immunol. 140(3):52-58 (1988).
Mittelman et al., "A phase I pharmacokinetic study of recombinant human tumor necrosis factor administered by a 5-day continuous infusion," Invest New Drugs. 10(3):183-190 (1992).
Miyazaki et al., "Predominance of T lymphocytes in pancreatic islets and spleen of pre-diabetic non-obese diabetic (NOD) mice: A longitudinal study," Clin Exp Immunol. 60:622-630 (1985).
Moreland et al., "Etanercept therapy in rheumatoid arthritis: a randomized, controlled trial," Ann Intern Med. 130(6):478-486 (1999).
Morrison, "Stem cell potential: Can anything make anything?" Curr Biol. 11:R7-R9 (2001).
Murthi et al., "Novel homeobox genes are differentially expressed in placental microvascular endothelial cells compared with macrovascular cells," Placenta. 29(7):624-630 (2008) (Abstract Only).
Nomikos et al., "Combined treatment with nicotinamide and desferrioxamine prevents islet allograft destruction in NOD mice," Diabetes. 35:1302-1304 (1986).
Offield et al., "PDX-1 is required for pancreatic outgrowth and differentiation of the rostral duodenum," Development. 122:983-995 (1996).
Ono et al., "IDDM in BB rats. Enhanced MHC Class I heavy-chain gene expression in pancreatic islets," Diabetes. 37:1411-1418 (1988).
Orlowski, "The multicatalytic proteinase complex, a major extralysosomal proteolytic system," Biochemistry. 29(45):10289-10297 (1990).
Osorio et al., "Beta-2 microglobulin gene disruption prolongs murine islet allograft survival in NOD mice," Transplant Proc. 26(2):752 (1994).
Palombella et al., "The ubiquitin-proteasome pathway is required for processing the NF-$_{kappa}$B1 precursor protein and the activation of NF-$_{kappa}$B," Cell. 78:773-785 (1994).

Paolillo et al., "The effect of Bacille Calmette-Guérin on the evolution of new enhancing lesions to hypointense T1 lesions in relapsing remitting MS," J Neurol. 250:247-248 (2003).
Pestano et al., "Inactivation of misselected CD8 T cells by CD8 gene methylation and cell death," Science. 284(5417):1187-91 (1999).
Petersen et al., "Bone marrow as a potential source of hepatic oval cells," Science. 284(5417):1168-70 (1999).
Pillay et al., "Antibodies in oncology," N Biotechnol. 28(5):518-529 (2011).
Pontesilli et al., "Circulating lymphocyte populations and autoantibodies in non-obese diabetic (Nod) mice: a longitudinal study," Clin Exp Immunol. 70(1):84-93 (1987).
Pozzilli, "BCG vaccine in insulin-dependent diabetes mellitus," Lancet. 349(9064):1520-1 (1997).
Prieto et al., "Apoptotic rate: A new indicator for the quantification of the incidence of apoptosis in cell cultures," Cytometry. 48(4):185-93 (2002).
Product Data Sheet for TNF RII/TNFRSF1 B Inhibition of TNP-alpha-induced Cyototoxicity and Neutralization by Human TNF RII/TNFRSF1B Antibody. Retrieved Aug. 1, 2017. R&D Systems Inc. (3 pages).
Qin et al., "BCG vaccination prevents insulin-dependent diabetes mellitus (IDDM) in NOD mice after disease acceleration with cyclophosphamide," J Autoimmun.10:271-278 (1997).
Qin et al., "Complete Freund's adjuvant-induced T cells prevent the development and adoptive transfer of diabetes in nonobese diabetic mice," J Immunol. 150(5):2072-80 (1993).
Quintana et al., "Experimental autoimmune myasthenia gravis in naïve non-obese diabetic (NOD/LTJ) mice: Susceptibility associated with natural IgG antibodies to the acetylcholine receptor," Int Immunol. 15(1):11-16 (2003).
Raab et al., "In vitro evaluation of methotrexate and azathioprine for antipsoriatic activity," Arch Derm Res. 253:77-84 (1975).
Rabinovitch et al., "TNF-alpha down-regulates type 1 cytokines and prolongs survival of syngeneic islet grafts in nonobese diabetic mice," J Immunol. 159(12):6298-6303 (1997).
Rabinovitch et al., "Tumor necrosis factor mediates the protective effect of Freund's adjuvant against autoimmune diabetes in BB rats," J Autoimmun. 8(3):357-366 (1995).
Rajagopalan et al., "Pathogenic anti-Dna autoantibody-inducing T helper cell lines from patients with active lupus nephritis: Isolation of CD4-8- T helper cell lines that express the gamma delta T-cell antigen receptor," Proc Natl Acad Sci USA. 87:7020-7024 (1990).
Raju et al., "Characterization and developmental expression of Tlx-1, the murine homolog of HOX11," Mech Dev. 44(1):51-64 (1993).
Ramiya et al., "Reversal of insulin-dependent diabetes using islets generated in vitro from pancreatic stem cells," Nat Med. 6(3):278-282 (2000).
Rath et al., "TNF-induced signaling in apoptosis," J Clin Immunol. 19(6):350-364 (1999).
Rechsteiner, "Ubiquitin-mediated pathways for intracellular proteolysis," Annu Rev Cell Biol. 3:1-30 (1987).
Rietze et al., "Purification of a pluripotent neural stem cell from the adult mouse brain," Nature. 412(6848):736-739 (2001).
Ristori et al., "Use of Bacille Calmette-Guérin (BCG) in multiple sclerosis," Neurology. 53:1588-1589 (1999).
Roberts et al., "Developmental expression of Hox11 and specification of splenic cell fate," Am J Pathol. 146(5):1089-1101 (1995).
Roberts et al., "Hox11 controls the genesis of the spleen," Nature. 368:747-749 (1994).
Robertson et al., "Preservation of insulin mRNA levels and insulin secretion in HIT cells by avoidance of chronic exposure to high glucose concentrations," J Clin Invest. 90:320-325 (1992).
Robinson et al., "A novel NOD-derived murine model of primary Sjögren's Syndrome," Arth Rheum. 41(1):150-156 (1998).
Robinson et al., "Elevated levels of cysteine protease activity in saliva and salivary glands of the nonobese diabetic (NOD) mouse model for Sjögren Syndrome," Proc Natl Acad Sci USA. 94:5767-5771 (1997).
Rolfe et al., "The ubiquitin-mediated proteolytic pathway as a therapeutic area," J Mol Med. 75:5-17 (1997).

(56) References Cited

OTHER PUBLICATIONS

Rosenthal, "Prometheus's vulture and the stem-cell promise," N Engl J Med. 349(3):267-74 (2003).
Ryu et al., "Reversal of established autoimmune diabetes by restoration of endogenous beta cell function," J Clin Invest. 108(1):63-72 (2001).
Sadelain et al., "Prevention of type I diabetes in NOD mice by adjuvant immunotherapy," Diabetes. 39:583-589 (1990).
Sandborn et al., "Antitumor necrosis factor therapy for inflammatory bowel disease: a review of agents, pharmacology, clinical results, and safety," Inflamm Bowel Dis. 5(2):119-33 (1999) (Abstract only).
Sandborn, "Strategies targeting tumor necrosis factor in Crohn's disease," Acta Gastroenterol Belg. 64(2):170-2 (2001) (Abstract only).
Sarin et al., "Cytotoxic effect of TNF and lymphotoxin on T lymphoblasts," J Immunol. 155:3716-3718 (1995).
Satoh et al., "Inhibition of type I diabetes in BB rats with recombinant human tumor necrosis factor-alpha," J Immunol. 145(5):1395-1399 (1990).
Satoh et al., "Recombinant human tumor necrosis factor alpha suppresses autoimmune diabetes in nonobese diabetic mice," J Clin Invest. 84:1345-1348 (1989).
Schaible, "Long term safety of infliximab," Can J Gastroenterol. 14(Suppl C):29C-32C (2000) (Abstract only).
Schatz et al., "Defective inducer T-cell function before the onset of insulin-dependent diabetes mellitus," J Autoimmun. 4:125-136 (1991).
Schmidt et al., "Interspecies exchange of beta2-microglobulin and associated MHC and differentiation antigens," Immunogenetics. 13(6):483-91 (1981).
Schuppan, "Current concepts of Celiac Disease pathogenesis," Gastroenterology. 119(1):234-242 (2000).
Sears et al., "NF-kappaB p105 processing via the ubiquitin-proteasome pathway," J Biol Chem. 273(3):1409-1419 (1998).
Sedger et al., "Poxvirus tumor necrosis factor receptor (TNFR)-like T2 proteins contain a conserved preligand assembly domain that inhibits cellular TNFR1-induced cell death," J Virol. 80(18):9300-9 (2006).
Serrano et al., "Non-HLA associations with autoimmune diseases," Autoimmun Rev. 5:209-214 (2006).
Serreze et al., "Th1 to Th2 cytokine shifts in nonobese diabetic mice: Sometimes an outcome, rather than the cause, of diabetes resistance elicited by immunostimulation," J Immunol. 166:1352-1359 (2001).
Serup et al., "Islet and stem cell transplantation for treating diabetes," BMJ. 322:29-32 (2001).
Serup, "Panning for pancreatic stem cells," Nat Genet. 25:134-135 (2000).
Shakoor et al., "Drug-induced systemic lupus erythematosus associated with etanercept therapy," Lancet. 359(9306):579-80 (2002) (Absract only).
Shehadeh et al., "Effect of adjuvant therapy on development of diabetes in mouse and man," Lancet. 343:706-707 (1994).
Shehadeh et al., "Repeated BCG vaccination is more effective than a single dose in preventing diabetes in non-obese diabetic (NOD) mice," Isr J Med Sci. 33(11):711-715 (1997).
Shihabuddin et al., "Adult spinal cord stem cells generate neurons after transplantation in the adult dentate gyrus," J Neurosci. 20(23):8727-8735 (2000).
Shohami et al., "Dual role of tumor necrosis factor alpha in brain injury," Cytokine Growth Factor Rev. 10:119-130 (1999).
Silva et al., "Prevention of autoimmune diabetes through immunostimulation with Q fever complement-fixing antigen," Ann NY Acad Sci. 1005:423-430 (2003).
Singh et al., "Can progression of IDDM be prevented in newly diagnosed patients by BCG immunotherapy?" Diabetes Metab Rev. 13(4):320-321 (1997).
Slack, "Stem cells in epithelial tissues," Science. 287:1431-1433 (2000).
Song et al., "Tumor necrosis factor-related apoptosis-inducing ligand (TRAIL) is an inhibitor of autoimmune inflammation and cell cycle progression," J Exp Med. 191(7):1095-1103 (2000).
Speiser et al., "Loss of ATP-dependent proteolysis with maturation of reticulocytes and erythrocytes," J Biol Chem. 257(23):14122-14127 (1982).
Sreenan et al., "Increased beta-Cell proliferation and reduced mass before diabetes onset in the nonobese diabetic mouse," Diabetes. 48:989-996 (1999).
Stephens et al., "Protection of NIT-1 pancreatic beta-cells from immune attack by inhibition of NF-kappaB," J Autoimmun. 10:293-298 (1997).
Storms et al., "Hoechst dye efflux reveals a novel CD7+CD34-lymphoid progenitor in human umbilical cord blood," Blood. 96(6):2125-2133 (2000).
Sun et al., "MHC class I multimers," Arthritis Res. 3(5):265-269 (2001).
Supplementary Partial European Search Report for European Application No. 04817543, dated Oct. 6, 2009 (4 pages).
Swale et al., "Etanercept-induced systemic lupus erythematosus," Clin Exp Dermatol. 28:604-607 (2003).
Swirski et al., "Identification of splenic reservoir monocytes and their deployment to inflammatory sites," available in PMC Jan. 7, 2010, published in final edited form as: Science. 325(5940):612-616 (2009) (12 pages).
Szodoray et al., "Programmed cell death in rheumatoid arthritis peripheral blood T-cell subpopulations determined by laser scanning cytometry," Lab Invest. 83(12):1839-1848 (2003).
Tamura et al., "In vivo differentiation of stem cells in the aorta-gonad-mesonephros region of mouse embryo and adult bone marrow," Exp Hematol. 30(8):957-966 (2002) (Abstract Only).
Tartaglia et al., "The two different receptors for tumor necrosis factor mediate distinct cellular responses," Proc Natl Acad Sci USA. 88:9292-9296 (1991).
Tavernier et al., "Analysis of the structure-function relationship of tumour necrosis factor. Human/mouse chimeric TNF proteins: general properties and epitope analysis," J Mol Biol. 211(2):493-501 (1990).
Technical Data Sheet for Purified Rat Anti-Human CD120b, BD Pharmingen™ (2011) (2 pages).
Terada et al., "Bone marrow cells adopt the phenotype of other cells by spontaneous cell fusion," Nature. 416:542-545 (2002).
Thomas et al., "Demyelination during anti-tumor necrosis factor alpha therapy with infliximab for Crohn's disease," Inflamm Bowel Dis. 10(1):28-31 (2004) (Abstract only).
Toma et al., "Isolation of multipotent adult stem cells from the dermis of mammalian skin," Nat Cell Bio. 3:778-784 (2001).
Totpal et al., "TNF and its receptor antibody agonist differ in mediation of cellular responses," J Immunol. 153:2248-2257 (1994).
Townsley et al., "Dominant-negative cyclin-selective ubiquitin carrier protein E2-C/UbcH10 blocks cells in metaphase," Proc Natl Acad Sci USA. 94:2362-2367 (1997).
Trad et al., "Clonal Progression during the T Cell-Dependent B Cell Antibody Response Depends on the Immunoglobulin DH Gene Segment Repertoire," Front Immunol. 5(385):1-11 (2014).
Tran et al., "Reversal of Sjögren's-like syndrome in non-obese diabetic mice," Ann Rheum Dis. 66:812-814 (2007).
Trowsdale et al., "Sequences encoded in the class II region of the MHC related to the 'ABC' superfamily of transporters," Nature. 348:741-744 (1990).
Ulaeto et al., "A T-cell dormant state in the autoimmune process of nonobese diabetic mice treated with complete Freund's adjuvant," Proc Natl Acad Sci USA. 89:3927-3931 (1992).
Van der Kooy et al., "Why stem cells?" Science. 287:1439-1441 (2000).
Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Van Noort et al., "Cell biology of autoimmune diseases," Int Rev Cytol. 178:127-206 (1998).

(56) References Cited

OTHER PUBLICATIONS

Van Zee et al., "A human tumor necrosis factor (TNF) alpha mutant that binds exclusively to the p55 TNF receptor produces toxicity in the baboon," J Exp Med. 179(4):1185-1191 (1994).
Vermeire et al., "Autoimmunity associated with anti-tumor necrosis factor alpha treatment in Crohn's disease: a prospective cohort study," Gastroenterology. 125(1):32-9 (2003) (Abstract only).
Vidal-Puig et al., "Tolerance to peripheral tissue Is transient and maintained by tissue-specific class I expression," Transplant Proc. 26(6):3314-6 (1994).
Vogel, "Stem cell research. Studies cast doubt on plasticity of adult cells," Science. 295:1989&1991 (2002).
Von Herrath et al., "In vivo treatment with a MHC class I-restricted blocking peptide can prevent virus-induced autoimmune diabetes," J Immunol. 161:5087-5096 (1998).
Wagner, "Making and using antibodies," <http://www-users.med.cornell.edu/~jawagne/Antibody_Approaches.html>, accessed Aug. 8, 2016 (7 pages).
Wang et al., "Prevention of recurrence of IDDM in islet-transplanted diabetic NOD mice by adjuvant immunotherapy," Diabetes. 41:114-117 (1992).
Watt et al., "Out of eden: stem cells and their niches," Science. 287:1427-1430 (2000).
Watt et al., "Specific alternative HOX11 transcripts are expressed in paediatric neural tumours and T-cell acute lymphoblastic leukaemia," Gene. 323:89-99 (2003) (Abstract only).
Waxman et al., "Demonstration of two distinct high molecular weight proteases in rabbit reticulocytes, one of which degrades ubiquitin conjugates," J Biol Chem. 262(6):2451-2457 (1987).
Weissman, "Translating stem and progenitor cell biology to the clinic: barriers and opportunities," Science. 287:1442-1446 (2000).
Welborn et al., "A human tumor necrosis factor p75 receptor agonist stimulates in vitro T cell proliferation but does not produce inflammation or shock in the baboon," J Exp Med. 184(1):165-171 (1996).
Wellik et al., "Hox11 paralogous genes are essential for metanephric kidney induction," Genes Dev. 16:1423-1432 (2002).
Wellik, "The role of Hox11 paralogous genes in prostate development," Grant Detail. (2009) (1 page)(Abstract only).
Weringer et al., "Identification of T cell subsets and Class I and Class II antigen expression in islet grafts and pancreatic islets of diabetic BioBreeding/Worcester rats," Am J Pathol. 132(2):292-303 (1988).
Wicker et al., "Transfer of autoimmune diabetes mellitus with splenocytes from nonobese diabetic (NOD) mice," Diabetes. 35:855-860 (1986).
Willis et al., "Type 1 Diabetes in insulin-treated adult-onset diabetic subjects," Diabetes Res Clin Pract. 42:49-53 (1998).
Wilson et al., "Bone-marrow haematopoietic-stem-cell niches," Nat Rev Immunol. 6(2):93-106 (2006).
Winston, "Embryonic stem cell research: the case for . . . ," Nat Med. 7(4):396-397 (2001).
Wong et al., "Identification of an MHC class I-restricted autoantigen in Type I Diabetes by screening an organ-specific cDNA library," Nat Med. 5(9):1026-1031 (1999).
Written Opinion for International Application No. PCT/US2004/037998, dated Feb. 28, 2008 (3 pages).
Xu et al., "MHC/peptide tetramer-based studies of T cell function," J Immunol Methods. 268:21-28 (2002).
Yagi et al., "Possible mechanism of the preventive effect of BCG against diabetes mellitus in NOD Mouse. I. Generation of suppressor macrophages in spleen cells of BCG-vaccinated mice," Cell Immunol. 138:130-141 (1991).
Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).
Yan et al., "Reduced expression of Tap1 and Lmp2 antigen-processing genes in the nonobese diabetic (NOD) mouse due to a mutation in their shared bidirectional promoter," J Immunol. 159:3068-3080 (1997).
Yang et al., "Effect of tumor necrosis factor alpha on insulin-dependent diabetes mellitus in NOD Mice. I. The early development of autoimmunity and the diabetogenic process," J Exp Med. 180:995-1004 (1994).
Ying et al., "Changing potency by spontaneous fusion," Nature. 416:545-548 (2002).
Yu et al., "Complex Interplay between Epitope Specificity and Isotype Dictates the Biological Activity of Antihuman CD40 Antibodies," Cancer Cell. 33:1-12 (2018) (17 pages).
Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).
Zöller et al., "Apoptosis resistance in peripheral blood lymphocytes of alopecia areata patients," Retrieved from Science Direct, published in: J Autoimmun. 23(3):241-256 (2004) (30 pages).
Okubo et al., "Homogeneous Expansion of Human T-regulatory Cells via Tumor Necrosis Factor Receptor 2," Sci Rep. 3:3153 (11 pages).
Faustman et al., "TNF Receptor 2 and Disease: Autoimmunity and Regenerative Medicine," Front Immunol. 4:478 (2013) (8 pages).
Ban et al., "Strategic Internal Covalent Cross-Linking of TNF Produces a Stable TNF Trimer With Improved TNFR2 Signaling," Mol Cell Ther. 3:7 (2015) (6 pages).
Torrey et al., "Targeting TNFR2 With Antagonistic Antibodies Inhibits Proliferation of Ovarian Cancer Cells and Tumor-Associated Tregs," Sci Signal. 10(462):eaaf8608 (2017) (13 pages).
Extended European Search Report for European Application No. 17796980.5, dated Mar. 5, 2020 (12 pages).

* cited by examiner

FIG. 1A. DNA and Amino Acid Sequences of TNFRAB1 Heavy Chain

TNFRAB1 Heavy Chain

DNA Sequence

GACCAGGCATCCCAGGGTCACCATGGAGTTAGTTTGGGCAGCAGATCCAGGGGCCAGTGGATAGA
CAGATGGGGGTGTCGTTTTGGCTGAGGAGACGGTGACCGCGGTCCCTGCGCCCAGACATCGAAG
TACCAGTAGCTGGAGTAACCATCAACCCTCTGTCGTGCACAGTAATACATGGCCGTGTCCTCAGACC
TCAGACTGCTCATTTGCAGGTACAGGGTGTTCTTGGCATTGTCTCTGGAGATGGTGAATCGCCCCTT
CACACTGTCTGGATAGTAGGTGTAACTACCACCACTACTAATGGTTGCGACCCACTCCAGCCTCTTC
TCCGGAGTCTGGCGAACCCAAGACATGACATAACTACTGAAAGTGAATCCAGAGGCTGCACAGGAG
AGTTTCAGGGACCCTCCAGGCTTCACTAAGCCTCCCCCTGACTCCTGCAGCTGCACCTCCGGAAGC
CTGAATTCTGCAGATATCCATCACACTGGCGGCCGCTCG-AGCATGCATCTAGAGGCCAT

(SEQ ID NO: 1)

Amino acid sequence

EVQLQESGGGLVKPGGSLKLSCAASGFTFSSYVMSWVRQTPEKRLEWVATISSGGSYTYYPDSVKGRF
TISRDNAKNTLYLQMSSLRSEDTAMYYCARQRVDGYSSYWYFDVWGAGTAVTVSS

(SEQ ID NO: 2)

FIG. 1B. DNA and Amino Acid Sequences of TNFRAB1 Light Chain

TNFRAB1 Light Chain

DNA sequence

CTCCGAGCGGCCGCCAGTGTGATGGATATCTGCAGAATTCAGGGGGACATTGTGCTGACCCAGTCT
CCAGCAATCATGTCTGCATCTCCAGGGGAGAAGGTCACCATAACCTGCAGTGCCAGCTCAAGTGTAT
ATTACATGTACTGGTTCCAGCAGAAGCCAGGCACTTCTCCCAAACTCTGGATTTATAGCACATCCAAC
CTGGCTTCTGGAGTCCCTGTTCGCTTCAGTGGCAGTGGCTCTGGGACCTCTTACTCTCTCACAATCA
GCCGAATGGAGGCTGAAGATGCTGCCACTTATTACTGCCAGCAAAGGAGGAATTACCCGTACACGTT
CGGAGGGGGGACCAAGTTGGAAATAAAACGGGCTGATGCTCCACCAACTGTATCCATCTTCCCACC
ATCCAGTGAGCAGTTACCTGAATTCCAGCACACTGGCGGCCGTTACTAGTGGATCCGAGCTCGGTA
CCAAGCTTGATGCATAGCTTGAGTATTCTAACGCGTCACCT 7/16

(SEQ ID NO: 3)

Amino acid sequence

DIVLTQSPAIMSASPGEKVTITCSASSSVYYMYWFQQKPGTSPKLWIYSTSNLASGVPVRFSGSGSGTSY
SLTISRMEAEDAATYYCQQRRNYPYTFGGGTKLEIKRA

(SEQ ID NO: 4)

FIG. 2A. Epitopes within TNFR2 bound by TNFRAB1

```
           10          20          30          40          50
       MAPVAVWAAL  AVGLELWAAA  HALPAQVAFT  PYAPEPGSTC  RLREYYDQTA
           60          70          80          90         100
       QMCCSKCSPG  QHAKVFCTKT  SDTVCDSCED  STYTQLWNWV  PECLSCGSRC
          110         120         130         140         150
       SSDQVETQAC  TREQNRICTC  RPGWYCALSK  QEGCRLCAPL  PKCHPGFGVA
          160         170         180         190         200
       RPGTETSDVV  RKAPCTIS    NTTSSTDICR  PHQICNVVAI  PGNASMDAVC
          210         220         230         240         250
       TSTSPTRSMA  PGAVHLPQPV  STRSQHTQPT  PEPSTAPSTS  FLLPMGPSPP
          260         270         280         290         300
       AEGSTGDFAL  PVGLIVGVTA  LGLLIIGVVN  CVIMTQVKKK  PLCLQREAKV
          310         320         330         340         350
       PHLPADKARG  TQGPEQQHLL  ITAPSSSSSS  LESSASALDR  RAPTRNQPQA
          360         370         380         390         400
       PGVEASGAGE  ARASTGSSDS  SPGGHGTQVN  VTCIVNVCSS  SDHSSQCSSQ
          410         420         430         440         450
       ASSTMGDTDS  SPSESPKDEQ  VPFSKEECAF  RSQLETPETL  LGSTEEKPLP
          460
       LGVPDAGMKP  S
```

FIG. 2B. Epitopes within TNFR2 bound by TNFRAB2

```
         10         20         30         40         50
  MAPVAVWAAL AVGLELWAAA HALPAQVAFT PYAPEPGSTC RLREYYDQTA
         60         70         80         90        100
  QMCCSKCSPG QHAKVFCTKT SDTVCDSCED STYTQLWNWV PECLSCGSRC
        110        120        130        140        150
  SSDQVETQAC TREQNRICTC RPGWYCALSK QEGCRLCAPL RKCRPGFGVA
        160        170        180        190        200
  RPGTETSDVV CKPCAPGTFS NTTSSTDICR PHQICNVVAI PGNASMDAVC
        210        220        230        240        250
  TSTSPTRSMA PGAVHLPQPV STRSQHTQPT PEPSTAPSTS FLLPMGPSPP
        260        270        280        290        300
  AEGSTGDFAL PVGLIVGVTA LGLLIIGVVN CVIMTQVKKK PLCLQREAKV
        310        320        330        340        350
  PHLPADKARG TQGPEQQHLL ITAPSSSSSS LESSASALDR RAPTRNQPQA
        360        370        380        390        400
  PGVEASGAGE ARASTGSSDS SPGGHGTQVN VTCIVNVCSS SDHSSQCSSQ
        410        420        430        440        450
  ASSTMGDTDS SPSESPKDEQ VPFSKEECAF RSQLETPETL LGSTEEKPLP
        460
  LGVPDAGMKP S
```

FIG. 3A. Epitope mapping of TNFRAB1

| SEQ ID NO. | Peptide Sequence | Structural Group | Raw luminescence data |
|---:|---|---|---:|
| 134 | SRCSSDQVETQGGSGGTREQNRICT2R | CYS.S | 177 |
| 135 | RCSSDQVETQAGGSGGTREQNRICT2R | CYS.S | 125 |
| 136 | CSSDQVETQA2GGSGGTREQNRICT2R | CYS.S | 179 |
| 137 | VPE2LS2GSRCGGSGGREQNRICT2RP | CYS.S | 318 |
| 138 | PE2LS2GSRCSGGSGGREQNRICT2RP | CYS.S | 291 |
| 139 | E2LS2GSRCSSGGSGGREQNRICT2RP | CYS.S | 323 |
| 140 | 2LS2GSRCSSDGGSGGREQNRICT2RP | CYS.S | 262 |
| 141 | LS2GSRCSSDQGGSGGREQNRICT2RP | CYS.S | 261 |
| 142 | S2GSRCSSDQVGGSGGREQNRICT2RP | CYS.S | 247 |
| 143 | 2GSRCSSDQVEGGSGGREQNRICT2RP | CYS.S | 228 |
| 144 | GSRCSSDQVETGGSGGREQNRICT2RP | CYS.S | 166 |
| 145 | SRCSSDQVETQGGSGGREQNRICT2RP | CYS.S | 157 |
| 146 | RCSSDQVETQAGGSGGREQNRICT2RP | CYS.S | 130 |
| 147 | CSSDQVETQA2GGSGGREQNRICT2RP | CYS.S | 250 |
| 148 | VPE2LS2GSRCGGSGGEQNRICT2RPG | CYS.S | 225 |
| 149 | PE2LS2GSRCSGGSGGEQNRICT2RPG | CYS.S | 229 |

FIG. 3A (Continued)

| 150 | E2LS2GSRCSSGGSGGEQNRICT2RPG | CYS.S | 152 |
|---|---|---|---|
| 151 | 2LS2GSRCSSDGGSGGEQNRICT2RPG | CYS.S | 214 |
| 152 | LS2GSRCSSDQGGSGGEQNRICT2RPG | CYS.S | 244 |
| 153 | S2GSRCSSDQVGGSGGEQNRICT2RPG | CYS.S | 235 |
| 154 | 2GSRCSSDQVEGGSGGEQNRICT2RPG | CYS.S | 221 |
| 155 | GSRCSSDQVETGGSGGEQNRICT2RPG | CYS.S | 202 |
| 156 | SRCSSDQVETQGGSGGEQNRICT2RPG | CYS.S | 222 |
| 157 | RCSSDQVETQAGGSGGEQNRICT2RPG | CYS.S | 183 |
| 158 | CSSDQVETQA2GGSGGEQNRICT2RPG | CYS.S | 248 |
| 159 | VPE2LS2GSRCGGSGGQNRICT2RPGW | CYS.S | 577 |
| 160 | PE2LS2GSRCSGGSGGQNRICT2RPGW | CYS.S | 543 |
| 161 | E2LS2GSRCSSGGSGGQNRICT2RPGW | CYS.S | 482 |
| 162 | 2LS2GSRCSSDGGSGGQNRICT2RPGW | CYS.S | 345 |
| 163 | LS2GSRCSSDQGGSGGQNRICT2RPGW | CYS.S | 291 |
| 164 | S2GSRCSSDQVGGSGGQNRICT2RPGW | CYS.S | 364 |
| 165 | 2GSRCSSDQVEGGSGGQNRICT2RPGW | CYS.S | 493 |
| 166 | GSRCSSDQVETGGSGGQNRICT2RPGW | CYS.S | 466 |
| 167 | SRCSSDQVETQGGSGGQNRICT2RPGW | CYS.S | 402 |
| 168 | RCSSDQVETQAGGSGGQNRICT2RPGW | CYS.S | 507 |
| 169 | CSSDQVETQA2GGSGGQNRICT2RPGW | CYS.S | 493 |

FIG. 3A (Continued)

| 170 | VPE2LS2GSRCGGSGGNRICT2RPGWY | CYS.S | 853 |
|---|---|---|---|
| 171 | PE2LS2GSRCSGGSGGNRICT2RPGWY | CYS.S | 928 |
| 172 | E2LS2GSRCSSGGSGGNRICT2RPGWY | CYS.S | 389 |
| 173 | 2LS2GSRCSSDGGSGGNRICT2RPGWY | CYS.S | 878 |
| 174 | LS2GSRCSSDQGGSGGNRICT2RPGWY | CYS.S | 822 |
| 175 | S2GSRCSSDQVGGSGGNRICT2RPGWY | CYS.S | 666 |
| 176 | 2GSRCSSDQVEGGSGGNRICT2RPGWY | CYS.S | 588 |
| 177 | GSRCSSDQVETGGSGGNRICT2RPGWY | CYS.S | 587 |
| 178 | SRCSSDQVETQGGSGGNRICT2RPGWY | CYS.S | 482 |
| 179 | RCSSDQVETQAGGSGGNRICT2RPGWY | CYS.S | 247 |
| 180 | CSSDQVETQA2GGSGGNRICT2RPGWY | CYS.S | 487 |
| 181 | VPE2LS2GSRCGGSGGRICT2RPGWY2 | CYS.S | 478 |
| 182 | PE2LS2GSRCSGGSGGRICT2RPGWY2 | CYS.S | 585 |
| 183 | E2LS2GSRCSSGGSGGRICT2RPGWY2 | CYS.S | 478 |
| 184 | 2LS2GSRCSSDGGSGGRICT2RPGWY2 | CYS.S | 436 |
| 185 | LS2GSRCSSDQGGSGGRICT2RPGWY2 | CYS.S | 546 |
| 186 | S2GSRCSSDQVGGSGGRICT2RPGWY2 | CYS.S | 465 |
| 187 | 2GSRCSSDQVEGGSGGRICT2RPGWY2 | CYS.S | 614 |
| 188 | GSRCSSDQVETGGSGGRICT2RPGWY2 | CYS.S | 594 |
| 189 | SRCSSDQVETQGGSGGRICT2RPGWY2 | CYS.S | 568 |
| 190 | RCSSDQVETQAGGSGGRICT2RPGWY2 | CYS.S | 543 |

FIG. 3A (Continued)

| 191 | CSSDQVETQA2GGSGGRICT2RPGWY2 | CY5.5 | 597 |
|---|---|---|---|
| 192 | VPE2LS2GSRCGGSGGICT2RPGWY2A | CY5.5 | 540 |
| 193 | PE2LS2GSRCSGGSGGICT2RPGWY2A | CY5.5 | 542 |
| 194 | E2LS2GSRCSSGGSGGICT2RPGWY2A | CY5.5 | 454 |
| 195 | 2GSRCSSDQVEGGSGGICT2RPGWY2A | CY5.5 | 402 |
| 196 | GSRCSSDQVETGGSGGICT2RPGWY2A | CY5.5 | 403 |
| 197 | SRCSSDQVETQGGSGGICT2RPGWY2A | CY5.5 | 388 |
| 198 | RCSSDQVETQAGGSGGICT2RPGWY2A | CY5.5 | 372 |
| 199 | CSSDQVETQA2GGSGGICT2RPGWY2A | CY5.5 | 454 |
| 200 | VPE2LS2GSRCGGSGGCT2RPGWY2AL | CY5.5 | 483 |
| 201 | PE2LS2GSRCSGGSGGCT2RPGWY2AL | CY5.5 | 697 |
| 202 | E2LS2GSRCSSGGSGGCT2RPGWY2AL | CY5.5 | 605 |
| 203 | 2LS2GSRCSSDGGSGGCT2RPGWY2AL | CY5.5 | 603 |
| 204 | LS2GSRCSSDQGGSGGCT2RPGWY2AL | CY5.5 | 510 |
| 205 | S2GSRCSSDQVGGSGGCT2RPGWY2AL | CY5.5 | 538 |
| 206 | 2GSRCSSDQVEGGSGGCT2RPGWY2AL | CY5.5 | 480 |
| 207 | GSRCSSDQVETGGSGGCT2RPGWY2AL | CY5.5 | 464 |
| 208 | SRCSSDQVETQGGSGGCT2RPGWY2AL | CY5.5 | 391 |
| 209 | RCSSDQVETQAGGSGGCT2RPGWY2AL | CY5.5 | 319 |
| 210 | CSSDQVETQA2GGSGGCT2RPGWY2AL | CY5.5 | 265 |

FIG. 3A (Continued)

| 211 | 2TREQNRI2TCGGSGGRPGWYCALSKQ | CYS.S | 101 |
|---|---|---|---|
| 212 | TREQNRI2TCRGGSGGRPGWYCALSKQ | CYS.S | 188 |
| 213 | REQNRI2TCRPGGSGGRPGWYCALSKQ | CYS.S | 228 |
| 214 | EQNRI2TCRPGGGSGGRPGWYCALSKQ | CYS.S | 263 |
| 215 | QNRI2TCRPGWGGSGGRPGWYCALSKQ | CYS.S | 240 |
| 216 | NRI2TCRPGWYGGSGGRPGWYCALSKQ | CYS.S | 426 |
| 217 | WY2ALSKQEGCGGSGG2APLRKCRPGF | CYS.S | 327 |
| 218 | Y2ALSKQEGCRGGSGG2APLRKCRPGF | CYS.S | 308 |
| 219 | 2ALSKQEGCRLGGSGG2APLRKCRPGF | CYS.S | 439 |
| 220 | ALSKQEGCRL2GGSGG2APLRKCRPGF | CYS.S | 560 |
| 221 | LSKQEGCRL2AGGSGG2APLRKCRPGF | CYS.S | 529 |
| 222 | SKQEGCRL2APGGSGG2APLRKCRPGF | CYS.S | 507 |
| 223 | KQEGCRL2APLGGSGG2APLRKCRPGF | CYS.S | 528 |
| 224 | QEGCRL2APLRGGSGG2APLRKCRPGF | CYS.S | 570 |
| 225 | EGCRL2APLRKGGSGG2APLRKCRPGF | CYS.S | 604 |
| 226 | WY2ALSKQEGCGGSGGAPLRKCRPGFG | CYS.S | 534 |
| 227 | Y2ALSKQEGCRGGSGGAPLRKCRPGFG | CYS.S | 553 |
| 228 | 2ALSKQEGCRLGGSGGAPLRKCRPGFG | CYS.S | 418 |
| 229 | ALSKQEGCRL2GGSGGAPLRKCRPGFG | CYS.S | 321 |
| 230 | LSKQEGCRL2AGGSGGAPLRKCRPGFG | CYS.S | 253 |
| 231 | SKQEGCRL2APGGSGGAPLRKCRPGFG | CYS.S | 220 |
| 232 | KQEGCRL2APLGGSGGAPLRKCRPGFG | CYS.S | 242 |

FIG. 3A (Continued)

| 233 | QEGCRL2APLRGGSGGAPLRKCRPGFG | CY5.5 | 340 |
|---|---|---|---|
| 234 | EGCRL2APLRKGGSGGAPLRKCRPGFG | CY5.5 | 312 |
| 235 | WY2ALSKQEGCGGSGGPLRKCRPGFGV | CY5.5 | 341 |
| 236 | Y2ALSKQEGCRGGSGGPLRKCRPGFGV | CY5.5 | 381 |
| 237 | 2ALSKQEGCRLGGSGGPLRKCRPGFGV | CY5.5 | 414 |
| 238 | ALSKQEGCRL2GGSGGPLRKCRPGFGV | CY5.5 | 446 |
| 239 | LSKQEGCRL2AGGSGGPLRKCRPGFGV | CY5.5 | 434 |
| 240 | SKQEGCRL2APGGSGGPLRKCRPGFGV | CY5.5 | 369 |
| 241 | KQEGCRL2APLGGSGGPLRKCRPGFGV | CY5.5 | 457 |
| 242 | QEGCRL2APLRGGSGGPLRKCRPGFGV | CY5.5 | 558 |
| 243 | EGCRL2APLRKGGSGGPLRKCRPGFGV | CY5.5 | 450 |
| 244 | WY2ALSKQEGCGGSGGLRKCRPGFGVA | CY5.5 | 336 |
| 245 | Y2ALSKQEGCRGGSGGRKCRPGFGVAR | CY5.5 | 463 |
| 246 | 2ALSKQEGCRLGGSGGRKCRPGFGVAR | CY5.5 | 443 |
| 247 | ALSKQEGCRL2GGSGGRKCRPGFGVAR | CY5.5 | 455 |
| 248 | LSKQEGCRL2AGGSGGRKCRPGFGVAR | CY5.5 | 474 |
| 249 | SKQEGCRL2APGGSGGRKCRPGFGVAR | CY5.5 | 430 |
| 250 | KQEGCRL2APLGGSGGRKCRPGFGVAR | CY5.5 | 430 |
| 251 | QEGCRL2APLRGGSGGRKCRPGFGVAR | CY5.5 | 426 |
| 252 | EGCRL2APLRKGGSGGRKCRPGFGVAR | CY5.5 | 358 |

Fig. 3B. Epitope mapping of TNFRAB2

| SEQ ID NO. | Peptide Sequence | Structural Group | Raw luminescence data |
|---|---|---|---|
| 34 | PE2LS2GSRCSGGSGGNRICT2RPGWY | CYS.S | 928 |
| 35 | 2LS2GSRCSSDGGSGGNRICT2RPGWY | CYS.S | 878 |
| 36 | VPE2LS2GSRCGGSGGNRICT2RPGWY | CYS.S | 853 |
| 37 | LS2GSRCSSDQGGSGGNRICT2RPGWY | CYS.S | 822 |
| 38 | PE2LS2GSRCSGGSGGCT2RPGWY2AL | CYS.S | 697 |
| 39 | S2GSRCSSDQVGGSGGNRICT2RPGWY | CYS.S | 666 |
| 40 | 2GSRCSSDQVEGGSGGRICT2RPGWY2 | CYS.S | 614 |
| 41 | E2LS2GSRCSSGGSGGCT2RPGWY2AL | CYS.S | 605 |
| 42 | EGCRL2APLRKGGSGG2APLRKCRPGF | CYS.S | 604 |
| 43 | 2LS2GSRCSSDGGSGGCT2RPGWY2AL | CYS.S | 603 |
| 44 | CSSDQVETQA2GGSGGRICT2RPGWY2 | CYS.S | 597 |
| 45 | GSRCSSDQVETGGSGGRICT2RPGWY2 | CYS.S | 594 |
| 46 | 2GSRCSSDQVEGGSGGNRICT2RPGWY | CYS.S | 588 |
| 47 | GSRCSSDQVETGGSGGNRICT2RPGWY | CYS.S | 587 |
| 48 | PE2LS2GSRCSGGSGGRICT2RPGWY2 | CYS.S | 585 |
| 49 | VPE2LS2GSRCGGSGGQNRICT2RPGW | CYS.S | 577 |
| 50 | QEGCRL2APLRGGSGG2APLRKCRPGF | CYS.S | 570 |
| 51 | SRCSSDQVETQGGSGGRICT2RPGWY2 | CYS.S | 568 |

FIG. 3B (Continued)

| 52 | ALSKQEGCRL2GGSGG2APLRKCRPGF | CYS.S | 560 |
|---|---|---|---|
| 53 | QEGCRL2APLRGGSGGPLRKCRPGFGV | CYS.S | 558 |
| 54 | Y2ALSKQEGCRGGSGGAPLRKCRPGFG | CYS.S | 553 |
| 55 | LS2GSRCSSDQGGSGGRICT2RPGWY2 | CYS.S | 546 |
| 56 | PE2LS2GSRCSGGSGGQNRICT2RPGW | CYS.S | 543 |
| 57 | RCSSDQVETQAGGSGGRICT2RPGWY2 | CYS.S | 543 |
| 58 | PE2LS2GSRCSGGSGGICT2RPGWY2A | CYS.S | 542 |
| 59 | VPE2LS2GSRCGGSGGICT2RPGWY2A | CYS.S | 540 |
| 60 | S2GSRCSSDQVGGSGGCT2RPGWY2AL | CYS.S | 538 |
| 61 | WY2ALSKQEGCGGSGGAPLRKCRPGFG | CYS.S | 534 |
| 62 | LSKQEGCRL2AGGSGG2APLRKCRPGF | CYS.S | 529 |
| 63 | KQEGCRL2APLGGSGG2APLRKCRPGF | CYS.S | 528 |
| 64 | LS2GSRCSSDQGGSGGCT2RPGWY2AL | CYS.S | 510 |
| 65 | RCSSDQVETQAGGSGGQNRICT2RPGW | CYS.S | 507 |
| 66 | SKQEGCRL2APGGSGG2APLRKCRPGF | CYS.S | 507 |
| 67 | 2GSRCSSDQVEGGSGGQNRICT2RPGW | CYS.S | 493 |
| 68 | CSSDQVETQA2GGSGGQNRICT2RPGW | CYS.S | 493 |

FIG. 3B (Continued)

| 69 | CSSDQVETQA2GGSGGNRICT2RPGWY | CYS.S | 487 |
|---|---|---|---|
| 70 | VPE2LS2GSRCGGSGGCT2RPGWY2AL | CYS.S | 483 |
| 71 | E2LS2GSRCSSGGSGGQNRICT2RPGW | CYS.S | 482 |
| 72 | SRCSSDQVETQGGSGGNRICT2RPGWY | CYS.S | 482 |
| 73 | 2GSRCSSDQVEGGSGGCT2RPGWY2AL | CYS.S | 480 |
| 74 | VPE2LS2GSRCGGSGGRICT2RPGWY2 | CYS.S | 478 |
| 75 | E2LS2GSRCSSGGSGGRICT2RPGWY2 | CYS.S | 478 |
| 76 | LSKQEGCRL2AGGSGGRKCRPGFGVAR | CYS.S | 474 |
| 77 | GSRCSSDQVETGGSGGQNRICT2RPGW | CYS.S | 466 |
| 78 | S2GSRCSSDQVGGSGGRICT2RPGWY2 | CYS.S | 465 |
| 79 | GSRCSSDQVETGGSGGCT2RPGWY2AL | CYS.S | 464 |
| 80 | Y2ALSKQEGCRGGSGGRKCRPGFGVAR | CYS.S | 463 |
| 81 | KQEGCRL2APLGGSGGPLRKCRPGFGV | CYS.S | 457 |
| 82 | ALSKQEGCRL2GGSGGRKCRPGFGVAR | CYS.S | 455 |
| 83 | E2LS2GSRCSSGGSGGICT2RPGWY2A | CYS.S | 454 |
| 84 | CSSDQVETQA2GGSGGICT2RPGWY2A | CYS.S | 454 |
| 85 | EGCRL2APLRKGGSGGPLRKCRPGFGV | CYS.S | 450 |
| 86 | ALSKQEGCRL2GGSGGPLRKCRPGFGV | CYS.S | 446 |
| 87 | 2ALSKQEGCRLGGSGGRKCRPGFGVAR | CYS.S | 443 |
| 88 | 2ALSKQEGCRLGGSGG2APLRKCRPGF | CYS.S | 439 |

FIG. 3B (Continued)

| 89  | 2LS2GSRCSSDGGSGGRICT2RPGWY2   | CY5.5 | 436 |
|-----|-------------------------------|-------|-----|
| 90  | LSKQEGCRL2AGGSGGPLRKCRPGFGV   | CY5.5 | 434 |
| 91  | SKQEGCRL2APGGSGGRKCRPGFGVAR   | CY5.5 | 430 |
| 92  | KQEGCRL2APLGGSGGRKCRPGFGVAR   | CY5.5 | 430 |
| 93  | QEGCRL2APLRGGSGGRKCRPGFGVAR   | CY5.5 | 426 |
| 94  | 2ALSKQEGCRLGGSGGAPLRKCRPGFG   | CY5.5 | 418 |
| 95  | 2ALSKQEGCRLGGSGGPLRKCRPGFGV   | CY5.5 | 414 |
| 96  | GSRCSSDQVETGGSGGICT2RPGWY2A   | CY5.5 | 403 |
| 97  | SRCSSDQVETQGGSGGQNRICT2RPGW   | CY5.5 | 402 |
| 98  | 2GSRCSSDQVEGGSGGICT2RPGWY2A   | CY5.5 | 402 |
| 99  | E2LS2GSRCSSGGSGGNRICT2RPGWY   | CY5.5 | 389 |
| 100 | SRCSSDQVETQGGSGGICT2RPGWY2A   | CY5.5 | 388 |
| 101 | Y2ALSKQEGCRGGSGGPLRKCRPGFGV   | CY5.5 | 381 |
| 102 | RCSSDQVETQAGGSGGICT2RPGWY2A   | CY5.5 | 372 |
| 103 | SKQEGCRL2APGGSGGPLRKCRPGFGV   | CY5.5 | 369 |
| 104 | S2GSRCSSDQVGGSGGQNRICT2RPGW   | CY5.5 | 364 |
| 105 | EGCRL2APLRKGGSGGRKCRPGFGVAR   | CY5.5 | 358 |
| 106 | 2LS2GSRCSSDGGSGGQNRICT2RPGW   | CY5.5 | 345 |
| 107 | WY2ALSKQEGCGGSGGPLRKCRPGFGV   | CY5.5 | 341 |
| 108 | QEGCRL2APLRGGSGGAPLRKCRPGFG   | CY5.5 | 340 |
| 109 | WY2ALSKQEGCGGSGG2APLRKCRPGF   | CY5.5 | 327 |

FIG. 3B (Continued)

| 110 | ALSKQEGCRL2GGSGGAPLRKCRPGFG | CYS.S | 321 |
|---|---|---|---|
| 111 | EGCRL2APLRKGGSGGAPLRKCRPGFG | CYS.S | 312 |
| 112 | Y2ALSKQEGCRGGSGG2APLRKCRPGF | CYS.S | 308 |
| 113 | LS2GSRCSSDQGGSGGQNRICT2RPGW | CYS.S | 291 |
| 114 | LSKQEGCRL2AGGSGGAPLRKCRPGFG | CYS.S | 253 |
| 115 | RCSSDQVETQAGGSGGNRICT2RPGWY | CYS.S | 247 |
| 116 | KQEGCRL2APLGGSGGAPLRKCRPGFG | CYS.S | 242 |
| 117 | SKQEGCRL2APGGSGGAPLRKCRPGFG | CYS.S | 220 |

FIG. 4. Visualization of epitopes bound by TNFR2 antibodies
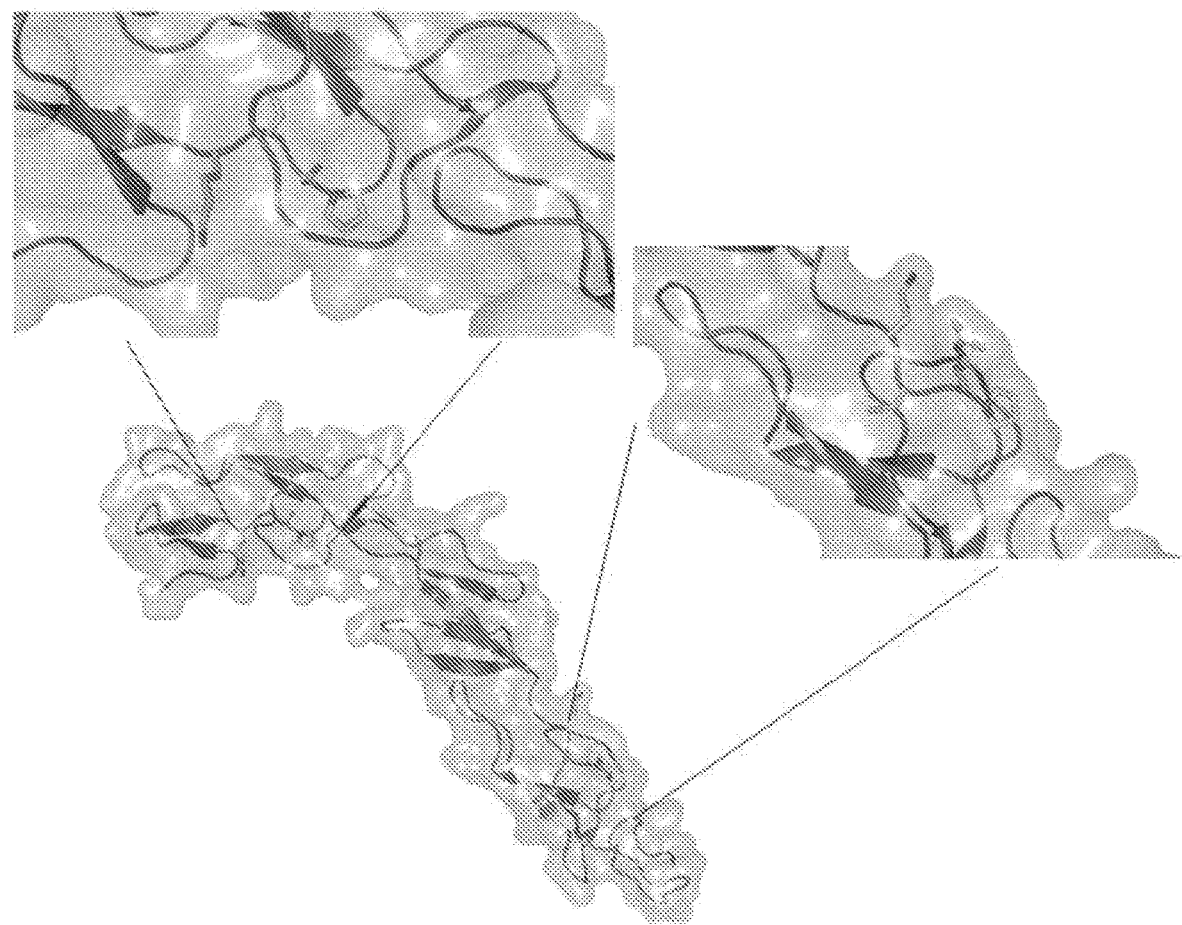

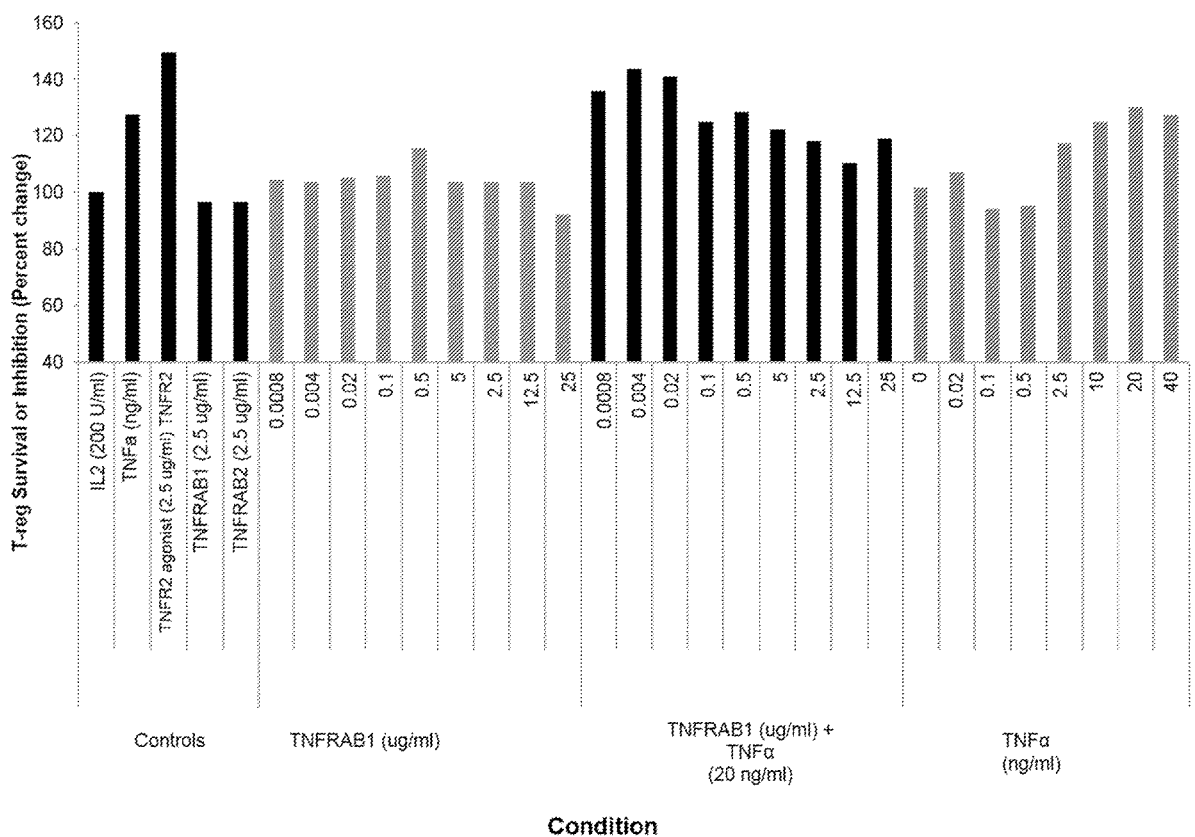
FIG. 5 T-reg Suppression Assay

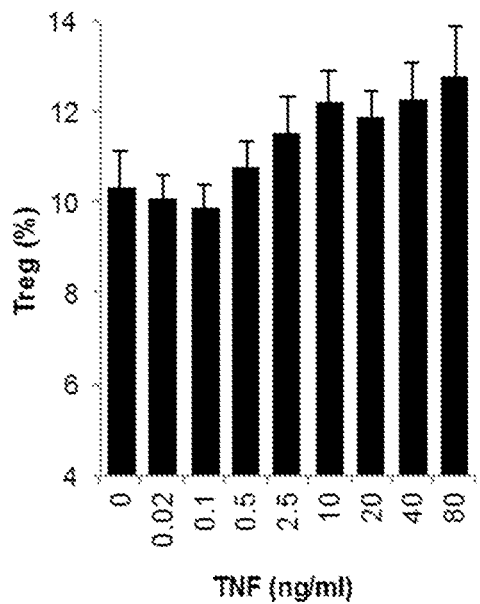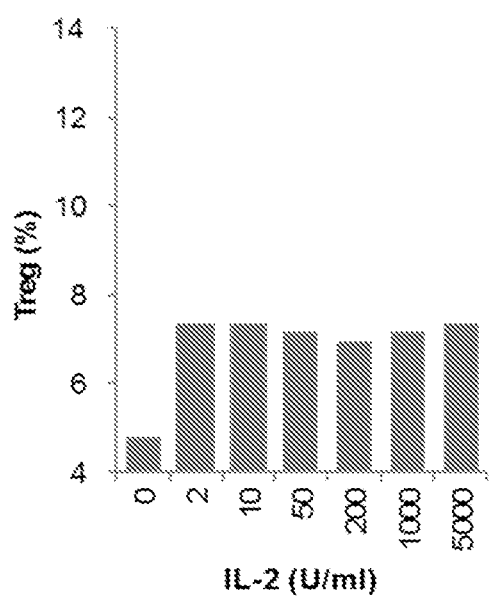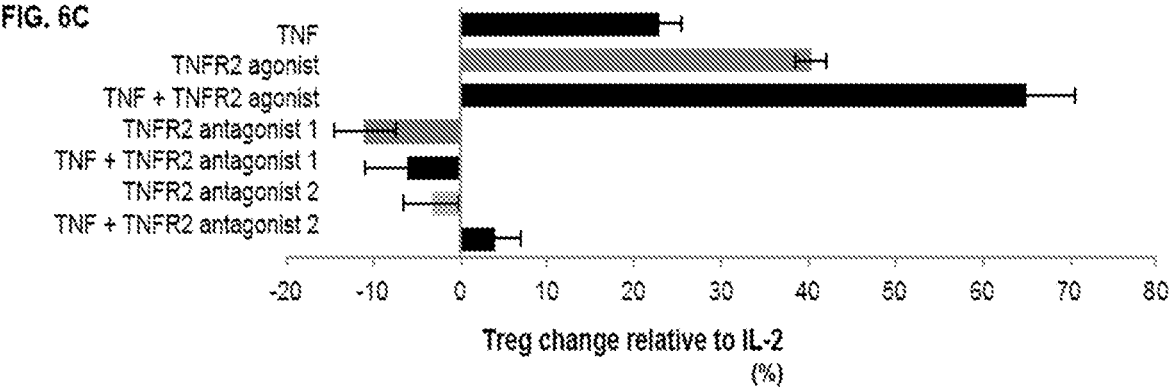

TNFR2 antagonist 1

TNFR2 antagonist 2

Lane
1. Precision Plus Protein Marker (10 ul)
2. Reduced (2.5 ug)
3. Non-reduced (2.5 ug)

TNFR2 antagonist 1 F(ab)'2

1. Perfect Protein™ marker (5 ul)
2. TNFR2 antagonist 1 (2.5 ug)
3. Purified F(ab')2 (15 ul of 1.5 ml)
4. Protein A column elution (15 ul of 1 ml)

TNFR2 antagonist 2 F(ab)'2

1. Precision Plus Protein marker (10 ul)
2. TNFR2 antagonist 2 (2.5 ug)
3. Digested IgG1 (15 ul of 2 ml)
4. Purified F(ab')2 (15 ul of 3 ml)
5. Final flow through + elution (15 ul of 1.5 ml)
6. Protein A column elution (15 ul of 500 ul)
7. Concentrated F(ab')2 (5 ul)

FIG. 13A

Binding affinity of antagonists to TNFR2

| TNFR2 antagonist | $k_{on}$ (1/Ms) | $k_{off}$ (1/s) | $K_D$ (M) |
|---|---|---|---|
| 1 | 4.98E+06 | 2.21E-04 | 4.44E-11 |
| 2 | 3.609(9)E+05 | 2.24E-04 | 6.21(2)E-10 |

$k_{on} = k_a$ — association rate constant
$k_{off} = k_d$ — dissociation rate constant
$K_D$ — equilibrium dissociation constant

FIG. 13B

Linear peptide mapping of TNFR2 antagonists

| Peptide | Position within SEQ ID NO: 7 | Sequence | TNFR2 antagonist 1 Affinity | TNFR2 antagonist 1 Reading | TNFR2 antagonist 2 Affinity | TNFR2 antagonist 2 Reading |
|---|---|---|---|---|---|---|
| TNFR2 | hTNFR2 (23-207) | 20kD | ++++ | 1.2 | ++++ | 1.2 |
| S04062 | hTNFR2 (1-20) | LPAQVAFTPYAPEPGSTCRL | - | 0 | - | 0 |
| S03931 | hTNFR2 (9-28) | PYAPEPGSTCRLREYYDQTA | - | 0 | - | 0 |
| S04063 | hTNFR2 (17-36) | TCRLREYYDQTAQMCCSKCS | - | 0 | - | 0 |
| S03933 | hTNFR2(26-45) | QTAQMCCSKCSPGQHAKVFC | + | 0.1 | - | 0 |
| S04064 | hTNFR2(34-53) | KCSPGQHAKVFCTKTSDTVC | - | 0 | - | 0 |
| S04065 | hTNFR2 (42-61) | KVFCTKTSDTVCDSCEDSTY | - | 0 | - | 0 |
| S04066 | hTNFR2 (50-69) | DTVCDSCEDSTYTQLWNWVP | - | 0 | - | 0 |
| S04067 | hTNFR2 (58-77) | DSTYTQLWNWVPECLSCGSR | - | 0 | - | 0 |
| S04068 | hTNFR2 (66-85) | NWVPECLSCGSRCSSDQVET | - | 0 | - | 0 |
| S04069 | hTNFR2 (74-93) | CGSRCSSDQVETQACTREQN | - | 0 | - | 0 |
| S04070 | hTNFR2 (82-101) | QVETQACTREQNRICTCRPG | - | 0 | - | 0 |
| S04071 | hTNFR2 (90-109) | REQNRICTCRPGWYCALSKQ | ++ | 0.5* | - | 0 |
| S04072 | hTNFR2(98-117) | CRPGWYCALSKQEGCRLCAP | ++ | 0.2* | - | 0 |
| S04073 | hTNFR2(106-125) | LSKQEGCRLCAPLRKCRPGF | +++++ | 1.2* | - | 0 |
| S03935 | hTNFR2 (108-127) | KQEGCRLCAPLRKCRPGFGV | +++++ | 1.2 | - | 0 |
| S04074 | hTNFR2(114-133) | LCAPLRKCRPGFGVARPGTE | +++++ | 1.2* | - | 0 |
| S04075 | hTNFR2 (122-141) | RPGFGVARPGTETSDVVCKP | - | 0 | - | 0 |
| S04076 | hTNFR2 (130-149) | PGTETSDVVCKPCAPGTFSN | - | 0 | - | 0 |
| S04077 | hTNFR2 (138-157) | VCKPCAPGTFSNTTSSTDIC | - | 0 | - | 0 |
| S04078 | hTNFR2 (146-165) | TFSNTTSSTDICRPHQICNV | - | 0 | - | 0 |
| S04079 | hTNFR2 (154-174) | TDICRPHQICNVVAIPGNAS | - | 0 | - | 0 |
| S04080 | hTNFR2 (162-181) | ICNVVAIPGNASMDAVCTST | - | 0 | - | 0 |
| S04081 | hTNFR2 (170-189) | GNASMDAVCTSTSPTRSMAP | - | 0 | - | 0 |

*Ratio (2x)

FIG. 13C

Linear peptide mapping of TNFR2 antagonists with TNF competition

| Peptide | Position within SEQ ID NO: 7 | Sequence | TNFR2 antagonist 1 Affinity | TNFR2 antagonist 1 Plus TNF | TNFR2 antagonist 2 Affinity | TNFR2 antagonist 2 Plus TNF |
|---|---|---|---|---|---|---|
| S03933 | hTNFR2(26-45) | QTAQMCCSKCSPGQHAKVFC | + | No effect | - | n/a |
| S04071 | hTNFR2 (90-109) | REQNRICTCRPGWYCALSKQ | ++ | No effect | - | n/a |
| S04072 | hTNFR2(98-117) | CRPGWYCALSKQEGCRLCAP | ++ | No effect | - | n/a |
| S04073 | hTNFR2(106-125) | LSKQEGCRLCAPLRKCRPGF | +++++ | No effect | - | n/a |
| S03935 | hTNFR2 (108-127) | KQEGCRLCAPLRKCRPGFGV | +++++ | No effect | - | n/a |
| S04074 | hTNFR2(114-133) | LCAPLRKCRPGFGVARPGTE | +++++ | No effect | - | n/a |

FIG. 15A TNFR2 antagonist
Antiparallel dimer
Parallel dimer
FIG. 15B
TNF-TNFR2 complex
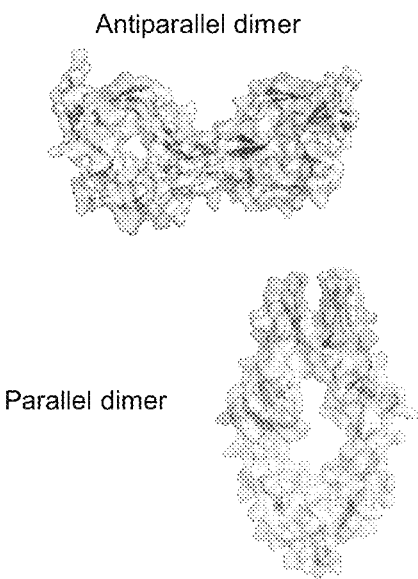
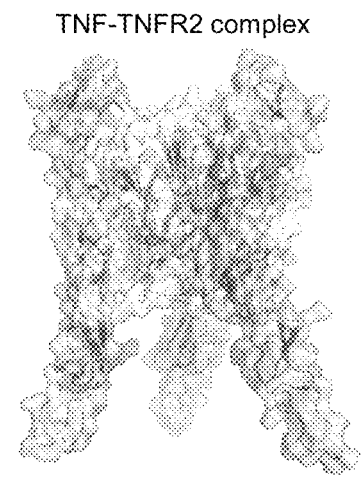
KCRPGFGV (SEQ ID NO: 20) and
CKPCAPGTF (SEQ ID NO: 21)
FIG. 15C
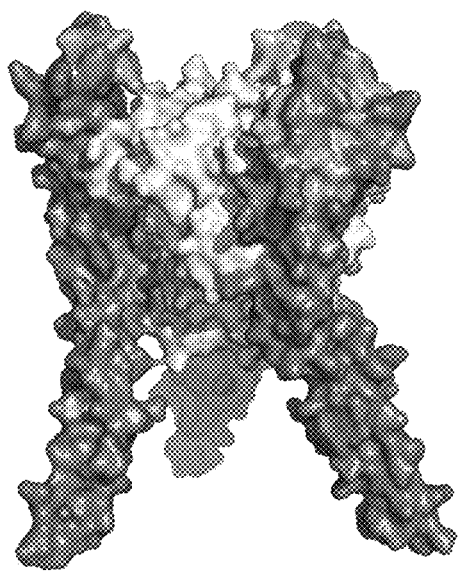

Prior Art

SEQUENCE LISTING

```
<160> NUMBER OF SEQ ID NOS: 283

<210> SEQ ID NO 1
<211> LENGTH: 523
<212> TYPE: DNA
<213> ORGANISM: Murine

<400> SEQUENCE: 1
gaccaggcat cccagggtca ccatggagtt agtttgggca gcagatccag gggccagtgg        60
atagacagat gggggtgtcg ttttggctga ggagacggtg accgcggtcc ctgcgcccca       120
```

```
gacatcgaag taccagtagc tggagtaacc atcaaccctc tgtcgtgcac agtaatacat    180
ggccgtgtcc tcagacctca gactgctcat ttgcaggtac agggtgttct tggcattgtc    240
tctggagatg gtgaatcgcc ccttcacact gtctggatag taggtgtaac taccaccact    300
actaatggtt gcgacccact ccagcctctt ctccggagtc tggcgaaccc aagacatgac    360
ataactactg aaagtgaatc cagaggctgc acaggagagt ttcagggacc ctccaggctt    420
cactaagcct ccccctgact cctgcagctg cacctccgga agcctgaatt ctgcagatat    480
ccatcacact ggcggccgct cgagcatgca tctagaggcc cat                     523
```

```
<210> SEQ ID NO 2
<211> LENGTH: 123
<212> TYPE: PRT
<213> ORGANISM: Murine

<400> SEQUENCE: 2
```

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Arg Val Asp Gly Tyr Ser Ser Tyr Trp Tyr Phe Asp Val
            100                 105                 110

Trp Gly Ala Gly Thr Ala Val Thr Val Ser Ser
        115                 120

```
<210> SEQ ID NO 3
<211> LENGTH: 508
<212> TYPE: DNA
<213> ORGANISM: Murine

<400> SEQUENCE: 3
```

```
ctccgagcgg ccgccagtgt gatggatatc tgcagaattc aggggacat tgtgctgacc      60 cagtctccag caatcatgtc tgcatctcca ggggagaagg tcaccataac ctgcagtgcc    120
agctcaagtg tatattacat gtactggttc cagcagaagc caggcacttc tcccaaactc    180
tggatttata gcacatccaa cctggcttct ggagtccctg ttcgcttcag tggcagtggc    240
tctgggacct cttactctct cacaatcagc cgaatggagg ctgaagatgc tgccacttat    300
tactgccagc aaaggaggaa ttacccgtac acgttcggag ggggaccaa gttggaaata    360 aaacgggctg atgctccacc aactgtatcc atcttccac catccagtga gcagttacct    420
gaattccagc acactggcgg ccgttactag tggatccgag ctcggtacca agcttgatgc    480
atagcttgag tattctaacg cgtcacct                                       508
```

```
<210> SEQ ID NO 4
<211> LENGTH: 108
<212> TYPE: PRT
<213> ORGANISM: Murine
```

-continued

<400> SEQUENCE: 4

Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Tyr Tyr Met
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Asn Tyr Pro Tyr Thr
                85                  90                  95

Phe Gly Gly Gly Thr Lys Leu Glu Ile Lys Arg Ala
            100                 105

<210> SEQ ID NO 5
<211> LENGTH: 454
<212> TYPE: DNA
<213> ORGANISM: Murine

<400> SEQUENCE: 5
gagcggccgc cagtgtgatg gatatctgca gaattcaggg ggacattgtg ctgacccaga      60
ctcctgcttc cttagctgta tctctggggc agagggccac catctcatgc agggccagca     120
aaagtgtcag tacatctggc tatagttata tgcactggta ccaacagaaa ccaggacagc     180
cacccaaact cctcatctat cttgcatcca acctagaatc tggggtccct gccaggttca     240
gtggcagtgg gtctgggaca gacttcaccc tcaacatcca tcctgtggag gaggaggatg     300
ctgcaaccta ttactgtcag cacagtaggg agcttcctcg gacgttcggt ggaggcacca     360
agctggaaat caaacgggct gatgctccac caactgtatc caccccctga attccagcaca    420
ctggcggccg ttactagtgg atccgagctc ggta                                 454

<210> SEQ ID NO 6
<211> LENGTH: 113
<212> TYPE: PRT
<213> ORGANISM: Murine

<400> SEQUENCE: 6

Asp Ile Val Leu Thr Gln Thr Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys Arg
            100                 105                 110

Ala

```
<210> SEQ ID NO 7
<211> LENGTH: 461
<212> TYPE: PRT
<213> ORGANISM: Homo sapiens

<400> SEQUENCE: 7
```

| | | | | | | | | | | | | | | | |
|---|---|---|---|---|---|---|---|---|---|---|---|---|---|---|---|
| Met | Ala | Pro | Val | Ala | Val | Trp | Ala | Ala | Leu | Ala | Val | Gly | Leu | Glu | Leu |
| 1 | | | | 5 | | | | | 10 | | | | | 15 | |
| Trp | Ala | Ala | Ala | His | Ala | Leu | Pro | Ala | Gln | Val | Ala | Phe | Thr | Pro | Tyr |
| | | | 20 | | | | | 25 | | | | | 30 | | |
| Ala | Pro | Glu | Pro | Gly | Ser | Thr | Cys | Arg | Leu | Arg | Glu | Tyr | Tyr | Asp | Gln |
| | | 35 | | | | | 40 | | | | | 45 | | | |
| Thr | Ala | Gln | Met | Cys | Cys | Ser | Lys | Cys | Ser | Pro | Gly | Gln | His | Ala | Lys |
| | 50 | | | | | 55 | | | | | 60 | | | | |
| Val | Phe | Cys | Thr | Lys | Thr | Ser | Asp | Thr | Val | Cys | Asp | Ser | Cys | Glu | Asp |
| 65 | | | | | 70 | | | | | 75 | | | | | 80 |
| Ser | Thr | Tyr | Thr | Gln | Leu | Trp | Asn | Trp | Val | Pro | Glu | Cys | Leu | Ser | Cys |
| | | | | 85 | | | | | 90 | | | | | 95 | |
| Gly | Ser | Arg | Cys | Ser | Ser | Asp | Gln | Val | Glu | Thr | Gln | Ala | Cys | Thr | Arg |
| | | | 100 | | | | | 105 | | | | | 110 | | |
| Glu | Gln | Asn | Arg | Ile | Cys | Thr | Cys | Arg | Pro | Gly | Trp | Tyr | Cys | Ala | Leu |
| | | | 115 | | | | | 120 | | | | | 125 | | |
| Ser | Lys | Gln | Glu | Gly | Cys | Arg | Leu | Cys | Ala | Pro | Leu | Arg | Lys | Cys | Arg |
| | 130 | | | | | 135 | | | | | 140 | | | | |
| Pro | Gly | Phe | Gly | Val | Ala | Arg | Pro | Gly | Thr | Glu | Thr | Ser | Asp | Val | Val |
| 145 | | | | | 150 | | | | | 155 | | | | | 160 |
| Cys | Lys | Pro | Cys | Ala | Pro | Gly | Thr | Phe | Ser | Asn | Thr | Thr | Ser | Ser | Thr |
| | | | | 165 | | | | | 170 | | | | | 175 | |
| Asp | Ile | Cys | Arg | Pro | His | Gln | Ile | Cys | Asn | Val | Val | Ala | Ile | Pro | Gly |
| | | | 180 | | | | | 185 | | | | | 190 | | |
| Asn | Ala | Ser | Met | Asp | Ala | Val | Cys | Thr | Ser | Thr | Ser | Pro | Thr | Arg | Ser |
| | | | 195 | | | | | 200 | | | | | 205 | | |
| Met | Ala | Pro | Gly | Ala | Val | His | Leu | Pro | Gln | Pro | Val | Ser | Thr | Arg | Ser |
| | 210 | | | | | 215 | | | | | 220 | | | | |
| Gln | His | Thr | Gln | Pro | Thr | Pro | Glu | Pro | Ser | Thr | Ala | Pro | Ser | Thr | Ser |
| 225 | | | | | 230 | | | | | 235 | | | | | 240 |
| Phe | Leu | Leu | Pro | Met | Gly | Pro | Ser | Pro | Ala | Glu | Gly | Ser | Thr | Gly | |
| | | | | 245 | | | | | 250 | | | | | 255 | |
| Asp | Phe | Ala | Leu | Pro | Val | Gly | Leu | Ile | Val | Gly | Val | Thr | Ala | Leu | Gly |
| | | | 260 | | | | | 265 | | | | | 270 | | |
| Leu | Leu | Ile | Ile | Gly | Val | Val | Asn | Cys | Val | Ile | Met | Thr | Gln | Val | Lys |
| | | | 275 | | | | | 280 | | | | | 285 | | |
| Lys | Lys | Pro | Leu | Cys | Leu | Gln | Arg | Glu | Ala | Lys | Val | Pro | His | Leu | Pro |
| | 290 | | | | | 295 | | | | | 300 | | | | |
| Ala | Asp | Lys | Ala | Arg | Gly | Thr | Gln | Gly | Pro | Glu | Gln | Gln | His | Leu | Leu |
| 305 | | | | | 310 | | | | | 315 | | | | | 320 |
| Ile | Thr | Ala | Pro | Ser | Ser | Ser | Ser | Ser | Ser | Leu | Glu | Ser | Ser | Ala | Ser |
| | | | | 325 | | | | | 330 | | | | | 335 | |
| Ala | Leu | Asp | Arg | Arg | Ala | Pro | Thr | Arg | Asn | Gln | Pro | Gln | Ala | Pro | Gly |
| | | | 340 | | | | | 345 | | | | | 350 | | |
| Val | Glu | Ala | Ser | Gly | Ala | Gly | Glu | Ala | Arg | Ala | Ser | Thr | Gly | Ser | Ser |
| | | | 355 | | | | | 360 | | | | | 365 | | |
| Asp | Ser | Ser | Pro | Gly | Gly | His | Gly | Thr | Gln | Val | Asn | Val | Thr | Cys | Ile |
| | 370 | | | | | 375 | | | | | 380 | | | | |

Val Asn Val Cys Ser Ser Asp His Ser Ser Gln Cys Ser Ser Gln
385                 390                 395                 400

Ala Ser Ser Thr Met Gly Asp Thr Asp Ser Ser Pro Glu Ser Pro
            405                 410                 415

Lys Asp Glu Gln Val Pro Phe Ser Lys Glu Glu Cys Ala Phe Arg Ser
        420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
        450                 455                 460

<210> SEQ ID NO 8
<211> LENGTH: 7
<212> TYPE: PRT
<213> ORGANISM: Homo sapiens

<400> SEQUENCE: 8

Asp Ser Thr Tyr Thr Gln Leu
1               5

<210> SEQ ID NO 9
<211> LENGTH: 8
<212> TYPE: PRT
<213> ORGANISM: Homo sapiens

<400> SEQUENCE: 9

Pro Glu Cys Leu Ser Cys Gly Ser
1               5

<210> SEQ ID NO 10
<211> LENGTH: 8
<212> TYPE: PRT
<213> ORGANISM: Homo sapiens

<400> SEQUENCE: 10

Arg Ile Cys Thr Cys Arg Pro Gly
1               5

<210> SEQ ID NO 11
<211> LENGTH: 8
<212> TYPE: PRT
<213> ORGANISM: Homo sapiens

<400> SEQUENCE: 11

Cys Ala Pro Leu Arg Lys Cys Arg
1               5

<210> SEQ ID NO 12
<211> LENGTH: 5
<212> TYPE: PRT
<213> ORGANISM: Homo sapiens

<400> SEQUENCE: 12

Lys Cys Ser Pro Gly
1               5

<210> SEQ ID NO 13
<211> LENGTH: 54
<212> TYPE: PRT
<213> ORGANISM: Homo sapiens

<400> SEQUENCE: 13

Cys Asp Ser Cys Glu Asp Ser Thr Tyr Thr Gln Leu Trp Asn Trp Val

```
                1               5                  10                 15
            Pro Glu Cys Leu Ser Cys Gly Ser Arg Cys Ser Ser Asp Gln Val Glu
                            20                  25                  30
            Thr Gln Ala Cys Thr Arg Glu Gln Asn Arg Ile Cys Thr Cys Arg Pro
                        35                  40                  45
            Gly Trp Tyr Cys Ala Leu
                        50
```

<210> SEQ ID NO 14
<211> LENGTH: 17
<212> TYPE: PRT
<213> ORGANISM: Homo sapiens

<400> SEQUENCE: 14

```
Cys Asp Ser Cys Glu Asp Ser Thr Tyr Thr Gln Leu Trp Asn Trp Val
1               5                   10                  15
Pro
```

<210> SEQ ID NO 15
<211> LENGTH: 18
<212> TYPE: PRT
<213> ORGANISM: Homo sapiens

<400> SEQUENCE: 15

```
Leu Trp Asn Trp Val Pro Glu Cys Leu Ser Cys Gly Ser Arg Cys Ser
1               5                   10                  15
Ser Asp
```

<210> SEQ ID NO 16
<211> LENGTH: 18
<212> TYPE: PRT
<213> ORGANISM: Homo sapiens

<400> SEQUENCE: 16

```
Thr Arg Glu Gln Asn Arg Ile Cys Thr Cys Arg Pro Gly Trp Tyr Cys
1               5                   10                  15
Ala Leu
```

<210> SEQ ID NO 17
<211> LENGTH: 20
<212> TYPE: PRT
<213> ORGANISM: Homo sapiens

<400> SEQUENCE: 17

```
Lys Gln Glu Gly Cys Arg Leu Cys Ala Pro Leu Arg Lys Cys Arg Pro
1               5                   10                  15
Gly Phe Gly Val
            20
```

<210> SEQ ID NO 18
<211> LENGTH: 20
<212> TYPE: PRT
<213> ORGANISM: Homo sapiens

<400> SEQUENCE: 18

```
Gln Thr Ala Gln Met Cys Cys Ser Lys Cys Ser Pro Gly Gln His Ala
1               5                   10                  15
Lys Val Phe Cys
            20
```

```
<210> SEQ ID NO 19
<211> LENGTH: 5
<212> TYPE: PRT
<213> ORGANISM: Homo sapiens

<400> SEQUENCE: 19

Lys Cys Arg Pro Gly
1               5

<210> SEQ ID NO 20
<211> LENGTH: 8
<212> TYPE: PRT
<213> ORGANISM: Homo sapiens

<400> SEQUENCE: 20

Lys Cys Arg Pro Gly Phe Gly Val
1               5

<210> SEQ ID NO 21
<211> LENGTH: 9
<212> TYPE: PRT
<213> ORGANISM: Homo sapiens

<400> SEQUENCE: 21

Cys Lys Pro Cys Ala Pro Gly Thr Phe
1               5

<210> SEQ ID NO 22
<211> LENGTH: 41
<212> TYPE: PRT
<213> ORGANISM: Homo sapiens

<400> SEQUENCE: 22

Ala Arg Pro Gly Thr Glu Thr Ser Asp Val Val Cys Lys Pro Cys Ala
1               5                   10                  15

Pro Gly Thr Phe Ser Asn Thr Thr Ser Ser Thr Asp Ile Cys Arg Pro
            20                  25                  30

His Gln Ile Cys Asn Val Val Ala Ile
        35                  40

<210> SEQ ID NO 23
<211> LENGTH: 7
<212> TYPE: PRT
<213> ORGANISM: Murine

<400> SEQUENCE: 23

Gly Phe Thr Phe Ser Ser Tyr
1               5

<210> SEQ ID NO 24
<211> LENGTH: 6
<212> TYPE: PRT
<213> ORGANISM: Murine

<400> SEQUENCE: 24

Ser Ser Gly Gly Ser Tyr
1               5

<210> SEQ ID NO 25
<211> LENGTH: 14
<212> TYPE: PRT
<213> ORGANISM: Murine

<400> SEQUENCE: 25
```

Gln Arg Val Asp Gly Tyr Ser Ser Tyr Trp Tyr Phe Asp Val
1               5                   10

<210> SEQ ID NO 26
<211> LENGTH: 10
<212> TYPE: PRT
<213> ORGANISM: Murine

<400> SEQUENCE: 26

Ser Ala Ser Ser Ser Val Tyr Tyr Met Tyr
1               5                   10

<210> SEQ ID NO 27
<211> LENGTH: 7
<212> TYPE: PRT
<213> ORGANISM: Murine

<400> SEQUENCE: 27

Ser Thr Ser Asn Leu Ala Ser
1               5

<210> SEQ ID NO 28
<211> LENGTH: 9
<212> TYPE: PRT
<213> ORGANISM: Murine

<400> SEQUENCE: 28

Gln Gln Arg Arg Asn Tyr Pro Tyr Thr
1               5

<210> SEQ ID NO 29
<211> LENGTH: 15
<212> TYPE: PRT
<213> ORGANISM: Murine

<400> SEQUENCE: 29

Arg Ala Ser Lys Ser Val Ser Thr Ser Gly Tyr Ser Tyr Met His
1               5                   10                  15

<210> SEQ ID NO 30
<211> LENGTH: 7
<212> TYPE: PRT
<213> ORGANISM: Murine

<400> SEQUENCE: 30

Leu Ala Ser Asn Leu Glu Ser
1               5

<210> SEQ ID NO 31
<211> LENGTH: 9
<212> TYPE: PRT
<213> ORGANISM: Murine

<400> SEQUENCE: 31

Gln His Ser Arg Glu Leu Pro Arg Thr
1               5

<210> SEQ ID NO 32
<211> LENGTH: 120
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 33
<211> LENGTH: 109
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 34
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 34

Pro Glu Xaa Leu Ser Xaa Gly Ser Arg Cys Ser Gly Gly Ser Gly Gly
1               5                   10                  15
```

Asn Arg Ile Cys Thr Xaa Arg Pro Gly Trp Tyr
            20                  25

<210> SEQ ID NO 35
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 35

Xaa Leu Ser Xaa Gly Ser Arg Cys Ser Ser Asp Gly Gly Ser Gly Gly
1               5                   10                  15

Asn Arg Ile Cys Thr Xaa Arg Pro Gly Trp Tyr
            20                  25

<210> SEQ ID NO 36
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 36

Val Pro Glu Xaa Leu Ser Xaa Gly Ser Arg Cys Gly Gly Ser Gly Gly
1               5                   10                  15

Asn Arg Ile Cys Thr Xaa Arg Pro Gly Trp Tyr
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES

```
<222> LOCATION: (22)..(22)
<223> OTHER INFORMATION: Xaa is Cys residue protected with ACM
      protecting group

<400> SEQUENCE: 37

Leu Ser Xaa Gly Ser Arg Cys Ser Ser Asp Gln Gly Gly Ser Gly Gly
1               5                   10                  15

Asn Arg Ile Cys Thr Xaa Arg Pro Gly Trp Tyr
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 38

Pro Glu Xaa Leu Ser Xaa Gly Ser Arg Cys Ser Gly Gly Ser Gly Gly
1               5                   10                  15

Cys Thr Xaa Arg Pro Gly Trp Tyr Xaa Ala Leu
            20                  25

<210> SEQ ID NO 39
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 39

Ser Xaa Gly Ser Arg Cys Ser Ser Asp Gln Val Gly Ser Gly Gly
1               5                   10                  15

Asn Arg Ile Cys Thr Xaa Arg Pro Gly Trp Tyr
            20                  25

<210> SEQ ID NO 40
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 40

Xaa Gly Ser Arg Cys Ser Ser Asp Gln Val Glu Gly Gly Ser Gly Gly
1               5                   10                  15

Arg Ile Cys Thr Xaa Arg Pro Gly Trp Tyr Xaa
            20                  25

<210> SEQ ID NO 41
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 41

Glu Xaa Leu Ser Xaa Gly Ser Arg Cys Ser Ser Gly Gly Ser Gly Gly
1               5                   10                  15

Cys Thr Xaa Arg Pro Gly Trp Tyr Xaa Ala Leu
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group
```

<400> SEQUENCE: 42

Glu Gly Cys Arg Leu Xaa Ala Pro Leu Arg Lys Gly Gly Ser Gly Gly
1               5                   10                  15

Xaa Ala Pro Leu Arg Lys Cys Arg Pro Gly Phe
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 43

Xaa Leu Ser Xaa Gly Ser Arg Cys Ser Ser Asp Gly Gly Ser Gly Gly
1               5                   10                  15

Cys Thr Xaa Arg Pro Gly Trp Tyr Xaa Ala Leu
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 44

Cys Ser Ser Asp Gln Val Glu Thr Gln Ala Xaa Gly Gly Ser Gly Gly
1               5                   10                  15

Arg Ile Cys Thr Xaa Arg Pro Gly Trp Tyr Xaa
            20                  25

<210> SEQ ID NO 45
<211> LENGTH: 27

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 45

Gly Ser Arg Cys Ser Ser Asp Gln Val Glu Thr Gly Gly Ser Gly Gly
1               5                   10                  15

Arg Ile Cys Thr Xaa Arg Pro Gly Trp Tyr Xaa
            20                  25

<210> SEQ ID NO 46
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 46

Xaa Gly Ser Arg Cys Ser Ser Asp Gln Val Glu Gly Gly Ser Gly Gly
1               5                   10                  15

Asn Arg Ile Cys Thr Xaa Arg Pro Gly Trp Tyr
            20                  25

<210> SEQ ID NO 47
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 47

Gly Ser Arg Cys Ser Ser Asp Gln Val Glu Thr Gly Gly Ser Gly Gly
1               5                   10                  15

Asn Arg Ile Cys Thr Xaa Arg Pro Gly Trp Tyr
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 48

Pro Glu Xaa Leu Ser Xaa Gly Ser Arg Cys Ser Gly Gly Ser Gly Gly
1               5                   10                  15

Arg Ile Cys Thr Xaa Arg Pro Gly Trp Tyr Xaa
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 49

Val Pro Glu Xaa Leu Ser Xaa Gly Ser Arg Cys Gly Gly Ser Gly Gly
1               5                   10                  15

Gln Asn Arg Ile Cys Thr Xaa Arg Pro Gly Trp
            20                  25

<210> SEQ ID NO 50
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 50

Gln Glu Gly Cys Arg Leu Xaa Ala Pro Leu Arg Gly Gly Ser Gly Gly
```

```
1               5                   10                  15
Xaa Ala Pro Leu Arg Lys Cys Arg Pro Gly Phe
            20                  25

<210> SEQ ID NO 51
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 51

Ser Arg Cys Ser Ser Asp Gln Val Glu Thr Gln Gly Gly Ser Gly Gly
1               5                   10                  15

Arg Ile Cys Thr Xaa Arg Pro Gly Trp Tyr Xaa
            20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 52

Ala Leu Ser Lys Gln Glu Gly Cys Arg Leu Xaa Gly Gly Ser Gly Gly
1               5                   10                  15

Xaa Ala Pro Leu Arg Lys Cys Arg Pro Gly Phe
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 53

Gln Glu Gly Cys Arg Leu Xaa Ala Pro Leu Arg Gly Gly Ser Gly Gly
1               5                   10                  15

Pro Leu Arg Lys Cys Arg Pro Gly Phe Gly Val
            20                  25
```

-continued

```
<210> SEQ ID NO 54
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 54

Tyr Xaa Ala Leu Ser Lys Gln Glu Gly Cys Arg Gly Gly Ser Gly Gly
1               5                   10                  15

Ala Pro Leu Arg Lys Cys Arg Pro Gly Phe Gly
            20                  25

<210> SEQ ID NO 55
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 55

Leu Ser Xaa Gly Ser Arg Cys Ser Ser Asp Gln Gly Gly Ser Gly Gly
1               5                   10                  15

Arg Ile Cys Thr Xaa Arg Pro Gly Trp Tyr Xaa
            20                  25

<210> SEQ ID NO 56
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 56

Pro Glu Xaa Leu Ser Xaa Gly Ser Arg Cys Ser Gly Gly Ser Gly Gly
1               5                   10                  15
```

Gln Asn Arg Ile Cys Thr Xaa Arg Pro Gly Trp
            20                  25

<210> SEQ ID NO 57
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 57

Arg Cys Ser Ser Asp Gln Val Glu Thr Gln Ala Gly Gly Ser Gly Gly
1               5                   10                  15

Arg Ile Cys Thr Xaa Arg Pro Gly Trp Tyr Xaa
            20                  25

<210> SEQ ID NO 58
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 58

Pro Glu Xaa Leu Ser Xaa Gly Ser Arg Cys Ser Gly Gly Ser Gly Gly
1               5                   10                  15

Ile Cys Thr Xaa Arg Pro Gly Trp Tyr Xaa Ala
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES

```
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 59

Val Pro Glu Xaa Leu Ser Xaa Gly Ser Arg Cys Gly Gly Ser Gly Gly
1               5                   10                  15

Ile Cys Thr Xaa Arg Pro Gly Trp Tyr Xaa Ala
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 60

Ser Xaa Gly Ser Arg Cys Ser Ser Asp Gln Val Gly Ser Gly Gly
1               5                   10                  15

Cys Thr Xaa Arg Pro Gly Trp Tyr Xaa Ala Leu
            20                  25

<210> SEQ ID NO 61
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 61

Trp Tyr Xaa Ala Leu Ser Lys Gln Glu Gly Cys Gly Gly Ser Gly Gly
1               5                   10                  15

Ala Pro Leu Arg Lys Cys Arg Pro Gly Phe Gly
            20                  25

<210> SEQ ID NO 62
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 62

Leu Ser Lys Gln Glu Gly Cys Arg Leu Xaa Ala Gly Gly Ser Gly Gly
1               5                   10                  15

Xaa Ala Pro Leu Arg Lys Cys Arg Pro Gly Phe
            20                  25

<210> SEQ ID NO 63
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 63

Lys Gln Glu Gly Cys Arg Leu Xaa Ala Pro Leu Gly Gly Ser Gly Gly
1               5                   10                  15

Xaa Ala Pro Leu Arg Lys Cys Arg Pro Gly Phe
            20                  25

<210> SEQ ID NO 64
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 64

Leu Ser Xaa Gly Ser Arg Cys Ser Ser Asp Gln Gly Gly Ser Gly Gly
1               5                   10                  15

Cys Thr Xaa Arg Pro Gly Trp Tyr Xaa Ala Leu
            20                  25
```

-continued

```
<210> SEQ ID NO 65
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 65

Arg Cys Ser Ser Asp Gln Val Glu Thr Gln Ala Gly Gly Ser Gly Gly
1               5                   10                  15

Gln Asn Arg Ile Cys Thr Xaa Arg Pro Gly Trp
            20                  25

<210> SEQ ID NO 66
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 66

Ser Lys Gln Glu Gly Cys Arg Leu Xaa Ala Pro Gly Gly Ser Gly Gly
1               5                   10                  15

Xaa Ala Pro Leu Arg Lys Cys Arg Pro Gly Phe
            20                  25

<210> SEQ ID NO 67
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 67

Xaa Gly Ser Arg Cys Ser Ser Asp Gln Val Glu Gly Gly Ser Gly Gly
1               5                   10                  15

Gln Asn Arg Ile Cys Thr Xaa Arg Pro Gly Trp
            20                  25

<210> SEQ ID NO 68
<211> LENGTH: 27
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 68

Cys Ser Ser Asp Gln Val Glu Thr Gln Ala Xaa Gly Gly Ser Gly Gly
1               5                   10                  15

Gln Asn Arg Ile Cys Thr Xaa Arg Pro Gly Trp
            20                  25

<210> SEQ ID NO 69
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 69

Cys Ser Ser Asp Gln Val Glu Thr Gln Ala Xaa Gly Gly Ser Gly Gly
1               5                   10                  15

Asn Arg Ile Cys Thr Xaa Arg Pro Gly Trp Tyr
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 70

Val Pro Glu Xaa Leu Ser Xaa Gly Ser Arg Cys Gly Gly Ser Gly Gly
1               5                   10                  15

Cys Thr Xaa Arg Pro Gly Trp Tyr Xaa Ala Leu
```

<210> SEQ ID NO 71
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM protecting group
<220> FEATURE:
<221> NAME/KEY: MOD_RES
<222> LOCATION: (5)..(5)
<223> OTHER INFORMATION: Xaa is Cys residue protected with ACM protecting group
<220> FEATURE:
<221> NAME/KEY: MOD_RES
<222> LOCATION: (23)..(23)
<223> OTHER INFORMATION: Xaa is Cys residue protected with ACM protecting group

<400> SEQUENCE: 71

Glu Xaa Leu Ser Xaa Gly Ser Arg Cys Ser Ser Gly Gly Ser Gly Gly
1               5                   10                  15

Gln Asn Arg Ile Cys Thr Xaa Arg Pro Gly Trp
            20                  25

<210> SEQ ID NO 72
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM protecting group

<400> SEQUENCE: 72

Ser Arg Cys Ser Ser Asp Gln Val Glu Thr Gln Gly Gly Ser Gly Gly
1               5                   10                  15

Asn Arg Ile Cys Thr Xaa Arg Pro Gly Trp Tyr
            20                  25

<210> SEQ ID NO 73
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM protecting group
<220> FEATURE:
<221> NAME/KEY: MOD_RES
<222> LOCATION: (19)..(19)
<223> OTHER INFORMATION: Xaa is Cys residue protected with ACM protecting group
<220> FEATURE:
<221> NAME/KEY: MOD_RES
<222> LOCATION: (25)..(25)
<223> OTHER INFORMATION: Xaa is Cys residue protected with ACM protecting group

<400> SEQUENCE: 73

```
Xaa Gly Ser Arg Cys Ser Ser Asp Gln Val Glu Gly Gly Ser Gly Gly
1               5                   10                  15

Cys Thr Xaa Arg Pro Gly Trp Tyr Xaa Ala Leu
            20                  25
```

<210> SEQ ID NO 74
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 74

```
Val Pro Glu Xaa Leu Ser Xaa Gly Ser Arg Cys Gly Gly Ser Gly Gly
1               5                   10                  15

Arg Ile Cys Thr Xaa Arg Pro Gly Trp Tyr Xaa
            20                  25
```

<210> SEQ ID NO 75
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 75

```
Glu Xaa Leu Ser Xaa Gly Ser Arg Cys Ser Ser Gly Gly Ser Gly Gly
1               5                   10                  15

Arg Ile Cys Thr Xaa Arg Pro Gly Trp Tyr Xaa
            20                  25
```

```
<210> SEQ ID NO 76
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 76

Leu Ser Lys Gln Glu Gly Cys Arg Leu Xaa Ala Gly Gly Ser Gly Gly
1               5                   10                  15

Arg Lys Cys Arg Pro Gly Phe Gly Val Ala Arg
            20                  25

<210> SEQ ID NO 77
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 77

Gly Ser Arg Cys Ser Ser Asp Gln Val Glu Thr Gly Gly Ser Gly Gly
1               5                   10                  15

Gln Asn Arg Ile Cys Thr Xaa Arg Pro Gly Trp
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 78

Ser Xaa Gly Ser Arg Cys Ser Ser Asp Gln Val Gly Gly Ser Gly Gly
1               5                   10                  15

Arg Ile Cys Thr Xaa Arg Pro Gly Trp Tyr Xaa
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 79

Gly Ser Arg Cys Ser Ser Asp Gln Val Glu Thr Gly Gly Ser Gly Gly
1               5                   10                  15

Cys Thr Xaa Arg Pro Gly Trp Tyr Xaa Ala Leu
            20                  25

<210> SEQ ID NO 80
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 80

Tyr Xaa Ala Leu Ser Lys Gln Glu Gly Cys Arg Gly Ser Gly Gly
1               5                   10                  15

Arg Lys Cys Arg Pro Gly Phe Gly Val Ala Arg
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 81

Lys Gln Glu Gly Cys Arg Leu Xaa Ala Pro Leu Gly Gly Ser Gly Gly
1               5                   10                  15

Pro Leu Arg Lys Cys Arg Pro Gly Phe Gly Val
            20                  25

<210> SEQ ID NO 82
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 82

Ala Leu Ser Lys Gln Glu Gly Cys Arg Leu Xaa Gly Gly Ser Gly Gly
1               5                   10                  15
```

Arg Lys Cys Arg Pro Gly Phe Gly Val Ala Arg
            20                  25

<210> SEQ ID NO 83
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 83

Glu Xaa Leu Ser Xaa Gly Ser Arg Cys Ser Ser Gly Gly Ser Gly Gly
1               5                   10                  15

Ile Cys Thr Xaa Arg Pro Gly Trp Tyr Xaa Ala
            20                  25

<210> SEQ ID NO 84
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 84

Cys Ser Ser Asp Gln Val Glu Thr Gln Ala Xaa Gly Gly Ser Gly Gly
1               5                   10                  15

Ile Cys Thr Xaa Arg Pro Gly Trp Tyr Xaa Ala
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES

```
<222> LOCATION: (6)..(6)
<223> OTHER INFORMATION: Xaa is Cys residue protected with ACM
      protecting group

<400> SEQUENCE: 85

Glu Gly Cys Arg Leu Xaa Ala Pro Leu Arg Lys Gly Gly Ser Gly Gly
1               5                   10                  15

Pro Leu Arg Lys Cys Arg Pro Gly Phe Gly Val
            20                  25

<210> SEQ ID NO 86
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 86

Ala Leu Ser Lys Gln Glu Gly Cys Arg Leu Xaa Gly Gly Ser Gly Gly
1               5                   10                  15

Pro Leu Arg Lys Cys Arg Pro Gly Phe Gly Val
            20                  25

<210> SEQ ID NO 87
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 87

Xaa Ala Leu Ser Lys Gln Glu Gly Cys Arg Leu Gly Gly Ser Gly Gly
1               5                   10                  15

Arg Lys Cys Arg Pro Gly Phe Gly Val Ala Arg
            20                  25

<210> SEQ ID NO 88
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 88

Xaa Ala Leu Ser Lys Gln Glu Gly Cys Arg Leu Gly Gly Ser Gly Gly
1               5                   10                  15

Xaa Ala Pro Leu Arg Lys Cys Arg Pro Gly Phe
            20                  25
```

```
<210> SEQ ID NO 89
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 89

Xaa Leu Ser Xaa Gly Ser Arg Cys Ser Ser Asp Gly Gly Ser Gly Gly
1               5                   10                  15

Arg Ile Cys Thr Xaa Arg Pro Gly Trp Tyr Xaa
            20                  25

<210> SEQ ID NO 90
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 90

Leu Ser Lys Gln Glu Gly Cys Arg Leu Xaa Ala Gly Gly Ser Gly Gly
1               5                   10                  15

Pro Leu Arg Lys Cys Arg Pro Gly Phe Gly Val
            20                  25

<210> SEQ ID NO 91
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 91

Ser Lys Gln Glu Gly Cys Arg Leu Xaa Ala Pro Gly Gly Ser Gly Gly
1               5                   10                  15

Arg Lys Cys Arg Pro Gly Phe Gly Val Ala Arg
            20                  25
```

```
<210> SEQ ID NO 92
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 92

Lys Gln Glu Gly Cys Arg Leu Xaa Ala Pro Leu Gly Gly Ser Gly Gly
 1               5                  10                  15

Arg Lys Cys Arg Pro Gly Phe Gly Val Ala Arg
            20                  25

<210> SEQ ID NO 93
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 93

Gln Glu Gly Cys Arg Leu Xaa Ala Pro Leu Arg Gly Gly Ser Gly Gly
 1               5                  10                  15

Arg Lys Cys Arg Pro Gly Phe Gly Val Ala Arg
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 94

Xaa Ala Leu Ser Lys Gln Glu Gly Cys Arg Leu Gly Gly Ser Gly Gly
 1               5                  10                  15

Ala Pro Leu Arg Lys Cys Arg Pro Gly Phe Gly
            20                  25

<210> SEQ ID NO 95
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 95

Xaa Ala Leu Ser Lys Gln Glu Gly Cys Arg Leu Gly Gly Ser Gly Gly
```

```
1               5                   10                  15
Pro Leu Arg Lys Cys Arg Pro Gly Phe Gly Val
            20                  25

<210> SEQ ID NO 96
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 96

Gly Ser Arg Cys Ser Ser Asp Gln Val Glu Thr Gly Gly Ser Gly Gly
1               5                   10                  15

Ile Cys Thr Xaa Arg Pro Gly Trp Tyr Xaa Ala
            20                  25

<210> SEQ ID NO 97
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 97

Ser Arg Cys Ser Ser Asp Gln Val Glu Thr Gln Gly Gly Ser Gly Gly
1               5                   10                  15

Gln Asn Arg Ile Cys Thr Xaa Arg Pro Gly Trp
            20                  25

<210> SEQ ID NO 98
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 98

Xaa Gly Ser Arg Cys Ser Ser Asp Gln Val Glu Gly Gly Ser Gly Gly
1               5                   10                  15
```

```
Ile Cys Thr Xaa Arg Pro Gly Trp Tyr Xaa Ala
            20                  25
```

<210> SEQ ID NO 99
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 99

```
Glu Xaa Leu Ser Xaa Gly Ser Arg Cys Ser Ser Gly Gly Ser Gly Gly
1               5                   10                  15

Asn Arg Ile Cys Thr Xaa Arg Pro Gly Trp Tyr
            20                  25
```

<210> SEQ ID NO 100
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 100

```
Ser Arg Cys Ser Ser Asp Gln Val Glu Thr Gln Gly Gly Ser Gly Gly
1               5                   10                  15

Ile Cys Thr Xaa Arg Pro Gly Trp Tyr Xaa Ala
            20                  25
```

<210> SEQ ID NO 101
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 101

```
Tyr Xaa Ala Leu Ser Lys Gln Glu Gly Cys Arg Gly Gly Ser Gly Gly
1               5                   10                  15
```

Pro Leu Arg Lys Cys Arg Pro Gly Phe Gly Val
            20                  25

<210> SEQ ID NO 102
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 102

Arg Cys Ser Ser Asp Gln Val Glu Thr Gln Ala Gly Gly Ser Gly Gly
1               5                   10                  15

Ile Cys Thr Xaa Arg Pro Gly Trp Tyr Xaa Ala
            20                  25

<210> SEQ ID NO 103
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 103

Ser Lys Gln Glu Gly Cys Arg Leu Xaa Ala Pro Gly Gly Ser Gly Gly
1               5                   10                  15

Pro Leu Arg Lys Cys Arg Pro Gly Phe Gly Val
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 104

Ser Xaa Gly Ser Arg Cys Ser Ser Asp Gln Val Gly Gly Ser Gly Gly
1               5                   10                  15

Gln Asn Arg Ile Cys Thr Xaa Arg Pro Gly Trp
            20                  25

<210> SEQ ID NO 105
<211> LENGTH: 27

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 105

Glu Gly Cys Arg Leu Xaa Ala Pro Leu Arg Lys Gly Gly Ser Gly Gly
1               5                   10                  15

Arg Lys Cys Arg Pro Gly Phe Gly Val Ala Arg
            20                  25

<210> SEQ ID NO 106
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 106

Xaa Leu Ser Xaa Gly Ser Arg Cys Ser Ser Asp Gly Ser Gly Gly
1               5                   10                  15

Gln Asn Arg Ile Cys Thr Xaa Arg Pro Gly Trp
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 107

Trp Tyr Xaa Ala Leu Ser Lys Gln Glu Gly Cys Gly Gly Ser Gly Gly
1               5                   10                  15

Pro Leu Arg Lys Cys Arg Pro Gly Phe Gly Val
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (7)..(7)
<223> OTHER INFORMATION: Xaa is Cys residue protected with ACM
      protecting group

<400> SEQUENCE: 108

Gln Glu Gly Cys Arg Leu Xaa Ala Pro Leu Arg Gly Gly Ser Gly Gly
1               5                   10                  15

Ala Pro Leu Arg Lys Cys Arg Pro Gly Phe Gly
            20                  25

<210> SEQ ID NO 109
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 109

Trp Tyr Xaa Ala Leu Ser Lys Gln Glu Gly Cys Gly Gly Ser Gly Gly
1               5                   10                  15

Xaa Ala Pro Leu Arg Lys Cys Arg Pro Gly Phe
            20                  25

<210> SEQ ID NO 110
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 110

Ala Leu Ser Lys Gln Glu Gly Cys Arg Leu Xaa Gly Gly Ser Gly Gly
1               5                   10                  15

Ala Pro Leu Arg Lys Cys Arg Pro Gly Phe Gly
            20                  25

<210> SEQ ID NO 111
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 111

Glu Gly Cys Arg Leu Xaa Ala Pro Leu Arg Lys Gly Gly Ser Gly Gly
1               5                   10                  15

Ala Pro Leu Arg Lys Cys Arg Pro Gly Phe Gly
            20                  25
```

<210> SEQ ID NO 112
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 112

Tyr Xaa Ala Leu Ser Lys Gln Glu Gly Cys Arg Gly Gly Ser Gly Gly
1               5                   10                  15

Xaa Ala Pro Leu Arg Lys Cys Arg Pro Gly Phe
            20                  25

<210> SEQ ID NO 113
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 113

Leu Ser Xaa Gly Ser Arg Cys Ser Ser Asp Gln Gly Gly Ser Gly Gly
1               5                   10                  15

Gln Asn Arg Ile Cys Thr Xaa Arg Pro Gly Trp
            20                  25

<210> SEQ ID NO 114
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 114

Leu Ser Lys Gln Glu Gly Cys Arg Leu Xaa Ala Gly Gly Ser Gly Gly
1               5                   10                  15

Ala Pro Leu Arg Lys Cys Arg Pro Gly Phe Gly
            20                  25

<210> SEQ ID NO 115
<211> LENGTH: 27
<212> TYPE: PRT
<213> ORGANISM: Artificial Sequence

```
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 115

Arg Cys Ser Ser Asp Gln Val Glu Thr Gln Ala Gly Gly Ser Gly Gly
1               5                   10                  15

Asn Arg Ile Cys Thr Xaa Arg Pro Gly Trp Tyr
            20                  25

<210> SEQ ID NO 116
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 116

Lys Gln Glu Gly Cys Arg Leu Xaa Ala Pro Leu Gly Gly Ser Gly Gly
1               5                   10                  15

Ala Pro Leu Arg Lys Cys Arg Pro Gly Phe Gly
            20                  25

<210> SEQ ID NO 117
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 117

Ser Lys Gln Glu Gly Cys Arg Leu Xaa Ala Pro Gly Gly Ser Gly Gly
1               5                   10                  15

Ala Pro Leu Arg Lys Cys Arg Pro Gly Phe Gly
            20                  25

<210> SEQ ID NO 118
<211> LENGTH: 5
<212> TYPE: PRT
<213> ORGANISM: Murine

<400> SEQUENCE: 118

Ala Asp Ala Ala Pro
1               5

<210> SEQ ID NO 119
<211> LENGTH: 5
<212> TYPE: PRT
<213> ORGANISM: Homo sapiens

<400> SEQUENCE: 119

Thr Val Ala Ala Pro
1               5
```

<210> SEQ ID NO 120
<211> LENGTH: 11
<212> TYPE: PRT
<213> ORGANISM: Murine

<400> SEQUENCE: 120

Ala Asp Ala Ala Pro Thr Val Ser Ile Phe Pro
1               5                   10

<210> SEQ ID NO 121
<211> LENGTH: 12
<212> TYPE: PRT
<213> ORGANISM: Homo sapiens

<400> SEQUENCE: 121

Thr Val Ala Ala Pro Ser Val Phe Ile Phe Pro Pro
1               5                   10

<210> SEQ ID NO 122
<211> LENGTH: 6
<212> TYPE: PRT
<213> ORGANISM: Homo sapiens

<400> SEQUENCE: 122

Gln Pro Lys Ala Ala Pro
1               5

<210> SEQ ID NO 123
<211> LENGTH: 13
<212> TYPE: PRT
<213> ORGANISM: Homo sapiens

<400> SEQUENCE: 123

Gln Pro Lys Ala Ala Pro Ser Val Thr Leu Phe Pro Pro
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Synthetic Construct

<400> SEQUENCE: 124

Gly Gly Ser Gly Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gly Gly Ser Gly Gly Gly Gly Ser Gly
1               5

<210> SEQ ID NO 126
<211> LENGTH: 13
<212> TYPE: PRT
<213> ORGANISM: Artificial Sequence
<220> FEATURE:
<223> OTHER INFORMATION: Synthetic Construct

```
<400> SEQUENCE: 126

Gly Gly Ser Gly Gly Gly Ser Gly Gly Gly Ser
1               5                   10

<210> SEQ ID NO 127
<211> LENGTH: 6
<212> TYPE: PRT
<213> ORGANISM: Murine

<400> SEQUENCE: 127

Ala Lys Thr Thr Ala Pro
1               5

<210> SEQ ID NO 128
<211> LENGTH: 6
<212> TYPE: PRT
<213> ORGANISM: Homo sapiens

<400> SEQUENCE: 128

Ala Ser Thr Lys Gly Pro
1               5

<210> SEQ ID NO 129
<211> LENGTH: 13
<212> TYPE: PRT
<213> ORGANISM: Murine

<400> SEQUENCE: 129

Ala Lys Thr Thr Ala Pro Ser Val Tyr Pro Leu Ala Pro
1               5                   10

<210> SEQ ID NO 130
<211> LENGTH: 13
<212> TYPE: PRT
<213> ORGANISM: Homo sapiens

<400> SEQUENCE: 130

Ala Ser Thr Lys Gly Pro Ser Val Phe Pro Leu Ala Pro
1               5                   10

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct

<400> SEQUENCE: 131

Gly Gly Gly Gly Ser Gly
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Gly Gly Gly Gly Ser Gly Gly Gly Gly Ser
1               5                   10

<210> SEQ ID NO 133
<211> LENGTH: 14
<212> TYPE: PRT
```

<213> ORGANISM: Artificial Sequence
<220> FEATURE:
<223> OTHER INFORMATION: Synthetic Construct

<400> SEQUENCE: 133

Gly Gly Gly Gly Ser Gly Gly Gly Ser Gly Gly Gly Gly
1               5                   10

<210> SEQ ID NO 134
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 134

Ser Arg Cys Ser Ser Asp Gln Val Glu Thr Gln Gly Gly Ser Gly Gly
1               5                   10                  15

Thr Arg Glu Gln Asn Arg Ile Cys Thr Xaa Arg
            20                  25

<210> SEQ ID NO 135
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 135

Arg Cys Ser Ser Asp Gln Val Glu Thr Gln Ala Gly Gly Ser Gly Gly
1               5                   10                  15

Thr Arg Glu Gln Asn Arg Ile Cys Thr Xaa Arg
            20                  25

<210> SEQ ID NO 136
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 136

Cys Ser Ser Asp Gln Val Glu Thr Gln Ala Xaa Gly Gly Ser Gly Gly
1               5                   10                  15

Thr Arg Glu Gln Asn Arg Ile Cys Thr Xaa Arg
            20                  25

<210> SEQ ID NO 137

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 137

Val Pro Glu Xaa Leu Ser Xaa Gly Ser Arg Cys Gly Gly Ser Gly Gly
1               5                   10                  15

Arg Glu Gln Asn Arg Ile Cys Thr Xaa Arg Pro
            20                  25

<210> SEQ ID NO 138
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 138

Pro Glu Xaa Leu Ser Xaa Gly Ser Arg Cys Ser Gly Gly Ser Gly Gly
1               5                   10                  15

Arg Glu Gln Asn Arg Ile Cys Thr Xaa Arg Pro
            20                  25

<210> SEQ ID NO 139
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
```

```
<222> LOCATION: (25)..(25)
<223> OTHER INFORMATION: Xaa is Cys residue protected with ACM
      protecting group

<400> SEQUENCE: 139

Glu Xaa Leu Ser Xaa Gly Ser Arg Cys Ser Ser Gly Gly Ser Gly Gly
1               5                   10                  15

Arg Glu Gln Asn Arg Ile Cys Thr Xaa Arg Pro
            20                  25

<210> SEQ ID NO 140
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 140

Xaa Leu Ser Xaa Gly Ser Arg Cys Ser Ser Asp Gly Gly Ser Gly Gly
1               5                   10                  15

Arg Glu Gln Asn Arg Ile Cys Thr Xaa Arg Pro
            20                  25

<210> SEQ ID NO 141
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 141

Leu Ser Xaa Gly Ser Arg Cys Ser Ser Asp Gln Gly Gly Ser Gly Gly
1               5                   10                  15

Arg Glu Gln Asn Arg Ile Cys Thr Xaa Arg Pro
            20                  25

<210> SEQ ID NO 142
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
```

```
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 142

Ser Xaa Gly Ser Arg Cys Ser Ser Asp Gln Val Gly Gly Ser Gly Gly
1               5                   10                  15

Arg Glu Gln Asn Arg Ile Cys Thr Xaa Arg Pro
            20                  25

<210> SEQ ID NO 143
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 143

Xaa Gly Ser Arg Cys Ser Ser Asp Gln Val Glu Gly Gly Ser Gly Gly
1               5                   10                  15

Arg Glu Gln Asn Arg Ile Cys Thr Xaa Arg Pro
            20                  25

<210> SEQ ID NO 144
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 144

Gly Ser Arg Cys Ser Ser Asp Gln Val Glu Thr Gly Gly Ser Gly Gly
1               5                   10                  15

Arg Glu Gln Asn Arg Ile Cys Thr Xaa Arg Pro
            20                  25

<210> SEQ ID NO 145
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 145

Ser Arg Cys Ser Ser Asp Gln Val Glu Thr Gln Gly Gly Ser Gly Gly
```

```
1               5                   10                  15
Arg Glu Gln Asn Arg Ile Cys Thr Xaa Arg Pro
            20                  25

<210> SEQ ID NO 146
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 146

Arg Cys Ser Ser Asp Gln Val Glu Thr Gln Ala Gly Gly Ser Gly Gly
1               5                   10                  15

Arg Glu Gln Asn Arg Ile Cys Thr Xaa Arg Pro
            20                  25

<210> SEQ ID NO 147
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 147

Cys Ser Ser Asp Gln Val Glu Thr Gln Ala Xaa Gly Gly Ser Gly Gly
1               5                   10                  15

Arg Glu Gln Asn Arg Ile Cys Thr Xaa Arg Pro
            20                  25

<210> SEQ ID NO 148
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 148

Val Pro Glu Xaa Leu Ser Xaa Gly Ser Arg Cys Gly Gly Ser Gly Gly
1               5                   10                  15
```

```
Glu Gln Asn Arg Ile Cys Thr Xaa Arg Pro Gly
            20                  25

<210> SEQ ID NO 149
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 149

Pro Glu Xaa Leu Ser Xaa Gly Ser Arg Cys Ser Gly Gly Ser Gly Gly
1               5                   10                  15

Glu Gln Asn Arg Ile Cys Thr Xaa Arg Pro Gly
            20                  25

<210> SEQ ID NO 150
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 150

Glu Xaa Leu Ser Xaa Gly Ser Arg Cys Ser Ser Gly Gly Ser Gly Gly
1               5                   10                  15

Glu Gln Asn Arg Ile Cys Thr Xaa Arg Pro Gly
            20                  25

<210> SEQ ID NO 151
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
```

```
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 151

Xaa Leu Ser Xaa Gly Ser Arg Cys Ser Ser Asp Gly Gly Ser Gly Gly
1               5                   10                  15

Glu Gln Asn Arg Ile Cys Thr Xaa Arg Pro Gly
            20                  25

<210> SEQ ID NO 152
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 152

Leu Ser Xaa Gly Ser Arg Cys Ser Ser Asp Gln Gly Gly Ser Gly Gly
1               5                   10                  15

Glu Gln Asn Arg Ile Cys Thr Xaa Arg Pro Gly
            20                  25

<210> SEQ ID NO 153
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 153

Ser Xaa Gly Ser Arg Cys Ser Ser Asp Gln Val Gly Ser Gly Gly
1               5                   10                  15

Glu Gln Asn Arg Ile Cys Thr Xaa Arg Pro Gly
            20                  25

<210> SEQ ID NO 154
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 154

Xaa Gly Ser Arg Cys Ser Ser Asp Gln Val Glu Gly Gly Ser Gly Gly
1               5                   10                  15

Glu Gln Asn Arg Ile Cys Thr Xaa Arg Pro Gly
            20                  25

<210> SEQ ID NO 155
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 155

Gly Ser Arg Cys Ser Ser Asp Gln Val Glu Thr Gly Gly Ser Gly Gly
1               5                   10                  15

Glu Gln Asn Arg Ile Cys Thr Xaa Arg Pro Gly
            20                  25

<210> SEQ ID NO 156
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 156

Ser Arg Cys Ser Ser Asp Gln Val Glu Thr Gln Gly Gly Ser Gly Gly
1               5                   10                  15

Glu Gln Asn Arg Ile Cys Thr Xaa Arg Pro Gly
            20                  25

<210> SEQ ID NO 157
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 157

Arg Cys Ser Ser Asp Gln Val Glu Thr Gln Ala Gly Gly Ser Gly Gly
1               5                   10                  15

Glu Gln Asn Arg Ile Cys Thr Xaa Arg Pro Gly
            20                  25
```

<210> SEQ ID NO 158
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 158

Cys Ser Ser Asp Gln Val Glu Thr Gln Ala Xaa Gly Gly Ser Gly Gly
1               5                   10                  15

Glu Gln Asn Arg Ile Cys Thr Xaa Arg Pro Gly
            20                  25

<210> SEQ ID NO 159
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 159

Val Pro Glu Xaa Leu Ser Xaa Gly Ser Arg Cys Gly Gly Ser Gly Gly
1               5                   10                  15

Gln Asn Arg Ile Cys Thr Xaa Arg Pro Gly Trp
            20                  25

<210> SEQ ID NO 160
<211> LENGTH: 27
<212> TYPE: PRT
<213> ORGANISM: Artificial Sequence
<220> FEATURE:
<223> OTHER INFORMATION: Xaa is Cys residue protected with ACM
      protecting group
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (23)..(23)

```
<223> OTHER INFORMATION: Xaa is Cys residue protected with ACM
      protecting group

<400> SEQUENCE: 160

Pro Glu Xaa Leu Ser Xaa Gly Ser Arg Cys Ser Gly Ser Gly Gly
1               5                   10                  15

Gln Asn Arg Ile Cys Thr Xaa Arg Pro Gly Trp
            20                  25

<210> SEQ ID NO 161
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 161

Glu Xaa Leu Ser Xaa Gly Ser Arg Cys Ser Ser Gly Gly Ser Gly Gly
1               5                   10                  15

Gln Asn Arg Ile Cys Thr Xaa Arg Pro Gly Trp
            20                  25

<210> SEQ ID NO 162
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 162

Xaa Leu Ser Xaa Gly Ser Arg Cys Ser Ser Asp Gly Gly Ser Gly Gly
1               5                   10                  15

Gln Asn Arg Ile Cys Thr Xaa Arg Pro Gly Trp
            20                  25

<210> SEQ ID NO 163
<211> LENGTH: 27
<212> TYPE: PRT
<213> ORGANISM: Artificial Sequence
<220> FEATURE:
```

<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 163

Leu Ser Xaa Gly Ser Arg Cys Ser Ser Asp Gln Gly Gly Ser Gly Gly
1               5                   10                  15

Gln Asn Arg Ile Cys Thr Xaa Arg Pro Gly Trp
            20                  25

<210> SEQ ID NO 164
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 164

Ser Xaa Gly Ser Arg Cys Ser Ser Asp Gln Val Gly Gly Ser Gly Gly
1               5                   10                  15

Gln Asn Arg Ile Cys Thr Xaa Arg Pro Gly Trp
            20                  25

<210> SEQ ID NO 165
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 165

Xaa Gly Ser Arg Cys Ser Ser Asp Gln Val Glu Gly Gly Ser Gly Gly
1               5                   10                  15

Gln Asn Arg Ile Cys Thr Xaa Arg Pro Gly Trp
            20                  25

<210> SEQ ID NO 166
<211> LENGTH: 27
<212> TYPE: PRT
<213> ORGANISM: Artificial Sequence
<220> FEATURE:
<223> OTHER INFORMATION: Synthetic Construct

```
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 166

Gly Ser Arg Cys Ser Ser Asp Gln Val Glu Thr Gly Gly Ser Gly Gly
1               5                   10                  15

Gln Asn Arg Ile Cys Thr Xaa Arg Pro Gly Trp
            20                  25

<210> SEQ ID NO 167
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 167

Ser Arg Cys Ser Ser Asp Gln Val Glu Thr Gln Gly Gly Ser Gly Gly
1               5                   10                  15

Gln Asn Arg Ile Cys Thr Xaa Arg Pro Gly Trp
            20                  25

<210> SEQ ID NO 168
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 168

Arg Cys Ser Ser Asp Gln Val Glu Thr Gln Ala Gly Gly Ser Gly Gly
1               5                   10                  15

Gln Asn Arg Ile Cys Thr Xaa Arg Pro Gly Trp
            20                  25

<210> SEQ ID NO 169
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 169

Cys Ser Ser Asp Gln Val Glu Thr Gln Ala Xaa Gly Gly Ser Gly Gly
1               5                   10                  15
```

Gln Asn Arg Ile Cys Thr Xaa Arg Pro Gly Trp
            20                  25

<210> SEQ ID NO 170
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 170

Val Pro Glu Xaa Leu Ser Xaa Gly Ser Arg Cys Gly Gly Ser Gly Gly
1               5                   10                  15

Asn Arg Ile Cys Thr Xaa Arg Pro Gly Trp Tyr
            20                  25

<210> SEQ ID NO 171
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 171

Pro Glu Xaa Leu Ser Xaa Gly Ser Arg Cys Ser Gly Gly Ser Gly Gly
1               5                   10                  15

Asn Arg Ile Cys Thr Xaa Arg Pro Gly Trp Tyr
            20                  25

<210> SEQ ID NO 172
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES

```
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 172

Glu Xaa Leu Ser Xaa Gly Ser Arg Cys Ser Ser Gly Gly Ser Gly Gly
1               5                   10                  15

Asn Arg Ile Cys Thr Xaa Arg Pro Gly Trp Tyr
            20                  25

<210> SEQ ID NO 173
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 173

Xaa Leu Ser Xaa Gly Ser Arg Cys Ser Ser Asp Gly Gly Ser Gly Gly
1               5                   10                  15

Asn Arg Ile Cys Thr Xaa Arg Pro Gly Trp Tyr
            20                  25

<210> SEQ ID NO 174
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 174

Leu Ser Xaa Gly Ser Arg Cys Ser Ser Asp Gln Gly Gly Ser Gly Gly
1               5                   10                  15

Asn Arg Ile Cys Thr Xaa Arg Pro Gly Trp Tyr
            20                  25

<210> SEQ ID NO 175
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 175

Ser Xaa Gly Ser Arg Cys Ser Ser Asp Gln Val Gly Gly Ser Gly Gly
1               5                   10                  15

Asn Arg Ile Cys Thr Xaa Arg Pro Gly Trp Tyr
            20                  25

<210> SEQ ID NO 176
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 176

Xaa Gly Ser Arg Cys Ser Ser Asp Gln Val Glu Gly Gly Ser Gly Gly
1               5                   10                  15

Asn Arg Ile Cys Thr Xaa Arg Pro Gly Trp Tyr
            20                  25

<210> SEQ ID NO 177
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 177

Gly Ser Arg Cys Ser Ser Asp Gln Val Glu Thr Gly Gly Ser Gly Gly
1               5                   10                  15

Asn Arg Ile Cys Thr Xaa Arg Pro Gly Trp Tyr
            20                  25

<210> SEQ ID NO 178
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
``` protecting group

<400> SEQUENCE: 178

Ser Arg Cys Ser Ser Asp Gln Val Glu Thr Gln Gly Gly Ser Gly Gly
1               5                   10                  15

Asn Arg Ile Cys Thr Xaa Arg Pro Gly Trp Tyr
            20                  25

<210> SEQ ID NO 179
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 179

Arg Cys Ser Ser Asp Gln Val Glu Thr Gln Ala Gly Gly Ser Gly Gly
1               5                   10                  15

Asn Arg Ile Cys Thr Xaa Arg Pro Gly Trp Tyr
            20                  25

<210> SEQ ID NO 180
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 180

Cys Ser Ser Asp Gln Val Glu Thr Gln Ala Xaa Gly Gly Ser Gly Gly
1               5                   10                  15

Asn Arg Ile Cys Thr Xaa Arg Pro Gly Trp Tyr
            20                  25

<210> SEQ ID NO 181
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group

```
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 181

Val Pro Glu Xaa Leu Ser Xaa Gly Ser Arg Cys Gly Gly Ser Gly Gly
1               5                   10                  15

Arg Ile Cys Thr Xaa Arg Pro Gly Trp Tyr Xaa
                20                  25

<210> SEQ ID NO 182
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 182

Pro Glu Xaa Leu Ser Xaa Gly Ser Arg Cys Ser Gly Gly Ser Gly Gly
1               5                   10                  15

Arg Ile Cys Thr Xaa Arg Pro Gly Trp Tyr Xaa
                20                  25

<210> SEQ ID NO 183
<211> LENGTH: 27
<212> TYPE: PRT
<213> ORGANISM: Artificial Sequence
<220> FEATURE:
<223> OTHER INFORMATION: Xaa is Cys residue protected with ACM
      protecting group
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group
```

<400> SEQUENCE: 183

Glu Xaa Leu Ser Xaa Gly Ser Arg Cys Ser Ser Gly Gly Ser Gly Gly
1               5                   10                  15

Arg Ile Cys Thr Xaa Arg Pro Gly Trp Tyr Xaa
            20                  25

<210> SEQ ID NO 184
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 184

Xaa Leu Ser Xaa Gly Ser Arg Cys Ser Ser Asp Gly Gly Ser Gly Gly
1               5                   10                  15

Arg Ile Cys Thr Xaa Arg Pro Gly Trp Tyr Xaa
            20                  25

<210> SEQ ID NO 185
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 185

Leu Ser Xaa Gly Ser Arg Cys Ser Ser Asp Gln Gly Gly Ser Gly Gly
1               5                   10                  15

Arg Ile Cys Thr Xaa Arg Pro Gly Trp Tyr Xaa
            20                  25

<210> SEQ ID NO 186
<211> LENGTH: 27
<212> TYPE: PRT

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 186

Ser Xaa Gly Ser Arg Cys Ser Ser Asp Gln Val Gly Gly Ser Gly Gly
1               5                   10                  15

Arg Ile Cys Thr Xaa Arg Pro Gly Trp Tyr Xaa
                20                  25

<210> SEQ ID NO 187
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 187

Xaa Gly Ser Arg Cys Ser Ser Asp Gln Val Glu Gly Gly Ser Gly Gly
1               5                   10                  15

Arg Ile Cys Thr Xaa Arg Pro Gly Trp Tyr Xaa
                20                  25

<210> SEQ ID NO 188
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 188

Gly Ser Arg Cys Ser Ser Asp Gln Val Glu Thr Gly Gly Ser Gly Gly
```

```
1               5                   10                  15
Arg Ile Cys Thr Xaa Arg Pro Gly Trp Tyr Xaa
            20                  25

<210> SEQ ID NO 189
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 189

Ser Arg Cys Ser Ser Asp Gln Val Glu Thr Gln Gly Gly Ser Gly Gly
1               5                   10                  15
Arg Ile Cys Thr Xaa Arg Pro Gly Trp Tyr Xaa
            20                  25

<210> SEQ ID NO 190
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 190

Arg Cys Ser Ser Asp Gln Val Glu Thr Gln Ala Gly Gly Ser Gly Gly
1               5                   10                  15
Arg Ile Cys Thr Xaa Arg Pro Gly Trp Tyr Xaa
            20                  25

<210> SEQ ID NO 191
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group
```

<400> SEQUENCE: 191

Cys Ser Ser Asp Gln Val Glu Thr Gln Ala Xaa Gly Gly Ser Gly Gly
1               5                   10                  15

Arg Ile Cys Thr Xaa Arg Pro Gly Trp Tyr Xaa
            20                  25

<210> SEQ ID NO 192
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 192

Val Pro Glu Xaa Leu Ser Xaa Gly Ser Arg Cys Gly Gly Ser Gly Gly
1               5                   10                  15

Ile Cys Thr Xaa Arg Pro Gly Trp Tyr Xaa Ala
            20                  25

<210> SEQ ID NO 193
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 193

Pro Glu Xaa Leu Ser Xaa Gly Ser Arg Cys Ser Gly Gly Ser Gly Gly
1               5                   10                  15

Ile Cys Thr Xaa Arg Pro Gly Trp Tyr Xaa Ala 20              25

<210> SEQ ID NO 194
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 194

Glu Xaa Leu Ser Xaa Gly Ser Arg Cys Ser Ser Gly Gly Ser Gly Gly
1               5                   10                  15

Ile Cys Thr Xaa Arg Pro Gly Trp Tyr Xaa Ala
            20                  25

<210> SEQ ID NO 195
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 195

Xaa Gly Ser Arg Cys Ser Ser Asp Gln Val Glu Gly Ser Gly Gly
1               5                   10                  15

Ile Cys Thr Xaa Arg Pro Gly Trp Tyr Xaa Ala
            20                  25

<210> SEQ ID NO 196
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)

```
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 196

Gly Ser Arg Cys Ser Ser Asp Gln Val Glu Thr Gly Gly Ser Gly Gly
1               5                   10                  15

Ile Cys Thr Xaa Arg Pro Gly Trp Tyr Xaa Ala
            20                  25

<210> SEQ ID NO 197
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 197

Ser Arg Cys Ser Ser Asp Gln Val Glu Thr Gln Gly Gly Ser Gly Gly
1               5                   10                  15

Ile Cys Thr Xaa Arg Pro Gly Trp Tyr Xaa Ala
            20                  25

<210> SEQ ID NO 198
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 198

Arg Cys Ser Ser Asp Gln Val Glu Thr Gln Ala Gly Gly Ser Gly Gly
1               5                   10                  15

Ile Cys Thr Xaa Arg Pro Gly Trp Tyr Xaa Ala
            20                  25

<210> SEQ ID NO 199
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
```

```
                      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 199

Cys Ser Ser Asp Gln Val Glu Thr Gln Ala Xaa Gly Gly Ser Gly Gly
1               5                   10                  15

Ile Cys Thr Xaa Arg Pro Gly Trp Tyr Xaa Ala
            20                  25

<210> SEQ ID NO 200
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 200

Val Pro Glu Xaa Leu Ser Xaa Gly Ser Arg Cys Gly Gly Ser Gly Gly
1               5                   10                  15

Cys Thr Xaa Arg Pro Gly Trp Tyr Xaa Ala Leu
            20                  25

<210> SEQ ID NO 201
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
```

```
<221> NAME/KEY: MOD_RES
<222> LOCATION: (25)..(25)
<223> OTHER INFORMATION: Xaa is Cys residue protected with ACM
      protecting group

<400> SEQUENCE: 201

Pro Glu Xaa Leu Ser Xaa Gly Ser Arg Cys Ser Gly Gly Ser Gly Gly
1               5                   10                  15

Cys Thr Xaa Arg Pro Gly Trp Tyr Xaa Ala Leu
            20                  25

<210> SEQ ID NO 202
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 202

Glu Xaa Leu Ser Xaa Gly Ser Arg Cys Ser Ser Gly Gly Ser Gly Gly
1               5                   10                  15

Cys Thr Xaa Arg Pro Gly Trp Tyr Xaa Ala Leu
            20                  25

<210> SEQ ID NO 203
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 203
```

-continued

```
Xaa Leu Ser Xaa Gly Ser Arg Cys Ser Ser Asp Gly Gly Ser Gly Gly
1               5                   10                  15

Cys Thr Xaa Arg Pro Gly Trp Tyr Xaa Ala Leu
            20                  25

<210> SEQ ID NO 204
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 204

Leu Ser Xaa Gly Ser Arg Cys Ser Ser Asp Gln Gly Gly Ser Gly Gly
1               5                   10                  15

Cys Thr Xaa Arg Pro Gly Trp Tyr Xaa Ala Leu
            20                  25

<210> SEQ ID NO 205
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 205

Ser Xaa Gly Ser Arg Cys Ser Ser Asp Gln Val Gly Gly Ser Gly Gly
1               5                   10                  15

Cys Thr Xaa Arg Pro Gly Trp Tyr Xaa Ala Leu
            20                  25

<210> SEQ ID NO 206
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
``` protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 206

Xaa Gly Ser Arg Cys Ser Ser Asp Gln Val Glu Gly Gly Ser Gly Gly
1               5                   10                  15

Cys Thr Xaa Arg Pro Gly Trp Tyr Xaa Ala Leu
            20                  25

<210> SEQ ID NO 207
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 207

Gly Ser Arg Cys Ser Ser Asp Gln Val Glu Thr Gly Gly Ser Gly Gly
1               5                   10                  15

Cys Thr Xaa Arg Pro Gly Trp Tyr Xaa Ala Leu
            20                  25

<210> SEQ ID NO 208
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 208

Ser Arg Cys Ser Ser Asp Gln Val Glu Thr Gln Gly Gly Ser Gly Gly
1               5                   10                  15

Cys Thr Xaa Arg Pro Gly Trp Tyr Xaa Ala Leu
            20                  25

<210> SEQ ID NO 209
<211> LENGTH: 27
<212> TYPE: PRT
<213> ORGANISM: Artificial Sequence
<220> FEATURE:
<223> OTHER INFORMATION: Synthetic Construct

```
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 209

Arg Cys Ser Ser Asp Gln Val Glu Thr Gln Ala Gly Gly Ser Gly Gly
1               5                   10                  15

Cys Thr Xaa Arg Pro Gly Trp Tyr Xaa Ala Leu
            20                  25

<210> SEQ ID NO 210
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 210

Cys Ser Ser Asp Gln Val Glu Thr Gln Ala Xaa Gly Gly Ser Gly Gly
1               5                   10                  15

Cys Thr Xaa Arg Pro Gly Trp Tyr Xaa Ala Leu
            20                  25

<210> SEQ ID NO 211
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 211

Xaa Thr Arg Glu Gln Asn Arg Ile Xaa Thr Cys Gly Gly Ser Gly Gly
1               5                   10                  15

Arg Pro Gly Trp Tyr Cys Ala Leu Ser Lys Gln
            20                  25

<210> SEQ ID NO 212
<211> LENGTH: 27
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 212

Thr Arg Glu Gln Asn Arg Ile Xaa Thr Cys Arg Gly Gly Ser Gly Gly
1               5                   10                  15

Arg Pro Gly Trp Tyr Cys Ala Leu Ser Lys Gln
            20                  25

<210> SEQ ID NO 213
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 213

Arg Glu Gln Asn Arg Ile Xaa Thr Cys Arg Pro Gly Gly Ser Gly Gly
1               5                   10                  15

Arg Pro Gly Trp Tyr Cys Ala Leu Ser Lys Gln
            20                  25

<210> SEQ ID NO 214
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 214

Glu Gln Asn Arg Ile Xaa Thr Cys Arg Pro Gly Gly Gly Ser Gly Gly
1               5                   10                  15

Arg Pro Gly Trp Tyr Cys Ala Leu Ser Lys Gln
            20                  25

<210> SEQ ID NO 215
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Cys residue protected with ACM
      protecting group

<400> SEQUENCE: 215

Gln Asn Arg Ile Xaa Thr Cys Arg Pro Gly Trp Gly Gly Ser Gly Gly
1               5                   10                  15

Arg Pro Gly Trp Tyr Cys Ala Leu Ser Lys Gln
```

```
                        20                  25

<210> SEQ ID NO 216
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 216

Asn Arg Ile Xaa Thr Cys Arg Pro Gly Trp Tyr Gly Gly Ser Gly Gly
1               5                   10                  15

Arg Pro Gly Trp Tyr Cys Ala Leu Ser Lys Gln
            20                  25

<210> SEQ ID NO 217
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 217

Trp Tyr Xaa Ala Leu Ser Lys Gln Glu Gly Cys Gly Gly Ser Gly Gly
1               5                   10                  15

Xaa Ala Pro Leu Arg Lys Cys Arg Pro Gly Phe
            20                  25

<210> SEQ ID NO 218
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 218

Tyr Xaa Ala Leu Ser Lys Gln Glu Gly Cys Arg Gly Gly Ser Gly Gly
```

```
1               5                   10                  15
Xaa Ala Pro Leu Arg Lys Cys Arg Pro Gly Phe
            20                  25

<210> SEQ ID NO 219
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 219

Xaa Ala Leu Ser Lys Gln Glu Gly Cys Arg Leu Gly Gly Ser Gly Gly
1               5                   10                  15

Xaa Ala Pro Leu Arg Lys Cys Arg Pro Gly Phe
            20                  25

<210> SEQ ID NO 220
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 220

Ala Leu Ser Lys Gln Glu Gly Cys Arg Leu Xaa Gly Gly Ser Gly Gly
1               5                   10                  15

Xaa Ala Pro Leu Arg Lys Cys Arg Pro Gly Phe
            20                  25

<210> SEQ ID NO 221
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 221

Leu Ser Lys Gln Glu Gly Cys Arg Leu Xaa Ala Gly Gly Ser Gly Gly
1               5                   10                  15
```

```
Xaa Ala Pro Leu Arg Lys Cys Arg Pro Gly Phe
            20                  25

<210> SEQ ID NO 222
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 222

Ser Lys Gln Glu Gly Cys Arg Leu Xaa Ala Pro Gly Gly Ser Gly Gly
1               5                   10                  15

Xaa Ala Pro Leu Arg Lys Cys Arg Pro Gly Phe
            20                  25

<210> SEQ ID NO 223
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 223

Lys Gln Glu Gly Cys Arg Leu Xaa Ala Pro Leu Gly Gly Ser Gly Gly
1               5                   10                  15

Xaa Ala Pro Leu Arg Lys Cys Arg Pro Gly Phe
            20                  25

<210> SEQ ID NO 224
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 224

Gln Glu Gly Cys Arg Leu Xaa Ala Pro Leu Arg Gly Gly Ser Gly Gly
1               5                   10                  15
```

Xaa Ala Pro Leu Arg Lys Cys Arg Pro Gly Phe
            20                  25

<210> SEQ ID NO 225
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 225

Glu Gly Cys Arg Leu Xaa Ala Pro Leu Arg Lys Gly Gly Ser Gly Gly
1               5                   10                  15

Xaa Ala Pro Leu Arg Lys Cys Arg Pro Gly Phe
            20                  25

<210> SEQ ID NO 226
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 226

Trp Tyr Xaa Ala Leu Ser Lys Gln Glu Gly Cys Gly Gly Ser Gly Gly
1               5                   10                  15

Ala Pro Leu Arg Lys Cys Arg Pro Gly Phe Gly
            20                  25

<210> SEQ ID NO 227
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 227

Tyr Xaa Ala Leu Ser Lys Gln Glu Gly Cys Arg Gly Gly Ser Gly Gly
1               5                   10                  15

Ala Pro Leu Arg Lys Cys Arg Pro Gly Phe Gly
            20                  25

<210> SEQ ID NO 228
<211> LENGTH: 27
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (1)..(1)
<223> OTHER INFORMATION: Xaa is Cys residue protected with ACM
      protecting group

<400> SEQUENCE: 228

Xaa Ala Leu Ser Lys Gln Glu Gly Cys Arg Leu Gly Gly Ser Gly Gly
1               5                   10                  15

Ala Pro Leu Arg Lys Cys Arg Pro Gly Phe Gly
            20                  25

<210> SEQ ID NO 229
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 229

Ala Leu Ser Lys Gln Glu Gly Cys Arg Leu Xaa Gly Gly Ser Gly Gly
1               5                   10                  15

Ala Pro Leu Arg Lys Cys Arg Pro Gly Phe Gly
            20                  25

<210> SEQ ID NO 230
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 230

Leu Ser Lys Gln Glu Gly Cys Arg Leu Xaa Ala Gly Gly Ser Gly Gly
1               5                   10                  15

Ala Pro Leu Arg Lys Cys Arg Pro Gly Phe Gly
            20                  25

<210> SEQ ID NO 231
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 231

Ser Lys Gln Glu Gly Cys Arg Leu Xaa Ala Pro Gly Gly Ser Gly Gly
1               5                   10                  15

Ala Pro Leu Arg Lys Cys Arg Pro Gly Phe Gly
            20                  25

<210> SEQ ID NO 232
<211> LENGTH: 27
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 232

Lys Gln Glu Gly Cys Arg Leu Xaa Ala Pro Leu Gly Gly Ser Gly Gly
1               5                   10                  15

Ala Pro Leu Arg Lys Cys Arg Pro Gly Phe Gly
            20                  25

<210> SEQ ID NO 233
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 233

Gln Glu Gly Cys Arg Leu Xaa Ala Pro Leu Arg Gly Gly Ser Gly Gly
1               5                   10                  15

Ala Pro Leu Arg Lys Cys Arg Pro Gly Phe Gly
            20                  25

<210> SEQ ID NO 234
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 234

Glu Gly Cys Arg Leu Xaa Ala Pro Leu Arg Lys Gly Gly Ser Gly Gly
1               5                   10                  15

Ala Pro Leu Arg Lys Cys Arg Pro Gly Phe Gly
            20                  25

<210> SEQ ID NO 235
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 235

Trp Tyr Xaa Ala Leu Ser Lys Gln Glu Gly Cys Gly Gly Ser Gly Gly
1               5                   10                  15

Pro Leu Arg Lys Cys Arg Pro Gly Phe Gly Val
```

20                  25

<210> SEQ ID NO 236
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 236

Tyr Xaa Ala Leu Ser Lys Gln Glu Gly Cys Arg Gly Gly Ser Gly Gly
1               5                   10                  15

Pro Leu Arg Lys Cys Arg Pro Gly Phe Gly Val
            20                  25

<210> SEQ ID NO 237
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 237

Xaa Ala Leu Ser Lys Gln Glu Gly Cys Arg Leu Gly Ser Gly Gly
1               5                   10                  15

Pro Leu Arg Lys Cys Arg Pro Gly Phe Gly Val
            20                  25

<210> SEQ ID NO 238
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 238

Ala Leu Ser Lys Gln Glu Gly Cys Arg Leu Xaa Gly Ser Gly Gly
1               5                   10                  15

Pro Leu Arg Lys Cys Arg Pro Gly Phe Gly Val
            20                  25

<210> SEQ ID NO 239
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 239

```
Leu Ser Lys Gln Glu Gly Cys Arg Leu Xaa Ala Gly Ser Gly Gly
1               5                   10                  15

Pro Leu Arg Lys Cys Arg Pro Gly Phe Gly Val
            20                  25
```

<210> SEQ ID NO 240
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 240

```
Ser Lys Gln Glu Gly Cys Arg Leu Xaa Ala Pro Gly Ser Gly Gly
1               5                   10                  15

Pro Leu Arg Lys Cys Arg Pro Gly Phe Gly Val
            20                  25
```

<210> SEQ ID NO 241
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 241

```
Lys Gln Glu Gly Cys Arg Leu Xaa Ala Pro Leu Gly Ser Gly Gly
1               5                   10                  15

Pro Leu Arg Lys Cys Arg Pro Gly Phe Gly Val
            20                  25
```

<210> SEQ ID NO 242
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 242

```
Gln Glu Gly Cys Arg Leu Xaa Ala Pro Leu Arg Gly Ser Gly Gly
1               5                   10                  15

Pro Leu Arg Lys Cys Arg Pro Gly Phe Gly Val
            20                  25
```

<210> SEQ ID NO 243
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES

```
<222> LOCATION: (6)..(6)
<223> OTHER INFORMATION: Xaa is Cys residue protected with ACM
      protecting group

<400> SEQUENCE: 243

Glu Gly Cys Arg Leu Xaa Ala Pro Leu Arg Lys Gly Gly Ser Gly Gly
1               5                   10                  15

Pro Leu Arg Lys Cys Arg Pro Gly Phe Gly Val
            20                  25

<210> SEQ ID NO 244
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 244

Trp Tyr Xaa Ala Leu Ser Lys Gln Glu Gly Cys Gly Gly Ser Gly Gly
1               5                   10                  15

Leu Arg Lys Cys Arg Pro Gly Phe Gly Val Ala
            20                  25

<210> SEQ ID NO 245
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 245

Tyr Xaa Ala Leu Ser Lys Gln Glu Gly Cys Arg Gly Gly Ser Gly Gly
1               5                   10                  15

Arg Lys Cys Arg Pro Gly Phe Gly Val Ala Arg
            20                  25

<210> SEQ ID NO 246
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 246

Xaa Ala Leu Ser Lys Gln Glu Gly Cys Arg Leu Gly Gly Ser Gly Gly
1               5                   10                  15

Arg Lys Cys Arg Pro Gly Phe Gly Val Ala Arg
            20                  25

<210> SEQ ID NO 247
<211> LENGTH: 27
<212> TYPE: PRT
```

<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 247

Ala Leu Ser Lys Gln Glu Gly Cys Arg Leu Xaa Gly Gly Ser Gly Gly
1               5                   10                  15

Arg Lys Cys Arg Pro Gly Phe Gly Val Ala Arg
            20                  25

<210> SEQ ID NO 248
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 248

Leu Ser Lys Gln Glu Gly Cys Arg Leu Xaa Ala Gly Gly Ser Gly Gly
1               5                   10                  15

Arg Lys Cys Arg Pro Gly Phe Gly Val Ala Arg
            20                  25

<210> SEQ ID NO 249
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 249

Ser Lys Gln Glu Gly Cys Arg Leu Xaa Ala Pro Gly Gly Ser Gly Gly
1               5                   10                  15

Arg Lys Cys Arg Pro Gly Phe Gly Val Ala Arg
            20                  25

<210> SEQ ID NO 250
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 250

Lys Gln Glu Gly Cys Arg Leu Xaa Ala Pro Leu Gly Gly Ser Gly Gly
1               5                   10                  15

Arg Lys Cys Arg Pro Gly Phe Gly Val Ala Arg
            20                  25

<210> SEQ ID NO 251
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 251

Gln Glu Gly Cys Arg Leu Xaa Ala Pro Leu Arg Gly Gly Ser Gly Gly
1               5                   10                  15

Arg Lys Cys Arg Pro Gly Phe Gly Val Ala Arg
            20                  25

<210> SEQ ID NO 252
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 252

Glu Gly Cys Arg Leu Xaa Ala Pro Leu Arg Lys Gly Gly Ser Gly Gly
1               5                   10                  15

Arg Lys Cys Arg Pro Gly Phe Gly Val Ala Arg
            20                  25

<210> SEQ ID NO 253
<211> LENGTH: 20
<212> TYPE: PRT
<213> ORGANISM: Homo sapiens

<400> SEQUENCE: 253

Arg Glu Gln Asn Arg Ile Cys Thr Cys Arg Pro Gly Trp Tyr Cys Ala
1               5                   10                  15

Leu Ser Lys Gln
            20

<210> SEQ ID NO 254
<211> LENGTH: 20
<212> TYPE: PRT
<213> ORGANISM: Homo sapiens

<400> SEQUENCE: 254

Cys Arg Pro Gly Trp Tyr Cys Ala Leu Ser Lys Gln Glu Gly Cys Arg
1               5                   10                  15

Leu Cys Ala Pro
            20

<210> SEQ ID NO 255
<211> LENGTH: 20
<212> TYPE: PRT
<213> ORGANISM: Homo sapiens

<400> SEQUENCE: 255

-continued

Leu Ser Lys Gln Glu Gly Cys Arg Leu Cys Ala Pro Leu Arg Lys Cys
1               5                   10                  15

Arg Pro Gly Phe
            20

<210> SEQ ID NO 256
<211> LENGTH: 20
<212> TYPE: PRT
<213> ORGANISM: Homo sapiens

<400> SEQUENCE: 256

Leu Cys Ala Pro Leu Arg Lys Cys Arg Pro Gly Phe Gly Val Ala Arg
1               5                   10                  15

Pro Gly Thr Glu
            20

<210> SEQ ID NO 257
<211> LENGTH: 8
<212> TYPE: PRT
<213> ORGANISM: Murine
<220> FEATURE:
<221> NAME/KEY: MISC_FEATURE
<222> LOCATION: (8)..(8)
<223> OTHER INFORMATION: Xaa is Leu or Ile

<400> SEQUENCE: 257

Gly Tyr Thr Phe Thr Asp Tyr Xaa
1               5

<210> SEQ ID NO 258
<211> LENGTH: 8
<212> TYPE: PRT
<213> ORGANISM: Murine

<400> SEQUENCE: 258

Val Asp Pro Glu Tyr Gly Ser Thr
1               5

<210> SEQ ID NO 259
<211> LENGTH: 14
<212> TYPE: PRT
<213> ORGANISM: Murine

<400> SEQUENCE: 259

Ala Arg Asp Asp Gly Ser Tyr Ser Pro Phe Asp Tyr Trp Gly
1               5                   10

<210> SEQ ID NO 260
<211> LENGTH: 6
<212> TYPE: PRT
<213> ORGANISM: Murine

<400> SEQUENCE: 260

Gln Asn Ile Asn Lys Tyr
1               5

<210> SEQ ID NO 261
<211> LENGTH: 9
<212> TYPE: PRT
<213> ORGANISM: Murine
<220> FEATURE:
<221> NAME/KEY: MISC_FEATURE
<222> LOCATION: (8)..(8)
<223> OTHER INFORMATION: Xaa is Leu or Ile

<400> SEQUENCE: 261

```
Cys Leu Gln Tyr Val Asn Leu Xaa Thr
1               5
```

<210> SEQ ID NO 262
<211> LENGTH: 4
<212> TYPE: PRT
<213> ORGANISM: Murine

<400> SEQUENCE: 262

```
Leu Leu Ile Arg
1
```

<210> SEQ ID NO 263
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (5)..(5)
<223> OTHER INFORMATION: Xaa is Asn, Gln, Ser, or Thr

<400> SEQUENCE: 263

```
Ser Ser Gly Xaa Xaa Tyr
1               5
```

<210> SEQ ID NO 264
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Gly or Ala
<220> FEATURE:
<221> NAME/KEY: MISC_FEATURE
<222> LOCATION: (7)..(7)
<223> OTHER INFORMATION: Xaa is Asn, Gln, Ser, or Thr

<400> SEQUENCE: 264

```
Val Asp Pro Glu Tyr Xaa Xaa Thr
1               5
```

<210> SEQ ID NO 265
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Arg, Lys, or His
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (7)..(7)

```
<223> OTHER INFORMATION: Xaa is Asn, Gln, Ser, or Thr
<220> FEATURE:
<221> NAME/KEY: MISC_FEATURE
<222> LOCATION: (9)..(9)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (12)..(12)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (13)..(13)
<223> OTHER INFORMATION: Xaa is Asp or Glu
<220> FEATURE:
<221> NAME/KEY: MISC_FEATURE
<222> LOCATION: (14)..(14)
<223> OTHER INFORMATION: Xaa is Ala, Val, Leu, Ile, Pro, Met, Trp, Phe,
      or Tyr

<400> SEQUENCE: 265

Gln Xaa Val Xaa Xaa Tyr Xaa Ser Xaa Trp Tyr Xaa Xaa Xaa
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Lys, Arg, or His
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Asn, Gln, Ser, or Thr
<220> FEATURE:
<221> NAME/KEY: MISC_FEATURE
<222> LOCATION: (7)..(7)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (10)..(10)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (11)..(11)
<223> OTHER INFORMATION: Xaa is Asp or Glu
<220> FEATURE:
<221> NAME/KEY: MISC_FEATURE
<222> LOCATION: (12)..(12)
<223> OTHER INFORMATION: Xaa is Ala, Val, Leu, Ile, Pro, Met, Trp, Phe,
      or Tyr

<400> SEQUENCE: 266

Ala Xaa Asp Xaa Xaa Xaa Xaa Ser Pro Xaa Xaa Xaa Trp Gly
1               5                   10

<210> SEQ ID NO 267
<211> LENGTH: 10
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is Ala, Val, Leu, Ile, Pro, Met, Trp, Phe,
      or Tyr

<400> SEQUENCE: 267

Ser Ala Ser Ser Ser Val Tyr Tyr Met Xaa
1               5                   10

<210> SEQ ID NO 268
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Ala, Val, Leu, Ile, Pro, Met, Trp, Phe,
      or Tyr

<400> SEQUENCE: 268

Gln Asn Ile Asn Lys Xaa
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa is Asn, Gln, Ser, or Thr

<400> SEQUENCE: 269

Ser Thr Ser Asn Leu Ala Xaa
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (9)..(9)
<223> OTHER INFORMATION: Xaa is Asn, Gln, Ser, or Thr

<400> SEQUENCE: 270

Gln Gln Arg Arg Asn Xaa Pro Tyr Xaa
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (4)..(4)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (8)..(8)
<223> OTHER INFORMATION: Xaa is Leu or Ile
<220> FEATURE:
<221> NAME/KEY: MISC_FEATURE
<222> LOCATION: (9)..(9)
<223> OTHER INFORMATION: Xaa is Asn, Gln, Ser, or Thr

<400> SEQUENCE: 271

Cys Leu Gln Xaa Val Asn Leu Xaa Xaa
1               5

<210> SEQ ID NO 272
<211> LENGTH: 9
<212> TYPE: PRT
<213> ORGANISM: Murine

<400> SEQUENCE: 272

Cys Leu Gln Tyr Val Asn Leu Leu Thr
1               5

<210> SEQ ID NO 273
<211> LENGTH: 9
<212> TYPE: PRT
<213> ORGANISM: Murine

<400> SEQUENCE: 273

Cys Leu Gln Tyr Val Asn Leu Ile Thr
1               5

<210> SEQ ID NO 274
<211> LENGTH: 8
<212> TYPE: PRT
<213> ORGANISM: Murine

<400> SEQUENCE: 274

Gly Tyr Thr Phe Thr Asp Tyr Leu
1               5

<210> SEQ ID NO 275
<211> LENGTH: 8
<212> TYPE: PRT
<213> ORGANISM: Murine

<400> SEQUENCE: 275

Gly Tyr Thr Phe Thr Asp Tyr Ile
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
```

```
<223> OTHER INFORMATION: Xaa is any amino acid

<400> SEQUENCE: 276

Gly Xaa Thr Phe Xaa Xaa Tyr
1               5

<210> SEQ ID NO 277
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid

<400> SEQUENCE: 277

Gly Xaa Thr Phe Xaa Xaa Tyr Xaa
1               5

<210> SEQ ID NO 278
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid

<400> SEQUENCE: 278

Xaa Arg Xaa Asp Gly Xaa Ser Xaa Tyr Xaa Xaa Phe Asp Xaa
1               5                   10

<210> SEQ ID NO 279
```

<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid

<400> SEQUENCE: 279

Xaa Arg Xaa Asp Gly Ser Tyr Xaa Xaa Phe Asp Xaa Xaa Xaa
1               5                   10

<210> SEQ ID NO 280
<211> LENGTH: 459
<212> TYPE: PRT
<213> ORGANISM: Bos taurus

<400> SEQUENCE: 280

Met Ala Pro Thr Ala Phe Trp Ala Ala Leu Ala Val Gly Leu Gln Phe
1               5                   10                  15

Trp Ala Ala Gly Arg Ala Val Pro Ala Gln Ala Val Phe Thr Pro Tyr
            20                  25                  30

Ile Pro Glu Pro Gly Ser Ser Cys Arg Gln Gln Glu Tyr Tyr Asn Gln
        35                  40                  45

Lys Ile Gln Met Cys Cys Ser Lys Cys Pro Pro Gly Tyr Arg Val Gln
    50                  55                  60

Ser Leu Cys Asn Met Thr Leu Asp Thr Ile Cys Ala Ser Cys Glu Ser
65                  70                  75                  80

Ser Thr Tyr Thr Gln Leu Trp Asn Leu Val Thr Ala Cys Phe Ser Cys
                85                  90                  95

Asn Ser Arg Cys Ser Ser Asp Gln Val Glu Thr Gln Ala Cys Thr Thr
            100                 105                 110

Lys Gln Asn Arg Ile Cys Thr Cys Lys Pro Gly Trp Tyr Cys Thr Leu
        115                 120                 125

Gly Arg Gln Glu Gly Cys Arg Leu Cys Val Ala Leu Arg Lys Cys Gly
    130                 135                 140

Pro Gly Phe Gly Val Ala Lys Pro Gly Thr Ala Thr Asn Val Ile
145                 150                 155                 160

Cys Ala Pro Cys Gly Pro Gly Thr Phe Ser Asp Thr Thr Ser Tyr Thr
                165                 170                 175

Asp Thr Cys Lys Pro His Arg Asn Cys Ser Ser Val Ala Ile Pro Gly
            180                 185                 190

Thr Ala Ser Thr Asp Ala Val Cys Thr Ser Val Leu Pro Thr Arg Lys
        195                 200                 205

Val Ala Arg Gly Pro Ala Thr Thr Arg Ser Gln His Met Glu Pro Thr
210                 215                 220

Leu Gly Pro Ser Thr Ala Pro Ser Thr Phe Phe Leu Leu Pro Lys Val
225                 230                 235                 240

Pro Ser Pro Pro Ser Ser Pro Val Glu Gln Pro Asn Thr Gly Asn Ile
                245                 250                 255

Ser Leu Pro Ile Glu Leu Ile Val Gly Val Thr Ala Leu Gly Leu Leu
            260                 265                 270

Leu Ile Val Val Val Asn Cys Val Ile Met Thr Gln Lys Lys Lys Lys
        275                 280                 285

Pro Phe Cys Leu Gln Gly Asp Ala Lys Val Pro His Leu Pro Ala Asn
290                 295                 300

Lys Ala Gln Gly Ala Pro Gly Pro Glu Gln Gln His Leu Leu Thr Thr
305                 310                 315                 320

Ala Pro Ser Ser Ser Ser Ser Leu Glu Ser Ser Thr Ser Ser Thr
                325                 330                 335

Asp Lys Arg Ala Pro Thr Arg Ser Gln Leu Gln Ser Pro Gly Val Glu
                340                 345                 350

Lys Ala Ser Thr Ser Gly Glu Ala Gln Thr Gly Cys Ser Ser Ser Glu
            355                 360                 365

Ala Ser Ser Gly Gly His Gly Thr Gln Val Asn Val Thr Cys Ile Val
        370                 375                 380

Asn Val Cys Ser Gly Pro Asp His Ser Ser Gln Cys Pro Ser Gln Ala
385                 390                 395                 400

Gly Ser Thr Arg Asp Thr Asp Ala Ser Thr Pro Asn Ser Pro Lys Glu
                405                 410                 415

Glu Gln Val Pro Phe Ser Lys Glu Glu Arg Pro Phe Gln Ser Gln Pro
            420                 425                 430

Gly Ala Pro Glu Thr Leu Leu Gln Gly Leu Glu Lys Pro Leu Pro
        435                 440                 445

Leu Gly Val Pro Asp Ala Gly Met Lys Pro Ser
    450                 455

<210> SEQ ID NO 281
<211> LENGTH: 458
<212> TYPE: PRT
<213> ORGANISM: Bison bison

<400> SEQUENCE: 281

Met Ala Pro Thr Ala Phe Trp Ala Ala Leu Ala Val Gly Leu Gln Phe
1               5                   10                  15

Trp Ala Ala Gly Arg Ala Val Pro Ala Gln Ala Val Phe Thr Pro Tyr
            20                  25                  30

Ile Pro Glu Pro Gly Ser Ser Cys Arg Gln Gln Glu Tyr Tyr Asn His
        35                  40                  45

Lys Ile Gln Met Cys Cys Ser Lys Cys Pro Pro Gly Tyr Arg Val Gln
    50                  55                  60

Ser Leu Cys Asn Thr Thr Leu Asp Thr Ile Cys Ala Ser Cys Glu Ser
65                  70                  75                  80

Ser Thr Tyr Thr Gln Leu Trp Asn Leu Val Thr Ala Cys Phe Ser Cys

```
                     85                  90                  95
Asn Ser Arg Cys Ser Ser Asp Gln Val Glu Thr Gln Ala Cys Thr Thr
                100                 105                 110
Lys Gln Asn Arg Ile Cys Thr Cys Lys Pro Gly Trp Tyr Cys Thr Leu
            115                 120                 125
Gly Arg Gln Glu Gly Cys Arg Leu Cys Val Ala Leu Arg Lys Cys Gly
        130                 135                 140
Pro Gly Phe Gly Val Ala Lys Pro Gly Thr Ala Thr Thr Asn Val Ile
145                 150                 155                 160
Cys Ala Pro Cys Gly Pro Gly Thr Phe Ser Asp Thr Thr Ser Tyr Thr
                165                 170                 175
Asp Thr Cys Lys Pro His Arg Asn Cys Ser Ser Val Ala Ile Pro Gly
            180                 185                 190
Thr Ala Ser Thr Asp Ala Val Cys Thr Ser Val Leu Pro Thr Arg Lys
        195                 200                 205
Val Ala Arg Gly Pro Ala Thr Thr Arg Ser Gln His Met Glu Pro Thr
    210                 215                 220
Leu Gly Pro Ser Thr Ala Pro Ser Thr Phe Phe Leu Leu Pro Lys Val
225                 230                 235                 240
Pro Ser Pro Pro Ser Ser Pro Val Glu Gln Pro Asn Ala Gly Asn Ile
                245                 250                 255
Ser Leu Pro Ile Glu Leu Ile Val Gly Val Thr Ala Leu Gly Leu Leu
            260                 265                 270
Leu Ile Val Val Val Asn Cys Val Ile Met Thr Gln Lys Lys Lys Lys
        275                 280                 285
Pro Phe Cys Leu Gln Gly Asp Ala Lys Val Pro His Leu Pro Ala Asn
    290                 295                 300
Lys Ala Gln Gly Ala Pro Gly Pro Glu Gln His Leu Leu Thr Thr
305                 310                 315                 320
Ala Pro Ser Ser Ser Ser Ser Leu Glu Ser Ser Thr Ser Ser Thr
                325                 330                 335
Asp Lys Arg Ala Pro Thr Arg Ser Gln Leu Gln Ser Pro Gly Val Glu
            340                 345                 350
Ala Asn Thr Ser Gly Glu Ala Gln Thr Gly Cys Ser Ser Ser Glu Ala
        355                 360                 365
Ser Ser Gly Gly His Gly Thr Gln Val Asn Val Thr Cys Ile Val Asn
    370                 375                 380
Val Cys Ser Gly Pro Asp His Ser Ser Gln Cys Pro Ser Gln Ala Gly
385                 390                 395                 400
Ser Thr Arg Asp Thr Asp Ala Ser Thr Pro Asn Ser Pro Lys Glu Glu
                405                 410                 415
Gln Val Pro Phe Ser Lys Glu Glu Arg Pro Phe Gln Ser Gln Pro Gly
            420                 425                 430
Ala Pro Glu Thr Leu Leu Gln Gly Leu Glu Glu Lys Pro Leu Pro Leu
        435                 440                 445
Gly Val Pro Asp Ala Gly Met Lys Pro Ser
    450                 455

<210> SEQ ID NO 282
<211> LENGTH: 474
<212> TYPE: PRT
<213> ORGANISM: Mus musculus

<400> SEQUENCE: 282
```

```
Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
            35                  40                  45

Arg Lys Ala Gln Met Cys Cys Ala Lys Cys Pro Pro Gly Gln Tyr Val
50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
                100                 105                 110

Lys Gln Gln Asn Arg Val Cys Ala Cys Glu Ala Gly Arg Tyr Cys Ala
            115                 120                 125

Leu Lys Thr His Ser Gly Ser Cys Arg Gln Cys Met Arg Leu Ser Lys
        130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
            165                 170                 175

Ser Thr Asp Val Cys Arg Pro His Arg Ile Cys Ser Ile Leu Ala Ile
                180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
            245                 250                 255

Gly Gly Ile Ser Leu Pro Ile Gly Leu Ile Val Gly Val Thr Ser Leu
            260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
        290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
        355                 360                 365

Ile Ser Asp Ser Ser His Gly Ser His Gly Thr His Val Asn Val Thr
        370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
            405                 410                 415

Ser Pro Lys Asp Glu Gln Val Pro Phe Ser Gln Glu Glu Cys Pro Ser
```

```
                   420                 425                 430
Gln Ser Pro Cys Glu Thr Thr Glu Thr Leu Gln Ser His Glu Lys Pro
            435                 440                 445

Leu Pro Leu Gly Val Pro Asp Met Gly Met Lys Pro Ser Gln Ala Gly
            450                 455                 460

Trp Phe Asp Gln Ile Ala Val Lys Val Ala
465                 470

<210> SEQ ID NO 283
<211> LENGTH: 474
<212> TYPE: PRT
<213> ORGANISM: Rattus norvegicus

<400> SEQUENCE: 283

Met Ala Pro Ala Ala Leu Trp Val Ala Leu Val Glu Leu Gln Leu
1               5                   10                  15

Trp Ala Thr Gly His Thr Val Pro Ala Lys Val Val Leu Thr Pro Tyr
                20                  25                  30

Lys Pro Glu Pro Gly Asn Gln Cys Gln Ile Ser Gln Glu Tyr Tyr Asp
            35                  40                  45

Lys Lys Ala Gln Met Cys Cys Ala Lys Cys Pro Pro Gly Gln Tyr Ala
50                  55                  60

Lys His Phe Cys Asn Lys Thr Ser Asp Thr Val Cys Ala Asp Cys Ala
65                  70                  75                  80

Ala Gly Met Phe Thr Gln Val Trp Asn His Leu His Thr Cys Leu Ser
                85                  90                  95

Cys Ser Ser Cys Ser Asp Asp Gln Val Glu Thr His Asn Cys Thr
            100                 105                 110

Lys Lys Gln Asn Arg Val Cys Ala Cys Asn Ala Asp Ser Tyr Cys Ala
            115                 120                 125

Leu Lys Leu His Ser Gly Asn Cys Arg Gln Cys Met Lys Leu Ser Lys
130                 135                 140

Cys Gly Pro Gly Phe Gly Val Ala Arg Ser Arg Thr Ser Asn Gly Asn
145                 150                 155                 160

Val Ile Cys Ser Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Ser Glu Ser Pro Thr
            195                 200                 205

Pro Ser Ala Val Pro Arg Thr Ile Tyr Val Ser Gln Pro Glu Pro Thr
210                 215                 220

Arg Ser Gln Pro Met Asp Gln Glu Pro Gly Pro Ser Gln Thr Pro His
225                 230                 235                 240

Ile Pro Val Ser Leu Gly Ser Thr Pro Ile Ile Glu Pro Ser Ile Thr
                245                 250                 255

Gly Gly Ile Ser Leu Pro Ile Gly Leu Ile Val Gly Leu Thr Thr Leu
            260                 265                 270

Gly Leu Leu Met Leu Gly Leu Ala Asn Cys Phe Ile Leu Val Gln Arg
            275                 280                 285

Lys Lys Lys Pro Ser Cys Leu Gln Arg Glu Thr Met Val Pro His Leu
290                 295                 300

Pro Asp Asp Lys Ser Gln Asp Ala Ile Gly Leu Glu Gln Gln His Leu
305                 310                 315                 320
```

```
Leu Thr Thr Ala Pro Ser Ser Ser Ser Ser Leu Glu Ser Ser Ala
            325             330             335
Ser Ala Gly Asp Arg Arg Ala Pro Pro Gly Gly His Pro Gln Ala Arg
            340             345             350
Val Thr Ala Glu Ala Gln Gly Ser Gln Glu Ala Cys Ala Gly Ser Arg
            355             360             365
Ser Ser Asp Ser Ser His Gly Ser His Gly Thr His Val Asn Val Thr
    370             375             380
Cys Ile Val Asn Val Cys Ser Ser Asp His Ser Ser Gln Cys Ser
385             390             395             400
Ser Gln Ala Ser Thr Thr Val Gly Asp Pro Asp Ala Asn Pro Ser Gly
            405             410             415
Ser Pro Lys Asp Glu Gln Val Pro Phe Ser Gln Glu Glu Cys Pro Ser
            420             425             430
Gln Ser Gln Trp Glu Thr Thr Glu Thr Leu Gln Asn His Asp Lys Pro
            435             440             445
Phe Pro Leu Gly Val Pro Asp Val Gly Met Lys Pro Asn Gln Pro Gly
    450             455             460
Trp Tyr Asp Gln Ile Ala Val Lys Val Pro
465             470
```

ANTAGONISTIC ANTI-TUMOR NECROSIS FACTOR RECEPTOR 2 ANTIBODIES

FIELD OF THE INVENTION

The invention relates to polypeptides, such as antibodies and antigen-binding fragments thereof, capable of antagonizing tumor necrosis factor receptor superfamily members, such as tumor necrosis factor receptor 2. The polypeptides of the invention can be used to modulate the activity of regulatory T-cells, such as in the field of immunotherapy for the treatment of cell proliferation disorders and infectious diseases.

BACKGROUND OF THE INVENTION

The use of naturally-occurring and genetically engineered T-lymphocytes is a prominent paradigm for ameliorating various human pathologies. For instance, while traditional therapeutic platforms for the treatment of cancer include surgical removal of tumor mass, radiation therapy, and administration of chemotherapeutics (Shewach, Chem. Rev., 109:2859-2861, 2009), the last decade has witnessed a resurgence in the application of adoptive immunotherapy to cancer treatment regimens. With the advent of chimeric antigen receptor (CAR-T) therapy, new methods have emerged for the infusion of autologous and allogeneic tumor-reactive T-cells to patients (June, J. Clin. Invest., 117:1466-1476, 2007). CAR-T therapies harness the resources of the adaptive immune response in order to promote cancer cell cytotoxicity and eradicate tumor material. A common motif in adoptive immunotherapy is the use of T-cells that exhibit the ability to selectively potentiate cytotoxicity in cells that display distinct tumor antigens. Examples of this technique include the administration of tumor-infiltrating lymphocytes (Dudley et al., J. Immunother., 26:332-342, 2003), as well as autologous or allogeneic T-cells that have been genetically re-engineered so as to exhibit reactivity with a tumor-specific antigen (Yee et al., PNAS., 99:16168-16173, 2002).

Despite the promise of T-lymphocyte-based cancer immunotherapy, the development of this therapeutic platform has been hindered by the natural propensity of the immune system to suppress immune attacks mounted on self cells. Cancer cells, like all nucleated human cells, express class I major histocompatability complex (MHC) proteins that distinguish these cells from foreign cells. In order to prevent cell fratricide, regulatory T-cells (T-reg cells) have evolved that suppress the activity of T-cells that exhibit reactivity against "self" MHC antigens. T-reg cells represent a heterogeneous class of T-cells that can be distinguished based on their unique surface protein presentation. The most well-understood populations of T-reg cells include CD4+, CD25+, FoxP3+T-reg cells and CD17+T-reg cells. The precise mechanisms by which these cells mediate suppression of autoreactive T-cells is the subject of ongoing investigations, though it has been shown that certain classes of T-reg cells inhibit production of the proliferation-inducing cytokine IL-2 in target T-cells and may additionally sequester IL-2 from autoreactive cells by virtue of the affinity of CD25 (a subdomain of the IL-2 receptor) for IL-2 (Josefowicz et al., Ann. Rev. Immun., 30:531-564, 2012).

Although T-reg cells play an important role in maintaining peripheral tolerance, the same biochemical features that underlie the ability of these cells to modulate autoreactive T-cell activity also serve to undermine adoptive immunotherapy and the natural immune response by suppressing the activity of tumor-reactive T lymphocytes. The development of chemical modulators of T-reg cell activity has been the subject of many pharmacological investigations, as access to an agent capable of inhibiting T-reg-mediated T-cell suppression could vastly improve the scope and efficacy of adoptive cancer immunotherapy, as well as improve the ability of the immune system to eradicate pathogenic organisms that give rise to infectious diseases.

Tumor necrosis factor receptor (TNFR) subtypes 1 and 2 have been identified on the T-reg cell surface as signal transduction molecules that dictate cell fate. The activation of TNFR1, for instance, potentiates the caspase signaling cascade and terminates in T-reg apoptosis, while activation of TNFR2 induces signaling through the mitogen-activated protein kinase (MAPK) signaling pathway, which orchestrates signaling through TRAF2/3 and the NFκB-mediated transcription of genes that promote escape from apoptosis and cell proliferation. Due to its role in directing cell survival and growth, TNFR2 represents an attractive target for preventing immune detection of tumor-reactive T lymphocytes. As such, there is currently a need for therapies that can prevent T-reg cell survival and proliferation for use in treatments targeting cell proliferation disorders, such as cancer, and a wide array of infectious diseases.

SUMMARY OF THE INVENTION

The invention provides antagonistic tumor necrosis factor receptor 2 (TNFR2) antibodies and antigen-binding fragments thereof, such as those that specifically bind epitopes within human TNFR2 that contain one or more residues of the KCRPG sequence (SEQ ID NO: 19) or equivalent epitopes in TNFR2 of non-human primates (e.g., bison or cattle, as described herein) and that do not specifically bind epitopes within human TNFR2 containing the KCSPG sequence (SEQ ID NO: 12) or equivalent epitopes in TNFR2 of non-human primates. The invention additionally features antibodies and antigen-binding fragments thereof that inhibit the activity of other TNFR superfamily members, such as antibodies and antigen-binding fragments thereof that bind these proteins in an anti-parallel dimer configuration. The antibodies and antigen-binding fragments thereof described herein can be used for the treatment of a variety of pathologies, including cancers and infectious diseases.

Disclosed herein are polypeptides, such as single-chain polypeptides, antibodies, or antigen-binding fragments thereof, capable of specifically binding human TNFR2 that contain a complementarity determining region-heavy chain 1 (CDR-H1) and a CDR-H2 derived from a neutral TNFR2 antibody and a CDR-H3 having the amino acid sequence $JZ^1JZ^2Z^4JZ^3JZ^5(J)_2Z^5Z^2Z^5$, $JZ^1JZ^2Z^4Z^3Z^5(J)_2Z^5Z^2Z^5(J)_2$, $JRJDGJSJY(J)_2FDJ$ (SEQ ID NO: 278), $JRJDGSY(J)_2FD(J)_3$ (SEQ ID NO: 279), $QZ^1VZ^2Z^4YZ^3SZ^5WYZ^5Z^2Z^5$ (SEQ ID NO: 265), or $AZ^1DZ^2Z^4Z^3Z^5SPZ^5Z^2Z^5WG$ (SEQ ID NO: 266), wherein each J is independently a naturally occurring amino acid;

each $Z^1$ is independently a naturally occurring amino acid containing a cationic side-chain at physiological pH, such as lysine, arginine, and histidine;

each $Z^2$ is independently a naturally occurring amino acid containing an anionic side-chain at physiological pH, such as aspartic acid and glutamic acid;

each $Z^3$ is independently a naturally occurring amino acid containing a polar, uncharged side-chain at physiological pH, such as serine, threonine, asparagine, and glutamine;

each $Z^4$ is independently a glycine or alanine; and each $Z^5$ is independently a naturally occurring amino acid containing a hydrophobic side-chain, such as alanine, valine, leucine, isoleucine, proline, and methionine, tryptophan, phenylalanine, and tyrosine. As used herein in the context of a polypeptide formula, numeric characters in subscript notation designate the quantity of the preceding amino acid present in the formula, and numeric characters in superscript notation designate the type of the preceding amino acid present in the formula.

Disclosed herein are polypeptides, such as single-chain polypeptides, antibodies, or antigen-binding fragments thereof, capable of specifically binding human TNFR2. The polypeptides (e.g., antibodies and antigen-binding fragments thereof) may contain one or more, or all, of the following CDRs:

(a) a CDR-H1 having the amino acid sequence $Z^4JZ^3Z^5(J)_2Z^5$ or $Z^4JZ^3Z^5(J)_2Z^5J$;

(b) a CDR-H2 having the amino acid sequence $(J)_3Z^4Z^3J$ or $(J)_5Z^4Z^3J$;

(c) a CDR-H3 having the amino acid sequence $JZ^1JZ^2Z^4JZ^3JZ^5(J)_2Z^5Z^2Z^5$ or $JZ^1JZ^2Z^4Z^3Z^5(J)_2Z^5Z^2Z^5(J)_2$;

(d) a CDR-L1 having the amino acid sequence $(J)_9Z^5$ or $(J)_5Z^5$;

(e) a CDR-L2 having the amino acid sequence $(J)_6Z^3$ or $(J)_2Z^3$; and (f) a CDR-L3 having the amino acid sequence $(J)_5Z^5(J)_2Z^3$ or $(J)_3Z^5(J)_4Z^3$;

wherein each J is independently a naturally occurring amino acid;

each $Z^1$ is independently a naturally occurring amino acid containing a cationic side-chain at physiological pH, such as lysine, arginine, and histidine;

each $Z^2$ is independently a naturally occurring amino acid containing an anionic side-chain at physiological pH, such as aspartic acid and glutamic acid;

each $Z^3$ is independently a naturally occurring amino acid containing a polar, uncharged side-chain at physiological pH, such as serine, threonine, asparagine, and glutamine;

each $Z^4$ is independently a glycine or alanine; and each $Z^5$ is independently a naturally occurring amino acid containing a hydrophobic side-chain, such as alanine, valine, leucine, isoleucine, proline, and methionine, tryptophan, phenylalanine, and tyrosine.

The antibody or antigen-binding fragment thereof may contain a non-native constant region (e.g., a human constant region), lack all or a portion of an Fc domain, lack all or a portion of a native Fc domain, or lack an Fc domain altogether.

Additionally disclosed herein are polypeptides (e.g., single-chain polypeptides, antibodies, and antigen-binding fragments thereof) capable of specifically binding human TNFR2, wherein the polypeptide (e.g., antibody or antigen-binding fragment thereof) contains one or more, or all, of the following CDRs:

(a) a CDR-H1 having the amino acid sequence $GJTF(J)_2Y$ (SEQ ID NO: 276) or $GJTF(J)_2YJ$ (SEQ ID NO: 277);

(b) a CDR-H2 having the amino acid sequence $(J)_3GSJ$ or $(J)_5GSJ$;

(c) a CDR-H3 having the amino acid sequence $JRJDGJSJY(J)_2FDJ$ (SEQ ID NO: 278) or $JRJDGSY(J)_2FD(J)_3$ (SEQ ID NO: 279);

(d) a CDR-L1 having the amino acid sequence $(J)_9Y$ or $(J)_5Y$;

(e) a CDR-L2 having the amino acid sequence $(J)_6S$ or $(J)_2S$; and (f) a CDR-L3 having the amino acid sequence $(J)_5Y(J)_2T$ or $(J)_3Y(J)_4T$;

wherein each J is independently a naturally occurring amino acid. The antibody or antigen-binding fragment thereof may contain a non-native constant region (e.g., a human constant region), lack all or a portion of an Fc domain, lack all or a portion of a native Fc domain, or lack an Fc domain altogether.

The invention also features polypeptides (e.g., single-chain polypeptides, antibodies, and antigen-binding fragments thereof) capable of specifically binding human TNFR2. The polypeptide (e.g., antibody or antigen-binding fragment thereof) may contain the following CDRs:

(a) a CDR-H1 having the amino acid sequence $Z^4FZ^3Z^5SSZ^5$ or $Z^4YZ^3Z^5TDZ^5X$;

(b) a CDR-H2 having the amino acid sequence $SSGZ^4Z^3Y$ (SEQ ID NO: 263) or $VDPEYZ^4Z^3T$ (SEQ ID NO: 264);

(c) a CDR-H3 having the amino acid sequence $QZ^1VZ^2Z^4YZ^3SZ^5WYZ^5Z^2Z^5$ (SEQ ID NO: 265) or $AZ^1DZ^2Z^4Z^3Z^5SPZ^5Z^2Z^5WG$ (SEQ ID NO: 266);

(d) a CDR-L1 having the amino acid sequence $SASSSVYYMZ^5$ (SEQ ID NO: 267) or $QNINKZ^5$ (SEQ ID NO: 268);

(e) a CDR-L2 having the amino acid sequence $STSNLAZ^3$ (SEQ ID NO: 269), $TYZ^3$, or $YTZ^3$; and (f) a CDR-L3 having the amino acid sequence $QQRRNZ^5PYZ^3$ (SEQ ID NO: 270) or $CLQZ^5VNLXZ^3$ (SEQ ID NO: 271);

wherein each $Z^1$ is independently an amino acid containing a cationic side-chain at physiological pH;

each $Z^2$ is independently an amino acid containing an anionic side-chain at physiological pH;

each $Z^3$ is independently an amino acid containing a polar, uncharged side-chain at physiological pH;

each $Z^4$ is independently a glycine or alanine;

each $Z^5$ is independently an amino acid containing a hydrophobic side-chain;

each X is independently leucine or isoleucine. The antibody or antigen-binding fragment thereof may contain a non-native constant region (e.g., a human constant region), lack all or a portion of an Fc domain, lack all or a portion of a native Fc domain, or lack an Fc domain altogether.

In another aspect, the invention features a polypeptide, such as a single-chain polypeptide, antibody, or antigen-binding fragment thereof, capable of specifically binding human TNFR2, wherein the polypeptide (e.g., single-chain polypeptide, antibody, or antigen-binding fragment thereof) contains the following CDRs:

(a) a CDR-H1 having the amino acid sequence GFTFSSY (SEQ ID NO: 23), GYTFTDYX (SEQ ID NO: 257), or an amino acid sequence having up to two amino acid substitutions (e.g., one or two amino acid substitutions, such as conservative amino acid substitutions) relative to these sequences;

(b) a CDR-H2 having the amino acid sequence SSGGSY (SEQ ID NO: 24), VDPEYGST (SEQ ID NO: 258), or an amino acid sequence having up to two amino acid substitutions (e.g., one or two amino acid substitutions, such as conservative amino acid substitutions) relative to these sequences;

(c) a CDR-H3 having the amino acid sequence QRVDGYSSYWYFDV (SEQ ID NO: 25), ARDDGSYSPFDYWG (SEQ ID NO: 259), or an amino acid sequence having up to two amino acid substitutions (e.g., one or two amino acid substitutions, such as conservative amino acid substitutions) relative to these sequences;

(d) a CDR-L1 having the amino acid sequence SASSSVYYMY (SEQ ID NO: 26), QNINKY (SEQ ID NO: 260), or an amino acid sequence having up to two amino acid substitutions (e.g., one or two amino acid substitutions, such as conservative amino acid substitutions) relative to these sequences;

(e) a CDR-L2 having the amino acid sequence STSNLAS (SEQ ID NO: 27), TYS, YTS, or an amino acid sequence having up to two amino acid substitutions (e.g., one or two amino acid substitutions, such as conservative amino acid substitutions) relative to SEQ ID NO: 27; and (f) a CDR-L3 having the amino acid sequence QQRRNY-PYT (SEQ ID NO: 28), CLQYVNLXT (SEQ ID NO: 261), or an amino acid sequence having up to two amino acid substitutions (e.g., one or two amino acid substitutions, such as conservative amino acid substitutions) relative to these sequences;

wherein each X is independently leucine or isoleucine. The antibody or antigen-binding fragment thereof may contain a non-native constant region (e.g., a human constant region), lack all or a portion of an Fc domain, lack all or a portion of a native Fc domain, or lack an Fc domain altogether. In some embodiments, the amino acid substitutions are conservative substitutions. In some embodiments, the amino acid substitutions are non-conservative substitutions.

In some embodiments, the polypeptide (e.g., single-chain polypeptide, antibody, or antigen-binding fragment thereof) contains one or more of the following CDRs:

(a) a CDR-L1 having the amino acid sequence SASSSVYYMY (SEQ ID NO: 26);

(b) a CDR-L2 having the amino acid sequence STSNLAS (SEQ ID NO: 27); and (c) a CDR-L3 having the amino acid sequence QQRRNY-PYT (SEQ ID NO: 28).

In some embodiments, the polypeptide single-chain polypeptide, antibody, or antigen-binding fragment thereof) contains one or more of the following CDRs:

(a) a CDR-L1 having the amino acid sequence QNINKY (SEQ ID NO: 260);

(b) a CDR-L2 having the amino acid sequence TYS or YTS; and (c) a CDR-L3 having the amino acid sequence CLQYVNLXT (SEQ ID NO: 261).

In some embodiments, the CDR-L2 of the antibody or antigen-binding fragment thereof has the amino acid sequence TYS. In some embodiments, the CDR-L2 of the antibody or antigen-binding fragment thereof has the amino acid sequence YTS. In some embodiments, the CDR-L3 has the amino acid sequence CLQYVNLLT (SEQ ID NO: 272). In some embodiments, the CDR-L3 has the amino acid sequence CLQYVNLIT (SEQ ID NO: 273).

In some embodiments, the polypeptide (e.g., single-chain polypeptide, antibody, or antigen-binding fragment thereof) contains one or more of the following CDRs:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25).

In some embodiments, the polypeptide single-chain polypeptide, antibody, or antigen-binding fragment thereof) contains one or more of the following CDRs:

(a) a CDR-H1 having the amino acid sequence GYTFTDYX (SEQ ID NO: 257);

(b) a CDR-H2 having the amino acid sequence VDPEYGST (SEQ ID NO: 258); and (c) a CDR-H3 having the amino acid sequence ARDDG-SYSPFDYWG (SEQ ID NO: 259).

In some embodiments, the CDR-H1 has the amino acid sequence GYTFTDYL (SEQ ID NO: 274). In some embodiments, the CDR-H1 has the amino acid sequence GYTFTDYI (SEQ ID NO: 275).

In some embodiments, the polypeptide (e.g., single-chain polypeptide, antibody, or antigen-binding fragment thereof) contains:

(a) a CDR-L1 having the amino acid sequence SASSSVYYMY (SEQ ID NO: 26);

(b) a CDR-L2 having the amino acid sequence STSNLAS (SEQ ID NO: 27); and.

(c) a CDR-L3 having the amino acid sequence QQRRNY-PYT (SEQ ID NO: 28).

The polypeptide single-chain polypeptide, antibody, or antigen-binding fragment thereof) may contain:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25).

In some embodiments, the polypeptide single-chain polypeptide, antibody, or antigen-binding fragment thereof) contains:

(a) a CDR-L1 having the amino acid sequence QNINKY (SEQ ID NO: 260);

(b) a CDR-L2 having the amino acid sequence TYS or YTS; and (c) a CDR-L3 having the amino acid sequence CLQYVNLXT (SEQ ID NO: 261).

In some embodiments, the polypeptide (e.g., single-chain polypeptide, antibody, or antigen-binding fragment thereof) contains:

(a) a CDR-H1 having the amino acid sequence GYTFTDYX (SEQ ID NO: 257);

(b) a CDR-H2 having the amino acid sequence VDPEYGST (SEQ ID NO: 258); and.

(c) a CDR-H3 having the amino acid sequence ARDDG-SYSPFDYWG (SEQ ID NO: 259).

In some embodiments, the polypeptide (e.g., single-chain polypeptide, antibody, or antigen-binding fragment thereof) includes a framework region that contains the amino acid sequence LLIR (SEQ ID NO: 262) bound to the N-terminus of the CDR-L2 region. In some embodiments, the polypeptide (e.g., antibody or antigen-binding fragment thereof) includes a framework region that contains the amino acid sequence TLE bound to the C-terminus of the CDR-L2 region.

The invention also features a polypeptide (e.g., single-chain polypeptide, antibody, or antigen-binding fragment thereof) that specifically binds TNFR2 and that contains a light chain amino acid sequence having at least 85% sequence identity to the amino acid sequence of SEQ ID NO: 4, and a non-native constant region. In some embodiments, the polypeptide (e.g., antibody or antigen-binding fragment thereof) contains a light chain amino acid sequence having at least 90% (e.g., 95%, 97%, 99%, or 100%) sequence identity to the amino acid sequence of SEQ ID NO: 4. The polypeptide (e.g., antibody or antigen-binding fragment thereof) may additionally contain a heavy chain sequence having at least 85% sequence identity to SEQ ID NO: 2. In some embodiments, the polypeptide (e.g., antibody or antigen-binding fragment thereof) may contain a heavy chain having at least 90% sequence identity to the amino acid sequence of SEQ ID NO: 2. For example, the polypeptide (e.g., antibody or antigen-binding fragment thereof) may contain a light chain having at least 85% sequence identity to the amino acid sequence of SEQ ID NO: 4 and a heavy chain having at least 85% sequence identity to the amino acid sequence of SEQ ID NO: 2. Optionally, the polypeptide (e.g., antibody or antigen-binding fragment thereof) may contain a light chain having at least 90% sequence identity to the amino acid sequence of SEQ ID NO: 4 and a heavy chain having at least 90% sequence identity to the amino acid sequence of SEQ ID NO: 2.

In another aspect, the invention provides constructs containing a first polypeptide domain and a second polypeptide domain, each of which contains a single-chain polypeptide of the invention. The first and second polypeptide domains may be the same. In some embodiments, the first and second polypeptide domains may be different. The first and second polypeptide domains may be bound by a linker, such as a linker containing an amide bond or a disulfide bridge. The constructs may lack a murine Fc domain.

Embodiments of the invention also feature an antibody or antigen-binding fragment thereof that specifically binds to a peptide comprising the amino acid sequence of any one of SEQ ID NOs: 11, 19, 20, and 34-117 with a $K_D$ of less than about 100 nM and does not bind a peptide comprising amino acids 56-60 (KCSPG) of SEQ ID NO: 7, and contains a non-native constant region (e.g., contains a human constant region), lacks all or a portion of an Fc domain, lacks all or a portion of a native Fc domain, or lacks an Fc domain altogether. The invention also features an antibody or antigen-binding fragment thereof that is capable of specifically binding human TNFR2, wherein the antibody or antigen-binding fragment thereof specifically binds a peptide comprising one or more of amino acids 142-146 of SEQ ID NO: 7 (KCRPG) and does not bind a peptide comprising amino acids 56-60 of SEQ ID NO: 7 (KCSPG), and contains a non-native constant region (e.g., contains a human constant region), lacks all or a portion of an Fc domain, lacks all or a portion of a native Fc domain, or lacks an Fc domain altogether. The antibody or antigen-binding fragment thereof may specifically bind the peptide containing one or more of amino acids 142-146 of SEQ ID NO: 7 (KCRPG) with a $K_D$ of less than about 10 nM. Optionally, the antibody or antigen-binding fragment thereof may specifically bind an epitope within amino acids 142-149 of SEQ ID NO: 7 (KCRPGFGV). Alternatively or additionally, the antibody or antigen-binding fragment thereof may specifically bind an epitope within amino acids 137-144 of SEQ ID NO: 7 (CAPLRKCR). In some cases, the antibody or antigen-binding fragment thereof may specifically bind an epitope containing at least five discontinuous or continuous residues within amino acids 150-190 of SEQ ID NO: 7 (RPGTETSDVVCKPCAPGTFSNTTSSTDI-CRPHQICNVVAI). The antibody or antigen-binding fragment thereof may optionally bind an epitope within amino acids 161-169 of SEQ ID NO: 7 (CKPCAPGTF). In other cases, the antibody or antigen-binding fragment thereof may bind an epitope containing at least five discontinuous or continuous residues within amino acids 75-128 of SEQ ID NO: 7 (CDSCEDSTYTQLWNWVPE-CLSCGSRCSSDQVETQACTREQNRICTCRPGWY-CAL). Particularly, the antibody or antigen-binding fragment thereof may bind epitope within one or more of amino acids 80-86 (DSTYTQL), 91-98 (PECLSCGS), and 116-123 (RICTCRPG) of SEQ ID NO: 7.

In some embodiments, the antibody or antigen-binding fragment thereof binds an epitope within amino acids 112-131 of SEQ ID NO: 7 (REQNRICTCRPGWYCALSKQ). The antibody or antigen-binding fragment thereof may bind an epitope within amino acids 120-139 of SEQ ID NO: 7 (CRPGWYCALSKQEGCRLCAP). Additionally or alternatively, the antibody or antigen-binding fragment thereof may bind an epitope within amino acids 128-147 of SEQ ID NO: 7 (LSKQEGCRLCAPLRKCRPGF). In some embodiments, the antibody or antigen-binding fragment thereof binds an epitope within amino acids 136-155 of SEQ ID NO: 7 (LCAPLRKCRPGFGVARPGTE).

The antibodies and antigen-binding fragments of the invention can inhibit TNFR2 signaling. In some embodiments, the antibody or antigen-binding fragment thereof reduces or inhibits the expression of one or more genes selected from the group consisting of CHUK, NFKBIE, NFKBIA, MAP3K11, TRAF2, TRAF3, relB, and cIAP2/BIRC3. In some embodiments, the antibody or antigen-binding fragment thereof inhibits NFκB activation. For instance, antagonistic TNFR2 antibodies or antigen-binding fragments thereof of the invention may reduce or inhibit the expression or post-translational modification (e.g., phosphorylation) of one or more of CHUK, NFKBIE, NFKBIA, MAP3K11, TRAF2, TRAF3, relB, or cIAP2/BIRC3, e.g., by 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% relative to the expression or post-translational modification (e.g., phosphorylation) of one or more of these molecules isolated from a sample not treated with an antagonistic TNFR2 antibody or antigen-binding fragment thereof of the invention. Exemplary assays that can be used to determine expression level and phosphorylation state are known in the art and include Western blot assays to determine protein content and quantitative reverse transcription polymerase chain reaction (RT-PCR) experiments to determine mRNA content. In preferred embodiments, anti-TNFR2 polypeptides (e.g., single-chain polypeptides, antibodies, or antigen-binding fragments thereof) are dominant TNFR2 antagonists and are thus capable of inhibiting TNFR2 activation even in the presence of a TNFR2 agonist (such as TNFα) or a growth-promoting agent, such as IL-2.

Antagonistic TNFR2 polypeptide (e.g., antibodies or antigen-binding fragments thereof) of the invention may bind TNFR2 with a $K_D$ of no greater than about 10 nM, no greater than 1 nM, or, in particular cases, with a $K_D$ of about 621 pM. For instance, antagonistic TNFR2 polypeptides (e.g., antibodies or antigen-binding fragments thereof) of the invention may bind TNFR2 or an epitope thereof as described herein with a $K_D$ of from about 1 pM to about 900 pM (e.g., about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 110 pM, 120 pM, 130 pM, 140 pM, 150 pM, 160 pM, 170 pM, 180 pM, 190 pM, or 200 pM, 300 pM, 310 pM, 320 pM, 330 pM, 340 pM, 350 pM, 360 pM, 370 pM, 380 pM, 390 pM, 400 pM, 410 pM, 420 pM, 430 pM, 440 pM, 450 pM, 460 pM, 470 pM, 480 pM, 490 pM, 500 pM, 510 pM, 520 pM, 530 pM, 540 pM, 550 pM, 560 pM, 570 pM, 580 pM, 590 pM, 600 pM, 610 pM, 620 pM, 630 pM, 640 pM, 650 pM, 660 pM, 670 pM, 680 pM, 690 pM, 700 pM, 710 pM, 720 pM, 730 pM, 740 pM, 750 pM, 760 pM, 770 pM, 780 pM, 790 pM, 800 pM, 810 pM, 820 pM, 830 pM, 840 pM, 850 pM, 860 pM, 870 pM, 880 pM, 890 pM, or 900 pM). In some embodiments, the polypeptide (e.g., antibody or antigen-binding fragment thereof) binds TNFR2 with a $K_D$ of about 44 pM, e.g., 44.4 pM. In certain instances, the TNFR2 antibodies or antigen-binding fragments thereof of the invention can bind TNFR2 to form an antibody-antigen complex with a $k_{on}$ of at least about $10^4$ $M^{-1}$ $s^{-1}$, and in some embodiments, with a $k_{on}$ of about $3.6 \times 10^5$ $M^{-1}s^{-1}$. For instance, antagonistic TNFR2 antibodies or antigen-binding fragments thereof of the invention may bind TNFR2 to form an antibody-antigen complex with a $k_{on}$ of from about $1 \times 10^4$ $M^{-1}$ $s^{-1}$ to about $1 \times 10^7$ $M^{-1}$ $s^{-1}$ (e.g., about $1 \times 10^4$ $M^{-1}$ $s^{-1}$, $5 \times 10^4$ $M^{-1}$ $s^{-1}$, $1 \times 10^5$ $M^{-1}$ $s^{-1}$, $5 \times 10^5$ $M^{-1}$ $s^{-1}$, $1 \times 10^6$ $M^{-1}$ $s^{-1}$, $5 \times 10^6$ $M^{-1}$ $s^{-1}$, or $1 \times 10^7$ $M^{-1}$ $s^{-1}$). In some embodiments, the antibody or antigen-binding fragment thereof can bind TNFR2 to form an antibody-antigen complex with a $k_{on}$ of about $5 \times 10^6$ $M^{-1}s^{-1}$, e.g., $4.98 \times 10^6$ $M^{-1}s^{-1}$. Antibodies or antigen-binding fragments thereof of the invention may bind TNFR2 to form an antibody-antigen complex, wherein the complex dissociates with a $k_{off}$ of no greater than about $10^{-3}$ $s^{-1}$. In some embodiments, the complex dissociates with a $k_{off}$ of no greater than about $10^{-4}$ $s^{-1}$, e.g., with a $k_{off}$ of about $3.0 \times 10^{-5}$ $s^{-1}$. For instance, antagonistic TNFR2 antibodies or antigen-binding fragments thereof of the invention may bind TNFR2 to form an antibody-antigen complex, wherein the complex dissociates with a $k_{off}$ of from about $1 \times 10^{-5}$ $s^{-1}$ to about $1 \times 10^{-3}$ $s^{-1}$ (e.g., about $1 \times 10^{-5}$ $s^-$, $5 \times 10^{-5}$ $s^{-1}$, $1 \times 10^{-4}$ $s^{-1}$, $5 \times 10^{-4}$ $s^{-1}$, or $1 \times 10^{-3}$ $s^{-1}$). In some embodiments, the antibodies or antigen-binding fragment thereof binds TNFR2 to form an antibody-antigen complex, wherein the complex dissociates with a $k_{off}$ of no greater than about $2.3 \times 10^{-4}$ $s^-$, e.g., about $2 \times 10^{-4}$ $S^-$. In some embodiments, the complex dissociates with a $k_{on}$ of about $2.21 \times 10^{-4}$ $S^-$.

Antagonistic TNFR2 polypeptides (e.g., antibodies and antigen-binding fragments thereof) of the invention may be capable of reducing or inhibiting the proliferation of a population of T-reg cells, and may do so optionally in the presence of a TNFR2 agonist, such as TNFα. In some embodiments, the antibody or antigen-binding fragment thereof is capable of reducing or inhibiting the proliferation of a population of cancer cells that express TNFR2, and may do so optionally in the presence of a TNFR2 agonist, such as TNFα. For instance, the cancer cells may be Hodgkin's lymphoma cells, cutaneous non-Hodgkin's lymphoma cells, T cell lymphoma cells, ovarian cancer cells, colon cancer cells, multiple myeloma cells, or renal cell carcinoma cells. In some embodiments, the antibody or antigen-binding fragment thereof is capable of reducing or inhibiting the proliferation of a population of myeloid-derived suppressor cells, and may optionally do so in the presence of a TNFR2 agonist, such as TNFα. In some embodiments, the antibody or antigen-binding fragment thereof is capable of selectively reducing or inhibiting the proliferation of a population of T-reg cells expressing $CD25^{Hi}$, such as a population of T-reg cells expressing $CD25^{Hi}$ and $CD45RA^{Low}$. For instance, the antibody or antigen-binding fragment thereof may be capable of reducing the proliferation of a population of T-reg cells expressing $CD25^{Hi}$ and $CD45RA^{Low}$ (i.e., a population of activated T-reg cells, or aT-reg cells) by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to a population of T-reg cells that does not express the $CD25^{Hi}$ and $CD45RA^{Low}$ proteins, such as a population of T-reg cells that expresses $CD25^{Med}$ and $CD45RA^{Hi}$ proteins (i.e., a population of resting T-reg cells, or rT-reg cells).

Antagonistic TNFR2 polypeptides (e.g., antibodies or antigen-binding fragments thereof) of the invention may additionally bind TNFR2 on the surface of a cancer cell, such as a tumor cell. Binding of TNFR2 on the cancer cell may inhibit or reduce proliferation of the cancer cell or may promote the apoptosis of the cancer cell.

Antagonistic TNFR2 polypeptides, such as single-chain polypeptides, antibodies, or antigen-binding fragments thereof, of the invention may also bind TNFR2 on the surface of a myeloid-derived suppressor cell (MDSC; e.g., a cell that expresses all or a subset of proteins and small molecules selected from the group consisting of B7-1 (CD80), B7-H1 (PD-L1), CCR2, CD1d, CD1d1, CD2, CD31 (PECAM-1), CD43, CD44, complement component C5a R1, F4/80 (EMR1), Fcγ RII (CD16), Fcγ RII (CD32), Fcγ RIIA (CD32a), Fcγ RIIB (CD32b), Fcγ RIIB/C (CD32b/c), Fcγ RIIC (CD32c), Fcγ RIIIA (CD16A), Fcγ RIIIB (CD16b), galectin-3, GP130, Gr-1 (Ly-6G), ICAM-1 (CD54), IL-1RI, IL-4Ra, IL-6Ra, integrin α4 (CD49d), integrin αL (CD11a), integrin αM (CD11b), M-CSFR, MGL1 (CD301a), MGL1/2 (CD301a/b), MGL2 (CD301 b), nitric oxide, PSGL-1 (CD162), L-selectin (CD62L), siglec-3 (CD33), transferrin receptor (TfR), VEGFR1 (Flt-1), and VEGFR2 (KDR or Flk-1). Particularly, MDSCs do not express proteins selected from the group consisting of B7-2 (CD86), B7-H4, CD11c, CD14, CD21, CD23 (FcεRII), CD34, CD35, CD40 (TNFRSF5), CD117 (c-kit), HLA-DR, and Sca-1 (Ly6). Binding of TNFR2 on the MDSC may inhibit or reduce proliferation of the MDSC or may promote the apoptosis of the MDSC.

Antagonistic TNFR2 polypeptides, such as single-chain polypeptides, antibodies, or antigen-binding fragments thereof, of the invention may demonstrate the ability to attenuate T-reg and/or cancer cell proliferation in the presence of a TNFR2 agonist, such as TNFα or an agonistic TNFR2 antibody, or growth-promoting molecules, such as IL-2. These antibodies or antigen-binding fragments thereof may bind TNFR2 and stabilize the dimeric, anti-parallel dimer conformation of this receptor and prevent phosphorylation and other post-translational modifications that occur during NFκB signaling.

Antagonistic TNFR2 polypeptides, such as single-chain polypeptides, antibodies, or antigen-binding fragments thereof, of the invention may reduce the total quantity of T-reg or cancer cells in a patient (such as a human patient) or within a sample (e.g., a sample isolated from a patient, such as a human patient undergoing treatment for cancer or an infectious disease as described herein relative to a sample isolated from a patient not undergoing such treatment or relative to a sample isolated from the patient prior to receiving this treatment).

In some embodiments, the antagonistic TNFR2 polypeptide (e.g., single-chain polypeptide, antibody, or antigen-binding fragment thereof) reduces expression of TNFR2, e.g., by a T-reg cell or a cancer cell (such as a Hodgkin's or cutaneous non-Hodgkin's lymphoma cell, T cell lymphoma cell, ovarian cancer cell, colon cancer cell, multiple myeloma cell, or renal cell carcinoma cell).

Antagonistic TNFR2 polypeptides, such as single-chain polypeptides, antibodies, and antigen-binding fragments thereof of the invention may inhibit the proliferation or reduce the total quantity of a population of T-reg cells in a patient (e.g., a human patient) or in a sample (e.g., a sample isolated from a human patient undergoing treatment for cancer or an infectious disease as described herein).

The invention also features a method of identifying a TNFR2 antagonist polypeptide (e.g., single-chain polypeptide, antibody, or antigen-binding fragment thereof) by:

(a) exposing a heterogeneous mixture of antibodies or fragments thereof to at least one peptide having the amino acid sequence of any one of SEQ ID NOs: 11, 19, 20, and 34-117, or a peptide containing between about 10 and about 30 continuous or discontinuous amino acids between positions 80 and 130 of SEQ ID NO: 7; and (b) retaining antibodies or fragments thereof that specifically bind said peptide and removing antibodies or fragments thereof that do not specifically bind said peptide, thereby producing an enriched antibody mixture comprising at least one TNFR2 antagonist antibody or antigen-binding fragment thereof.

In some embodiments, one may determine the amino acid sequence of one or more of the antibodies or antigen-binding fragments thereof in the enriched antibody mixture. Optionally, the peptide may be bound to a surface, and in some embodiments, the antibody or antigen-binding fragment thereof can be expressed on the surface of a phage, bacterial cell, or yeast cell. In alternative cases, the antibody or antigen-binding fragment thereof is expressed as one or more polypeptide chains non-covalently bound to ribosomes or covalently bound to mRNA or cDNA. In particular cases, the peptide can be conjugated to a detectable label, such as a fluorescent molecule, epitope tag, or radiolabel. In some cases, the fluorescent molecule may be green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, or cyanine. In certain embodiments, the epitope tag may be maltose-binding protein, glutathione-S-transferase, a poly-histidine tag, a FLAG-tag, a myc-tag, human influenza hemagglutinin (HA) tag, biotin, or streptavidin. In addition, in some embodiments steps (a) and (b) above may be sequentially repeated one or more times.

The invention also features a method of producing a TNFR2 antagonist antibody or antigen-binding fragment thereof by immunizing a non-human mammal with a peptide comprising the sequence of any one of SEQ ID NOs: 11, 19, 20, and 34-117, or a peptide containing between about 10 and about 30 continuous or discontinuous amino acids between positions 80 and 130 of SEQ ID NO: 7, and collecting serum containing the TNFR2 antagonist antibody or antigen-binding fragment thereof. Exemplary non-human mammals that can be immunized include a rabbit, mouse, rat, goat, guinea pig, hamster, horse, and sheep. In some embodiments, the peptide used for immunization may contain the amino acid sequence KCRPG (SEQ ID NO: 19). In some cases, the peptide used for immunization may contain the amino acid sequence CAPLRKCR (SEQ ID NO: 11). Optionally, the peptide may contain the amino acid sequence KCRPGFGV (SEQ ID NO: 20).

The invention features an antibody or antigen-binding fragment thereof produced by any of the above-described methods. In some embodiments, the antibody or antigen-binding fragment thereof may be a monoclonal antibody or antigen-binding fragment thereof, a polyclonal antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a F(ab')$_2$ molecule, and a tandem scFv (taFv). In some embodiments, the antibody or antigen-binding fragment thereof is a F(ab')$_2$ molecule. In some embodiments, the antibody or antigen-binding fragment thereof has an isotype selected from the group consisting of IgG, IgA, IgM, IgD, and IgE.

In some embodiments, an antibody or antigen-binding fragment thereof of the invention may be conjugated to a therapeutic agent, such as a cytotoxic agent.

The invention features a polynucleotide encoding an antibody or antigen-binding fragment thereof of the invention, as well as a vector containing such a polynucleotide. The vector may be an expression vector, such as a eukaryotic expression vector, or a viral vector, such as an adenovirus (Ad, such as serotype 5, 26, 35, or 48 adenovirus), retrovirus (such as a γ-retrovirus or a lentivirus), poxvirus, adeno-associated virus, baculovirus, herpes simplex virus, or a vaccinia virus (such as a modified vaccinia Ankara (MVA). The invention also features host cells, such as prokaryotic and eukaryotic (e.g., mammalian) cells containing a vector of the invention.

The invention also features a method of producing a polypeptide (e.g., single-chain polypeptide, construct, antibody, or antigen-binding fragment) of the invention by expressing a polynucleotide encoding the single-chain polypeptide, construct, antibody, or antigen-binding fragment thereof in a host cell and recovering the single-chain polypeptide, antibody, or antigen-binding fragment thereof from host cell medium.

The invention also features a method of inhibiting an immune response mediated by a regulatory T cell, as well as a method of treating a cell proliferation disorder in a human, by administering a single-chain polypeptide, construct, antibody, or antigen-binding fragment thereof, polynucleotide, vector, or host cell of the invention to the human in need of treatment. Additionally, the invention features invention also features a composition containing a single-chain polypeptide, construct, antibody, or antigen-binding fragment thereof, polynucleotide, vector, or host cell of the invention for inhibiting an immune response mediated by a regulatory T cell, as well as for treating a cell proliferation disorder in a human.

In some embodiments, the cell proliferation disorder is a cancer, such as leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, or throat cancer. In particular cases, the cell proliferation disorder may be a cancer selected from the group consisting of acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T-cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

The invention also features methods of treating Hodgkin's or cutaneous non-Hodgkin's lymphoma, T cell lymphoma, ovarian cancer, colon cancer, multiple myeloma, or renal cell carcinoma by administration of an antagonistic TNFR2 polypeptide (e.g., single-chain polypeptide, construct, antibody, or antigen-binding fragment thereof), a polynucleotide, vector, or host cell of the invention of the invention to a patient (e.g., a mammalian patient, such as a human patient). For instance, the invention provides a method of treating ovarian cancer by administration of an antagonistic TNFR2 antibody or antigen-binding fragment thereof of the invention to a patient (e.g., a mammalian patient, such as a human patient). The invention additionally features a composition containing a single-chain polypeptide, construct, antibody, or antigen-binding fragment thereof, polynucleotide, vector, or host cell of the invention for treating Hodgkin's or cutaneous non-Hodgkin's lymphoma, T cell lymphoma, ovarian cancer, colon cancer, multiple myeloma, or renal cell carcinoma in a patient (e.g., a human patient).

The invention also features a method of treating an infectious disease in a patient (e.g., a human patient) by administering a single-chain polypeptide, construct, antibody, or antigen-binding fragment thereof, polynucleotide, vector, or host cell of the invention to the human in need of treatment, as well as a composition containing a single-chain polypeptide, construct, antibody, or antigen-binding fragment thereof, polynucleotide, vector, or host cell of the invention for treating an infectious disease in a patient (e.g., a human patient). In some embodiments, the infectious disease may be caused by a virus, a bacterium, a fungus, or a parasite. For instance, viral infections that can be treated according to the methods of the invention include hepatitis C virus, Yellow fever virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus, Negishi virus, Meaban virus, Saumarez Reef virus, Tyuleniy virus, Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, cell fusing agent virus, Ippy virus, Lassa virus, lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabia virus, Tacaribe virus, Tamiami virus, Whitewater Arroyo virus, Chapare virus, Lujo virus, Hantaan virus, Sin Nombre virus, Dugbe virus, Bunyamwera virus, Rift Valley fever virus, La Crosse virus, California encephalitis virus, Crimean-Congo hemorrhagic fever (CCHF) virus, Ebola virus, Marburg virus, Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus, smallpox virus, monkeypox virus, vaccinia virus, herpes simplex virus, human herpes virus, cytomegalovirus (CMV), Epstein-Barr virus (EBV), Varicella-Zoster virus, Kaposi's sarcoma associated-herpesvirus (KSHV), influenza virus, severe acute respiratory syndrome (SARS) virus, rabies virus, vesicular stomatitis virus (VSV), human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, mumps virus, poliovirus, human enterovirus (A, B, C, and D), hepatitis A virus, coxsackievirus, hepatitis B virus, human papilloma virus, adeno-associated virus, astrovirus, JC virus, BK virus, SV40 virus, Norwalk virus, rotavirus, human immunodeficiency virus (HIV), human T-lymphotropic virus Types I and II, and transmissible spongiform encephalopathy, such as chronic wasting disease.

In some embodiments, bacterial infections that can be treated according to the methods of the invention include those caused by a bacterium belonging to a genus selected from the group consisting of *Salmonella, Streptococcus, Bacillus, Listeria, Corynebacterium, Nocardia, Neisseria, Actinobacter, Moraxella, Enterobacteriacece* (e.g., *E. coli*, such as O157:H7), *Pseudomonas, Escherichia, Klebsiella, Serratia, Enterobacter, Proteus, Salmonella, Shigella, Yersinia, Haemophilus, Bordatella, Legionella, Pasteurella, Francisella, Brucella, Bartonella, Clostridium, Vibrio, Campylobacter*, and *Staphylococcus*. In addition, parasitic infections that can be treated according to the methods of the invention include those caused by *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis*, and *Histomonas meleagridis*. Exemplary helminthic parasites include *Richuris trichiura, Ascaris lumbricoides, Enterobius vermicularis, Ancylostoma duodenale, Necator americanus, Strongyloides stercoralis, Wuchereria bancrofti*, and *Dracunculus medinensis, Schistosoma mansoni, Schistosoma haematobium, Schistosoma japonicum, Fasciola hepatica, Fasciola gigantica, Heterophyes, Paragonimus westermani, Taenia solium, Taenia saginata, Hymenolepis nana*, or *Echinococcus granulosus*.

The invention also features kits, such as a kit that contains a single-chain polypeptide, construct, antibody, or antigen-binding fragment of the invention (e.g., an antagonist TNFR2 antibody), a polynucleotide of the invention, a vector of the invention, or a host cell of the invention. In some cases, kits of the invention may contain instructions for transfecting a vector of the invention into a host cell of the invention. Optionally, kits may contain instructions for (and optionally, a reagent that can be used for) expressing a single-chain polypeptide, construct, antibody, or antigen-binding fragment of the invention in a host cell of the invention. A kit of the invention may also contain instructions for administering an antibody or antigen-binding fragment of the invention, a polynucleotide of the invention, a vector of the invention, or a host cell of the invention to a human patient. Optionally a kit may contain instructions for making or using an antibody or antigen-binding fragment of the invention, a polynucleotide of the invention, a vector of the invention, or a host cell of the invention.

The invention additionally features a polypeptide (e.g., a single-chain polypeptide, antibody, or antigen-binding fragment thereof) that specifically binds a tumor necrosis factor receptor superfamily (TNFRS) member in an anti-parallel dimer conformation. The polypeptide (e.g., single-chain polypeptide, antibody, or antigen-binding fragment thereof) may optionally contain a non-native constant region. For instance, the single-chain polypeptide, antibody, or antigen-binding fragment thereof may inhibit trimerization of the TNFRS member, e.g., in the presence of a TNFRS member agonist, such as a cognate TNFRS member ligand. The single-chain polypeptide, antibody, or antigen-binding fragment thereof may inhibit NFκB signaling in a cell, such as a eukaryotic cell (e.g., a mammalian cell, such as a human or bovine cell). In some embodiments, the single-chain polypeptide, antibody, or antigen-binding fragment thereof reduces or inhibits the expression of one or more genes selected from the group consisting of CHUK, NFKBIE, NFKBIA, MAP3K11, TRAF2, TRAF3, relB, and cIAP2/BIRC3. The TNFRS member may, e.g., be selected from the group consisting of TNFR1, TNFR2, Fas, DCR3, DR3, TRAIL-R1(DR4), TRAIL-R2 (DR5), TRAIL-R3, TRAIL-R4, DR6, EDAR, CD271, OPG, RANK, LTβR, TWEAK-R, HVEM, CD27, CD30, CD40, CD137, OX40, GITR, BCMA, TACI, BAFFR, EDAR2, TROY, and RELT. For instance, polypeptides (e.g., single-chain polypeptides, antibodies, or antigen-binding fragments thereof) of the invention may bind TNFR2 in an anti-parallel dimer conformation, e.g., thereby preventing TNFα-mediated trimerization and activation of this receptor.

The invention additionally features a method of treating a disease mediated by signaling through a TNFRS member in a patient (e.g., a human patient) by administering to the human the single-chain polypeptide, antibody, or antigen-binding fragment thereof that specifically binds a TNFRS member in an anti-parallel dimer conformation as described above. Additionally, the method features a composition containing a single-chain polypeptide, antibody, or antigen-binding fragment thereof that specifically binds a TNFRS member in an anti-parallel dimer conformation for treating a disease mediated by signaling through a TNFRS member in a patient (e.g., a human patient). In some embodiments, the TNFRS member is TNFR1, TNFR2, Fas, DCR3, DR3, TRAIL-R1 (DR4), TRAIL-R2 (DR5), TRAIL-R3, TRAIL-R4, DR6, EDAR, CD271, OPG, RANK, LTβR, TWEAK-R, HVEM, CD27, CD30, CD40, CD137, OX40, GITR, BCMA, TACI, BAFFR, EDAR2, TROY, or RELT. In some embodiments, the TNFRS member is TNFR2. The disease mediated by signaling through a TNFRS member, such as TNFR2, may be a cancer. For instance, the cancer may be Hodgkin's lymphoma, cutaneous non-Hodgkin's lymphoma, T cell lymphoma, ovarian cancer, colon cancer, multiple myeloma, or renal cell carcinoma.

Definitions

As used herein, the term "about" refers to a value that is no more than 10% above or below the value being described. For example, the term "about 5 nM" indicates a range of from 4.5 nM to 5.5 nM.

As used herein, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen-binding fragments of antibodies, including e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) that are capable of specifically binding to a target protein. Fab and F(ab')$_2$ fragments lack the Fc fragment of an intact antibody, clear more rapidly from the circulation of the animal, and may have less non-specific tissue binding than an intact antibody (see Wahl et al., J. Nucl. Med. 24:316, 1983; incorporated herein by reference).

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546, 1989), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single-chain Fv (scFv); see, e.g., Bird et al., Science 242: 423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the terms "anti-tumor necrosis factor receptor 2 antibody," "TNFR2 antibody," "anti-TNFR2 antibody portion," and/or "anti-TNFR2 antibody fragment" and the like include any protein or peptide-containing molecule that includes at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that is capable of specifically binding to TNFR2. TNFR2 antibodies also include antibody-like protein scaffolds, such as the tenth fibronectin type III domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, e.g., the CDRs of a TNFR2 monoclonal antibody onto the fibronectin scaffold by replacing residues of the BC, DE, and FG loops of $^{10}$Fn3 with residues from the CDR-H1, CDR-H2, or CDR-H3 regions of a TNFR2 monoclonal antibody.

As used herein, the terms "antagonist TNFR2 antibody" and "antagonistic TNFR2 antibody" refer to TNFR2 antibodies that are capable of inhibiting or reducing activation of TNFR2 and/or attenuating one or more signal transduction pathways mediated by TNFR2. For example, antagonistic TNFR2 antibodies can inhibit or reduce the growth and proliferation of a population of regulatory T-cells. Antagonistic TNFR2 antibodies may inhibit or reduce TNFR2 activation by blocking TNFR2 from binding TNFα. In this way, antagonistic TNFR2 antibodies may block the trimerization of TNFR2 that would otherwise be induced by interacting with TNFα, thus resulting in suppression of TNFR2 activity.

As used herein, the term "bispecific antibodies" refers to monoclonal, often human or humanized antibodies that have binding specificities for at least two different antigens. In the invention, one of the binding specificities can be directed towards TNFR2, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the term "chimeric" antibody refers to an antibody having variable sequences derived from an immunoglobulin of one source organism, such as rat or mouse, and constant regions derived from an immunoglobulin of a different organism (e.g., a human). Methods for producing chimeric antibodies are known in the art. See, e.g., Morrison, 1985, Science 229(4719): 1202-7; Oi et al, 1986, BioTechniques 4:214-221; Gillies et al, 1985, J. Immunol. Methods 125:191-202; U.S. Pat. Nos. 5,807,715; 4,816,567; and 4,816,397; incorporated herein by reference.

As used herein, the term "complementarity determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The invention includes antibodies comprising modifications in these hybrid hypervariable positions. The variable domains of native heavy and light chains each comprise four framework regions that primarily adopt a β-sheet configuration, connected by three CDRs, which form loops that connect, and in some cases form part of, the β-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |

TABLE 1-continued

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "conjugate" refers to a compound formed by the chemical bonding of a reactive functional group of one molecule with an appropriately reactive functional group of another molecule.

As used herein, the term "derivatized antibodies" refers to antibodies that are modified by a chemical reaction so as to cleave residues or add chemical moieties not native to an isolated antibody. Derivatized antibodies can be obtained by glycosylation, acetylation, pegylation, phosphorylation, amidation, derivatization by addition of known chemical protecting/blocking groups, proteolytic cleavage, linkage to a cellular ligand or other protein. Any of a variety of chemical modifications can be carried out by known techniques, including, without limitation, specific chemical cleavage, acetylation, formylation, metabolic synthesis of tunicamycin, etc. using established procedures. Additionally, the derivative can contain one or more non-natural amino acids, e.g., using amber suppression technology (see, e.g., U.S. Pat. No. 6,964,859; incorporated herein by reference).

As used herein, the term "diabodies" refers to bivalent antibodies comprising two polypeptide chains, in which each polypeptide chain includes $V_H$ and $V_L$ domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain. In order to fold into their native structure, peptides configured in this way typically trimerize so as to position the VH and VL domains of neighboring peptide chains spatially proximal to one another to permit proper folding (see Holliger et al., Proc. Natl. Acad. Sci. USA 90:6444-48, 1993; incorporated herein by reference).

As used herein, a "dominant antagonist" of TNFR2 is an antagonist (e.g., an antagonistic polypeptide, such as a single-chain polypeptide, antibody, or antigen-binding fragment thereof) that is capable of inhibiting TNFR2 activation even in the presence of a TNFR2 agonist, such as TNFα, or IL-2. For example, a TNFR2 antagonist is a dominant antagonist if the $IC_{50}$ of the antagonist increases by less than 200% (e.g., less than 200%, 100%, 50%, 45%, 40%, 35%, 30%, 25%, 20%, 15%, 10%, 5%, 1%, or less) in the presence of a TNFR2 agonist (e.g., TNFα) or IL-2 relative to the $IC_{50}$ of the antagonist as measured in the same assay in the absence of a TNFR2 agonist, such as TNFα, or IL-2. Inhibition of TNFR2 activation can be assessed, for instance, by measuring the inhibition of proliferation of a population of TNFR2+ cells, such as T-reg cells, cancer cells that express TNFR2, or myeloid-derived suppressor cells, as well as by measuring the inhibition of NFκB signaling (e.g., by monitoring the reduction in expression of one or more genes selected from the group consisting of CHUK, NFK-BIE, NFKBIA, MAP3K11, TRAF2, TRAF3, relB, and cIAP2/BIRC3 in a conventional gene expression assay). Cell proliferation assays and gene expression assays that can be used to monitor TNFR2 activation are described herein, for instance, in Examples 9 and 12, respectively.

As used herein, a "dual variable domain immunoglobulin" ("DVD-Ig") refers to an antibody that combines the target-binding variable domains of two monoclonal antibodies via linkers to create a tetravalent, dual-targeting single agent. (Gu et al., Meth. Enzymol., 502:25-41, 2012; incorporated by reference herein). Suitable linkers for use in the light chains of the DVDs of the invention include those identified on Table 2.1 on page 30 of Gu et al.: the short K chain linkers ADAAP (SEQ ID NO: 118) (murine) and TVAAP (SEQ ID NO: 119) (human); the long K chain linkers ADAAPTVSIFP (SEQ ID NO: 120) (murine) and TVAAPSVFIFPP (SEQ ID NO: 121) (human); the short A chain linker QPKAAP (SEQ ID NO: 122) (human); the long A chain linker QPKAAPSVTLFPP (SEQ ID NO: 123) (human); the GS-short linker GGSGG (SEQ ID NO: 124), the GS-medium linker GGSGGGGSG (SEQ ID NO: 125), and the GS-long linker GGSGGGGSGGGGS (SEQ ID NO: 126) (all GS linkers are murine and human). Suitable linkers for use in the heavy chains of the DVDs include those identified on Table 2.1 on page 30 of Gu & Ghayur, 2012, Methods in Enzymology 502:25-41, incorporated by reference herein: the short linkers AKTTAP (SEQ ID NO: 127) (murine) and ASTKGP (SEQ ID NO: 128) (human); the long linkers AKTTAPSVYPLAP (SEQ ID NO: 129) (murine) and ASTKGPSVFPLAP (SEQ ID NO: 130) (human); the GS-short linker GGGGSG (SEQ ID NO: 131), the GS-medium linker GGGGSGGGGS (SEQ ID NO: 132), and the GS-long linker GGGGSGGGGSGGGG (SEQ ID NO: 133) (all GS linkers are murine and human).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "framework region" or "FW region" includes amino acid residues that are adjacent to the CDRs. FW region residues may be present in, for example, human antibodies, rodent-derived antibodies (e.g., murine antibodies), humanized antibodies, primatized antibodies, chimeric antibodies, antibody fragments (e.g., Fab fragments), single-chain antibody fragments (e.g., scFv fragments), antibody domains, and bispecific antibodies, among others.

As used herein, the term "fusion protein" refers to a protein that is joined via a covalent bond to another molecule. A fusion protein can be chemically synthesized by, e.g., an amide-bond forming reaction between the N-terminus of one protein to the C-terminus of another protein. Alternatively, a fusion protein containing one protein covalently bound to another protein can be expressed recombinantly in a cell (e.g., a eukaryotic cell or prokaryotic cell) by expression of a polynucleotide encoding the fusion protein, for example, from a vector or the genome of the cell. A fusion protein may contain one protein that is covalently bound to a linker, which in turn is covalently bound to another molecule. Examples of linkers that can be used for the formation of a fusion protein include peptide-containing linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

As used herein, the term "heterospecific antibodies" refers to monoclonal, preferably human or humanized, antibodies that have binding specificities for at least two different antigens. Traditionally, the recombinant production of heterospecific antibodies is based on the co-expression of two immunoglobulin heavy chain-light chain pairs, where the two heavy chains have different specificities (Milstein et al., Nature 305:537, 1983). Similar procedures are disclosed, e.g., in WO 93/08829, U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759; 5,601,819; 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986); incorporated herein by reference. Heterospecific antibodies can include Fc mutations that enforce correct chain association in multi-specific antibodies, as described by Klein et al, mAbs 4(6):653-663, 2012; incorporated herein by reference.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A human antibody can be produced in a human cell (e.g., by recombinant expression), or by a non-human animal or a prokaryotic or eukaryotic cell that is capable of expressing functionally rearranged human immunoglobulin (e.g., heavy chain and/or light chain) genes. Further, when a human antibody is a single-chain antibody, it can include a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. See U.S. Pat. Nos. 4,444,887 and 4,716,111; and PCT publications WO 1998/46645; WO 1998/50433; WO 1998/24893; WO 1998/16654; WO 1996/34096; WO 1996/33735; and WO 1991/10741; incorporated herein by reference. Human antibodies can also be produced using transgenic mice that are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598; incorporated by reference herein.

As used herein, the term "humanized" antibodies refers to forms of non-human (e.g., murine) antibodies that are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin. All or substantially all of the FR regions may also be those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., Nature 332:323-7, 1988; U.S. Pat. Nos. 5,530,101; 5,585,089; 5,693,761; 5,693,762; and 6,180,370 to Queen et al; EP239400; PCT publication WO 91/09967; U.S. Pat. No. 5,225,539; EP592106; and EP519596; incorporated herein by reference.

As used herein, the term "hydrophobic side-chain" refers to an amino acid side-chain that exhibits low solubility in water relative due to, e.g., the steric or electronic properties of the chemical moieties present within the side-chain. Examples of amino acids containing hydrophobic side-chains include those containing unsaturated aliphatic hydrocarbons, such as alanine, valine, leucine, isoleucine, proline, and methionine, as well as amino acids containing aromatic ring systems that are electrostatically neutral at physiological pH, such as tryptophan, phenylalanine, and tyrosine.

As used herein, the term "monoclonal antibody" refers to an antibody that is derived from a single clone, including any eukaryotic, prokaryotic, or phage clone, and not the method by which it is produced.

As used herein, the term "multi-specific antibodies" refers to antibodies that exhibit affinity for more than one target antigen. Multi-specific antibodies can have structures similar to full immunoglobulin molecules and include Fc regions, for example IgG Fc regions. Such structures can include, but not limited to, IgG-Fv, IgG-(scFv)$_2$, DVD-Ig, (scFv)$_2$-(scFv)$_2$-Fc and (scFv)$_2$-Fc-(scFv)$_2$. In case of IgG-(scFv)$_2$, the scFv can be attached to either the N-terminal or the C– terminal end of either the heavy chain or the light chain. Exemplary multi-specific molecules that include Fc regions and into which anti-TNFR2 antibodies or antigen-binding fragments thereof can be incorporated have been reviewed by Kontermann, 2012, mAbs 4(2):182-197, Yazaki et al, 2013, Protein Engineering, Design & Selection 26(3): 187-193, and Grote et al, 2012, in Proetzel & Ebersbach (eds.), Antibody Methods and Protocols, Methods in Molecular Biology vol. 901, chapter 16:247-263; incorporated herein by reference. In some embodiments, antibody fragments can be components of multi-specific molecules without Fc regions, based on fragments of IgG or DVD or scFv. Exemplary multi-specific molecules that lack Fc regions and into which antibodies or antibody fragments can be incorporated include scFv dimers (diabodies), trimers (triabodies) and tetramers (tetrabodies), Fab dimers (conjugates by adhesive polypeptide or protein domains) and Fab trimers (chemically conjugated), are described by Hudson and Souriau, 2003, Nature Medicine 9:129-134; incorporated herein by reference.

As used herein, the term "myeloid-derived suppressor cell" or "MDSC" refers to a cell of the immune system that modulates the activity of a variety of effector cells and antigen-presenting cells, such as T-cells, NK cells, dendritic cells, and macrophages, among others. Myeloid derived suppressor cells are distinguished by their gene expression profile, and express all or a subset of proteins and small molecules selected from the group consisting of B7-1 (CD80), B7-H1 (PD-L1), CCR2, CD1d, CD1d1, CD2, CD31 (PECAM-1), CD43, CD44, complement component C5a R1, F4/80 (EMR1), Fcγ RII (CD16), Fcγ RII (CD32), Fcγ RIIA (CD32a), Fcγ RIIB (CD32b), Fcγ RIIB/C (CD32b/c), Fcγ RIIC (CD32c), Fcγ RIIIA (CD16A), Fcγ RIIIB (CD16b), galectin-3, GP130, Gr-1 (Ly-6G), ICAM-1 (CD54), IL-1 RI, IL-4Rα, IL-6Rα, integrin α4 (CD49d), integrin αL (CD11a), integrin αM (CD11b), M-CSFR, MGL1 (CD301a), MGL1/2 (CD301a/b), MGL2 (CD301b), nitric oxide, PSGL-1 (CD162), L-selectin (CD62L), siglec-3 (CD33), transferrin receptor (TfR), VEGFR1 (Flt-1), and VEGFR2 (KDR or Flk-1). Particularly, MDSCs do not express proteins selected from the group consisting of B7-2 (CD86), B7-H4, CD11c, CD14, CD21, CD23 (FcεRII), CD34, CD35, CD40 (TNFRSF5), CD117 (c-kit), HLA-DR, and Sca-1 (Ly6).

As used herein, the term "neutral TNFR2 polypeptide" refers to a polypeptide (such as a single-chain polypeptide, an antibody, or an antibody fragment) that binds TNFR2 and does not exert an antagonistic or an agonistic effect on TNFR2 activation. For instance, a TNFR2 polypeptide is a neutral TNFR2 polypeptide if the polypeptide binds TNFR2 and neither potentiates nor suppresses TNFR2 activation, for instance, as assessed by measuring the proliferation of a population of TNFR2-expressing cells (e.g., T-reg cells, TNFR2+ cancer cells, and/or MDSCs) and/or by measuring the expression of one or more NFκB target genes, such as CHUK, NFKBIE, NFKB1A, MAP3K11, TRAF2, TRAF3, relB, and/or cIAP2/BIRC3. Exemplary assays for measuring cell proliferation and gene expression are described, e.g., in Examples 9 and 12, respectively.

As used herein, the term "non-native constant region" refers to an antibody constant region that is derived from a source that is different from the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region).

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, the term "primatized antibody" refers to an antibody comprising framework regions from primate-derived antibodies and other regions, such as CDRs and constant regions, from antibodies of a non-primate source. Methods for producing primatized antibodies are known in the art. See e.g., U.S. Pat. Nos. 5,658,570; 5,681,722; and 5,693,780; incorporated herein by reference.

As used herein, the term "operatively linked" in the context of a polynucleotide fragment is intended to mean that the two polynucleotide fragments are joined such that the amino acid sequences encoded by the two polynucleotide fragments remain in-frame.

As used herein, the term "pharmacokinetic profile" refers to the absorption, distribution, metabolism, and clearance of a drug over time following administration of the drug to a patient.

As used herein, a "recessive antagonist" of TNFR2 is an antagonist (e.g., an antagonistic polypeptide, such as a single-chain polypeptide, antibody, or antigen-binding fragment thereof) that inhibits TNFR2 activation to a significantly lesser extent in the presence of a TNFR2 agonist, such as TNFα, or IL-2 relative to the extent of inhibition of the same antagonist as measured in the absence of a TNFR2 agonist, such as TNFα, or IL-2. For example, a TNFR2 antagonist is a recessive antagonist if the $IC_{50}$ of the antagonist increases by, e.g., 10-fold, 20-fold, 30-fold, 40-fold, 50-fold, 60-fold, 70-fold, 80-fold, 90-fold, 100-fold, or more in the presence of a TNFR2 agonist (e.g., TNFα) or IL-2 relative to the $IC_{50}$ of the antagonist as measured in the same assay the absence of a TNFR2 agonist, such as TNFα, or IL-2. Inhibition of TNFR2 activation can be assessed, for instance, by measuring the inhibition of proliferation of a population of TNFR2+ cells, such as T-reg cells, cancer cells that express TNFR2, or myeloid-derived suppressor cells, as well as by measuring the inhibition of NFκB signaling (e.g., by monitoring the reduction in expression of one or more genes selected from the group consisting of CHUK, NFK-BIE, NFKBIA, MAP3K11, TRAF2, TRAF3, relB, and cIAP2/BIRC3 in a conventional gene expression assay). Cell proliferation assays and gene expression assays that can be used to monitor TNFR2 activation are described herein, for instance, in Examples 9 and 12, respectively.

As used herein, the term "regulatory sequence" includes promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990); incorporated herein by reference.

As used herein, the term "scFv" refers to a single-chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). scFv molecules are known in the art and are described, e.g., in U.S. Pat. No. 5,892,019, Flo et al., (Gene 77:51, 1989); Bird et al., (Science 242:423, 1988); Pantoliano et al., (Biochemistry 30:10117, 1991); Milenic et al., (Cancer Research 51:6363, 1991); and Takkinen et al., (Protein Engineering 4:837, 1991). The VL and VH domains of a scFv molecule can be derived from one or more antibody molecules. It will also be understood by one of ordinary skill in the art that the variable regions of the scFv molecules of the invention can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively or in addition, mutations are made to CDR amino acid residues to optimize antigen binding using art recognized techniques. scFv fragments are described, for example, in WO 2011/084714; incorporated herein by reference.

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 pM and 100 nM). An antibody or antigen-binding fragment thereof that does not exhibit specific binding to a particular antigen or epitope thereof will exhibit a $K_D$ of greater than 100 nM (e.g., greater than 500 nm, 1 μM, 100 μM, 500 M, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As used herein, the terms "subject" and "patient" refer to an organism that receives treatment for a particular disease or condition as described herein (such as cancer or an infectious disease). Examples of subjects and patients include mammals, such as humans, primates, pigs, goats, rabbits, hamsters, cats, dogs, guinea pigs, members of the bovidae family (such as cattle, bison, buffalo, elk, and yaks, among others), cows, sheep, horses, and bison, among others, receiving treatment for diseases or conditions, for example, cell proliferation disorders, such as cancer or infectious diseases.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE—dextran transfection and the like.

As used herein, the terms "treat" or "treatment" refer to therapeutic treatment, in which the object is to prevent or slow down (lessen) an undesired physiological change or disorder, such as the progression of a cell proliferation disorder, such as cancer, or an infectious disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be prevented.

As used herein, the terms "tumor necrosis factor receptor superfamily," "TNFR superfamily," or "TNFRS" refer to a group of type I transmembrane proteins with a carboxy-terminal intracellular domain and an amino-terminal extracellular domain characterized by a common cysteine rich domain (CRD). The TNFR superfamily includes receptors that mediate cellular signaling as a consequence of binding to one or more ligands in the TNF superfamily. The TNFR superfamily can be divided into two subgroups: receptors containing the intracellular death domain and those lacking this domain. The death domain is an 80 amino acid motif that propagates apoptotic signal transduction cascades following receptor activation. Exemplary TNFR super family members that contain the intracellular death domain include TNFR1, while TNFR2 represents a TNFR super family protein that does not contain this domain. Members of the TNFR superfamily include TNFR1, TNFR2, RANK, CD30, CD40, Lymphotoxin beta receptor (LT-13R), OX40, Fas receptor, Decoy receptor 3 (DCR3), CD27, 4-1BB, Death receptor 4 (DR4), Death receptor 5 (DR5), Decoy receptor 1 (DCR1), Decoy receptor 2 (DCR2), Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6 (DR6), Death receptor 3 (DR3), and Ectodysplasin A2 receptor.

As used herein the term "variable region CDR" includes amino acids in a CDR or complementarity determining region as identified using sequence or structure based methods. As used herein, the term "CDR" or "complementarity determining region" refers to the noncontiguous antigen-binding sites found within the variable regions of both heavy and light chain polypeptides. These particular regions have been described by Kabat et al., J. Biol. Chem. 252:6609-6616, 1977 and Kabat, et al., Sequences of Proteins of Immunological Interest, Fifth Edition, U.S. Department of Health and Human Services, NIH Publication No. 91-3242, 1991; by Chothia et al., (J. Mol. Biol. 196:901-917, 1987), and by MacCallum et al., (J. Mol. Biol. 262:732-745, 1996) where the definitions include overlapping or subsets of amino acid residues when compared against each other. In certain embodiments, the term "CDR" is a CDR as defined by Kabat based on sequence comparisons.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/11026; incorporated herein by reference. Expression vectors of the invention contain a polynucleotide sequence as well as, e.g., additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors of the invention may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "VH" refers to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain of a native antibody has at the amino terminus a variable domain (VH) followed by a number of constant domains. Each light chain of a native antibody has a variable domain at the amino terminus (VL) and a constant domain at the carboxy terminus.

BRIEF DESCRIPTION OF THE FIGURES

FIGS. 1A and 1B show the DNA and amino acid sequences of the heavy and light chains of the antagonistic TNFR2 antibody TNFRAB1. FIG. 1A shows the DNA sequence that encodes the heavy chain of TNFRAB1 (top) and amino acid sequence of the heavy chain (bottom). The amino acid sequences of the three complementarity-determining regions (CDRs) are shown in bold. FIG. 1B shows the DNA sequence that encodes the light chain of TNFRAB1 (top) and amino acid sequence of the light chain (bottom). The amino acid sequences of the three CDRs are shown in bold.

FIGS. 2A and 2B show the amino acid sequence of human TNFR2 (SEQ ID NO: 7). Notably, human TNFR2 is numbered herein starting with an N-terminal methionine at position 1 and concluding with a C-terminal serine at position 461 (SEQ ID NO: 7). All references to amino acid positions within TNFR2 are made in the context of the TNFR2 numbering scheme shown in FIGS. 2A and 2B. (FIG. 2A) Shaded residues KCRPGFGV (SEQ ID NO: 20) define an epitope that is specifically bound by the antagonistic TNFR2 antibody TNFRAB1. Significantly, the ability of TNFRAB1 to selectively bind residues within this region without binding underlined residues KCSPG (SEQ ID NO: 12) promotes antagonism of TNFR2 signaling. The poor (or lack of) affinity of the antibodies of the invention for residues within the region of, or near, the underlined residues is consistent with the antagonistic activity of these antibodies, as binding to epitopes containing the underlined residues has been correlated with attenuation of the inhibitory activity among TNFR2 antibodies. TNFRAB1 additionally binds an epitope that includes shaded residues CKPCAPGTF (SEQ ID NO: 21). Though these residues are not consecutive in primary sequence with the KCRPG motif, they are likely spatially proximal in the three dimensional tertiary structure of TNFR2 and may be appropriately positioned for interaction with an antagonistic TNFR2 antibody of the invention (see FIG. 4). (FIG. 2B) Shaded residues CAPLRKRCR (SEQ ID NO: 11) define an epitope that is specifically bound by the antagonistic TNFR2 antibody TNFRAB2. TNFRAB2 may additionally bind one or more regions that include the residues DSTYTQL (SEQ ID NO: 8), PECLSCGS (SEQ ID NO: 9), and RICTCRPG (SEQ ID NO: 10), which may be part of a discontinuous epitope. Though these residues are not consecutive in primary sequence, they are likely spatially proximal in the three dimensional tertiary structure of TNFR2 and may be appropriately positioned for interaction with an antagonistic TNFR2 antibody of the invention.

FIGS. 3A and 3B are tables showing the raw data obtained from enzyme-linked immunosorbant assay (ELISA) experiments that were conducted to determine the affinity of TNFRAB1 and TNFRAB2 for various continuous and discontinuous epitopes within TFNR2 (see Example 1). Raw luminescence values are shown in the fourth column of the tables (right). The peptide sequences shown represent those that contain a portion of the conformational epitope within TNFR2 that interacts with TNFRAB1 (FIG. 3A) or TNFRAB2 (FIG. 3B). Amino acid residues with the single-digit code "2" designate cysteine residues that were chemically protected at the thiol position with an acetamidomethyl (ACM) moiety during peptide synthesis. These residues are not reactive with bromomethyl-containing electrophiles and were therefore not cross-linked during the cyclization and bicyclization phases of peptide synthesis. The third column in the tables indicates the general structure of the peptide scaffold. "CYS.S" indicates a 27-residue peptide in which positions 1-11 and 17-27 of the peptide represent 11-residue peptides derived from TNFR2 that contain cysteine residues that form disulfide bridges in the native protein based on information available for UniProt entry P20333. The sequence Gly-Gly-Ser-Gly-Gly (SEQ ID NO: 124) was incorporated into positions 12-16 of peptides of this group. Native Cys residues that do not form disulfide bridges were protected with acetamidomethyl (ACM) protecting groups and are designated with the single-digit code "2".

FIG. 4 is a schematic illustrating the conformational epitopes within TNFR2 that may interact with antagonist TNFR2 antibodies, such as TNFRAB1 and TNFRAB2, as well as residues that do not interact with antagonist TNFR2 antibodies. The KCSPG motif (SEQ ID NO: 12) is shown in the expansion at the top left of the figure; the KCRPG (SEQ ID NO: 19) motif is shown in the expansion at the right of the figure. Exterior surface of the protein designates the van der Waals surface of TNFR2. FIG. 4 is a rendering of a monomer of TNFR2 isolated from the X-ray crystal structure of TNFR2 (PDB ID: 3ALQ, Mukai, et al., Sci. Signal., 3:ra83, 2010).

FIG. 5 is a graph showing that TNFRAB1 suppresses the growth of cultured T-reg cells in vitro. Values represent the fraction of viable T-reg cells relative to untreated control cells that remained in culture after exposure of the cells to a particular condition. Bars shown on the far left represent T-reg cells treated with either IL-2 at 200 U/ml (control), TNFα (20 ng/ml), TNFR2 agonist (2.5 pg/ml), antagonistic TNFR2 antibody TNFRAB1 (2.5 pg/ml), or antagonistic TNFR2 antibody TNFRAB2 (2.5 pg/ml). Bars shown second from the left demonstrate the dose-dependent variation in T-reg viability upon treatment of cells with TNFRAB1. Bars shown second from the right show the ability of TNFRAB1 to inhibit the growth-promoting activity of TNFα. T-reg cells were treated with a constant concentration of TNFα (20 ng/ml) and varying concentrations of TNFRAB1 (from 0.0008 to 25 pg/ml). TNFRAB1 was capable of suppressing TNFα-induced proliferation in a concentration-dependent manner, indicating that TNFRAB1 antagonizes TNFR2. Bars shown on the far right demonstrate the effect of TNFα on the growth of T-reg cells. Incubation of T-reg cells with 20 ng/ml TNFα resulted in approximately 130% proliferation relative to untreated cells.

FIG. 6A is a graph showing the ability of TNFα to induce aT-reg cell proliferation in a dose-dependent manner. FIG. 6B is a graph showing the ability of IL-2 to induce aT-reg cell proliferation in a dose-dependent manner. Incubation of freshly isolated human CD4+ cells for up to 48 hours with TNFα and IL-2 (200 U/ml) induces T-cell expansion in a dose-dependent manner and the presence of IL-2 is important for promoting T-reg expansion. FIG. 6C is a graph showing the effect of TNFα and dominant antagonistic TNFR2 antibodies TNFRAB1 and TNFRAB2 on T-reg cell proliferation. Values on the x-axis represent the percent change in the quantity of T-reg cells relative to a sample treated with IL-2.

FIG. 13A is a table showing the kinetic and thermodynamic parameters of the binding of TNFRAB1 and TNFRAB2 to TNFR2. Association rate constants are shown in units of $M^{-1}s^{-1}$, dissociation rate constants are shown in units of $s^{-1}$, and equilibrium constants are shown in units of M. FIG. 13B is a table showing the affinity of TNFRAB1 and TNFRAB2 for various linear peptide sequences within human TNFR2. Relative affinity is indicated as a series of "+" symbols, such that higher quantities of this symbol represent elevated affinity values. Raw data derived from ELISA binding experiments are provided in the "Reading" column. FIG. 13C is a table showing the effect of TNFα on the affinity of TNFRAB1 and TNFRAB2 for various linear peptide sequences within human TNFR2. Relative affinity is indicated as a series of "+" symbols, such that higher quantities of this symbol represent elevated affinity values. Raw data derived from ELISA binding experiments are provided in the "Reading" column.

FIG. 15A is a structural model showing a three-dimensional structure of the anti-parallel dimer and parallel dimer of human TNFR2. FIG. 15B is a structural model showing the three-dimensional structure of the TNFα-TNFR2 complex. Shaded residues represent amino acids within human TNFR2 that are bound by TNFRAB1. Proteins are portrayed in ribbon form beneath a Van der Waals surface. The data described herein clearly shows that for the full antibody or the F(ab')$_2$ fragment thereof to bind to TNFR2 in an anti-parallel conformation, the TNFR2 receptor would bind the antibody or fragment thereof at the indicated amino acid motifs. The binding sites of the parallel dimer are too close to one another and would thus preclude antibody binding. Moreover, the trimeric TNFα-TNFR2 complex masks the epitopes bound by antagonistic TNFR2 antibodies, as these residues are located within the interior of the trimeric structure. FIG. 15C is an image showing the known and published trimeric structural model of TNFR2 as a trimer with contained trimer TNF. Also shown in this structure are shaded residues that represent amino acids within human TNFR2 that are bound by the recessive-antagonist TNFR2 antibodies A and B.

FIGS. 18B and 18C are reproduced from Naismith et al. Structure 4:1251-1262 (1996), the disclosure of which is incorporated herein by reference in its entirety.

DETAILED DESCRIPTION

Antagonistic TNFR2 polypeptides (e.g., single-chain polypeptides, antibodies, and antigen-binding fragments) of the invention inhibit the activation of TNFR2 on TNFR2-expressing cells by binding this receptor (e.g., on the exterior surface of a T-reg cell, a cancer cell that expresses TNFR2, or a myeloid-derived suppressor cell (MDSC), and thus prevent the protein from recruiting its cognate ligand, TNFα. TNFα potentiates TNFR2 signaling by nucleating a trimer of TNFR2 proteins. It is this trimerization event that brings individual TNFR2 proteins into close proximity and initiates signaling via the MAPK/NFκB/TRAF2/3 pathway, which ultimately leads to cell growth and escape from apoptosis. TNFR2-binding polypeptides (e.g., single-chain polypeptides, antibodies, and antibody fragments) can antagonize this interaction by binding the receptor and preventing TNFα from triggering this structural change. For instance, one mechanism by which this may occur is through the formation of an anti-parallel TNFR2 dimer, which is an inactive structural form of the receptor.

Figure 18A:
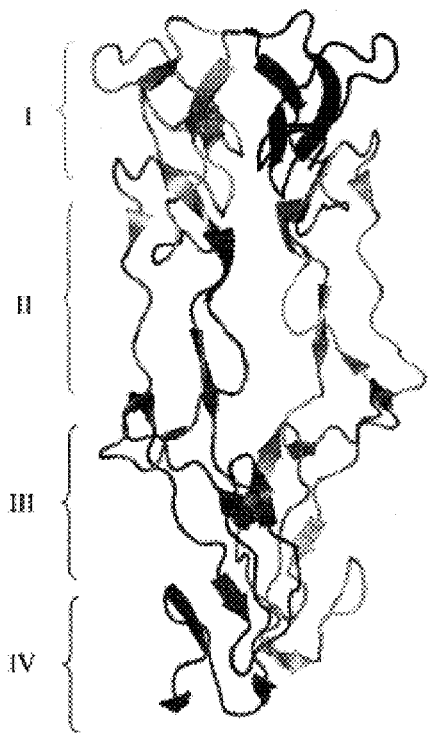
FIG. 18A is a structural model of a TNFRS member, the human death receptor 3 (DR3), shown in an anti-parallel dimer conformation. The four cysteine-rich domains of DR3 are indicated by Roman numerals I-IV. The structural model is reproduced from Tengchuan, Original Archival Copy of Thesis, Structural Characterization of TNF Receptors and Ligands, Chicago, Ill., 2008, the disclosure of which is incorporated herein by reference in its entirety.
Figure 18B:
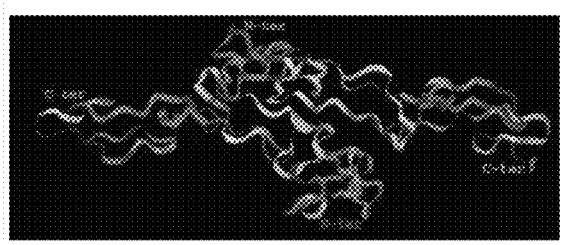
FIG. 18B is a structural model showing TNFR1 in an anti-parallel dimer conformation. In this model, the N-terminus of one TNFR1 monomer is located near the center of the other TNFR1 monomer.
Figure 18C:
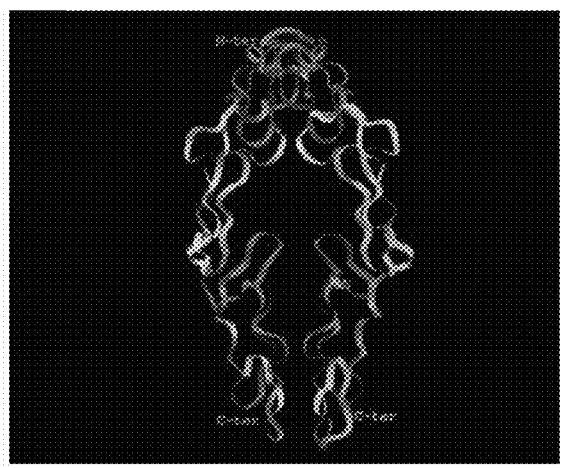
FIG. 18C is a structural model showing TNFR1 in an alternative anti-parallel dimer conformation. In this model, the N-termini of the TNFR1 monomers and the C-termini of the TNFR1 monomers are located proximal to one another.

Polypeptides (e.g., single-chain polypeptides, antibodies, and antigen-binding fragments) of the invention may be used to inhibit the activity of other members of the tumor necrosis factor receptor superfamily (TNFRS). For instance, antibodies and antigen-binding fragments thereof of the invention may bind a TNFRS member, such as DR3 or TNFR1, in an anti-parallel dimer conformation. By binding a TNFRS member in an anti-parallel dimer structure, antibodies or antigen-binding fragments thereof form a complex with the TNFRS member in which receptor residues that bind a cognate ligand, such as TNFα in the case of TNFR2, are sequestered within the interior of the complex. Thus, antibodies or antigen-binding fragments thereof of the invention may prevent ligand-mediated trimerization, and hence activation, of a TNFRS member by forming a complex with the TNFRS member that sterically precludes the endogenous ligand from accessing its cognate binding sites within the receptor. Exemplary TNFRS members that are known to adopt an anti-parallel dimer conformation include TNFR1, TNFR2, Fas, DCR3, DR3, TRAIL-R1 (DR4), TRAIL-R2 (DR5), TRAIL-R3, TRAIL-R4, DR6, EDAR, CD271, OPG, RANK, LTβR, TWEAK-R, HVEM, CD27, CD30, CD40, CD137, OX40, GITR, BCMA, TACI, BAFFR, EDAR2, TROY, and RELT, among others. Polypeptides (e.g., single-chain polypeptides, antibodies, and antigen-binding fragments) of the invention may therefore be used to bind a TNFRS member, such as TNFR2, in an anti-parallel dimer conformation in order to inhibit the activity of the TNFRS member in a target cell, such as a T-reg cell, a TNFR2+ cancer cell, or a myeloid-derived suppressor cell. For instance, antagonistic polypeptides, such as single-chain polypeptides, antibodies, or antigen-binding fragments thereof of the invention may bind DR3 in an anti-parallel dimer conformation (e.g., as shown in FIG. 18A) and/or TNFR1 in an anti-parallel dimer conformation (e.g., as shown in FIG. 18B). Antagonistic polypeptides (e.g., single-chain polypeptides, antibodies, and antigen-binding fragments) of the invention may bind TNFRS members such as DR3 and/or TNFR1 in an anti-parallel conformation as shown in FIGS. 18A and 18B, thus rendering cognate ligand binding sites sterically inaccessible and attenuating TNFRS member-mediated signaling. For instance, antagonistic DR3 antibodies or antigen-binding fragments thereof of the invention may bind an epitope within residues 138-150 of the DR3 amino acid sequence (GENBANK™ Accession No. AAQ88676.1). Antagonistic TNFR1 antibodies or antigen-binding fragments thereof of the invention may bind an epitope within residues 185-197 of the TNFR1 amino acid sequence (GENBANK™ Accession No. NP_001056).

Polypeptides (e.g., single-chain polypeptides, antibodies, and antigen-binding fragments) of the invention may be dominant antagonists (e.g., dominant TNFR2 antagonistic polypeptides, such as single-chain polypeptides, antibodies, or antigen-binding fragments thereof). Dominant antagonistic TNFR2 polypeptides are those that are capable of binding TNFR2 (e.g., in an anti-parallel dimer conformation) and inhibiting TNFR2-mediated signal transduction even in the presence of an agonist, such as TNFα, or IL-2. For example, in the presence of a TNFR2 agonist, a dominant antagonistic TNFR2 polypeptide may inhibit the proliferation of a population of cells, such as T-reg cells, cancer cells that express TNFR2, or myeloid-derived suppressor cells by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to a population of such cells that is not treated with a dominant antagonistic TNFR2 polypeptide. In contrast, recessive antagonistic TNFR2 polypeptides are capable of binding TNFR2 and inhibiting TNFR2-mediated signaling, but the ability of these polypeptides to do so is attenuated in the presence of a TNFR2 agonist. For instance, the $IC_{50}$ of a recessive antagonistic TNFR2 polypeptide as measured in the presence of a TNFR2 agonist, such as TNFα, or IL-2, in a T-reg cell death assay, a TNFR2+ cancer cell death assay, or a myeloid-derived suppressor cell death assay may be augmented, e.g., by 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to that of a dominant antagonistic TNFR2 polypeptide. Examples of cell death assays that can be used to measure the antagonistic effects of TNFR2 antibodies are described herein, e.g., in Example 9, below. Dominant antagonistic TNFR2 polypeptides, such as single-chain polypeptides, antibodies, or antigen-binding fragments thereof of the invention may therefore be used to suppress the proliferation of a TNFR2-expressing cell (e.g., a T-reg cell, a TNFR2+ cancer cell, such as an ovarian cancer cell, or a myeloid-derived suppressor cell) even in the presence of a growth-inducing signal, such as TNFα or IL-2.

Polypeptides (e.g., single-chain polypeptides, antibodies, and antigen-binding fragments) of the invention can be used to attenuate the activity (e.g., proliferation) of T-reg cells that typically accompanies T-cell-mediated cytotoxicity against self cells, such as the attack of a tumor cell by a T-lymphocyte. Antagonistic TNFR2 polypeptides can be administered to a mammalian subject, such as a human (e.g., by any of a number of routes of administration described herein) in order to prolong the duration of an adaptive immune response, such as a response against a cancer cell or a pathogenic organism. In this way, antagonistic TNFR2 polypeptides of the invention may synergize with existing techniques to enhance T-lymphocyte-based therapy for cancer and for infectious diseases. For instance, TNFR2 antagonists of the invention may be administered to suppress T-reg cell activity, thereby enhancing the cytotoxic effect of tumor reactive T-cells. TNFR2 antagonists may also synergize with existing strategies to promote tumor-reactive T-cell survival, such as lymphodepletion and growth factor therapy, and in turn prolong the duration of anti-tumor reactivity in vivo. Antagonistic TNFR2 polypeptides (e.g., single-chain polypeptides, antibodies, and antigen-binding fragments) can also be used to treat a broad array of infectious diseases in a mammalian subject (e.g., a human), as inhibition of T-reg growth and proliferation promotes the activity of CD8+T-lymphocytes capable of mounting an attack on pathogenic organisms. Additionally, antagonistic TNFR2 polypeptides, such as single-chain polypeptides, antibodies, and antigen-binding fragments thereof, of the invention can be used to treat a wide variety of infectious diseases, such as *Mycobacterium tuberculosis*, in an agricultural farm animal (e.g., a bovine mammal, pig, cow, horse, sheep, goat, cat, dog, rabbit, hamster, guinea pig, or other non-human mammal).

Antagonistic TNFRS Member Polypeptides

TNFRS member proteins exhibit conformational properties typified by TNFR2. For instance, these receptors are known to adopt an anti-parallel dimer conformation, and are activated upon trimerization induced by binding to a cognate ligand. The amino acid sequences and three-dimensional structures of TNFRS member proteins are known in the art. For instance, structural studies of unliganded TNFα receptors have revealed that these proteins adopt an anti-parallel dimer conformation, as described, e.g., in Naismith et al. J. Biol. Chem. 290:13303 (1995), the disclosure of which is incorporated herein by reference in its entirety. Additionally, it has been shown that the human death receptor 3 (DR3) adopts an anti-parallel dimer conformation (Tengchuan, Original Archival Copy of Thesis, Structural Characterization of TNF Receptors and Ligands, Chicago, Ill., 2008, the disclosure of which is incorporated herein by reference in its entirety). Similarly, the TRAIL receptor is known to form an anti-parallel dimer (Shirley et al. Rec. Pat. Anticanc. Drug Disc. 6:311 (2011), the disclosure of which is incorporated herein by reference in its entirety). TRAF6 has additionally been shown to adopt this structural conformation (Marienfeld et al. Mol. Cell. Biol. 26:9209 (2006); Yin et al. Biochem. 48:10558 (2009); and Yin et al. Nat. Struct. Mol. Biol. 16:658 (2009), the disclosures of each of which are incorporated herein by reference in their entirety). NGFR has been shown to adopt an anti-parallel dimer conformation (Bibel et al. Genes Dev. 14:2919 (2000), the disclosure of which is incorporated herein by reference in its entirety). Additionally, CD40 is known to exhibit this structural motif (Smulski et al. J. Biol. Chem. 288:10914 (2013), the disclosure of which is incorporated herein by reference in its entirety). Additionally, CD137 has been shown to exist in an anti-parallel dimer state (Vinay et al. CD137 Pathway: Immunology and Diseases, New York, N.Y., 2006, the disclosure of which is incorporated herein by reference in its entirety). FAS, CD40, OX40, and CD27 have additionally been shown to adopt an anti-parallel dimer conformation (Tartaglia et al. J. Biol. Chem. 267:4304 (1992), the disclosure of which is incorporated herein by reference in its entirety). BAFF-R has also been found to exhibit this structural motif (Kim et al., Nat. Struct. Biol. 10:342 (2003), the disclosure of which is incorporated herein by reference in its entirety).

Polypeptides (e.g., single-chain polypeptides, antibodies, and antigen-binding fragments) that bind amino acid sequences within a TNFRS member protein that share sequence or structural homology with one or more of the KCRPGFGV (SEQ ID NO: 20), CKPCAPGTF (SEQ ID NO: 21), CAPLRKCR (SEQ ID NO: 11), DSTYTQL (SEQ ID NO: 8), PECLSCGS (SEQ ID NO: 9), or RICTCRPG (SEQ ID NO: 10) motifs within human TNFR2 may bind and stabilize the TNFRS member protein in an anti-parallel dimer conformation. For instance, epitopes within a TNFRS member protein that have at least 85% sequence identity (e.g., 85%, 90%, 95%, 97%, 99%, or 100% sequence identity) to one of the aforementioned amino acid sequences within human TNFR2 can be identified using conventional protein sequence alignment techniques known in the art. Antagonistic TNFRS member polypeptides that bind one or more of these homologous epitopes can then be developed using a variety of library screening and in vitro display techniques as described herein (for instance, see Example 15, below). Antagonistic TNFRS member polypeptides (e.g., single-chain polypeptides, antibodies, and antigen-binding fragments) developed in this manner may bind the TNFRS member protein in an anti-parallel dimer conformation, thereby rendering cognate ligand binding sites sterically inaccessible and thus precluding receptor trimerization and activation. In particular, single-chain polypeptides, antibodies, or antigen-binding fragments thereof that specifically bind a TNFRS member and stabilize an anti-parallel dimer confirmation have binding specificity to only a single TNFRS member and do not cross-react with other TNFRS members.

Antagonistic TNFR2 Polypeptides

The anti-TFNR2 polypeptides (e.g., single-chain polypeptides, antibodies, and antigen-binding fragments) of the invention are capable of interacting with and inhibiting the activity of TNFR2. Thus, the anti-TNFR2 antibodies of the invention can selectively antagonize the TNFα-TNFR2 interaction rather than promote TNFR2 signaling. This is particularly important for therapeutic applications, e.g., cancer immunotherapy, as TNFR2 activation upon association with TNFα leads to propagation of the MAPK and TRAF2/3 signal cascade and activation of NFκB-mediated transcription of genes involved in T-reg cell growth and escape from apoptosis (Faustman, et al., Nat. Rev. Drug Disc., 9:482-493, 2010). The TNFR2 polypeptides of the invention may bind TNFR2 with high affinity and may sterically sequester the receptor from TNFα rather than allow TNFα binding to TNFR2 initiate TNFR2 signaling, e.g., by binding TNFR2 in an anti-parallel dimer conformation in which TNFα binding sites are sterically inaccessible. The antibodies of the invention can therefore be used to suppress T-reg cell growth and proliferation and can be administered to a mammalian subject, such as a human patient with a cell proliferation disorder or an infectious disease, in order to enhance the effectiveness of an immune response (e.g., an immune response against cancerous cells or pathogenic organisms) in the patient.

Antagonistic TNFR2 single-chain polypeptides, antibodies, or antigen-binding fragments thereof of the invention may additionally bind and inactivate TNFR2 on the surface of a cancer cell, such as a tumor cell. For instance, antagonistic TNFR2 single-chain polypeptides, antibodies, and antigen-binding fragments thereof described herein may bind TNFR2 on the surface a Hodgkin's or cutaneous non-Hodgkin's lymphoma cell, T cell lymphoma cell, ovarian cancer cell, colon cancer cell, multiple myeloma cell, or renal cell carcinoma cell, among others. The ability of antagonistic TNFR2 single-chain polypeptides, antibodies, and antigen-binding fragments thereof of the invention to bind TNFR2 directly on a cancer cell provides another pathway by which these molecules may attenuate cancer cell survival and proliferation. For instance, an antagonistic TNFR2 single-chain polypeptide, antibody, or antigen-binding fragment thereof of the invention, such as an antibody or antigen-binding fragment thereof that contains one or more of the heavy chain and/or light chain CDRs of TNFRAB1 or TNFRAB2 (or a CDR that has at least 85% sequence identity (e.g., 85%, 90%, 95%, 97%, 99%, or 100% sequence identity) to a heavy chain and/or light chain CDR of TNFRAB1 or TNFRAB2, may bind TNFR2 directly on the surface of a cancer cell (e.g., a cutaneous T cell lymphoma cell, ovarian cancer cell, colon cancer cell, or multiple myeloma cell, such as an ovarian cancer cell) in order to diminish the ability of the cell to proliferate.

Antagonistic TNFR2 polypeptides (e.g., single-chain polypeptides, antibodies, and antigen-binding fragments) of the invention may demonstrate the ability to attenuate T-reg and/or cancer cell proliferation even in the presence of a TNFR2 agonist, such as TNFα or an agonistic TNFR2 antibody, or growth-promoting molecules, such as IL-2. Without being limited by mechanism, antagonistic TNFR2 single-chain polypeptides, antibodies, or antigen-binding fragments thereof of the invention may exhibit this property due to the ability of these antibodies or antigen-binding fragments thereof to bind TNFR2 and stabilize the dimeric, anti-parallel dimer conformation of this receptor. This structural configuration is not capable of potentiating NFκB signaling. By maintaining TNFR2 in an inactive structural state, antagonistic TNFR2 single-chain polypeptides, antibodies, or antigen-binding fragments thereof of the invention may prevent TNFR2 agonists from restoring cell growth.

Another property that may be exhibited by antagonistic TNFR2 polypeptides (e.g., single-chain polypeptides, antibodies, and antigen-binding fragments) is the ability to not only reduce T-reg cell, TNFR2+ cancer cell, and/or MDSC proliferation, but also to reduce the total quantity of T-reg cells, TNFR2+ cancer cells, and/or MDSCs within a sample (e.g., within a patient, such as a human patient). Antagonistic TNFR2 single-chain polypeptides, antibodies, or antigen-binding fragments thereof of the invention may be capable of reducing the total quantity of T-reg cells, cancer cells (such as cutaneous T cell lymphoma cells, ovarian cancer cells, colon cancer cells, renal cell carcinoma cells or multiple myeloma cells, among others), and/or MDSCs in a sample treated with an antagonist TNFR2 polypeptide (such as a sample isolated from a human patient undergoing treatment for cancer or an infectious disease as described herein) by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to a sample not treated with an antagonist TNFR2 antibody or antigen-binding fragment thereof.

The ability of antagonistic TNFR2 polypeptides (e.g., single-chain polypeptides, antibodies, and antigen-binding fragments) of the invention to attenuate T-reg and/or cancer cell growth may be due to the ability of these polypeptides to diminish the quantity of soluble TNFR2 within a sample (e.g., a sample isolated from a human patient undergoing treatment for cancer or an infectious disease as described herein). Soluble TNFR2 can be secreted by, e.g., T-reg cells, and can interfere with the ability of TNFR2 antagonists to localize to TNFR2 at the surface of a T-reg cell, TNFR2+ cancer cell, or MDSC by binding and sequestering such antagonists in the extracellular environment. By reducing TNFR2 secretion, antagonistic TNFR2 single-chain polypeptides, antibodies, or antigen-binding fragments thereof of the invention may render T-reg cells, TNFR2+ cancer cells, and/or MDSCs increasingly susceptible to therapeutic molecules, such as an antagonistic TNFR2 antibody or antigen-binding fragment thereof, and/or additional anti-cancer agents described herein or known in the art that may be used in conjunction with the compositions and methods of the invention.

Antagonistic TNFR2 polypeptides (e.g., single-chain polypeptides, antibodies, and antigen-binding fragments) of the invention may be capable of inhibiting the proliferation or reducing the total quantity of a population of T-reg cells in a sample (e.g., a sample isolated from a human patient undergoing treatment for cancer or an infectious disease as described herein) and may act selectively on T-reg cells in an actively-dividing state. Antagonistic TNFR2 single-chain polypeptides, antibodies, or antigen-binding fragments thereof of the invention may selectively target active T-reg cells that express $CD25^{Hi}$ and $CD45RA^{Low}$, e.g., over resting T-reg cells that express $CD25^{Med}$ and $CD45RA^{Hi}$. For instance, antagonistic TNFR2 polypeptides (e.g., single-chain polypeptides, antibodies, and antigen-binding fragments) of the invention may be capable of reducing the proliferation of a population of T-reg cells expressing $CD25^{Hi}$ and $CD45RA^{Low}$ by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to a population of T-reg cells that does not express the $CD25^{Hi}$ and $CD45RA^{Low}$ proteins, such as a population of T-reg cells that expresses $CD25^{Med}$ and $CD45RA^{Hi}$ proteins.

Antagonistic TNFR2 antibodies of the invention may inhibit, e.g., T-reg, cancer cell, and/or MDSC growth with a similar potency as that exhibited by antigen-binding fragments of such antibodies. For instance, removal of the Fc region of an antagonistic TNFR2 antibody of the invention may not alter the ability of the molecule to attenuate the proliferation or reduce the total quantity of T-reg cells and/or cancer cells in a sample (e.g., a sample isolated from a human patient undergoing treatment for cancer or an infectious disease as described herein). Antagonistic TNFR2 antibodies and antigen-binding fragments thereof of the invention may function by a pathway distinct from antibody-dependent cellular cytotoxicity (ADCC), in which an Fc region is required to recruit effector proteins in order to induce cell death. Additionally, antagonistic TNFR2 antibodies or antigen-binding fragments thereof may not be susceptible to a loss of inhibitory capacity in the presence of cross-linking agents. Antagonistic TNFR2 antibodies or antigen-binding fragments thereof of the invention may therefore exhibit therapeutic activity in a variety of isotypes, such as IgG, IgA, IgM, IgD, or IgE, or in a variety of forms, such as a monoclonal antibody or antigen-binding fragment thereof, a polyclonal antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a F(ab')$_2$ molecule, and a tandem scFv (taFv).

Specific Binding Properties of Antagonistic TNFR2 Polypeptides

The specific binding of a single-chain polypeptide, antibody or antibody fragment of the invention to human TNFR2 can be determined by any of a variety of established methods. The affinity can be represented quantitatively by various measurements, including the concentration of antibody needed to achieve half-maximal inhibition of the TNFα-TNFR2 interaction in vitro ($IC_{50}$) and the equilibrium constant ($K_D$) of the polypeptide-TNFR2 complex dissociation. The equilibrium constant, $K_D$, that describes the interaction of TNFR2 with a polypeptide of the invention is the chemical equilibrium constant for the dissociation reaction of a TNFR2-antibody complex into solvent-separated TNFR2 and antibody molecules that do not interact with one another.

Polypeptides (e.g., single-chain polypeptides, antibodies, and antigen-binding fragments) of the invention include those that specifically bind to TNFR2 with a $K_D$ value of less than 100 nM (e.g., 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, or 1 nM). In some embodiments, antibodies of the invention are those that specifically bind to TNFR2 with a $K_D$ value of less than 1 nM (e.g., (e.g., 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, 10 pM, 5 pM, or 1 pM).

Polypeptides (e.g., single-chain polypeptides, antibodies, and antigen-binding fragments) of the invention can also be characterized by a variety of in vitro binding assays. Examples of experiments that can be used to determine the $K_D$ or $IC_{50}$ of a TNFR2 single-chain polypeptide, antibody, or fragment thereof include, e.g., surface plasmon resonance, isothermal titration calorimetry, fluorescence anisotropy, and ELISA-based assays, among others. ELISA represents a particularly useful method for analyzing antibody activity, as such assays typically require minimal concentrations of antibodies. A common signal that is analyzed in a typical ELISA assay is luminescence, which is typically the result of the activity of a peroxidase conjugated to a secondary antibody that specifically binds a primary antibody (e.g., a TNFR2 antibody of the invention). Polypeptides of the invention are capable of binding TNFR2 and epitopes derived thereof, such as epitopes containing one or more of residues 142-146 of SEQ ID NO: 7 within human TNFR2 (KCRPG, as shown in FIGS. 2A and 2B), as well as isolated peptides derived from TNFR2 that structurally pre-organize various residues in a manner that may simulate the conformation of these amino acids in the native protein. For instance, polypeptides of the invention may bind peptides containing the amino acid sequence of any one of SEQ ID NOs: 11, 19, 20, and 34-117, or a peptide containing between about 10 and about 30 continuous or discontinuous amino acids between positions 80 and 130 of SEQ ID NO: 7. In a direct ELISA experiment, this binding can be quantified, e.g., by analyzing the luminescence that occurs upon incubation of an HRP substrate (e.g., 2,2'-azino-di-3-ethylbenzthiazoline sulfonate) with an antigen-antibody complex bound to a HRP-conjugated secondary antibody. For instance, polypeptides of the invention may induce a luminescence response of about 400 absorbance units or more when incubated with surface-immobilized antigen and a HRP-conjugated secondary antibody in the presence of an HRP substrate (see, e.g., Example 3). In some embodiments, the luminescence observed can be from about 400 to about 900 absorbance units (e.g., 400-900 absorbance units, 500-800 absorbance units, or 600-700 absorbance units). In particular cases, the luminescence observed can be from about 600 to about 900 absorbance units (e.g., 600-900 absorbance units or 700-800 absorbance units).

Kinetic Properties of Antagonistic TNFR2 Polypeptides

In addition to the thermodynamic parameters of a TNFR2-polypeptide interaction, it is also possible to quantitatively characterize the kinetic association and dissociation of a single-chain polypeptide, antibody, or antibody fragment of the invention with TNFR2. This can be done, e.g., by monitoring the rate of antibody-antigen complex formation according to established procedures. For example, one can use surface plasmon resonance (SPR) to determine the rate constants for the formation ($k_{on}$) and dissociation ($k_{off}$) of an antibody-TNFR2 complex. These data also enable calculation of the equilibrium constant of ($K_D$) of antibody-TNFR2 complex dissociation, since the equilibrium constant of this unimolecular dissociation can be expressed as the ratio of the $k_{off}$ to $k_{on}$ values. SPR is a technique that is particularly advantageous for determining kinetic and thermodynamic parameters of receptor-antibody interactions since the experiment does not require that one component be modified by attachment of a chemical label. Rather, the receptor is typically immobilized on a solid metallic surface which is treated in pulses with solutions of increasing concentrations of antibody. Antibody-receptor binding induces distortion in the angle of reflection of incident light at the metallic surface, and this change in refractive index over time as antibody is introduced to the system can be fit to established regression models in order to calculate the association and dissociation rate constants of an antibody-receptor interaction.

Polypeptides (e.g., single-chain polypeptides, antibodies, and antigen-binding fragments) of the invention exhibit high $k_{on}$ and low $k_{off}$ values upon interaction with TNFR2, consistent with high-affinity receptor binding. For example, polypeptides of the invention may exhibit $k_{on}$ values in the presence of TNFR2 of greater than $10^4$ $M^{-1}$ $s^{-1}$ (e.g., $1.0\times10^4$ $M^{-1}s^{-1}$, $1.5\times10^4$ $M^{-1}s^{-1}$, $2.0\times10^4$ $M^{-1}s^{-1}$, $2.5\times10^4$ $M^{-1}$ $s^{-1}$, $3.0\times10^4$ $M^{-1}$ $s^{-1}$, $3.5\times10^4$ $M^{-1}$ $s^{-1}$, $4.0\times10^4$ $M^{-1}s^{-1}$, $4.5\times10^4$ $M^{-1}$ $s^{-1}$, $5.0\times10^4$ $M^{-1}$ $s^{-1}$, $5.5\times10^4$ $M^{-1}$ $s^{-1}$, $6.0\times10^4$ $M^{-1}$ $s^{-1}$, $6.5\times10^4$ $M^{-1}$ $s^{-1}$, $7.0\times10^4$ $M^{-1}s^{-1}$, $7.5\times10^4$ $M^{-1}s^{-1}$, $8.0\times10^4$ $M^{-1}s^{-1}$, $8.5\times10^4$ $M^{-1}s^{-1}$, $9.0\times10^4$ $M^{-1}$ $s^{-1}$, $9.5\times10^4$ $M^{-1}$ $s^{-1}$, $1.0\times10^5$ $M^{-1}s^{-1}$, $1.5\times10^5$ $M$-$s^{-1}$, $2.0\times10^5$ $M^{-1}s^{-1}$, $2.5\times10^5$ $M^{-1}s^{-1}$, $3.0\times10^5$ $M^{-1}s^{-1}$, $3.5\times10^5$ $M^{-1}$ $s^{-1}$, $4.0\times10^5$ $M^{-1}s^{-1}$, $4.5\times10^5$ $M^{-1}s^{-1}$, $5.0\times10^5$ $M^{-1}s^{-1}$, $5.5\times10^5$ $M^{-1}s^{-1}$, $6.0\times10^5$ $M^{-1}$ $s^{-1}$, $6.5\times10^5$ $M^{-1}$ $s^{-1}$, $7.0\times10^5$ $M^{-1}s^{-1}$, $7.5\times10^5$ $M^{-1}s^{-1}$, $8.0\times10^5$ $M^{-1}s^{-1}$, $8.5\times10^5$ $M^{-1}$ $s^{-1}$, $9.0\times10^5$ $M^{-1}s^{-1}$, $9.5\times10^5$ $M$-$s^{-1}$, or $1.0\times10^6$ $M^{-1}s^{-1}$). Polypeptides of the invention exhibit low $k_{off}$ values when bound to TNFR2, since antibodies are capable of interacting with distinct TNFR2 epitopes with a high affinity. Residues within these epitopes form strong intermolecular contacts with TFNR2, which serves to slow the dissociation of the polypeptide-TNFR2 complex. This high receptor affinity is manifested in low $k_{off}$ values. For instance, antibodies of the invention may exhibit $k_{off}$ values of less than $10^{-3}$ $s^{-1}$ when complexed to TNFR2 (e.g., $1.0\times10^{-3}$ $s^{-1}$, $9.5\times10^{-4}$ $S^{-1}$, $9.0\times10^{-4}$ $s^{-1}$, $8.5\times10^{-4}$ $s^{-1}$, $8.0\times10^{-4}$ $s^{-1}$, $7.5\times10^{-4}$ $s^{-1}$, $7.0\times10^{-4}$ $s^{-1}$, $6.5\times10^{-4}s^{-1}$, $6.0\times10^{-4}$ $s^{-1}$, $5.5\times10^{-4}$ $S^{-1}$, $5.0\times10^{-4}$ $s^{-1}$, $4.5\times10^{-4}$ $s^{-1}$, $4.0\times10^{-4}$ $s^{-1}$, $3.5\times10^{-4}$ $S^{-1}$, $3.0\times10^{-4}$ $s^{-1}$, $2.5\times10^{-4}$ $s^{-1}$, $2.0\times10^{-4}$ $S^{-1}$, $1.5\times10^{-4}$ $S^{-1}$, $1.0\times10^{-4}$ $S^{-1}$, $9.5\times10^{-5}$ $s^{-1}$, $9.0\times10^{-5}$ $s^{-1}$, $8.5\times10^{-5}$ $s^{-1}$, $8.0\times10^{-5}$ $s^{-1}$, $7.5\times10^{-5}$ $s^{-1}$, $7.0\times10^{-5}$ $s^{-1}$, $6.5\times10^{-5}$ $s^{-1}$, $6.0\times10^{-5}$ $s^{-1}$, $5.5\times10^{-5}$ $s^{-1}$, $5.0\times10^{-5}$ $s^{-1}$, $4.5\times10^{-5}$ $s^{-1}$, $4.0\times10^{-5}s^{-1}$, $3.5\times10^{-5}$ $s^{-1}$, $3.0\times10^{-5}$ $s^{-1}$, $2.5\times10^{-5}$ $s^{-1}$, $2.0\times10^{-5}$ $s^{-1}$, $1.5\times10^{-5}$ $s^{-1}$, or $1.0\times10^{-5}$ $s^{-1}$).

Epitopes within TNFR2 Bound by Antagonistic TNFR2 Polypeptides

The high affinities of polypeptides (e.g., single-chain polypeptides, antibodies, and antigen-binding fragments) of the invention for TNFR2 coupled with the rapid onset of polypeptide-TNFR2 complex formation and the slow dissociation of these complexes render these polypeptides well-suited for therapeutic applications as suppressors of T-reg cell growth and proliferation. The high $k_{on}$ values, for instance, indicate that polypeptides (e.g., single-chain polypeptides, antibodies, and antigen-binding fragments) of the invention are capable of localizing to the surface of a TNFR2-expressing cell (e.g., a T-reg cell) and rapidly associating with TNFR2, thereby preventing receptor activation that may otherwise be induced by TNFα (e.g., by inhibiting the trimerization of TNFR2 by TNFα). Moreover, the slow dissociation of the polypeptide-TNFR2 complex can be indicative of a long half-life of the complex in vivo, which results in stable, sustained down-regulation of the growth of the TNFR2-expressing cell (e.g., sustained down-regulation of T-reg growth). These ideal thermodynamic and kinetic parameters of TNFR2 binding are consistent with the strong intermolecular contacts that are established upon association of polypeptides of the invention with TNFR2.

Among the difficulties in developing anti-TNFR2 polypeptides (e.g., single-chain polypeptides, antibodies, and antigen-binding fragments) that are capable of antagonizing TNFR2 has been the elucidation of epitopes within TNFR2 that participate in antagonistic complex formation rather than epitopes that promote signal transduction. Various discrete peptide fragments found within the TNFR2 primary structure bind antagonistic antibodies of the invention by virtue of the spatial orientation of these residues in the native conformation of the receptor. Significantly, these residues have been difficult to identify, as many isolated linear TNFR2-derived peptides do not appear to interact with antagonistic TNFR2 polypeptides (e.g., single-chain polypeptides, antibodies, and antibody fragments) due to the different conformations these peptides exhibit when structurally pre-organized within the full-length protein and when isolated in solution. Epitope mapping analysis using constrained cyclic and bicyclic peptides derived from various regions of TNFR2 indicates that antagonistic TNFR2 antibodies of the invention bind epitopes from distinct regions of the TNFR2 amino acid sequence in a conformation-dependent manner. Particularly important epitopes that bind antagonistic TNFR2 polypeptides of the invention and promote receptor antagonism are those that contain one or more residues of the KCRPG motif (SEQ ID NO: 19), located at positions 142-146 of SEQ ID NO: 7 within human TNFR2. One or more of these residues reside within larger epitopes (e.g., residues 142-149 of SEQ ID NO: 7, shown in FIG. 2A, and residues 137-144 of SEQ ID NO: 7, shown in FIG. 2B) that may interact with antagonistic TNFR2 antibodies of the invention. The knowledge of those residues that selectively bind antagonistic TNFR2 polypeptides can be used to identify and design a wide array of antagonistic TNFR2 antibodies and antigen-binding fragments thereof using library screening techniques, e.g., those described herein or known in the art. For instance, structurally rigidified peptides containing one or more the residues within the KCRPG sequence (e.g., peptides having the sequence of SEQ ID NOs: 42, 50, 52-54, and 61-63) can be used to screen and select for polypeptides (e.g., single-chain polypeptides, antibodies, and antibody-like scaffolds) that bind these epitopes with high affinity and selectivity.

Several distinct residues within TNFR2 bind antagonistic TNFR2 polypeptides, such as single-chain polypeptides, antibodies, and antibody fragments, of the invention and establish strong intermolecular contacts with these antibodies. Notably, functional antagonistic TNFR2 polypeptides of the invention selectively bind an epitope containing one or more residues of amino acids 142-146 of SEQ ID NO: 7 within human TNFR2 (KCRPG, SEQ ID NO: 19). The spatial orientation of this epitope is shown in FIG. 4. Antagonistic TNFR2 polypeptides (e.g., single-chain polypeptides, antibodies, and antigen-binding fragments) of the invention are capable of selectively binding an epitope of TNFR2 that contains one or more of these residues and distinctly do not exhibit specific binding to an epitope containing residues 56-60 of SEQ ID NO: 7 within human TNFR2 (KCSPG, SEQ ID NO: 12). For instance, polypeptides (e.g., single-chain polypeptides, antibodies and antibody fragments) of the invention do not exhibit specific binding to epitopes that include one or more, or all, of residues 48-67 of SEQ ID NO: 7 within human TNFR2 (QTAQMCCSKCSPGQHAKVFC, SEQ ID NO: 18), as well as epitopes that exhibit at least 85% sequence identity (e.g., 85%, 90%, 95%, 97%, 99%, or 100% sequence identity) to this sequence and epitopes that contain conservative amino acid substitutions relative to this sequence (so long as the amino acid sequence KCSPG is present in the epitope). Polypeptides that exhibit the ability to bind an epitope containing one or more residues of amino acids 142-146 of SEQ ID NO: 7 within human TNFR2 and an epitope containing residues 56-60 of SEQ ID NO: 7 within human TNFR2 have been shown to lack inhibitory (antagonistic) activity. As such, the ability of a TNFR2 antibody to discriminate among these epitopes and specifically interact with an epitope including one or more of residues 142-146 of SEQ ID NO: 7 within human TNFR2 and to not engage in specific binding with an epitope composed of residues 56-60 of SEQ ID NO: 7 within human TNFR2 characterizes polypeptides (e.g., single-chain polypeptides, antibodies, and antigen-binding fragments) of the invention that antagonize TNFR2 signaling.

One exemplary procedure that can be used to predict the inhibitory activity of a TNFR2 single-chain polypeptide, antibody, or antibody fragment of the invention is to compare the affinity of the polypeptide for a peptide containing the KCRPG motif (e.g., a linear peptide having the sequence KQEGCRLCAPLRKCRPGFGV, SEQ ID NO: 17) to the affinity of the same antibody or antibody fragment for a peptide containing the KCSPG sequence (e.g., a linear peptide having the sequence QTAQMCCSKCSPGQHAKVFC, SEQ ID NO: 18). For instance, antagonistic TNFR2 antibody TNFRAB1 specifically binds the peptide fragment defined by residues 130-149 of SEQ ID NO: 7 within human TNFR2 (KQEGCRLCAPLRKCRPGFGV, SEQ ID NO: 17) with a 40-fold greater affinity than the peptide fragment defined by residues 48-67 of SEQ ID NO: 7 within human TNFR2 (QTAQMCCSKCSPGQHAKVFC, SEQ ID NO: 18). Antagonistic TNFR2 polypeptides (e.g., single-chain polypeptides, antibodies, and antigen-binding fragments) of the invention bind an epitope containing one or more residues of the KCRPG sequence (SEQ ID NO: 19) with an affinity that is at least 10-fold greater than the affinity of the same single-chain polypeptide, antibody, or antigen-binding fragment for a peptide that contains the KCSPG sequence of human TNFR2 (SEQ ID NO: 12). For example, antagonistic TNFR2 polypeptides (e.g., single-chain polypeptides, antibodies, and antigen-binding fragments thereof) of the invention bind an epitope containing one or more residues of the KCRPG sequence (SEQ ID NO: 19) of human TNFR2 with an affinity that is 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more than 1000-fold greater than the affinity of the same single-chain polypeptide, antibody, or antigen-binding fragment for a peptide that contains the KCSPG sequence (SEQ ID NO: 12) of human TNFR2. Polypeptides (e.g., single-chain polypeptides, antibodies, or antigen-binding fragments thereof) that bind epitopes containing one or more residues of the KCRPG sequence (amino acids 142-146 of SEQ ID NO: 7 within human TNFR2) and epitopes containing the KCSPG motif (amino acids 56-60 of SEQ ID NO: 7 within human TNFR2) with similar affinity (e.g., less than a 10-fold difference in affinity) are not considered antagonistic TNFR2 polypeptides of the invention.

In addition to one or more residues of amino acids 142-146 of SEQ ID NO: 7, polypeptides of the invention may also bind one or more residues of a larger epitope that includes at least five continuous or discontinuous residues from positions 130-149 of SEQ ID NO: 7 within human TNFR2 (KQEGCRLCAPLRKCRPGFGV, SEQ ID NO: 17), or an epitope that exhibits at least 85% sequence identity (e.g., 85%, 90%, 95%, 97%, 99%, or 100% sequence identity) to this sequence and epitopes that contain conservative amino acid substitutions relative to this sequence. For example, antagonistic TNFR2 antibodies or antibody fragments of the invention may specifically bind an epitope containing residues 142-149 of SEQ ID NO: 7 within human TNFR2 (KCRPGFGV, SEQ ID NO: 20), or an epitope that exhibits at least 85% sequence identity (e.g., 85%, 90%, 95%, 97%, 99%, or 100% sequence identity) to this sequence (so long as one or more residues of the KCRPG sequence is present in the epitope). Additionally or alternatively, antagonistic TNFR2 antibodies of the invention may specifically bind an epitope including residues 137-144 of SEQ ID NO: 7 within human TNFR2 (CAPLRKCR, SEQ ID NO: 11), or an epitope that exhibits at least 85% sequence identity (e.g., 85%, 90%, 95%, 97%, 99%, or 100% sequence identity) to this sequence (so long as one or more residues of the KCRPG sequence is present in the epitope).

Antagonistic TNFR2 single-chain polypeptides, antibodies, and antibody fragments of the invention may optionally bind a downstream epitope composed of at least five continuous or discontinuous residues from positions 150-190 of SEQ ID NO: 7 within human TNFR2 (ARPGTETSDVVCKPCAPGTFSNTTSSTDI-CRPHQICNVVAI, SEQ ID NO: 22), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. For example, in some embodiments, antagonistic TNFR2 polypeptides of the invention may specifically bind an epitope that includes residues from positions 161-169 of SEQ ID NO: 7 within human TNFR2 (CKPCAPGTF, SEQ ID NO: 21), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

In addition to interacting with the one or more residues of the KCRPG motif (SEQ ID NO: 19), antagonistic TNFR2 polypeptides of the invention may also specifically bind an epitope within human TNFR2 that includes at least five continuous or discontinuous residues from positions 75-128 of SEQ ID NO: 7 within human TNFR2 (CDSCED-STYTQLWNWVPECLSCGSRCSSDQVETQACTREQN-RICTCRPGWYCAL, SEQ ID NO: 13), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. Anti-TNFR2 polypeptides (e.g., single-chain polypeptides, antibodies, and antigen-binding fragments) of the invention may also specifically bind an epitope within human TNFR2 that includes at least five continuous or discontinuous residues from positions 75-91 of SEQ ID NO: 7 within human TNFR2 (CDSCEDSTYTQLWNWVP, SEQ ID NO: 14), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. In some embodiments, anti-TNFR2 polypeptides (e.g., single-chain polypeptides, antibodies, and antigen-binding fragments) of the invention may specifically bind an epitope that includes residues at positions 80-86 of SEQ ID NO: 7 within human TNFR2 (DSTYTQL, SEQ ID NO: 8), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. Antagonistic TNFR2 polypeptides (e.g., single-chain polypeptides, antibodies, and antigen-binding fragments) of the invention also may specifically bind an epitope that includes at least five continuous or discontinuous residues from positions 86-103 of SEQ ID NO: 7 within human TNFR2 (LWNWVPE-CLSCGSRCSSD, SEQ ID NO: 15), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. In some embodiments, polypeptides (e.g., single-chain polypeptides, antibodies, and antigen-binding fragments) of the invention may specifically bind an epitope that includes residues from positions 91-98 of SEQ ID NO: 7 within human TNFR2 (PECLSCGS, SEQ ID NO: 9), as well as an epitope that exhibits at least 85% sequence identity (e.g., 85%, 90%, 95%, 97%, 99%, or 100% sequence identity) to this sequence and epitopes that contain conservative amino acid substitutions relative to this sequence. The polypeptides (e.g., single-chain polypeptides, antibodies, and antigen-binding fragments) of the invention may also specifically bind an epitope that include at least five continuous or discontinuous residues from positions 111-128 of SEQ ID NO: 7 within human TNFR2 (TREQN-RICTCRPGWYCAL, SEQ ID NO: 16), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. In some embodiments, polypeptides (e.g., single-chain polypeptides, antibodies, and antigen-binding fragments) of the invention may specifically bind an epitope that includes residues from positions 116-123 of SEQ ID NO: 7 within human TNFR2 (RICTCRPG, SEQ ID NO: 10), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. For example, antagonistic TNFR2 single-chain polypeptides, antibodies, and antibody fragments of the invention may specifically bind an epitope containing residues 116-123 of SEQ ID NO: 7 within human TNFR2 (RICTCRPG, SEQ ID NO: 10) and residues 137-144 of SEQ ID NO: 7 within human TNFR2 (CAPLRKCR, SEQ ID NO: 11).

Antagonistic TNFR2 polypeptides of the invention may bind an epitope within amino acids 112-131 of SEQ ID NO: 7 (REQNRICTCRPGWYCALSKQ), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. Additionally or alternatively, antagonistic TNFR2 single-chain polypeptides, antibodies, or antigen-binding fragments thereof of the invention may bind an epitope within amino acids 120-139 of SEQ ID NO: 7 (CRPGWYCALSKQEGCRLCAP), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. Antagonistic TNFR2 polypeptides of the invention may bind an epitope within amino acids 128-147 of SEQ ID NO: 7 (LSKQEGCRLCAPLRKCRPGF), as well as epitopes that exhibit at least 85% sequence identity (e.g., 85%, 90%, 95%, 97%, 99%, or 100% sequence identity) to this sequence and epitopes that contain conservative amino acid substitutions relative to this sequence. Antagonistic TNFR2 polypeptides of the invention may optionally bind an epitope within amino acids 136-155 of SEQ ID NO: 7 (LCAPLRKCRPGFGVARPGTE), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

Antagonistic TNFR2 Polypeptides that Bind TNFR2 from Non-Human Animals

In addition to binding epitopes within human TFNR2 that contain the KCRPG motif, antagonistic TNFR2 polypeptides (e.g., single-chain polypeptides, antibodies, and antigen-binding fragments) of the invention also include those that specifically bind epitopes containing the equivalent motif within TNFR2 derived from non-human animals, such as non-human mammals, e.g., in a cow, bison, mouse, or rat, among others. The location of sequences equivalent to the human KCRPG motif in TNFR2 derived from exemplary non-human mammals is shown in Table 2, below:

TABLE 2

Location of sequences equivalent to KCRPG in TNFR2 from non-human mammals

| Source of TNFR2 | Sequence equivalent to KCRPG | Amino acid positions of equivalent sequence within TNFR2 | SEQ ID NO. of full-length TNFR2 sequence | Genbank Accession No. of full-length TNFR2 sequence |
|---|---|---|---|---|
| Human | KCRPG | 142-146 | 7 | P20333.3 |
| Cattle | KCGPG | 142-146 | 280 | AAI05223 |
| Bison | KCGPG | 142-146 | 281 | XP_010848145 |
| Mouse | KCGPG | 144-148 | 282 | AAA39752.1 |
| Rat | KCGPG | 144-148 | 283 | Q80WY6 |

Epitopes within TNFR2 derived from the non-human mammals discussed above that may be bound by antagonistic TNFR2 polypeptides (e.g., single-chain polypeptides, antibodies, and antigen-binding fragments) of the invention are summarized in the sequence alignment below. This sequence alignment shows partial sequences of TNFR2 derived from human, cattle, bison, mouse, and rat, as well as epitopes (highlighted in grey) equivalent to the human KCRPG motif.

```
Alignment of partial TNFR2 sequences derived from human and select non-human mammals
     Human:    1    MAPVAVWAALAVGLELWAAAHALPAQVAFTPYAPEPGSTCRL--REYYDQTAQMCCSKCSPGQHAKVFCTKTSDTVCDSC      78
     Cattle:   1    MAPTAFWAALAVGLQFWAAGRAVPAQAVFTPYIPEPGSSCRQ--QEYYNQKIQMCCSKCPPGYRVQSLCNMTLDTICASC      78
     Bison:    1    MAPTAFWAALAVGLQFWAAGRAVPAQAVFTPYIPEPGSSCRQ--QEYYNHKIQMCCSKCPPGYRVQSLCNTTLDTICASC      78
     Mouse:    1    MAPAALWVALVFELQLWATGHTVPAQVVLTPYKPEPGYECQIS-QEYYDRKAQMCCAKCPPGQYVKHFCNKTSDTVCADC      79
     Rat:      1    MAPAALWVALVVELQLWATGHTVPAKVVLTPYKPEPGNQCQIS-QEYYDKKAQMCCAKCPPGQYAKHFCNKTSDTVCADC      79

Human:   79    EDSTYTQLWNWVPECLSCGSRCSSDQVETQACTREQNRICTCRPGWYCALSKQEG-CRLCAPLRKCRPGFGVARPGTETS     157
     Cattle:  79    ESSTYTQLWNLVTACFSCNSRCSSDQVETQACTTKQNRICTCKPGWYCTLGRQEG-CRLCVALRKCGPGFGVAKPGTATT     157
     Bison:   79    ESSTYTQLWNLVTACFSCNSRCSSDQVETQACTTKQNRICTCKPGWYCTLGRQEG-CRLCVALRKCGPGFGVAKPGTATT     157
     Mouse:   80    EASMYTQVWNQFRTCLSCCSSSCTTDQVEIRACTKQQNRVCACEAGRYCALKTHSGSCRQCMRLSKCGPGFGVASSRAPNG    159
     Rat:     80    AAGMFTQVWNHLHTCLSCSSSCSDDQVETHNCTKKQNRVCACNADSYCALKLHSGNCRQCMKLSKCGPGFGVARSRTSNG    159
```

-continued

| | | | |
|---|---|---|---|
| Human: | 158 | DVVCKPCAPGTFSNTTSSTDICRPHQICNVVAIPGNASMDAVCT------STSPTRSMAPGAVHLPQPVSTRSQHTQPTP | 231 |
| Cattle: | 158 | NVICAPCGPGTFSDTTSYTDTCKPHRNCSSVAIPGTASTDAVCT------SVLPTRKVARG------PATTRSQHMEPTL | 225 |
| Bison: | 158 | NVICAPCGPGTFSDTTSYTDTCKPHRNCSSVAIPGTASTDAVCT------SVLPTRKVARG------PATTRSQHMEPTL | 225 |
| Mouse: | 160 | NVLCKACAPGTFSDTTSSTDVCRPHRICSILAIPGNASTDAVCAPESPTLSAIPR------TLYVSQPEPTRSQPLDQEP | 233 |
| Rat: | 160 | NVICSACAPGTFSDTTSSTDVCRPHRICSILAIPGNASTDAVCASESPTPSAVPR------TIYVSQPEPTRSQPMDQEP | 233 |
| Human: | 232 | EPSTAPSTSFLLPMGPSPPA----EGSTGDFALPVGLIVGVTALGLLIIGVVNCVIMTQVKKKPLCLQREAKVPHLPADK | 307 |
| Cattle: | 226 | GPSTAPSTFFLLPKVPSPPSSPVEQPNTGNISLPIELIVGVTALGLLLIVVVNCVIMTQKKKKPFCLQGDAKVPHLPANK | 305 |
| Bison: | 226 | GPSTAPSTFFLLPKVPSPPSSPVEQPNAGNISLPIELIVGVTALGLLLIVVVNCVIMTQKKKKPFCLQGDAKVPHLPANK | 305 |
| Mouse: | 234 | GPSQTPS---ILTSLGSTPI--IEQSTKGGISLPIGLIVGVTSLGLLMLGLVNCIILVQRKKKPSCLQRDAKVPHVPDEK | 308 |
| Rat: | 234 | GPSQTPH---IPVSLGSTPI--IEPSITGGISLPIGLIVGLTTLGLLMLGLANCFILVQRKKKPSCLQRETMVPHLPDDK | 308 |
| Human: | 308 | ARGTQGPEQQHLLITAPSSSSSSLESSASALDRRAPTRNQPQAPGVE-ASGAGEARASTGSSDSSPGGHGTQVNVTCIVN | 386 |
| Cattle: | 306 | AQGAPGPEQQHLLTTAPSSSSSSLESSTSSTDKRAPTRSQLQSPGVEKASTSGEAQTGCSSSEASSGGHGTQVNVTCIVN | 385 |
| Bison: | 306 | AQGAPGPEQQHLLTTAPSSSSSSLESSTSSTDKRAPTRSQLQSPGVE-ANTSGEAQTGCSSSEASSGGHGTQVNVTCIVN | 384 |
| Mouse: | 309 | SQDAVGLEQQHLLTTAPSSSSSSLESSASAGDRRAPPGGHPQARVMAEAQGFQEARASSRISDSSHGSHGTHVNVTCIVN | 388 |
| Rat: | 309 | SQDAIGLEQQHLLTTAPSSSSSSLESSASAGDRRAPPGGHPQARVTAEAQGSQEACAGSRSSDSSHGSHGTHVNVTCIVN | 388 |

The Antagonistic TNFR2 Antibody TNFRAB 1

A representative antagonistic TNFR2 polypeptide (e.g., single-chain polypeptide, antibody, or antigen-binding fragment thereof) of the invention can be based on TNFRAB1, also referred to herein as TNFR2 antagonist 1, which is a murine antibody that antagonizes the TNFRα-TNFR2 interaction and is capable of suppressing TNFα-mediated T-reg cell proliferation (see, e.g., FIG. 5). The variable regions of TNFRAB1 (e.g., the heavy and light chain CDRs), and variants thereof that exhibit substantially similar specific binding properties to TNFRAB1, can be used to make an antagonistic TNFR2 antibody or antigen-binding fragment thereof of the invention, e.g., by replacing the mouse constant region of TNFRAB1 with a non-native constant region (e.g., a constant region from a human antibody) using methods known in the art or described herein.

Polypeptides (e.g., single-chain polypeptides, antibodies, and antigen-binding fragments) of the invention may exhibit binding properties that are the same as or similar to those of TNFRAB1. These properties are as follows: In the presence of TNFR2, TNFRAB1 exhibits a high $k_{on}$ value of $4.98\times10^{6}$ $M^{-1}$ $s^{-1}$, as well as a low $k_{off}$ of $2.21\times10^{-4}$ $s^{-1}$ and a $K_D$ of about 44.4 pM in complex with TNFR2. The high affinity of TNFRAB1 for TNFR2 coupled with the rapid formation and the slow dissociation of the TNFRAB1-TNFR2 complex is consistent with the strong intermolecular contacts that underlie this protein-protein interaction. TNFRAB1 binds to distinct epitopes within the primary structure of TNFR2 that are spatially aligned in the native conformation of the receptor. The KCRPGFGV motif (SEQ ID NO: 20), and specifically, the KCRPG sequence (SEQ ID NO: 19), has been identified as a particularly important component of the functional epitope that establishes strong intermolecular contacts with TNFRAB1 as determined by epitope mapping analysis (FIGS. 2 and 3). The interaction of these residues with anti-TNFR2 polypeptides of the invention selectively promotes antagonistic activity. Significantly, a TNFR2 epitope including amino acid residues 56-60 of SEQ ID NO: 7 within human TNFR2 (KCSPG, SEQ ID NO: 12) is distinctly not a part of the conformational epitope that is specifically bound by TNFRAB1 or antagonistic TNFR2 polypeptides of the invention, as specific binding to both of these epitopes has been shown to lead to a loss of, or significant reduction in, antagonistic activity. As such, TNFR2 polypeptides (e.g., single-chain polypeptides, antibodies, and antigen-binding fragments) that specifically bind both of these epitopes (KCSPG and an epitope containing at least the KCR sequence, and more specifically, the KCRPG sequence of human TNFR2) are not considered antagonistic TNFR2 polypeptides of the invention.

In addition to binding an epitope contained within the sequence KCRPGFGV (SEQ ID NO: 20), TNFRAB1 also binds to a downstream epitope contained within a sequence defined by positions 161-169 of SEQ ID NO: 7 within human TNFR2 (CKPCAPGTF, SEQ ID NO: 21). Anti-TNFR2 single-chain polypeptides, antibodies, and antibody fragments of the invention may also bind this epitope or a larger region within TNFR2 containing this epitope (e.g., a sequence that includes at least five continuous or discontinuous residues from positions 150-190 of SEQ ID NO: 7 within human TNFR2 (ARPGTETSDVVCKPCAPGTFSNTTSSTDICRPHQICNVVAI, SEQ ID NO: 22).

TNFRAB1 contains two heavy chains, as well as two light chains, as shown in FIGS. 1A and 1B. The heavy chains of TNFRAB1 contain the following amino acid sequence (CDRs are indicated in bold):

(SEQ ID NO: 2)
EVQLQESGGGLVKPGGSLKLSCAASGFTFSSYVMSWVRQTPEKRLEWVAT
ISSGGSYTYYPDSVKGRFTISRDNAKNTLYLQMSSLRSEDTAMYYCARQR
VDGYSSYWYFDVWGAGTAVTVSS

The sequence of the TNFRAB1 light chain is as follows (CDRs are indicated in bold):

(SEQ ID NO: 4)
DIVLTQSPAIMSASPGEKVTITCSASSSVYYMYWFQQKPGTSPKLWIYST
SNLASGVPVRFSGSGSGTSYSLTISRMEAEDAATYYCQQRRNYPYTFGGG
TKLEIKRA

The Antagonistic TNFR2 Antibody TNFRAB2

A representative antagonistic TNFR2 polypeptide (e.g., single-chain polypeptide, antibody, or antigen-binding fragment thereof) of the invention can be based on TNFRAB2, also referred to herein as TNFR2 antagonist 2, an antibody that selectively binds and inhibits TNFR2 by virtue of specifically binding various epitopes within this receptor. For instance, antagonistic TNFR2 single-chain polypeptides, antibodies, or antigen-binding fragments thereof of the invention may exhibit binding properties that are the same as or similar to those of TNFRAB2. These properties are as follows: In the presence of TNFR2, TNFRAB2 exhibits a high $k_{on}$ value of $3.6099\times10^{5}$ $M^{-1}s^{-1}$, as well as a low $k_{off}$ of $2.24\times10^{-4}$ $s^{-1}$ and a $K_D$ of about 621 pM in complex with TNFR2. An epitope containing residues 137-144 of SEQ ID NO: 7 within human TNFR2 (CAPLRKCR, SEQ ID NO: 11) has been identified as a particularly important component of the functional epitope that establishes strong intermolecular contacts with TNFRAB2 as determined by epitope mapping analysis (see, e.g., Example 1 and FIGS. 2B and 3B). Included in the invention are TNFR2 antibodies and antibody fragments that specifically bind this epitope.

In addition to binding an epitope containing residues CAPLRKCR (SEQ ID NO: 11), TNFRAB2 also binds to epitopes that include one or more residues within positions 80-86 of SEQ ID NO: 7 within human TNFR2 (DSTYTQL, SEQ ID NO: 8), positions 91-98 of SEQ ID NO: 7 within human TNFR2 (PECLSCGS, SEQ ID NO: 9), as well as positions 116-123 of SEQ ID NO: 7 within human TNFR2 (RICTCRPG, SEQ ID NO: 10). TNFR2 single-chain polypeptides, antibodies, and antibody fragments of the invention may also bind one or more of these epitopes. Polypeptides of the invention can be designed and identified using the knowledge of the epitopes specifically bound by TNFRAB2. For instance, one can use any of a variety of in vitro peptide display techniques or combinatorial antibody library screens as described herein or known in the art in order to screen for polypeptides (e.g., single-chain polypeptides, antibodies, and antigen-binding fragments thereof) capable of binding these epitopes with high affinity and selectivity.

In addition, TNFR2 polypeptides of the invention include those that contain one or more of the heavy and light chain CDRs or heavy and light chain variable regions of TNFRAB2 and a constant region that is non-native to that of TNFRAB2 (e.g., a constant region from a human antibody). The heavy chain and light chain CDRs of TNFRAB2 are shown below:

```
TNFRAB2 CDR-H1:
                         (SEQ ID NO: 257)
GYTFTDY(L/I)

TNFRAB2 CDR-H2:
                         (SEQ ID NO: 258)
VDPEYGST

TNFRAB2 CDR-H3:
                         (SEQ ID NO: 259)
ARDDGSYSPFDYWG

TNFRAB2 CDR-L1:
                         (SEQ ID NO: 260)
QNINKY

TNFRAB2 CDR-L2:
TYS
or

YTS

TNFRAB2 CDR-L3:
                         (SEQ ID NO: 261)
CLQYVNL(L/I)T
```

As shown above, the CDR-H1 sequence of TNFRAB2 may contain either a leucine or isoleucine residue at the eighth position of this region. Similarly, the TNFRAB2 CDR-L2 may include a TYS or YTS tripeptide, and the TNFRAB2 CDR-L3 may contain either a leucine or isoleucine residue at the eighth position of this region. Notably, the CDR-L2 of TNFRAB2 is flanked by the N-terminal framework residues LLIR (SEQ ID NO: 262) and the C-terminal framework residues TLE. Accordingly, antagonistic TNFR2 antibodies or antigen-binding fragments thereof of the invention include those that contain one or more of the above CDRs of TNFRAB2, as well as N-terminal LLIR (SEQ ID NO: 262) and C-terminal TLE residues that flank the CDR-L2 sequence of the antagonistic TNFR2 antibody or antigen-binding fragment thereof.

Molecular Determinants of TNFR2 Affinity and Antagonism

Notably, there are distinct sequence similarities between the CDRs of the antagonistic TNFR2 antibodies TNFRAB1 and TNFRAB2. An analysis of the residues common to the CDRs of both antibodies provides insight into the molecular features of antibodies that bind TNFR2 and exhibit an antagonistic effect. Epitope mapping analysis has shown that both TNFRAB1 and TNFRAB2 bind to TNFR2 in an anti-parallel dimer configuration. These antibodies bind an epitope within TNFR2 that contains residues 142-146 of SEQ ID NO: 7 and do not bind epitopes containing residues 56-60 of SEQ ID NO: 7. The structural similarities between corresponding CDR-H and CDR-L regions provide a basis for predicting residue substitutions that may preserve or enhance TNFR2 affinity and antagonism. Inspection of the heavy chain and light chain CDR sequences of these antibodies demonstrates that several residues and physicochemical characteristics are conserved within corresponding CDR sequences, while other positions within these CDRs can be varied significantly without loss of affinity and antagonistic function. For instance, the CDR-H1 sequences of TNFRAB1 and TNFRAB2 are shown below:

```
GFTFSSY         (TNFRAB1 CDR-H1, SEQ ID NO: 23)

GYTFTDY(L/I)    (TNFRAB2 CDR-H1, SEQ ID NO: 257)

G-TF--Y-        (Consensus sequence)
```

Alignment of the sequences reveals a shared GXTFXXY motif, wherein "X" designates any amino acid. These CDR-H1 sequences feature a conserved glycine residue at the first position and conserved threonine, phenylalanine, and tyrosine residues at the third, fourth, and seventh positions, respectively. Inspection of these sequences demonstrates that the CDR-H1 region is tolerant of substitutions at the remaining positions. Side-chains of varying polarity are tolerated at the second position, for example, as both phenylalanine, containing an unsubstituted and hydrophobic phenyl moiety, and tyrosine, containing a protic hydroxyl substituent, are found in this position in the CDR-H1 region of TNFRAB1 and TNFRAB2, respectively. Additionally, while the fifth and sixth positions are occupied by polar serine residues in the CDR-H1 of TNFRAB1, these positions feature a threonine, containing an additional hydrophobic methyl substituent, and aspartic acid, which is anionic at physiological pH, in TNFRAB2. This diversity demonstrates that these positions can be substituted with amino acids of diverse electrostatic properties without loss of TNFR2 affinity and antagonism.

Sequence analysis of the CDR-H2 regions of TNFRAB1 and TNFRAB2 similarly reveals a set of conserved amino acids at various positions throughout these regions:

| | |
|---|---|
| SSG--GSY | (TNFRAB1 CDR-H2, SEQ ID NO: 24) |
| VDPEYGST | (TNFRAB2 CDR-H2, SEQ ID NO: 258) |
| -----GS- | (Consensus sequence) |

Analysis of this sequence alignment demonstrates that the CDR-H2 sequences exhibit a conserved GS motif at the C-terminal end of the CDR-H2 region, with side-chains of variable molecular size, polarity, and electrostatic charge tolerated at the remaining positions. Additionally, alignment of the corresponding CDR-H3 sequences of TNFRAB1 and TNFRAB2 is shown below:

| | |
|---|---|
| QRVDGYSSYWYFDV | (TNFRAB1 CDR-H3, SEQ ID NO: 25) |
| ARDDG-S-YSPFDYWG | (TNFRAB2 CDR-H3, SEQ ID NO: 259) |
| -R-DG-S-Y--FD--- | (Consensus sequence) |

A similar analysis of the CDR-H3 sequences of TNFRAB1 and TNFRAB2 reveals conserved arginine, aspartic acid, glycine, serine, tyrosine, and phenylalanine residues throughout this CDR. Notably, residues of varying steric and electrostatic properties are tolerated in the remaining positions. For instance, the first position of the CDR-H3 sequence tolerates amino acid residues of contrasting size and hydrogen bond-forming tendencies, as the first position of CDR-H3 in TNFRAB1 features a polar glutamine residue containing a carboxamide side-chain with hydrogen bond donor and acceptor moieties, while an alanine residue bearing an unfunctionalized methyl side-chain is found at the corresponding position in TNFRAB2. Additionally, the third position in the above CDR-H3 sequences features a hydrophobic valine in TNFRAB1 and an anionic aspartic acid moiety in the corresponding position of TNFRAB2.

A similar analysis reveals molecular features common to the CDR-L sequences of TNFRAB1 and TNFRAB2. For instance, the CDR-L1 sequences of TNFRAB1 and TNFRAB2 are shown below:

| | |
|---|---|
| SASSSVYYMY | (TNFRAB1 CDR-L1, SEQ ID NO: 26) |
| Q-N--INK-Y | (TNFRAB2 CDR-L1, SEQ ID NO: 260) |
| Y | (Consensus residue) |

Inspection of these sequences reveals that a hydroxyl-containing tyrosine residue is featured at the final position of CDR-L1, while residues of varying physicochemical properties are tolerated at the remaining positions. Similarly, analysis of the CDR-L2 regions of TNFRAB1 and TNFRAB2 reveals a conserved amino acid at the final position in both regions:

| | |
|---|---|
| STSNLAS | (TNFRAB1 CDR-L2, SEQ ID NO: 27) |
| TY----S or<br>YT----S | (TNFRAB2 CDR-L2) |
| S | (Consensus residue) |

Analysis of the above sequence alignment demonstrates that serine residues are featured at the third position of these CDR-L2 sequences, while substitutions are widely tolerated at the remaining residues. Similarly, the CDR-L3 sequences of TNRAB1 and TNFRAB2 are as follows:

| | |
|---|---|
| Q-QRRNYPY------T | (TNFRAB1 CDR-L3, SEQ ID NO: 28) |
| CLQ---YVNL(L/I)T | (TNFRAB2 CDR-L3, SEQ ID NO: 261) |
| ------Y--------T | (Consensus sequence) |

Analysis of the CDR-L3 sequences of TNFRAB1 and TNFRAB2 reveals a preference for tyrosine and threonine residues at distinct positions within these regions, while amino acids of a wide range of physicochemical characteristics are tolerated at other positions, including residues with cationic side-chains (Arg), conformationally restricted side-chains (Pro), and side-chains of varying polarity (e.g., Gln, Asn, Leu, and Val). Collectively, the shared structural features of the above CDR-H and CDR-L sequences provide insight into those residues that are important for selectively binding one or more residues of the KCRPG epitope of TNFR2 (positions 142-146 of SEQ ID NO: 7, shown in SEQ ID NO: 19) in an anti-parallel dimer configuration and demonstrate that certain amino acids can be varied while retaining affinity and antagonistic activity.

Antagonistic TNFR2 polypeptides of the invention (e.g., single-chain polypeptides, antibodies, or antigen-binding fragments thereof) may therefore have heavy chain and light chain CDRs that contain the above consensus sequences. For instance, TNFR2 antagonists of the invention may have a CDR-H1 having the amino acid sequence $Z^4JZ^3Z^5(J)_2Z^5$ or $Z^4JZ^3Z^5(J)_2Z^5J$; a CDR-H2 having the amino acid sequence $(J)_3Z^4Z^3J$ or $(J)_5Z^4Z^3J$; a CDR-H3 having the amino acid sequence $JZ^1JZ^2Z^4JZ^3JZ^5(J)_2Z^5Z^2Z^5$ or $JZ^1JZ^2Z^4Z^3Z^5(J)_2Z^5Z^2Z^5(J)_2$; a CDR-L1 having the amino acid sequence $(J)_9Z^5$ or $(J)_5Z^5$; a CDR-L2 having the amino acid sequence $(J)_6Z^3$ or $(J)_2Z^3$; and a CDR-L3 having the amino acid sequence $(J)_5Z^5(J)_2Z^3$ or $(J)_3Z^5(J)_4Z^3$; wherein each J is independently a naturally occurring amino acid; each $Z^1$ is independently a naturally occurring amino acid containing a cationic side-chain at physiological pH; each $Z^2$ is independently a naturally occurring amino acid containing an anionic side-chain at physiological pH; each $Z^3$ is independently a naturally occurring amino acid containing a polar, uncharged side-chain at physiological pH; each $Z^4$ is independently a glycine or alanine; and each $Z^5$ is independently a naturally occurring amino acid containing a hydrophobic side-chain.

In some embodiments, antagonistic TNFR2 polypeptides of the invention (e.g., single-chain polypeptides, antibodies, or antigen-binding fragments thereof) may have a CDR-H1 having the amino acid sequence $GJTF(J)_2Y$ (SEQ ID NO: 276) or $GJTF(J)_2YJ$ (SEQ ID NO: 277); a CDR-H2 having the amino acid sequence $(J)_3GSJ$ or $(J)_5GSJ$; a CDR-H3 having the amino acid sequence $JRJDGJSJY(J)_2FDJ$ (SEQ ID NO: 278) or $JRJDGSY(J)_2FD(J)_3$ (SEQ ID NO: 279); a CDR-L1 having the amino acid sequence $(J)_9Y$ or $(J)_5Y$; a CDR-L2 having the amino acid sequence $(J)_6S$ or $(J)_2S$; and a CDR-L3 having the amino acid sequence $(J)_5Y(J)_2T$ or $(J)_3Y(J)_4T$; wherein each J is independently a naturally occurring amino acid.

Antagonistic TNFR2 polypeptides of the invention (e.g., single-chain polypeptides, antibodies, or antigen-binding fragments thereof) may have a CDR-H1 having the amino acid sequence $Z^4FZ^3Z^5SSZ^5$ or $Z^4YZ^3Z^5TDZ^5X$; a CDR-H2 having the amino acid sequence $SSGZ^4Z^3Y$ (SEQ ID NO: 263) or $VDPEYZ^4Z^3T$ (SEQ ID NO: 264); a CDR-H3 having the amino acid sequence $QZ^1VZ^2Z^4YZ^3SZ^5WYZ^5Z^2Z^5$ (SEQ ID NO: 265) or $AZ^1DZ^2Z^4Z^3Z^5SPZ^5Z^2Z^5WG$ (SEQ ID NO: 266); a CDR-L1 having the amino acid sequence $SASSSVYYMZ^5$ (SEQ ID NO: 267) or $QNINKZ^5$ (SEQ ID NO: 268); a CDR-L2 having the amino acid sequence $STSNLAZ^3$ (SEQ ID NO: 269), $TYZ^3$, or $YTZ^3$; and a CDR-L3 having the amino acid sequence $QQRRNZ^5PYZ^3$ (SEQ ID NO: 270) or $CLQZ^5VNLXZ^3$ (SEQ ID NO: 271); wherein each $Z^1$ is independently an amino acid containing a cationic side-chain at physiological pH; each $Z^2$ is independently an amino acid containing an anionic side-chain at physiological pH; each $Z^3$ is independently an amino acid containing a polar, uncharged side-chain at physiological pH; each $Z^4$ is independently a glycine or alanine; each $Z^5$ is independently an amino acid containing a hydrophobic side-chain; and each X is independently leucine or isoleucine.

In some embodiments, antagonistic TNFR2 polypeptides of the invention (e.g., single-chain polypeptides, antibodies, or antigen-binding fragments thereof) may have a CDR-H1 having the amino acid sequence GFTFSSY (SEQ ID NO: 23), GYTFTDYX (SEQ ID NO: 257), or an amino acid sequence having up to two amino acid substitutions relative to these sequences; a CDR-H2 having the amino acid sequence SSGGSY (SEQ ID NO: 24), VDPEYGST (SEQ ID NO: 258), or an amino acid sequence having up to two amino acid substitutions relative to these sequences; a CDR-H3 having the amino acid sequence QRVDGYSSYWYFDV (SEQ ID NO: 25), ARDDGSYS-PFDYWG (SEQ ID NO: 259), or an amino acid sequence having up to two amino acid substitutions relative to these sequences; a CDR-L1 having the amino acid sequence SASSSVYYMY (SEQ ID NO: 26), QNINKY (SEQ ID NO: 260), or an amino acid sequence having up to two amino acid substitutions relative to these sequences; a CDR-L2 having the amino acid sequence STSNLAS (SEQ ID NO: 27), TYS, YTS, or an amino acid sequence having up to two amino acid substitutions relative to SEQ ID NO: 27; and a CDR-L3 having the amino acid sequence QQRRNYPYT (SEQ ID NO: 28), CLQYVNLXT (SEQ ID NO: 261), or an amino acid sequence having up to two amino acid substitutions relative to these sequences.

Humanized, Primatized, and Chimeric Antibodies Derived from TNFRAB1 and/or TNFRAB2

Antibodies of the invention include human, humanized, primatized, and chimeric antibodies that contain one or more of the CDRs of TNFRAB1, or a CDR that exhibits at least 85% sequence identity (e.g., 90%, 95%, 97%, 99%, or 100% sequence identity) to any of these CDRs or sequences that contain conservative mutations relative to these CDRs. Antibodies of the invention also include human, humanized, primatized, and chimeric antibodies that contain one or more of the CDRs of TNFRAB2, or a CDR that exhibits at least 85% sequence identity (e.g., 90%, 95%, 97%, 99%, or 100% sequence identity) to any of these CDRs or sequences that contain conservative mutations relative to these CDRs. For instance, antibodies of the invention also include human, humanized, primatized, and chimeric antibodies that contain one or more CDRs that are identical to the above CDRs except for conservative amino acid substitutions. In some embodiments, a humanized, primatized, or chimeric antibody may contain one or more of the CDRs of TNFRAB1, or a CDR that exhibits at least 85% sequence identity (e.g., 90%, 95%, 97%, 99%, or 100% sequence identity) to any of the CDRs of TNFRAB1 or sequences that contain conservative mutations relative to these CDRs, and one or more CDRs of TNFRAB2, or a CDR that exhibits at least 85% sequence identity (e.g., 90%, 95%, 97%, 99%, or 100% sequence identity) to any of the CDRs of TNFRAB2 or sequences that contain conservative mutations relative to these CDRs. For example, antagonistic TNFR2 antibodies of the invention can be generated by incorporating any of the above CDRs into the framework regions (e.g., FW1, FW2, FW3, and FW4) of a human antibody. Exemplary framework regions that can be used for the development of a humanized anti-TNFR2 antibody containing one or more of the above CDRs include, without limitation, those described in U.S. Pat. Nos. 7,732,578, 8,093,068, and WO 2003/105782; incorporated herein by reference.

One strategy that can be used to design humanized antibodies of the invention is to align the sequences of the heavy chain variable region and light chain variable region of an antagonistic TNFR2 antibody, such as TNFRAB1 or TNFRAB2, with the heavy chain variable region and light chain variable region of a consensus human antibody. Consensus human antibody heavy chain and light chain sequences are known in the art (see e.g., the "VBASE" human germline sequence database; see also Kabat, et al., Sequences of Proteins of Immunological Interest, Fifth Edition, U.S. Department of Health and Human Services, NIH Publication No. 91-3242, 1991; Tomlinson et al., J. Mol. Biol. 227:776-98, 1992; and Cox et al, Eur. J. Immunol. 24:827-836, 1994; incorporated herein by reference). In this way, the variable domain framework residues and CDRs can be identified by sequence alignment (see Kabat, supra). One can substitute one or more CDRs of the heavy chain and/or light chain variable domains of consensus human antibody with one or more corresponding CDRs of an antagonistic TNFR2 antibody, such as TNFRAB1 or TNFRAB2, in order to produce a humanized TNFR2 antibody. Exemplary variable domains of a consensus human antibody include the heavy chain variable domain: EVQLVESGGGLVQPGGSLRLSCAASGFTFSDYAM-SWVRQAPGKGLEWVAVISENGSDTYYADSVKGR FTISRDDSKNTLYLQMNSLRAEDTAVYYCARDRG-GAVSYFDVWGQGTLVTVSS (SEQ ID NO: 32) and the light chain variable domain: DIQMTQSPSSL-SASVGDRVTITCRASQDVSSY-LAWYQQKPGKAPKLLIYAASSLESGVPSRFSGSGSGT DFTLTISSLQPEDFATYYCQQYNSLPY-TFGQGTKVEIKRT (SEQ ID NO: 33) identified in U.S. Pat. No. 6,054,297; incorporated herein by reference (CDRs are shown in bold were determined according to the method of Chothia, et al., J. Mol. Biol, 196:901-917, 1987). These amino acid substitutions can be made, for example, by recombinant expression of polynucleotides encoding the heavy and light chains of a humanized antibody in a host cell using methods known in the art or described herein.

Similarly, this strategy can also be used to produce primatized anti-TNFR2 antibodies, as one can substitute the CDRs of the heavy and/or light chain variable domains of a primate antibody consensus sequence with one or more corresponding CDRs of TNFRAB1 and/or TNFRAB2. Consensus primate antibody sequences known in the art (see e.g., U.S. Pat. Nos. 5,658,570; 5,681,722; and 5,693,780; incorporated herein by reference).

In some embodiments, it may be desirable to import particular framework residues in addition to CDR sequences from a TNFR2 antibody, such as TNFRAB1 or TNFRAB2, into the heavy and/or light chain variable domains of a human antibody. For instance, U.S. Pat. No. 6,054,297 identifies several instances when it may be advantageous to retain certain framework residues from a particular antibody heavy chain or light chain variable region in the resulting humanized antibody. In some embodiments, framework residues may engage in non-covalent interactions with the antigen and thus contribute to the affinity of the antibody for the target antigen. In other cases, individual framework residues may modulate the conformation of a CDR, and thus indirectly influence the interaction of the antibody with the antigen. Alternatively, certain framework residues may form the interface between VH and VL domains, and may therefore contribute to the global antibody structure. In other cases, framework residues may constitute functional glycosylation sites (e.g., Asn-X-Ser/Thr) which may dictate antibody structure and antigen affinity upon attachment to carbohydrate moieties. In cases such as those described above, it may be beneficial to retain certain framework residues of a TNFR2 antibody (e.g., TNFRAB1 or TNFRAB2) in the antagonistic antibodies and antigen-binding fragments thereof of the invention, such as humanized antibodies, as various framework residues may promote high epitope affinity and improved biochemical activity of the antibody or antigen-binding fragment thereof.

Antibodies of the invention also include antibody fragments, Fab domains, F(ab') molecules, F(ab')$_2$ molecules, single-chain variable fragments (scFvs), tandem scFv fragments, diabodies, triabodies, dual variable domain immunoglobulins, multi-specific antibodies, bispecific antibodies, and heterospecific antibodies that contain one or more of the CDRs of TNFRAB1 or TNFRAB2 (e.g., a CDR containing the amino acid sequence of any one of SEQ ID NOs: 23-28) or a CDR that exhibits at least 85% sequence identity (e.g., 90%, 95%, 97%, 99%, or 100% sequence identity) to any of these CDRs. Antibodies and antigen-binding fragments thereof of the invention include those that also contain CDRs having between one and three amino acid substitutions (e.g., conservative or nonconservative substitutions) relative to the CDR sequences of TNFRAB1 or TNFRAB2. These molecules can be expressed recombinantly, e.g., by incorporating polynucleotides encoding these proteins into expression vectors for transfection in a eukaryotic or prokaryotic cell using techniques described herein or known in the art, or synthesized chemically, e.g., by solid-phase peptide synthesis methods described herein or known in the art.

Antibodies of the invention additionally include antibody-like scaffolds that contain one or more of the CDRs of TNFRAB1 or TNFRAB2, or a CDR that exhibits at least 85% sequence identity (e.g., 90%, 95%, 97%, 99%, or 100% sequence identity) to any of these CDRs or sequences that contain between one and three amino acid substitutions (e.g., conservative or nonconservative substitutions) relative to the CDR sequences of TNFRAB1 or TFNRAB2. Examples of antibody-like scaffolds include proteins that contain a tenth fibronectin type III domain ($^{10}$Fn3), which contains BC, DE, and FG structural loops analogous to canonical antibodies. It has been shown that the tertiary structure of the $^{10}$Fn3 domain resembles that of the variable region of the IgG heavy chain, and one of skill in the art can graft, e.g., one or more CDRs of TNFRAB1 and/or TNFRAB2, or sequences having at least 85% sequence identity (e.g., 90%, 95%, 97%, 99%, or 100% sequence identity) to any of these CDRs or sequences containing conserved amino acid substitutions relative to these CDRs onto the fibronectin scaffold by replacing residues of the BC, DE, and FG loops of $^{10}$Fn3 with residues of TNFRAB1 and/or TNFRAB2 CDRs. This can be achieved by recombinant expression of a modified $^{10}$Fn3 domain in a prokaryotic or eukaryotic cell (e.g., using the vectors and techniques described herein). Examples of using the $^{10}$Fn3 domain as an antibody-like scaffold for the grafting of CDRs from antibodies onto the BC, DE, and FG structural loops are reported in WO 2000/034784, WO 2009/142773, WO 2012/088006, and U.S. Pat. No. 8,278,419; incorporated herein by reference.

Antagonistic TNFR2 Single-Chain Polypeptides

TNFR2 antagonists of the invention may be in the form of a single-chain polypeptide, such as a single-chain polypeptide that contains one, two, or three heavy chain CDRs of a monoclonal TNFR2 antagonist antibody described herein (e.g., TNFRAB1 or TNFRAB2), and/or one, two, or three light chain CDRs of a monoclonal TNFR2 antagonist antibody described herein (e.g., TNFRAB1 or TNFRAB2). Single-chain polypeptides may be in the form of an antibody fragment, e.g., an antibody fragment described herein or known in the art, such as a scFv fragment. Single chain polypeptides may alternatively contain one or more CDRs described herein covalently bound to one another using conventional bond-forming techniques known in the art, for instance, by an amide bond, a thioether bond, a carbon-carbon bond, or by a linker, such as a peptide linker or a multi-valent electrophile (e.g., a bis(bromomethyl) arene derivative, such as a bis(bromomethyl)benzene or bis(bromomethyl)pyridine) described herein or known in the art.

For instance, antagonistic TNFR2 single-chain polypeptides of the invention may have one or more heavy chain and light chain CDRs that contain the above-described consensus sequences that promote selective binding to TNFR2 epitopes, such as the KCRPG motif (SEQ ID NO: 19), and induce TNFR2 antagonism. For instance, antagonistic TNFR2 single-chain polypeptides of the invention may have a CDR-H1 having the amino acid sequence $Z^4JZ^3Z^5(J)_2Z^5$ or $Z^4JZ^3Z^5(J)_2Z^5J$; a CDR-H2 having the amino acid sequence $(J)_3Z^4Z^3J$ or $(J)_5Z^4Z^3J$; a CDR-H3 having the amino acid sequence $JZ^1JZ^2Z^4JZ^3JZ^5(J)_2Z^5Z^2Z^5$ or $JZ^1JZ^2Z^4Z^3Z^5(J)_2Z^5Z^2Z^5(J)_2$; a CDR-L1 having the amino acid sequence $(J)_9Z^5$ or $(J)_5Z^5$; a CDR-L2 having the amino acid sequence $(J)_6Z^3$ or $(J)_2Z^3$; and/or a CDR-L3 having the amino acid sequence $(J)_5Z^5(J)_2Z^3$ or $(J)_3Z^5(J)_4Z^3$; wherein each J is independently a naturally occurring amino acid; each $Z^1$ is independently a naturally occurring amino acid containing a cationic side-chain at physiological pH; each $Z^2$ is independently a naturally occurring amino acid containing an anionic side-chain at physiological pH; each $Z^3$ is independently a naturally occurring amino acid containing a polar, uncharged side-chain at physiological pH; each $Z^4$ is independently a glycine or alanine; and each $Z^5$ is independently a naturally occurring amino acid containing a hydrophobic side-chain.

In some embodiments, antagonistic TNFR2 single-chain polypeptides of the invention may have a CDR-H1 having the amino acid sequence $GJTF(J)_2Y$ (SEQ ID NO: 276) or $GJTF(J)_2YJ$ (SEQ ID NO: 277); a CDR-H2 having the amino acid sequence $(J)_3GSJ$ or $(J)_5GSJ$; a CDR-H3 having the amino acid sequence $JRJDGJSJY(J)_2FDJ$ (SEQ ID NO: 278) or $JRJDGSY(J)_2FD(J)_3$ (SEQ ID NO: 279); a CDR-L1 having the amino acid sequence $(J)_9Y$ or $(J)_5Y$; a CDR-L2 having the amino acid sequence $(J)_6S$ or $(J)_2S$; and/or a CDR-L3 having the amino acid sequence $(J)_5Y(J)_2T$ or $(J)_3Y(J)_4T$; wherein each J is independently a naturally occurring amino acid.

Antagonistic TNFR2 single-chain polypeptides of the invention may have a CDR-H1 having the amino acid sequence $Z^4FZ^3Z^5SSZ^5$ or $Z^4YZ^3Z^5TDZ^5X$; a CDR-H2 having the amino acid sequence $SSGZ^4Z^3Y$ (SEQ ID NO: 263) or $VDPEYZ^4Z^3T$ (SEQ ID NO: 264); a CDR-H3 having the amino acid sequence $QZ^1VZ^2Z^4YZ^3SZ^5WYZ^5Z^2Z^5$ (SEQ ID NO: 265) or $AZ^1DZ^2Z^4Z^3Z^5SPZ^5Z^2Z^5WG$ (SEQ ID NO: 266); a CDR-L1 having the amino acid sequence $SASSSVYYMZ^5$ (SEQ ID NO: 267) or $QNINKZ^5$ (SEQ ID NO: 268); a CDR-L2 having the amino acid sequence $STSNLAZ^3$ (SEQ ID NO: 269), $TYZ^3$, or $YTZ^3$; and/or a CDR-L3 having the amino acid sequence $QQRRNZ^5PYZ^3$ (SEQ ID NO: 270) or $CLQZ^5VNLXZ^3$ (SEQ ID NO: 271); wherein each $Z^1$ is independently an amino acid containing a cationic side-chain at physiological pH; each $Z^2$ is independently an amino acid containing an anionic side-chain at physiological pH; each $Z^3$ is independently an amino acid containing a polar, uncharged side-chain at physiological pH; each $Z^4$ is independently a glycine or alanine; each $Z^5$ is independently an amino acid containing a hydrophobic side-chain; and each X is independently leucine or isoleucine.

In some embodiments, antagonistic TNFR2 single-chain polypeptides of the invention may have a CDR-H1 having the amino acid sequence GFTFSSY (SEQ ID NO: 23), GYTFTDYX (SEQ ID NO: 257), or an amino acid sequence having up to two amino acid substitutions relative to these sequences; a CDR-H2 having the amino acid sequence SSGGSY (SEQ ID NO: 24), VDPEYGST (SEQ ID NO: 258), or an amino acid sequence having up to two amino acid substitutions relative to these sequences; a CDR-H3 having the amino acid sequence QRVDGYSSYWYFDV (SEQ ID NO: 25), ARDDGSYSPFDYWG (SEQ ID NO: 259), or an amino acid sequence having up to two amino acid substitutions relative to these sequences; a CDR-L1 having the amino acid sequence SASSSVYYMY (SEQ ID NO: 26), QNINKY (SEQ ID NO: 260), or an amino acid sequence having up to two amino acid substitutions relative to these sequences; a CDR-L2 having the amino acid sequence STSNLAS (SEQ ID NO: 27), TYS, YTS, or an amino acid sequence having up to two amino acid substitutions relative to SEQ ID NO: 27; and/or a CDR-L3 having the amino acid sequence QQRRNYPYT (SEQ ID NO: 28), CLQYVNLXT (SEQ ID NO: 261), or an amino acid sequence having up to two amino acid substitutions relative to these sequences.

Single-chain polypeptides can be produced by a variety of recombinant and synthetic techniques, such as by recombinant gene expression or solid-phase peptide synthesis procedures described herein or known in the art. For instance, one of skill in the art can design polynucleotides encoding, e.g., two or more of the above CDRs operably linked to one another in frame so as to produce a continuous, single-chain peptide containing these CDRs. Optionally, the CDRs may be separated by a spacer, such as by a framework region (e.g., a framework sequence described herein or a framework region of a germline consensus sequence of a human antibody) or a flexible linker, such as a poly-glycine or glycine/serine linker described herein or known in the art. When produced by chemical synthesis methods, native chemical ligation can optionally be used as a strategy for the synthesis of long peptides (e.g., greater than 50 amino acids). Native chemical ligation protocols are known in the art and have been described, e.g., by Dawson et al. (Science, 266:776-779, 1994); incorporated herein by reference. A detailed description of techniques for the production of single-chain polypeptides, full-length antibodies, and antibody fragments is provided in the sections that follow.

Nucleic Acids and Expression Systems

Antagonistic TNFR2 polypeptides (e.g., single-chain polypeptides, antibodies, or antigen-binding fragments thereof) of the invention can be prepared by any of a variety of established techniques. For instance, an antagonistic TNFR2 polypeptides (e.g., single-chain polypeptides, antibodies, or antigen-binding fragments thereof) of the invention can be prepared by recombinant expression of one or more immunoglobulin light and heavy chain genes in a host cell. For instance, to express an antibody recombinantly, a host cell can be transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel et al., eds., Greene Publishing Associates, 1989), and in U.S. Pat. No. 4,816,397; incorporated herein by reference.

Vectors for Expression of Antagonistic TNFR2 Polypeptides

Viral genomes provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments of the invention include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In *Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030); incorporated herein by reference.

Genome Editing Techniques

In addition to viral vectors, a variety of additional methods have been developed for the incorporation of genes, e.g., those encoding antibody light and heavy chains, single-chain polypeptides, single-chain variable fragments (scFvs), tandem scFvs, Fab domains, F(ab')$_2$ domains, diabodies, and triabodies, among others, into the genomes of target cells for polypeptide expression. One such method that can be used for incorporating polynucleotides encoding anti-TNFR2 polypeptides (e.g., single-chain polypeptides, antibodies, or antigen-binding fragments thereof) into prokaryotic or eukaryotic cells includes transposons. Transposons are polynucleotides that encode transposase enzymes and contain a polynucleotide sequence or gene of interest flanked by excision sites at the 5' and 3' positions. Once a transposon has been delivered into a cell, expression of the transposase gene commences and results in active enzymes that cleave the gene of interest from the transposon. This activity is mediated by the site-specific recognition of transposon excision sites by the transposase. In some embodiments, these excision sites may be terminal repeats or inverted terminal repeats. Once excised from the transposon, the gene of interest can be integrated into the genome of a prokaryotic or eukaryotic cell by transposase-catalyzed cleavage of similar excision sites that exist within nuclear genome of the cell. This allows the gene encoding, e.g., an anti-TNFR2 antibody or fragment or domain thereof to be inserted into the cleaved nuclear DNA at the excision sites, and subsequent ligation of the phosphodiester bonds that join the gene of interest to the DNA of the prokaryotic or eukaryotic cell genome completes the incorporation process. In some embodiments, the transposon may be a retrotransposon, such that the gene encoding the antibody is first transcribed to an RNA product and then reverse-transcribed to DNA before incorporation in the prokaryotic or eukaryotic cell genome. Exemplary transposon systems include the piggybac transposon (described in detail in WO 2010/085699) and the sleeping beauty transposon (described in detail in US20050112764); incorporated herein by reference.

Another useful method for the integration of nucleic acid molecules encoding anti-TNFR2 polypeptides (e.g., single-chain polypeptides, antibodies, or antigen-binding fragments thereof) into the genome of a prokaryotic or eukaryotic cell is the clustered regularly interspaced short palindromic repeats (CRISPR)/Cas system, which is a system that originally evolved as an adaptive defense mechanism in bacteria and archaea against infection by viruses. The CRISPR/Cas system consists of palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al., Nat. Biotech., 31:227-229, 2013) and can be used as an efficient means of site-specifically editing eukaryotic or prokaryotic genomes in order to cleave DNA prior to the incorporation of a polynucleotide encoding an anti-TNFR2 polypeptide of the invention. The use of CRISPR/Cas to modulate gene expression has been described in U.S. Pat. No. 8,697,359, which is incorporated herein by reference.

Alternative methods for site-specifically cleaving genomic DNA prior to the incorporation of a polynucleotide encoding a TNFR2 antibody or antibody fragment of the invention include the use of zinc finger nucleases and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. Zinc finger nucleases and TALENs for use in genome editing applications are described in Urnov et al. (Nat. Rev. Genet., 11:636-646, 2010); and in Joung et al., (Nat. Rev. Mol. Cell. Bio. 14:49-55, 2013); incorporated herein by reference. Additional genome editing techniques that can be used to incorporate polynucleotides encoding antibodies of the invention into the genome of a prokaryotic or eukaryotic cell include the use of ARCUS™ meganucleases that can be rationally designed so as to site-specifically cleave genomic DNA. The use of these enzymes for the incorporation of polynucleotides encoding antagonistic TNFR2 polypeptides (e.g., single-chain polypeptides, antibodies, or antibody fragments) of the invention into the genome of a prokaryotic or eukaryotic cell is particularly advantageous in view of the structure-activity relationships that have been established for such enzymes. Single-chain meganucleases can thus be modified at certain amino acid positions in order to create nucleases that selectively cleave DNA at desired locations. These single-chain nucleases have been described extensively, e.g., in U.S. Pat. Nos. 8,021,867 and 8,445,251; incorporated herein by reference.

Polynucleotide Sequence Elements

To express antagonistic TNFR2 polypeptides (e.g., single-chain polypeptides, antibodies, or antibody fragments thereof) of the invention, polynucleotides encoding partial or full-length light and heavy chains, or CDRs thereof, e.g., obtained as described above, can be inserted into expression vectors such that the genes are operatively linked to transcriptional and translational control sequences. The expression vector and expression control sequences are chosen to be compatible with the expression host cell used. Polynucleotides encoding, e.g., the light chain gene and the heavy chain of a TNFR2 antibody can be inserted into separate vectors, or, optionally, both polynucleotides can be incorporated into the same expression vector using established techniques described herein or known in the art.

In addition to polynucleotides encoding the heavy and light chains of an antibody (or a polynucleotide encoding a single-chain polypeptide or an antibody fragment, such as a scFv molecule), the recombinant expression vectors of the invention may carry regulatory sequences that control the expression of the antibody chain genes in a host cell. The design of the expression vector, including the selection of regulatory sequences, may depend on such factors as the choice of the host cell to be transformed or the level of expression of protein desired. For instance, suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. Nos. 5,168,062, 4,510,245, and 4,968,615.

In addition to the antibody chain or CDR genes and regulatory sequences, the recombinant expression vectors of the invention can carry additional sequences, such as sequences that regulate replication of the vector in host cells (e.g., origins of replication) and selectable marker genes. A selectable marker gene facilitates selection of host cells into which the vector has been introduced (see e.g., U.S. Pat. Nos. 4,399,216, 4,634,665 and 5,179,017). For example, typically the selectable marker gene confers resistance to cytotoxic drugs, such as G418, puromycin, blasticidin, hygromycin or methotrexate, to a host cell into which the vector has been introduced. Suitable selectable marker genes include the dihydrofolate reductase (DHFR) gene (for use in DHFR host cells with methotrexate selection/amplification) and the neo gene (for G418 selection). In order to express the light and heavy chains of a TNFR2 antibody or a TNFR2 antibody fragment, the expression vector(s) containing polynucleotides encoding the heavy and light chains can be transfected into a host cell by standard techniques.

Polynucleotides Encoding Modified Antagonistic TNFR2 Polypeptides

In some embodiments, antagonistic TNFR2 polypeptides (e.g., single-chain polypeptides, antibodies, or antibody fragments of the invention) may be similar to TNFRAB1 or TNFRAB2 but feature differences in the sequence of one or more CDRs. In other cases, the polypeptides of the invention may be similar to TNFRAB1 or TNFRAB2 but feature differences in one or more framework regions. For instance, one or more framework regions of TNFRAB1 or TNFRAB2 may be substituted with the framework region of a human antibody. Exemplary framework regions include, for example, human framework regions described in U.S. Pat. No. 7,829,086, and primate framework regions as described in EP 1945668; incorporated herein by reference. Alternatively, polypeptides (e.g., single-chain polypeptides, antibodies, or antigen-binding fragments thereof) of the invention may be similar to TNFRAB1 or TNFRAB2 but exhibit differences in the sequence of one or more CDRs and differences in one or more framework regions. To generate nucleic acids encoding such TNFR2 antagonist polypeptides, DNA fragments encoding, e.g., one or more CDRs, or at least one, or both, of the light chain variable regions and the heavy chain variable regions can be produced by chemical synthesis (e.g., by solid-phase polynucleotide synthesis techniques), in vitro gene amplification (e.g., by polymerase chain reaction techniques), or by replication of the polynucleotide in a host organism. For instance, nucleic acids encoding anti-TNFR2 polypeptides of the invention may be obtained by amplification and modification of germline DNA or cDNA encoding light and heavy chain variable sequences so as to incorporate the CDRs of TNFRAB1 or TNFRAB2 into the framework residues of a consensus antibody. In some embodiments, a humanized antagonistic TNFR2 antibody may include one or more CDRs of TFNRAB1, or a variant thereof that has at least 85% sequence identity (e.g., 90%, 95%, 97%, 99%, or 100% sequence identity) to any of these CDRs or sequences that contain between one and three amino acid substitutions (e.g., conservative or nonconservative substitutions) relative to the CDR sequences of TNFRAB1, and one or more CDRs of TNFRAB2, or a variant thereof that has at least 85% sequence identity (e.g., 90%, 95%, 97%, 99%, or 100% sequence identity) to any of these CDRs or sequences that contain between one and three amino acid substitutions (e.g., conservative or nonconservative substitutions) relative to the CDR sequences of TFNRAB2. This can be achieved, for example, by performing site-directed mutagenesis of germline DNA or cDNA and amplifying the resulting polynucleotides using the polymerase chain reaction (PCR) according to established procedures. Germline DNA sequences for human heavy and light chain variable region genes are known in the art (see, e.g., the "VBASE" human germline sequence database; see also Kabat et al., Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al., Eur. J. Immunol. 24:827-836, 1994; incorporated herein by reference). Chimeric nucleic acid constructs encoding human heavy and light chain variable regions containing one or more of the CDRs of TNFRAB1 and TNFRAB2 can be produced, e.g., using established cloning techniques known in the art. Additionally, a polynucleotide encoding the heavy or light chain variable region of TNFRAB1 or TFNRAB2 can be synthesized and used as a template for mutagenesis to generate a variant as described herein using routine mutagenesis techniques. Alternatively, a DNA fragment encoding the variant can be directly synthesized (e.g., by established solid-phase nucleic acid chemical synthesis procedures).

Once DNA fragments encoding TNFRAB1, TNFRAB2, TNFRAB1-related, or TFNRAB2-related CDRs or VH and VL segments are obtained, these DNA fragments can be further manipulated by standard recombinant DNA techniques, e.g., to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the $V_H$ region of an anti-TNFR2 antibody of the invention can be converted to a full-length heavy chain gene (as well as a Fab heavy chain gene), e.g., by operatively linking the $V_H$-encoding DNA to another DNA molecule encoding heavy chain constant region domains (CH1, CH2, CH3, and, optionally, CH4). The sequences of human heavy chain constant region genes are known in the art (see e.g., Kabat et al., Sequences of Proteins of Immunological Interest, Fifth Edition, U.S. Department of Health and Human Services, NIH Publication No. 91-3242, 1991) and DNA fragments encompassing these regions can be obtained by standard PCR amplification. The heavy chain constant region can be an IgG1, IgG2, IgG3, IgG4, IgA, IgE, IgM or IgD constant region, and in certain embodiments is an IgG1 constant region. For a Fab fragment heavy chain gene, the VH-encoding DNA can be operatively linked to another DNA molecule encoding only the heavy chain CH1 domain.

The isolated DNA encoding the VL region of an anti-TNFR2 polypeptide (e.g., single-chain polypeptide, antibody, or antigen-binding fragment thereof) of the invention can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., Sequences of Proteins of Immunological Interest, Fifth Edition (U.S. Department of Health and Human Services, NIH Publication No. 91-3242, 1991)) and DNA fragments encompassing these regions can be obtained, e.g., by amplification in a prokaryotic or eukaryotic cell of a polynucleotide encoding these regions, by PCR amplification, or by chemical polynucleotide synthesis. The light chain constant region can be a kappa (κ) or lambda (λ) constant region, but in certain embodiments is a kappa constant region. To create a scFv gene, the VH and VL-encoding DNA fragments are operatively linked to another fragment encoding a flexible linker, e.g., a polynucleotide encoding a flexible, hydrophilic amino acid sequence, such as the amino acid sequence $(Gly_4Ser)_3$, such that the $V_H$ and $V_L$ sequences can be expressed as a contiguous single-chain protein, with the $V_L$ and $V_H$ regions joined by the linker (see e.g., Bird et al., Science 242:423-426, 1988; Huston et al., Proc. Natl. Acad. Sci. USA 85:5879-5883, 1988; McCafferty et al., Nature 348:552-554, 1990).

Recombinant DNA technology can also be used to remove some or all of the DNA encoding either or both of the light and heavy chains that is not necessary for binding to TNFR2. The molecules expressed from such truncated DNA molecules are also encompassed by the polypeptides of the invention. In addition, bifunctional polypeptides (e.g., bifunctional antibodies) can be produced in which one heavy and one light chain are derived from TNFRAB1 and/or TNFRAB2 and the other heavy and light chain are specific for an antigen other than TNFR2. Such antibodies can be generated, e.g., by crosslinking a heavy chain and light chain of TNFRAB1 and/or TNFRAB2 to a heavy chain and light chain of a second antibody by standard chemical crosslinking methods (e.g., by disulfide bond formation). Bifunctional antibodies can also be made by expressing a nucleic acid molecule engineered to encode a bifunctional antibody in a prokaryotic or eukaryotic cell.

Dual specific antibodies, i.e., antibodies that bind TNFR2 and a different antigen using the same binding site, can be produced by mutating amino acid residues in the light chain and/or heavy chain CDRs. In some embodiments, dual specific antibodies that bind two antigens, such as TNFR2 and a second cell-surface receptor, can be produced by mutating amino acid residues in the periphery of the antigen binding site (Bostrom et al., Science 323: 1610-1614, 2009). Dual functional antibodies can be made by expressing a polynucleotide engineered to encode a dual specific antibody.

Modified antagonistic TNFR2 antibodies and antibody fragments of the invention can also be produced by chemical synthesis (e.g., by the methods described in Solid Phase Peptide Synthesis, 2nd ed., 1984 The Pierce Chemical Co., Rockford, 111; incorporated herein by reference). Variant antibodies can also be generated using a cell-free synthetic platform (see, e.g., Chu et al., Biochemia No. 2, 2001 (Roche Molecular Biologicals); incorporated herein by reference).

Host Cells for Expression of Antagonistic TNFR2 Polypeptides

It is possible to express the polypeptides (e.g., single-chain polypeptides, antibodies, and antigen-binding fragments thereof) of the invention in either prokaryotic or eukaryotic host cells. In some embodiments, expression of polypeptides (e.g., single-chain polypeptides, antibodies, or antigen-binding fragments thereof) is performed in eukaryotic cells, e.g., mammalian host cells, for optimal secretion of a properly folded and immunologically active antibody. Exemplary mammalian host cells for expressing the recombinant polypeptides (e.g., single-chain polypeptides, antibodies, or antigen-binding fragments thereof) of the invention include Chinese Hamster Ovary (CHO cells) (including DHFR CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), NSO myeloma cells, COS cells, 293 cells, and SP2/0 cells. Additional cell types that may be useful for the expression of single-chain polypeptides, antibodies, and fragments thereof include bacterial cells, such as BL-21(DE3) *E. coli* cells, which can be transformed with vectors containing foreign DNA according to established protocols. Additional eukaryotic cells that may be useful for expression of polypeptides include yeast cells, such as auxotrophic strains of *S. cerevisiae*, which can be transformed and selectively grown in incomplete media according to established procedures known in the art. When recombinant expression vectors encoding antibody genes (e.g., genes encoding one or more CDRs, an antibody heavy chain, or an antibody light chain) are introduced into mammalian host cells, the antibodies are produced by culturing the host cells for a period of time sufficient to allow for expression of the antibody in the host cells or secretion of the antibody into the culture medium in which the host cells are grown.

Polypeptides (e.g., single-chain polypeptides, antibodies, and antigen-binding fragments thereof) can be recovered from the culture medium using standard protein purification methods. Host cells can also be used to produce portions of intact antibodies, such as Fab fragments or scFv molecules. The invention also includes methods in which the above procedure is varied according to established protocols known in the art. For example, it can be desirable to transfect a host cell with DNA encoding either the light chain or the heavy chain (but not both) of an anti-TNFR2 antibody of this invention in order to produce an antigen-binding fragment of the antibody.

Once an anti-TNFR2 polypeptide (e.g., single-chain polypeptide, antibody, or antigen-binding fragment) thereof of the invention has been produced by recombinant expression, it can be purified by any method known in the art, such as a method useful for purification of an immunoglobulin molecule, for example, by chromatography (e.g., ion exchange, affinity, particularly by affinity for TNFR2 after Protein A or Protein G selection, and sizing column chromatography), centrifugation, differential solubility, or by any other standard technique for the purification of proteins. Further, the anti-TNFR2 polypeptides (e.g., single-chain polypeptides, antibodies, and antigen-binding fragments thereof) of the invention can be fused to heterologous polypeptide sequences described herein or otherwise known in the art to facilitate purification or to produce therapeutic conjugates (see "Antibody conjugates," below).

Once isolated, an anti-TNFR2 antibody or antigen-binding fragments thereof can, if desired, be further purified, e.g., by high performance liquid chromatography (see, e.g., Fisher, Laboratory Techniques in Biochemistry and Molecular Biology (Work and Burdon, eds., Elsevier, 1980); incorporated herein by reference), or by gel filtration chromatography, such as on a Superdex™ 75 column (Pharmacia Biotech AB, Uppsala, Sweden).

Platforms for Generating and Affinity-Maturing Antagonistic Anti-TNFR2 Polypeptides Mapping Epitopes of TNFR2 that Promote Receptor Antagonism Antagonistic TNFR2 polypeptides (e.g., single-chain polypeptides, antibodies and antigen-binding fragments thereof) of the invention can be produced by screening libraries of polypeptides (e.g., single-chain polypeptides, antibodies, and antigen-binding fragments thereof) for functional molecules that are capable of binding epitopes within TNFR2 that selectively promote receptor antagonism rather than receptor activation. Linear peptides isolated from the TNFR2 protein may not adopt the same three dimensional conformations as those peptide sequences located within the protein. TNFR2 provides a structurally rigidified framework that biases the conformations of individual peptide fragments and reinforces these spatial orientations by establishing intramolecular contacts (e.g., hydrogen bonds, dipole-dipole interactions, salt bridges) and by differentially positioning various regions for exposure to solvent depending on the relative hydrophilicity and lipophilicity of these areas (Mukai et al., Sci. Signal., 3:ra83-ra83, 2010). The conformational constraint of a peptide fragment within TNFR2 can be achieved by incorporating the amino acid residues of a TNFR2 epitope (e.g., an epitope that promotes receptor antagonism) into a structurally pre-organized peptide scaffold, such as a cyclic, bicyclic, tricyclic, or tetrayclic peptide. Cyclic and polycyclic peptides such as these confine a peptide fragment to a distinct three-dimensional conformation. This can be achieved by synthesizing peptide epitopes isolated from TNFR2 by established chemical synthetic methods (e.g., by solid-phase peptide synthesis as described herein) and incorporating cysteine residues into the sequence at the N- and C-terminal positions or at various internal positions within the peptide chain. It may be advantageous to incorporate cysteine residues that are chemically protected at the thiol moiety with a protecting group that can be removed under conditions different from those used to remove other protecting groups within the peptide being synthesized and different from those used to assemble the peptide chain. Exemplary orthogonal protecting groups for the cysteine thiol include the 4-methyltrityl group and 4-methoxtrityl group, each of which can be removed using dilute trifluoracetic acid (examples are described, e.g., in Isidro-Llobet et al., Chem Rev., 109:2455-2504, 2009).

After introducing a cysteine residue into a synthetic peptide fragment derived from an epitope within TNFR2, the peptide can be cyclized by treating the peptide with a multivalent electrophile, such as a bis(bromomethyl) or tris(bromomethyl)arene derivative. Alternative multivalent thiol-reactive electrophiles can be used, e.g., 1,5-difluoro-2,4-dinitrobenzene, acyclic dibromoalkanes, and others (see, e.g., Jo et al., J. Am. Chem. Soc., 134:17704-17713, 2012; incorporated herein by reference). In some embodiments, it may be advantageous to prevent the participation of a cysteine residue in the synthetic peptide fragment in a cyclization reaction. For instance, it may be desirable to synthesize a polycyclic peptide containing multiple cysteine residues such that only select cysteine thiols participate in the intramolecular crosslinking process. To prevent unwanted participation of these additional Cys thiol groups in the coupling reaction, a simple approach is for instance to use Fmoc-Cys(Acm) (Fmoc-acetamidomethyl-L-cysteine) for introduction of a protected Cys residue during the course of peptide synthesis. Alternatively, Fmoc-Cys(StBu)-OH can be used, and/or the corresponding t-butyloxycarbonyl (Boc)-protected amino acids. The Acm or StBu group is not removed during the course of a normal TFA deprotection-cleavage reaction but requires oxidative (e.g., iodine, 12) treatment in case of Acm group, or reductive treatment (e.g., 3-mercaptoethanol (excess) or 1,4-dithiothreiotol (excess)) in case of the StBu group to give the reduced sulfhydryl form of the peptide, which can either be used directly or subsequently oxidized to the corresponding cystinyl peptide. In one embodiment, a peptide is used which contains at least one Cys derivative, such as Cys(Acm) or Cys(StBu), to allow selective deprotection of a Cys-thiol group. Selective deprotection of a Cys-thiol group renders the Cys-thiol group available for reacting at a desired moment, such as following completion of peptide chain assembly and prior to the deprotection of other residues within the peptide (see, e.g., WO 2008/013454; incorporated herein by reference).

As an example, libraries of cyclic and polycyclic peptides containing individual fragments isolated from TNFR2 and combinations of fragments from distinct regions of TNFR2 can be synthesized by techniques such as those described above in order to incorporate cysteine residues at various positions within the peptide scaffold and using different electrophilic crosslinking reagents (see, e.g., Example 1 and FIG. 3, SEQ ID NOs: 34-117). These peptides can be immobilized on a solid surface and screened for molecules that bind antagonistic TNFR2 polypeptides (e.g., single-chain polypeptides, antibodies, or antigen-binding fragments thereof) such as TNFRAB1 or TNFRAB2, using an ELISA-based screening platform using established procedures. Using this assay, for instance, peptides that specifically bind TNFRAB1 and/or TNFRAB2 with high affinity therefore contain residues within epitopes of TNFR2 that preferentially bind TNFRAB1 and/or TNFRAB2 and may structurally pre-organize these residues such that they resemble the conformations of the corresponding peptide in the native protein. Cyclic and polycyclic peptides thus obtained (e.g., peptides having the sequence of any one of SEQ ID NOs: 11, 19, 20, and 34-117, or a peptide containing between about 10 and about 30 continuous or discontinuous amino acids between positions 80 and 130 of SEQ ID NO: 7) can be used to screen libraries of antibodies and antigen-binding fragments thereof in order to identify anti-TNFR2 polypeptides of the invention. Moreover, since these constrained peptides act as surrogates for epitopes within TNFR2 that promote receptor antagonism, polypeptides (e.g., single-chain polypeptides, antibodies, and antigen-binding fragments thereof) generated using this screening technique may bind the corresponding epitopes in TNFR2 and are expected to be antagonistic of receptor activity.

Screening of Libraries for Antagonistic TNFR2 Polypeptides

Methods for high throughput screening of polypeptide (e.g., single-chain polypeptide, antibody, or antibody fragment) libraries for molecules capable of binding epitopes within TNFR2 (e.g., epitopes presented by peptides having the sequence of any one of SEQ ID NOs: 11, 19, 20, and 34-117, or a peptide containing between about 10 and about 30 continuous or discontinuous amino acids between positions 80 and 130 of SEQ ID NO: 7) include, without limitation, display techniques including phage display, bacterial display, yeast display, mammalian display, ribosome display, mRNA display, and cDNA display. The use of phage display to isolate ligands that bind biologically relevant molecules has been reviewed, e.g., in Felici et al. (Biotechnol. Annual Rev. 1:149-183, 1995), Katz (Annual Rev. Biophys. Biomol. Struct. 26:27-45, 1997), and Hoogenboom et al. (Immunotechnology 4:1-20, 1998). Several randomized combinatorial peptide libraries have been constructed to select for polypeptides that bind different targets, e.g., cell surface receptors or DNA (reviewed by Kay (Perspect. Drug Discovery Des. 2, 251-268, 1995), Kay et al., (Mol. Divers. 1:139-140, 1996)). Proteins and multimeric proteins have been successfully phage-displayed as functional molecules (see EP 0349578A, EP 4527839A, EP 0589877A; Chiswell and McCafferty (Trends Biotechnol. 10, 80-84 1992)). In addition, functional antibody fragments (e.g. Fab, single-chain Fv [scFv]) have been expressed (McCafferty et al. (Nature 348: 552-554, 1990), Barbas et al. (Proc. Natl. Acad Sci. USA 88:7978-7982, 1991), Clackson et al. (Nature 352:624-628, 1991)). These references are hereby incorporated by reference in their entirety.

(i) Phage Display Techniques

As an example, phage display techniques can be used in order to screen libraries of polypeptides, such as single-chain polypeptides, antibodies, and antigen-binding fragments thereof, for functional molecules capable of binding cyclic or polycyclic peptides containing epitopes within TNFR2 that promote receptor antagonism (e.g., peptides having the sequence of any one of SEQ ID NOs: 11, 19, 20, and 34-117, and particularly those that contain the KCRPG motif, as in SEQ ID NOs: 42, 50, 52-54, and 61-63). For instance, libraries of polynucleotides encoding single-chain antibody fragments, such as scFv fragments, that contain randomized hypervariable regions can be obtained using established procedures (e.g., solid-phase polynucleotide synthesis or error-prone PCR techniques, see McCullum et al. (Meth. Mol. Biol., 634:103-109, 2010); incorporated herein by reference). These randomized polynucleotides can subsequently be incorporated into a viral genome such that the randomized antibody chains encoded by these genes are expressed on the surface of filamentous phage, e.g., by a covalent bond between the antibody chain and a coat protein (e.g., pill coat protein on the surface of M13 phage). This provides a physical connection between the genotype and phenotype of the antibody chain. In this way, libraries of phage that display diverse antibody chains containing random mutations in hypervariable regions can be screened for the ability of the exterior antibody chains to bind TNFR2 epitopes (e.g., peptides having the sequence of any one of SEQ ID NOs: 11, 19, 20, and 34-117, or a peptide containing between about 10 and about 30 continuous or discontinuous amino acids between positions 80 and 130 of SEQ ID NO: 7) that are immobilized to a surface using established procedures. For instance, cyclic peptides such as those represented by SEQ ID NOs: 42, 50, 52-54, and 61-63, which contain the KCRPG motif, can be physically bound to the surface of a microtiter plate by forming a covalent bond between the peptide and an epitope tag (e.g., biotin) and incubating the peptide in wells of a microtiter plate that have been previously coated with a complementary tag (e.g., avidin) that binds the tag attached to the peptide with high affinity. Suitable epitope tags include, without limitation, maltose-binding protein, glutathione-S-transferase, a poly-histidine tag, a FLAG-tag, a myc-tag, human influenza hemagglutinin (HA) tag, biotin, streptavidin. Peptides containing the epitopes presented by these molecules are capable of being immobilized on surfaces containing such complementary molecules as maltose, glutathione, a nickel-containing complex, an anti-FLAG antibody, an anti-myc antibody, an anti-HA antibody, streptavidin, or biotin, respectively. In this way, phage can be incubated with a surface containing an immobilized TNFR2-derived peptide for a time suitable to allow binding of the antibody to the constrained peptide and in the presence of an appropriate buffer system (e.g., one that contains physiological salt concentration, ionic strength, and is maintained at physiological pH by a buffering agent). The surface can then be washed (e.g., with phosphate buffer containing 0.1% Tween-20) so as to remove phage that do not present antibody chains that interact with the TNFR2-derived peptides with an affinity greater than a particular threshold value.

The affinity of the polypeptides that remain after this initial panning (i.e., screening) step can be modulated by adjusting the conditions of the washing step (e.g., by including mildly acidic or basic components, or by including other TNFR2-derived peptides at a low concentration in order to compete with immobilized peptides for antigen-binding sites). In this way, the population of phage that remains bound to the surfaces of the microtiter plate following the washing step is enriched for phage that bind TNFR2-derived peptide epitopes that promote receptor antagonism. The remaining phage can then be amplified by eluting the phage from the surface containing these peptides (e.g., by altering the ambient pH, ionic strength, or temperature) so as to diminish protein-protein interaction strength. The isolated phage can then be amplified, e.g., by infecting bacterial cells, and the resulting phage can optionally be subjected to panning by additional iterations of screening so as to further enrich the population of phage for those harboring higher-affinity anti-TNFR2 polypeptides. Following these panning stages, phage that display high-affinity antibodies or antigen-binding fragments thereof can subsequently be isolated and the genomes of these phage can be sequenced in order to identify the polynucleotide and polypeptide sequences of the encoded antibodies. Phage display techniques such as this can be used to generate, e.g., antibody chains, such as scFv fragments, tandem scFv fragments, and other antigen-binding fragments of the invention that can be used as antagonists of TNFR2. Exemplary phage display protocols for the identification of antibody chains and antigen-binding fragments thereof that bind a particular antigen with high affinity are well-established and are described, e.g., in U.S. Pat. No. 7,846,892, WO 1997/002342, U.S. Pat. No. 8,846,867, and WO 2007/132917; incorporated herein by reference. Similar phage display techniques can be used to generate antibody-like scaffolds (e.g., $^{10}$Fn3 domains) of the invention that bind epitopes within TNFR2 that promote receptor antagonism (e.g., epitopes presented by peptides with the sequence of any one of SEQ ID NOs: 11, 19, 20, and 34-117, and particularly those that contain the KCRPG motif, as in SEQ ID NOs: 42, 50, 52-54, and 61-63). Exemplary phage display protocols for the identification of antibody-like scaffold proteins are described, e.g., in WO 2009/086116; incorporated herein by reference).

(ii) Cell-Based Display Techniques

Other in vitro display techniques that exploit the linkage between genotype and phenotype of a solvent-exposed polypeptide (e.g., single-chain polypeptide, antibody, or antigen-binding fragment thereof) include yeast and bacterial display. Yeast display techniques are established in the art and are often advantageous in that high quantities of antibodies (often up to 30,000) can be presented on the surface of an individual yeast cell (see, e.g., Boder et al. (Nat Biotechno. 15:553, 1997); incorporated herein by reference). The larger size of yeast cells over filamentous phage enables an additional screening strategy, as one can use flow cytometry to both analyze and sort libraries of yeast. For instance, established procedures can be used to generate libraries of bacterial cells or yeast cells that express polypeptides, such as single-chain polypeptides, antibodies, or antibody fragments, containing randomized hypervariable regions (see, e.g., see U.S. Pat. No. 7,749,501 and US 2013/0085072; the teachings of each which are incorporated herein by reference). For instance, large libraries of yeast cells that express polynucleotides encoding naïve scFv fragments can be made using established procedures (de Bruin et al., Nat Biotechnol 17:397, 1999; incorporated herein by reference). Yeast cells expressing these polynucleotides can then be incubated with two different fluorescent molecules during the panning steps: one dye that binds conserved residues within the antibody and thus reflects the amount of antibody displayed, and another dye that fluoresces at a different wavelength and binds the antigen and thus indicates the amount of antigen bound. In these cases, it is useful to use a cyclic or polycyclic peptide containing the sequence of any one of SEQ ID NOs: 11, 19, 20, and 34-117 (and particularly those that contain the KCRPG motif, as in SEQ ID NOs: 42, 50, 52-54, and 61-63) that has been conjugated to an epitope tag (e.g., biotin), optionally at a residue that is not expected to interfere with antibody-antigen binding. This enables a fluorescent dye labeled with a complementary tag (e.g., avidin) to localize to the antibody-antigen complex. This results in great flexibility and immediate feedback on the progress of a selection. In contrast to phage display, by normalizing to antibody display levels, antibodies with higher affinities, rather than greater expression levels can easily be selected. In fact, it is possible to distinguish and sort antibodies whose affinities differ by only two-fold (VanAntwerp and Wittrup (*Biotechnol Prog* 16:31, 2000)).

(iii) Nucleotide Display Techniques

Display techniques that utilize in vitro translation of randomized polynucleotide libraries also provide a powerful approach to generating anti-TNFR2 antibodies of the invention. For instance, randomized DNA libraries encoding single-chain polypeptides, antibodies, or antigen-binding fragments thereof that contain mutations within designated hypervariable regions can be obtained, e.g., using established PCR-based mutagenesis techniques as described herein. The polynucleotides of these libraries may contain transcription regulating sequences, such as promoters and transcription terminating sequences, and may additionally encode sequences that increase the rate of translation of the resulting mRNA construct (e.g., IRES sequences, 5' and 3' UTRs, a poly-adenylation tract, etc). These polynucleotide libraries can be incubated in an appropriately buffered solution containing RNA polymerase and RNA nucleoside triphosphates (NTPs) in order to enable transcription of the DNA sequences to competent mRNA molecules, which can subsequently be translated by large and small ribosomal subunits, aminoacyl tRNA molecules, and translation initiation and elongation factors present in solution (e.g., using the PURExpress® In Vitro Protein Synthesis Kit, New England Biolabs®). Designed mRNA modifications can enable the antibody product to remain covalently bound to the mRNA template by a chemical bond to puromycin (e.g., see Keefe (Curr. Protoc. Mol. Biol., Chapter 24, Unit 24.5, 2001); incorporated herein by reference). This genotype-phenotype linkage can thus be used to select for antibodies that bind a TNFR2-derived peptide (e.g., a peptide that has the sequence of any one of SEQ ID NOs: 11, 19, 20, and 34-117, and particularly those that contain the KCRPG motif, as in SEQ ID NOs: 42, 50, 52-54, and 61-63) by incubating mRNA:antibody fusion constructs with a peptide immobilized to a surface and panning in a fashion similar to phage display techniques (see, e.g., WO 2006/072773; incorporated herein by reference).

Optionally, polypeptides (e.g., single-chain polypeptides, antibodies, or antigen-binding fragments thereof) of the invention can be generated using a similar technique, except the polypeptide product may be bound non-covalently to the ribosome-mRNA complex rather than covalently via a puromycin linker. This platform, known as ribosome display, has been described, e.g., in U.S. Pat. No. 7,074,557; incorporated herein by reference. Alternatively, antibodies can be generated using cDNA display, a technique analogous to mRNA display with the exception that cDNA, rather than mRNA, is covalently bound to an antibody product via a puromycin linker. cDNA display techniques offer the advantage of being able to perform panning steps under increasingly stringent conditions, e.g., under conditions in which the salt concentration, ionic strength, pH, and/or temperature of the environment is adjusted in order to screen for antibodies with particularly high affinity for TNFR2-derived peptides. This is due to the higher natural stability of double-stranded cDNA over single-stranded mRNA. cDNA display screening techniques are described, e.g., in Ueno et al. (Methods Mol. Biol., 805:113-135, 2012); incorporated herein by reference.

In addition to generating anti-TNFR2 polypeptides of the invention, in vitro display techniques (e.g., those described herein and those known in the art) also provide methods for improving the affinity of an anti-TNFR2 polypeptide of the invention. For instance, rather than screening libraries of single-chain polypeptides, antibodies, and fragments thereof containing completely randomized hypervariable regions, one can screen narrower libraries of single-chain polypeptides, antibodies, and antigen-binding fragments thereof that feature targeted mutations at specific sites within hypervariable regions. This can be accomplished, e.g., by assembling libraries of polynucleotides encoding antibodies or antigen-binding fragments thereof that encode random mutations only at particular sites within hypervariable regions. These polynucleotides can then be expressed in, e.g., filamentous phage, bacterial cells, yeast cells, mammalian cells, or in vitro using, e.g., ribosome display, mRNA display, or cDNA display techniques in order to screen for polypeptides, such as single-chain polypeptides, antibodies, or antigen-binding fragments thereof that specifically bind TNFR2 epitopes (e.g., peptides containing the sequence of any one of SEQ ID NOs: 11, 19, 20, and 34-117, and particularly those that contain the KCRPG motif, as in SEQ ID NOs: 42, 50, 52-54, and 61-63) with improved binding affinity. Yeast display is particularly well-suited for affinity maturation, and has been used previously to improve the affinity of a single-chain antibody to a $K_D$ of 48 fM (Boder et al. (Proc Natl Acad Sci USA 97:10701, 2000)).

Additional in vitro techniques that can be used for the generation and affinity maturation of antagonistic TNFR2 antibodies of the invention include the screening of combinatorial libraries of polypeptides, such as single-chain polypeptides, antibodies, or antigen-binding fragments thereof for functional molecules capable of specifically binding TNFR2-derived peptides (e.g., a peptide having the amino acid sequence of any one of SEQ ID NOs: 11, 19, 20, and 34-117, such as SEQ ID NOs: 42, 50, 52-54, and 61-63). Combinatorial polypeptide libraries, such as antibody or antibody fragment libraries, can be obtained, e.g., by expression of polynucleotides encoding randomized hypervariable regions of an antibody or antigen-binding fragment thereof in a eukaryotic or prokaryotic cell. This can be achieved, e.g., using gene expression techniques described herein or known in the art. Heterogeneous mixtures of antibodies can be purified, e.g., by Protein A or Protein G selection, sizing column chromatography), centrifugation, differential solubility, and/or by any other standard technique for the purification of proteins. Libraries of combinatorial libraries thus obtained can be screened, e.g., by incubating a heterogeneous mixture of these antibodies with a peptide derived from TNFR2 that has been immobilized to a surface (e.g., a peptide having the amino acid sequence of any one of SEQ ID NOs: 11, 19, 20, and 34-117 immobilized to the surface of a solid-phase resin or a well of a microtiter plate) for a period of time sufficient to allow antibody-antigen binding. Non-binding antibodies or fragments thereof can be removed by washing the surface with an appropriate buffer (e.g., a solution buffered at physiological pH (approximately 7.4) and containing physiological salt concentrations and ionic strength, and optionally containing a detergent, such as TWEEN-20). Antibodies that remain bound can subsequently be detected, e.g., using an ELISA-based detection protocol (see, e.g., U.S. Pat. No. 4,661,445; incorporated herein by reference).

Additional techniques for screening combinatorial libraries of polypeptides for those that specifically bind TNFR2-derived peptides (e.g., a peptide containing the amino acid sequence of any one of SEQ ID NOs: 11, 19, 20, and 34-117, such as SEQ ID NOs: 42, 50, 52-54, and 61-63) include the screening of one-bead-one-compound libraries of single-chain polypeptides or antibody fragments. Single-chain polypeptides and antibody fragments can be chemically synthesized on a solid bead (e.g., using established split-and-pool solid-phase peptide synthesis protocols) composed of a hydrophilic, water-swellable material such that each bead displays a single antibody fragment. Heterogeneous bead mixtures can then be incubated with a TNFR2-derived peptide that is optionally labeled with a detectable moiety (e.g., a fluorescent dye) or that is conjugated to an epitope tag (e.g., biotin, avidin, FLAG tag, HA tag) that can later be detected by treatment with a complementary tag (e.g., avidin, biotin, anti-FLAG antibody, anti-HA antibody, respectively). Beads containing antibody fragments that specifically bind a TNFR2-derived peptide (e.g., a peptide containing the amino acid sequence of any one of SEQ ID NOs: 11, 19, 20, and 34-117, such as SEQ ID NOs: 42, 50, 52-54, and 61-63) can be identified by analyzing the fluorescent properties of the beads following incubation with a fluorescently-labeled antigen or complementary tag (e.g., by confocal fluorescent microscopy or by fluorescence-activated bead sorting; see, e.g., Muller et al. (J. Biol. Chem., 16500-16505, 1996); incorporated herein by reference). Beads containing antibody fragments that specifically bind TNFR2-derived peptides can thus be separated from those that do not contain high-affinity antibody fragments. The sequence of an antibody fragment that specifically binds a TNFR2-derived peptide can be determined by techniques known in the art, including, e.g., Edman degradation, tandem mass spectrometry, matrix-assisted laser-desorption time-of-flight mass spectrometry (MALDI-TOF MS), nuclear magnetic resonance (NMR), and 2D gel electrophoresis, among others (see, e.g., WO 2004/062553; incorporated herein by reference).

Negative Screens of Polypeptides

In addition to the above-described methods for screening for a single-chain polypeptide, antibody, or antibody fragment that specifically binds to an epitope derived from human TNFR2 containing the KCR or KCRPG motif, one can additionally perform negative screens in order to eliminate single-chain polypeptides, antibodies, or antibody fragments that may also bind an epitope that contains the KCSPG sequence. For instance, mixtures of single-chain polypeptides, antibodies, or antibody fragments isolated as a result of any of the above-described screening techniques can be screened for single-chain polypeptides, antibodies, or antibody fragments that also specifically bind to a peptide derived from human TNFR2 that contains the KCSPG motif, such as a peptide containing residues 48-67 of SEQ ID NO: 7 (QTAQMCCSKCSPGQHAKVFC, SEQ ID NO: 18). This can be accomplished using any of the above-described methods or variations thereof, e.g., such that the single-chain polypeptides, antibodies, or antibody fragments being screened are those that were previously identified as being capable of specifically binding a peptide containing one or more residues of the KCRPG sequence (e.g., at least the KCR sequence). Exemplary techniques useful for a negative screen include those described above or known in the art, such as phage display, yeast display, bacterial display, ribosome display, mRNA display, cDNA display, or surface-based combinatorial library screens (e.g., in an ELISA format). This screening technique represents a useful strategy for identifying an antagonistic TNFR2 single-chain polypeptides, antibodies, and antibody fragments, as polypeptides capable of binding TNFR2 epitopes containing the KCSPG sequence and one or more residues of the KCRPG sequence have been shown to lack, or to have significantly reduced, antagonistic activity.

Immunization of a Non-Human Mammal

Another strategy that can be used to produce antagonistic TNFR2 antibodies or antibody fragments of the invention includes immunizing a non-human mammal. Examples of non-human mammals that can be immunized in order to produce antagonistic TNFR2 antibodies and fragments thereof of the invention include rabbits, mice, rats, goats, guinea pigs, hamsters, horses, and sheep, as well as non-human primates. For instance, established procedures for immunizing primates are known in the art (see, e.g., WO 1986/6004782; incorporated herein by reference). Immunization represents a robust method of producing monoclonal antibodies by exploiting the antigen specificity of B lymphocytes. For example, monoclonal antibodies can be prepared by the Kohler-Millstein procedure (described, e.g., in EP 0110716; incorporated herein by reference), wherein spleen cells from a non-human animal (e.g., a primate) immunized with a peptide that presents a TNFR2-derived antigen that promotes receptor antagonism (e.g., a peptide containing the amino acid sequence of any one of SEQ ID NOs: 11, 19, 20, and 34-117, such as SEQ ID NOs: 42, 50, 52-54, and 61-63). A clonally-expanded B lymphocyte produced by immunization can be isolated from the serum of the animal and subsequently fused with a myeloma cell in order to form a hybridoma. Hybridomas are particularly useful agents for antibody production, as these immortalized cells can provide a lasting supply of an antigen-specific antibody. Antibodies from such hybridomas can subsequently be isolated using techniques known in the art, e.g., by purifying the antibodies from the cell culture medium by affinity chromatography, using reagents such as Protein A or Protein G.

Antagonistic TNFR2 Polypeptide Conjugates

Prior to administration of antagonistic TNFR2 polypeptides of the invention to a mammalian subject (e.g., a human), it may be desirable to conjugate the polypeptide (e.g., single-chain polypeptide, antibody, or antigen-binding fragment thereof) to a second molecule, e g., to modulate the activity of the polypeptide in vivo. Antagonistic TNFR2 single-chain polypeptides, antibodies, and fragments thereof can be conjugated to other molecules at either the N-terminus or C-terminus of a light or heavy chain of the polypeptide using any one of a variety of established conjugation strategies that are well-known in the art. Examples of pairs of reactive functional groups that can be used to covalently tether an antagonistic TNFR2 single-chain polypeptide, antibody, or fragment thereof to another molecule include, without limitation, thiol pairs, carboxylic acids and amino groups, ketones and amino groups, aldehydes and amino groups, thiols and alpha,beta-unsaturated moieties (such as maleimides or dehydroalanine), thiols and alpha-halo amides, carboxylic acids and hydrazides, aldehydes and hydrazides, and ketones and hydrazides.

Antagonistic TNFR2 single-chain polypeptides, antibodies, and fragments thereof can be covalently appended directly to another molecule by chemical conjugation as described. Alternatively, fusion proteins containing antagonistic TNFR2 single-chain polypeptides, antibodies, and fragments thereof can be expressed recombinantly from a cell (e.g., a eukaryotic cell or prokaryotic cell). This can be accomplished, for example, by incorporating a polynucleotide encoding the fusion protein into the nuclear genome of a cell (e.g., using techniques described herein or known in the art). Optionally, single-chain polypeptides, antibodies, and fragments thereof of the invention can be joined to a second molecule by forming a covalent bond between the antibody and a linker. This linker can then be subsequently conjugated to another molecule, or the linker can be conjugated to another molecule prior to ligation to the anti-TNFR2 single-chain polypeptide, antibody, or fragment thereof. Examples of linkers that can be used for the formation of a conjugate include polypeptide linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Fusion proteins containing polypeptide linkers can be made using chemical synthesis techniques, such as those described herein, or through recombinant expression of a polynucleotide encoding the fusion protein in a cell (e.g., a prokaryotic or eukaryotic cell). Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

Drug-Polypeptide Conjugates

An antagonistic TNFR2 polypeptide (e.g., single-chain polypeptide, antibody, or antigen-binding fragment thereof) of the invention can additionally be conjugated to, admixed with, or administered separately from a therapeutic agent, such as a cytotoxic molecule. Conjugates of the invention may be applicable to the treatment or prevention of a disease associated with aberrant cell proliferation, such as a cancer described herein. Exemplary cytotoxic agents that can be conjugated to, admixed with, or administered separately from an antagonistic TNFR2 polypeptide include, without limitation, antineoplastic agents such as: acivicin; aclarubicin; acodazole hydrochloride; acronine; adozelesin; adriamycin; aldesleukin; altretamine; ambomycin; a. metantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; camptothecin; caracemide; carbetimer; carboplatin; carmustine; carubicin hydrochloride; carzelesin; cedefingol; chlorambucil; cirolemycin; cisplatin; cladribine; combretestatin a-4; crisnatol mesylate; cyclophosphamide; cytarabine; dacarbazine; daca (n-[2-(dimethyl-amino) ethyl]acridine-4-carboxamide); dactinomycin; daunorubicin hydrochloride; daunomycin; decitabine; dexormaplatin; dezaguanine; dezaguanine mesylate; diaziquone; docetaxel; dolasatins; doxorubicin; doxorubicin hydrochloride; droloxifene; droloxifene citrate; dromostanolone propionate; duazomycin; edatrexate; eflornithine hydrochloride; ellipticine; elsamitrucin; enloplatin; enpromate; epipropidine; epirubicin hydrochloride; erbulozole; esorubicin hydrochloride; estramustine; estramustine phosphate sodium; etanidazole; ethiodized oil i 131; etoposide; etoposide phosphate; etoprine; fadrozole hydrochloride; fazarabine; fenretinide; floxuridine; fludarabine phosphate; fluorouracil; 5-fdump; flurocitabine; fosquidone; fostriecin sodium; gemcitabine; gemcitabine hydrochloride; gold au 198; homocamptothecin; hydroxyurea; idarubicin hydrochloride; ifosfamide; ilmofosine; interferon alfa-2a; interferon alfa-2b; interferon alfa-nl; interferon alfa-n3; interferon beta-i a; interferon gamma-i b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peploycinsulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rhizoxin; rhizoxin d; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; thymitaq; tiazofurin; tirapazamine; tomudex; top53; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadenosine; 2' deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; cisplatin; carboplatin; ormaplatin; oxaliplatin; C1-973; DWA 2114R; JM216; JM335; Bis(platinum); tomudex; azacitidine; cytarabine; gemcitabine; 6-mercaptopurine; 6-thioguanine; hypoxanthine; teniposide 9-amino camptothecin; topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-hydroxyphenyl) retinamide; 13-cis retinoic acid; 3-methyl TTNEB; 9-cis retinoic acid; fludarabine (2-F-ara-AMP); or 2-chlorodeoxyadenosine (2-Cda).

Other therapeutic compounds that can be conjugated to, admixed with, or administered separately from an antagonistic TNFR2 single-chain polypeptide, antibody, or antigen-binding fragment thereof of the invention in order to treat, prevent, or study the progression of a disease associated with aberrant cell proliferation include, but are not limited to, cytotoxic agents such as 20-pi-1,25 dihydroxyvitamin D3; 5-ethynyluracil; abiraterone; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single-chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Labeled Anti-TNFR2 Polypeptides

In some embodiments, antagonistic TNFR2 single-chain polypeptides, antibodies, or antigen-binding fragments thereof may be conjugated to another molecule (e.g., an epitope tag) for the purpose of purification or detection. Examples of such molecules that are useful in protein purification include those that present structural epitopes capable of being recognized by a second molecule. This is a common strategy that is employed in protein purification by affinity chromatography, in which a molecule is immobilized on a solid support and exposed to a heterogeneous mixture containing a target protein conjugated to a molecule capable of binding the immobilized compound. Examples of epitope tag molecules that can be conjugated to antagonistic TNFR2 single-chain polypeptides, antibodies, or fragments thereof for the purposes of molecular recognition include, without limitation, maltose-binding protein, glutathione-S- transferase, a poly-histidine tag, a FLAG-tag, a myc-tag, human influenza hemagglutinin (HA) tag, biotin, streptavidin. Conjugates containing the epitopes presented by these molecules are capable of being recognized by such complementary molecules as maltose, glutathione, a nickel-containing complex, an anti-FLAG antibody, an anti-myc antibody, an anti-HA antibody, streptavidin, or biotin, respectively. For example, one can purify an antagonistic TNFR2 single-chain polypeptide, antibody, or fragment thereof of the invention that has been conjugated to an epitope tag from a complex mixture of other proteins and biomolecules (e.g., DNA, RNA, carbohydrates, phospholipids, etc) by treating the mixture with a solid-phase resin containing an complementary molecule that can selectively recognize and bind the epitope tag of the antagonistic anti-TNFR2 antibody or fragment thereof. Examples of solid-phase resins include agarose beads, which are compatible with purifications in aqueous solution.

An antagonistic TNFR2 polypeptide of the invention can also be covalently appended to a fluorescent molecule, e.g., to detect the antibody or antigen-binding fragment thereof by fluorimetry and/or by direct visualization using fluorescence microscopy. Exemplary fluorescent molecules that can be conjugated to polypeptides of the invention include green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, and cyanine. Additional examples of fluorescent molecules suitable for conjugation to polypeptides of the invention are well-known in the art and have been described in detail in, e.g., U.S. Pat. Nos. 7,417,131 and 7,413,874, each of which is incorporated by reference herein.

Antagonistic TNFR2 polypeptides containing a fluorescent molecule are particularly useful for monitoring the cell-surface localization properties of polypeptides, such as single-chain polypeptides, antibodies, and fragments thereof of the invention. For instance, one can expose cultured mammalian cells (e.g., T-reg cells) to antagonistic TNFR2 single-chain polypeptides, antibodies, or fragments thereof of the invention that have been covalently conjugated to a fluorescent molecule and subsequently analyze these cells using conventional fluorescent microscopy techniques known in the art. Confocal fluorescent microscopy is a particularly powerful method for determining cell-surface localization of antagonistic anti-TNFR2 single-chain polypeptides, antibodies, or fragments thereof, as individual planes of a cell can be analyzed in order to distinguish antibodies or fragments thereof that have been internalized into a cell's interior, e.g., by receptor-mediated endocytosis, from those that are bound to the external face of the cell membrane. Additionally, cells can be treated with antagonistic TNFR2 antibodies conjugated to a fluorescent molecule that emits visible light of a particular wavelength (e.g., fluorescein, which fluoresces at about 535 nm) and an additional fluorescent molecule that is known to localize to a particular site on the T-reg cell surface and that fluoresces at a different wavelength (e.g., a molecule that localizes to CD25 and that fluoresces at about 599 nm). The resulting emission patterns can be visualized by confocal fluorescence microscopy and the images from these two wavelengths can be merged in order to reveal information regarding the location of the antagonistic TNFR2 single-chain polypeptide, antibody, or antigen-binding fragment thereof on the T-reg cell surface with respect to other receptors.

Bioluminescent proteins can also be incorporated into a fusion protein for the purposes of detection and visualization of an antagonistic anti-TNFR2 polypeptide. Bioluminescent proteins, such as Luciferase and aequorin, emit light as part of a chemical reaction with a substrate (e.g., luciferin and coelenterazine). Exemplary bioluminescent proteins suitable for use as a diagnostic sequence and methods for their use are described in, e.g., U.S. Pat. Nos. 5,292,658, 5,670,356, 6,171,809, and 7,183,092, each of which is herein incorporated by reference. Antagonistic TNFR2 single-chain polypeptides, antibodies, or fragments thereof labeled with bioluminescent proteins are a useful tool for the detection of antibodies of the invention following an in vitro assay. For instance, the presence of an antagonistic TNFR2 antibody that has been conjugated to a bioluminescent protein can be detected among a complex mixture of additional proteins by separating the components of the mixture using gel electrophoresis methods known in the art (e.g., native gel analysis) and subsequently transferring the separated proteins to a membrane in order to perform a Western blot. Detection of the antagonistic TNFR2 antibody among the mixture of other proteins can be achieved by treating the membrane with an appropriate Luciferase substrate and subsequently visualizing the mixture of proteins on film using established protocols.

The polypeptides (e.g., single-chain polypeptides, antibodies, and fragments thereof) of the invention can also be conjugated to a molecule comprising a radioactive nucleus, such that an antibody or fragment thereof of the invention can be detected by analyzing the radioactive emission pattern of the nucleus. Alternatively, an antagonistic TNFR2 antibody or fragment thereof can be modified directly by incorporating a radioactive nucleus within the antibody during the preparation of the protein. Radioactive isotopes of methionine ($^{35}$S), nitrogen ($^{15}$N), or carbon ($^{13}$C) can be incorporated into antibodies or fragments thereof of the invention by, e.g., culturing bacteria in media that has been supplemented with nutrients containing these isotopes. Optionally, tyrosine derivatives containing a radioactive halogen can be incorporated into an antagonistic TNFR2 antibody or fragment thereof by, e.g., culturing bacterial cells in media supplemented with radiolabeled tyrosine. It has been shown that tyrosine functionalized with a radioactive halogen at the C2 position of the phenol system are rapidly incorporated into elongating polypeptide chains using the endogenous translation enzymes in vivo (U.S. Pat. No. 4,925,651; incorporated herein by reference). The halogens include fluorine, chlorine, bromine, iodine, and astatine. Additionally, antagonistic TNFR2 antibodies or fragments thereof can be modified following isolation and purification from cell culture by functionalizing antibodies or fragments thereof of the invention with a radioactive isotope. The halogens represent a class of isotopes that can be readily incorporated into a purified protein by aromatic substitution at tyrosine or tryptophan, e.g., via reaction of one or more of these residues with an electrophilic halogen species. Examples of radioactive halogen isotopes include $^{18}$F, $^{75}$Br, $^{77}$Br, $^{122}$I, $^{123}$I, $^{124}$I, $^{125}$I, $^{129}$I, $^{131}$I, or $^{211}$At.

Another alternative strategy for the incorporation of a radioactive isotope is the covalent attachment of a chelating group to the antagonistic anti-TNFR2 polypeptide (e.g., single-chain polypeptide, antibody, or fragment thereof). Chelating groups can be covalently appended to an antagonistic TNFR2 polypeptide by attachment to a reactive functional group, such as a thiol, amino group, alcohol, or carboxylic acid. The chelating groups can then be modified to contain any of a variety of metallic radioisotopes, including, without limitation, such radioactive nuclides as $^{125}$I, $^{67}$Ga, $^{111}$In, $^{99}$Tc, $^{169}$Yb, $^{186}$Re, $^{123}$I, $^{124}$I, $^{125}$I, $^{131}$I, $^{99m}$Tc, $^{111}$In, $^{64}$Cu, $^{67}$Cu, $^{186}$Re, $^{188}$Re, $^{177}$Lu, $^{90}$Y, $^{77}$As, $^{72}$As, 86Y, $^{89}$Zr, $^{211}$At, $^{212}$Bi, $^{213}$Bi, or $^{225}$Ac.

In some embodiments, it may be desirable to covalently conjugate the polypeptides (e.g., single-chain polypeptides, antibodies, or fragments thereof) of the invention with a chelating group capable of binding a metal ion from heavy elements or rare earth ions, such as $Gd^{3+}$, $Fe^{3+}$, $Mn^{3+}$, or $Cr^{2+}$. Conjugates containing chelating groups that are coordinated to such paramagnetic metals are useful as in MRI imaging applications. Paramagnetic metals include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). In this way, antagonistic TNFR2 antibodies can be detected by MRI spectroscopy. For instance, one can administer antagonistic TNFR2 antibodies or fragments thereof conjugated to chelating groups bound to paramagnetic ions to a mammalian subject (e.g., a human patient) in order to monitor the distribution of the antibody following administration. This can be achieved by administration of the antibody to a patient by any of the administration routes described herein, such as intravenously, and subsequently analyzing the location of the administered antibody by recording an MRI of the patient according to established protocols.

Antagonistic TNFR2 polypeptides (e.g., single-chain polypeptides, antibodies, or fragments thereof) can additionally be conjugated to other molecules for the purpose of improving the solubility and stability of the protein in aqueous solution. Examples of such molecules include PEG, PSA, bovine serum albumin (BSA), and human serum albumin (HSA), among others. For instance, one can conjugate an antagonistic TNFR2 antibody or fragment thereof to carbohydrate moieties in order to evade detection of the antibody or fragment thereof by the immune system of the patient receiving treatment. This process of hyperglycosylation reduces the immunogenicity of therapeutic proteins by sterically inhibiting the interaction of the protein with B-cell receptors in circulation. Alternatively, antagonistic TNFR2 antibodies or fragments thereof can be conjugated to molecules that prevent clearance from human serum and improve the pharmacokinetic profile of antibodies of the invention. Exemplary molecules that can be conjugated to or inserted within anti-TNFR2 antibodies or fragments thereof of the invention so as to attenuate clearance and improve the pharmacokinetic profile of these antibodies and fragments include salvage receptor binding epitopes. These epitopes are found within the Fc region of an IgG immunoglobulin and have been shown to bind Fc receptors and prolong antibody half-life in human serum. The insertion of salvage receptor binding epitopes into anti-TNFR2 antibodies or fragments thereof can be achieved, e.g., as described in U.S. Pat. No. 5,739,277; incorporated herein by reference.

Modified Antagonistic TFNR2 Polypeptides

In addition to conjugation to other therapeutic agents and labels for identification or visualization, anti-TNFR2 polypeptides (e.g., single-chain polypeptides, antibodies, or fragments thereof) of the invention can also be modified so as to improve their pharmacokinetic profile, biophysical stability, or inhibitory capacity. For instance, any cysteine residue not involved in maintaining the proper conformation of the anti-TNFR2 antibody or fragment thereof may be substituted with an isosteric or isoelectronic amino acid (e.g., serine) in order to improve the oxidative stability of the molecule and prevent aberrant crosslinking. Conversely, cystine bond(s) may be added to the antibody or fragment thereof to improve its stability (particularly where the antibody is an antibody fragment, such as an Fv fragment). This can be accomplished, e.g., by altering a polynucleotide encoding the antibody heavy and light chains or a polynucleotide encoding an antibody fragment so as to encode one or more additional pairs of cysteine residues that can form disulfide bonds under oxidative conditions in order to reinforce antibody tertiary structure (see, e.g., U.S. Pat. No. 7,422,899; incorporated herein by reference).

Another useful modification that may be made to anti-TNFR2 polypeptides (e.g., single-chain polypeptides, antibodies, or fragments thereof) of the invention includes altering the glycosylation profile of these antibodies and fragments thereof. This can be achieved, e.g., by substituting, inserting, or deleting amino acids in an antagonistic TNFR2 antibody so as to insert or remove a glycosylation site. Glycosylation of antibodies typically occurs in N-linked or O-linked fashion. N-linked glycosylation is a process whereby the attachment of a carbohydrate moiety to an antibody occurs at the side-chain of an asparagine residue. Consensus amino acid sequences for N-linked glycosylation include the tripeptide sequences asparagine-X-serine (NXS) and asparagine-X-threonine (NXT), where X is any amino acid except proline. The insertion of either of these tripeptide sequences in a polypeptide (e.g., an anti-TNFR2 antibody) creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine are also competent substrates for glycoside formation. Addition of glycosylation sites to an anti-TNFR2 antibody can thus be accomplished by altering the amino acid sequence of the antibody (e.g., using recombinant expression techniques as described herein) such that it contains one or more of the above-described tripeptide sequences to promote N-linked glycosylation, or one or more serine or threonine residues to the sequence of the original antibody engender O-linked glycosylation (see, e.g., U.S. Pat. No. 7,422,899; incorporated herein by reference).

In alternative cases, it may be desirable to modify the antibody or fragment thereof of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. For instance, cysteine residues may be introduced in the Fc region of an anti-TNFR2 antibody or fragment thereof (e.g., by recombinant expression techniques as described herein), so as to facilitate additional inter-chain disulfide bond formation in this region. The homodimeric antibody thus generated may have increased conformational constraint, which may foster improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described, for example, in Wolff et al. (Canc. Res., 53:2560-2565, 1993); incorporated herein by reference. Alternatively, an antibody can be engineered which has dual Fc regions and may thereby have enhanced complement lysis and ADCC capabilities (see Stevenson et al. (Anti-Canc. Drug Des., 3:219-230, 1989); incorporated herein by reference).

The serum half-life of anti-TNFR2 polypeptides (e.g., single-chain polypeptides, antibodies, or fragments thereof) of the invention can be improved in some embodiments by incorporating one more amino acid modifications, such as by altering the CH1 or CL region of the Fab domain to introduce a salvage receptor motif, e.g., that found in the two loops of a CH2 domain of an Fc region of an IgG. Such alterations are described, for instance, in U.S. Pat. Nos. 5,869,046 and 6,121,022; incorporated herein by reference. Additional framework modifications can also be made to reduce immunogenicity of the antibody or fragment thereof or to reduce or remove T cell epitopes that reside therein, as described for instance in US2003/0153043; incorporated herein by reference.

Methods of Treatment

Methods of Treating Cell Proliferation Disorders

Antagonistic TNFR2 polypeptides (e.g., single-chain polypeptides, antibodies, or fragments thereof) of the invention are useful therapeutics for the treatment of a wide array of cancers and cell proliferation disorders. Antagonistic TNFR2 polypeptides (e.g., single-chain polypeptides, antibodies, or fragments thereof) can be administered to a mammalian subject, such as a human, suffering from a cell proliferation disorder, such as cancer, e.g., to enhance the effectiveness of the adaptive immune response against the target cancer cells. In particular, antagonistic TNFR2 polypeptides (e.g., single-chain polypeptides, antibodies, or fragments thereof) of the invention can be administered to a mammalian subject, such as a human, to reduce or inhibit T-reg cell growth and activation, which allows tumor-infiltrating T-lymphocytes to localize to cells presenting tumor-associated antigens and to promote cytotoxicity. In addition, polypeptides of the invention may synergize with existing adoptive T-cell therapy platforms, as one of the limitations on the effectiveness of this strategy has been the difficulty of prolonging cytotoxicity of tumor-reactive T-cells following infusion into a mammalian subject (e.g., a human). Polypeptides of the invention may also promote the activity of allogeneic T-lymphocytes, which may express foreign MHC proteins and may be increasingly susceptible to inactivation by the host immune system. For example, antibodies and antigen-binding fragments thereof of the invention can mitigate the T-reg-mediated depletion of tumor-reactive T-cells by suppressing the growth and proliferation of T-reg cells that typically accompanies T-cell infusion. For instance, polypeptides (e.g., single-chain polypeptides, antibodies, or fragments thereof) of the invention may be capable of reducing the growth of a population of T-reg cells by about 50% to about 200% relative to untreated cells (e.g., 50%, 75%, 100%, 125%, 150%, 175%, or 200%). The reduction in cellular growth occurs even in the presence of TNFα. In some embodiments, polypeptides (e.g., single-chain polypeptides, antibodies, or fragments thereof) of the invention may be capable of restricting the growth of a population of T-reg cells in the presence of TNFα to between 90% and 150% relative to untreated cells (e.g., 90%, 100%, 110%, 120%, 130%, 140%, or 150%, as described, e.g., in Example 4). Antagonistic TNFR2 polypeptides (e.g., single-chain polypeptides, antibodies, or fragments thereof) of the invention are also capable of restricting the proliferation of a population of T-reg cells to less than 70% (e.g., 60%, 50%, 40%, 30%, 20%, 10%, 5%, or 1%) of that of an untreated population of T-reg cells. Antagonistic TNFR2 polypeptides (e.g., single-chain polypeptides, antibodies, or fragments thereof) of the invention are also capable of decreasing the survival of a population of T-reg cells by about 10% (e.g., by about 20%, 30%, 40%, or 50%, or more) relative to an untreated population of T-reg cells.

Antagonistic TNFR2 polypeptides of the invention can be administered to a mammalian subject (e.g., a human) suffering from cancer in order to improve the condition of the patient by promoting the immune response against cancer cells and tumorogenic material. Antibodies of the invention can be administered to a subject, e.g., via any of the routes of administration described herein. Polypeptides of the invention can also be formulated with excipients, biologically acceptable carriers, and may be optionally conjugated to, admixed with, or co-administered separately (e.g., sequentially) with additional therapeutic agents, such as anti-cancer agents. Cancers that can be treated by administration of polypeptides (e.g., single-chain polypeptides, antibodies, or fragments thereof) of the invention include such cancers as leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, and throat cancer. Particular cancers that can be treated by administration of antibodies or antigen-binding fragments thereof of the invention include, without limitation, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T-cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

For example, antagonistic TNFR2 polypeptides (e.g., single-chain polypeptides, antibodies, or fragments thereof) of the invention, such as variants of TNFRAB1 and TNFRAB2 having a non-native constant region, e.g., humanized TNFRAB1 and TNFRAB2 antibodies, and fragments thereof (e.g., Fab fragments), can be administered to a patient (e.g., a mammalian patient, such as a human patient) in order to treat Hodgkin's or cutaneous non-Hodgkin's lymphoma, T cell lymphoma, ovarian cancer, colon cancer, multiple myeloma, or renal cell carcinoma.

An anti-TNFR2 polypeptide (e.g., single-chain polypeptide, antibody, or antigen-binding fragment thereof) of the invention can also be co-administered with a therapeutic antibody that exhibits reactivity towards a cancer cell. In this way, antagonistic TNFR2 polypeptides of the invention may synergize not only with the adaptive immune response, e.g., by prolonging T-lymphocyte tumor reactivity, but also with other inhibitors of tumor cell growth. Examples of additional therapeutic antibodies that can be used to treat cancer and other cell proliferation disorders include those that exhibit reactivity with a tumor antigen or a cell-surface protein that is overexpressed on the surface of a cancer cell. Exemplary antibodies that can be admixed, co-administered, or sequentially administered with antagonistic TNFR2 polypeptides of the invention include, without limitation, Trastuzamb (HERCEPTIN®), Bevacizumab (AVASTIN®), Cetuximab (ERBITUX®), Panitumumab (VECTIBIX®), Ipilimumab (YERVOY®), Rituximab (RITUXAN® and MABTHERA®), Alemtuzumab (CAMPATH®), Ofatumumab (ARZERRA®), Gemtuzumab ozogamicin (MYLOTARG®), Brentuximab vedotin (ADCETRIS®), $^{90}$Y-Ibritumomab Tiuxetan (ZEVALIN®), and $^{131}$I-Tositumomab (BEXXAR®), which are described in detail in Scott et al. (Cancer Immun., 12:14-21, 2012); incorporated herein by reference.

A physician having ordinary skill in the art can readily determine an effective amount of an antagonistic TNFR2 polypeptide for administration to a mammalian subject (e.g., a human) in need thereof. For example, a physician could start prescribing doses of a polypeptide of the invention at levels lower than that required in order to achieve the desired therapeutic effect and gradually increase the dosage until the desired effect is achieved. Alternatively, a physician may begin a treatment regimen by administering an antagonistic TFNR2 antibody or antibody fragment at a high dose and subsequently administer progressively lower doses until a therapeutic effect is achieved (e.g., a reduction in the volume of one or more tumors, a decrease in the population of T-reg cells, or remission of a cell proliferation disorder). In general, a suitable daily dose of an antibody or antigen-binding fragment thereof of the invention will be an amount of the antibody which is the lowest dose effective to produce a therapeutic effect. A single-chain polypeptide, antibody, or antigen-binding fragment thereof of the invention may be administered by injection, e.g., by intravenous, intramuscular, intraperitoneal, or subcutaneous injection, optionally proximal to the site of the target tissue (e.g., a tumor). A daily dose of a therapeutic composition of an antibody or antigen-binding fragment thereof of the invention may be administered as a single dose or as two, three, four, five, six or more doses administered separately at appropriate intervals throughout the day, week, month, or year, optionally, in unit dosage forms. While it is possible for an antibody or fragment thereof of the invention to be administered alone, it may also be administered as a pharmaceutical formulation in combination with excipients, carriers, and optionally, additional therapeutic agents.

Polypeptides (e.g., single-chain polypeptides, antibodies, or fragments thereof) of the invention can be monitored for their ability to attenuate the progression of a cell proliferation disease, such as cancer, by any of a variety of methods known in the art. For instance, a physician may monitor the response of a mammalian subject (e.g., a human) to treatment with an antibody, antibody fragment, or single-chain polypeptide of the invention by analyzing the volume of one or more tumors in the patient. For example, polypeptides (e.g., single-chain polypeptides, antibodies, or fragments thereof) of the invention may be capable of reducing tumor volume by between 1% and 100% (e.g., 1%, 5%, 10%, 20%, 30%, 40%, 50%, 60%, 70%, 80%, 90%, 95%, 99%, or 100%). Alternatively, a physician may monitor the responsiveness of a subject (e.g., a human) t to treatment with antagonistic TNFR2 single-chain polypeptides, antibodies, or antigen-binding fragments thereof of the invention by analyzing the T-reg cell population in the lymph of a particular subject. For instance, a physician may withdraw a sample of blood from a mammalian subject (e.g., a human) and determine the quantity or density of a population of T-reg cells (e.g., CD4+CD25+FOXP3+T-reg cells or CD17+ T-reg cells) using established procedures, such as fluorescence activated cell sorting.

Methods of Treating Infectious Diseases

Antagonistic TNFR2 polypeptides (e.g., single-chain polypeptides, antibodies, or fragments thereof) of the invention can also be used for treating infectious diseases, such as those caused by any one or more of a virus, a bacterium, a fungus, or a parasite. For instance, antagonistic TNFR2 polypeptides (e.g., single-chain polypeptides, antibodies, or fragments thereof) can be administered to a mammalian subject (e.g., a human) suffering from an infectious disease in order to treat the disease, as well as to alleviate one or more symptoms of the disease.

For example, antagonistic TNFR2 polypeptides (e.g., single-chain polypeptides, antibodies, or fragments thereof) of the invention can be used for treating, or alleviating one or more symptoms of, viral infections in a mammalian subject, such as a human, that are caused by, e.g., a member of the Flaviviridae family (e.g., a member of the *Flavivirus, Pestivirus,* and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parané virus, Pichinde virus, Pirital virus, Sabia virus, Tacaribe virus, Tamiami virus, Whitewater Arroyo virus, Chapare virus, and Lujo virus; a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxviridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively); Friend Leukemia Virus; and transmissible spongiform encephalopathy, such as chronic wasting disease. Particularly, methods of the invention include administering an antagonistic TNFR2 antibody (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1 and/or TNFRAB2) to a human in order to treat an HIV infection (such as a human suffering from AIDS).

Antagonistic TNFR2 polypeptides (e.g., single-chain polypeptides, antibodies, or fragments thereof) of the invention can also be used for treating, or alleviating one or more symptoms of, bacterial infections in a mammalian subject (e.g., a human). Examples of bacterial infections that may be treated by administration of an antagonistic TNFR2 antibody or antibody fragment of the invention include, without limitation, those caused by bacteria within the genera *Streptococcus, Bacillus, Listeria, Corynebacterium, Nocardia, Neisseria, Actinobacter, Moraxella, Enterobacteriacece* (e.g., *E. coli*, such as O157:H7), *Pseudomonas* (such as *Pseudomonas aeruginosa*), *Escherichia, Klebsiella, Serratia, Enterobacter, Proteus, Salmonella, Shigella, Yersinia, Haemophilus, Bordetella* (such as *Bordetella pertussis*), *Legionella, Pasteurella, Francisella, Brucella, Bartonella, Clostridium, Vibrio, Campylobacter, Staphylococcus, Mycobacterium* (such as *Mycobacterium tuberculosis* and *Mycobacterium avium paratuberculosis*, and *Helicobacter* (such as *Helicobacter pylori* and *Helicobacter hepaticus*). Particularly, methods of the invention include administering an antagonistic TNFR2 antibody (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1 and/or TNFRAB2) to a human or a non-human mammal in order to treat a *Mycobacterium tuberculosis* infection. Particular methods of the invention include administering an antagonistic TNFR2 antibody (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1 and/or TNFRAB2) to bovine mammals or bison in order to treat a *Mycobacterium tuberculosis* infection. Additionally, methods of the invention include administering an antagonistic TNFR2 antibody (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1 and/or TNFRAB2) to a human or a non-human mammal in order to treat a *Mycobacterium avium* paratuberculosis infection. Particular methods of the invention include administering an antagonistic TNFR2 antibody (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1 and/or TNFRAB2) to bovine mammals or bison in order to treat a *Mycobacterium avium* paratuberculosis infection.

Antagonistic TNFR2 polypeptides (e.g., single-chain polypeptides, antibodies, or fragments thereof) of the invention can also be administered to a mammalian subject (e.g., a human) for treating, or alleviating one or more symptoms of, parasitic infections caused by a protozoan parasite (e.g., an intestinal protozoa, a tissue protozoa, or a blood protozoa) or a helminthic parasite (e.g., a nematode, a helminth, an adenophorea, a secementea, a trematode, a fluke (blood flukes, liver flukes, intestinal flukes, and lung flukes), or a cestode). Exemplary protozoan parasites that can be treated according to the methods of the invention include, without limitation, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Leishmania major, Toxoplasma gondii, Plasmodium vivax, Plasmodium ovale, Plasmodium malariae, Plasmodium falciparum, Plasmodium yoelli, Trichomonas vaginalis*, and *Histomonas meleagridis*. Exemplary helminthic parasites include *richuris trichiura, Ascaris lumbricoides, Enterobius vermicularis, Ancylostoma duodenale, Necator americanus, Strongyloides stercoralis, Wuchereria bancrofti*, and *Dracunculus medinensis, Schistosoma mansoni, Schistosoma haematobium, Schistosoma japonicum, Fasciola hepatica, Fasciola gigantica, Heterophyes, Paragonimus westermani, Taenia solium, Taenia saginata, Hymenolepis nana*, and *Echinococcus granulosus*. Additional parasitic infections that can be treated according to the methods of the invention include *Onchocercas volvulus*.

Antagonistic TNFR2 polypeptides (e.g., single-chain polypeptides, antibodies, or fragments thereof) can also be administered to a mammalian subject (e.g., a human) in order to treat, or to alleviate one or more symptoms of, fungal infections. Examples of fungal infections that may be treated according to the methods of the invention include, without limitation, those caused by, e.g., *Aspergillus, Candida, Malassezia, Trichosporon, Fusarium, Acremonium, Rhizopus, Mucor, Pneumocystis*, and *Absidia*. Exemplary fungal infections that can be treated according to the methods of the invention also include *Pneumocystis carinii, Paracoccidioides brasiliensis* and *Histoplasma capsulatum*.

Pharmaceutical Compositions

Therapeutic compositions containing an antagonistic TNFR2 polypeptide, such as a single-chain polypeptide, antibody, or antigen-binding fragment thereof of the invention can be prepared using methods known in the art. For example, such compositions can be prepared using, e.g., physiologically acceptable carriers, excipients or stabilizers (*Remington's Pharmaceutical Sciences* 16th edition, Osol, A. Ed. (1980); incorporated herein by reference), and in a desired form, e.g., in the form of lyophilized formulations or aqueous solutions. The compositions can also be prepared so as to contain the active agent (e.g., an antagonistic anti-TNFR2 antibody or fragment thereof) at a desired concentration. For example, a pharmaceutical composition of the invention may contain at least 10% (e.g., 10%, 20%, 30%, 40%, 50%, 60%, 70%, 80%, 90%, 95%, 97%, 98%, 99%, 99.5%, 99.9%, or 100%) active agent by weight (w/w).

Additionally, an active agent (e.g., an antagonistic TNFR2 antibody or fragment thereof of the invention) that can be incorporated into a pharmaceutical formulation can itself have a desired level of purity. For example, an antibody or antigen-binding fragment thereof of the invention may be characterized by a certain degree of purity after isolating the antibody from cell culture media or after chemical synthesis, e.g., of a single-chain antibody fragment (e.g., scFv) by established solid-phase peptide synthesis methods or native chemical ligation as described herein. An antagonistic TNFR2 antibody of the invention may be at least 10% pure prior to incorporating the antibody into a pharmaceutical composition (e.g., 10%, 20%, 30%, 40%, 50%, 60%, 70%, 80%, 90%, 95%, 97%, 98%, 99%, 99.5%, 99.9%, 99.99%, or 100% pure).

Pharmaceutical compositions of anti-TNFR2 polypeptides (e.g., single-chain polypeptides, antibodies, or fragments thereof) of the invention can be prepared for storage as lyophilized formulations or aqueous solutions by mixing the antibody having the desired degree of purity with optional pharmaceutically acceptable carriers, excipients or stabilizers typically employed in the art, e.g., buffering agents, stabilizing agents, preservatives, isotonifiers, non-ionic detergents, antioxidants, and other miscellaneous additives. See, e.g., Remington's Pharmaceutical Sciences, 16th edition (Osol, ed. 1980; incorporated herein by reference). Such additives must be nontoxic to the recipients at the dosages and concentrations employed.

Buffering Agents

Buffering agents help to maintain the pH in the range which approximates physiological conditions. They can be present at concentration ranging from about 2 mM to about 50 mM. Suitable buffering agents for use with antagonistic TNFR2 polypeptides (e.g., single-chain polypeptides, antibodies, or fragments thereof) of the invention include both organic and inorganic acids and salts thereof such as citrate buffers {e.g., monosodium citrate-disodium citrate mixture, citric acid-trisodium citrate mixture, citric acid-monosodium citrate mixture, etc.), succinate buffers {e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers {e.g., fumaric acid-monosodium fumarate mixture, fumaric acid-disodium fumarate mixture, monosodium fumarate-disodium fumarate mixture, etc.), gluconate buffers {e.g., gluconic acid-sodium glyconate mixture, gluconic acid-sodium hydroxide mixture, gluconic acid-potassium glyuconate mixture, etc.), oxalate buffer {e.g., oxalic acid-sodium oxalate mixture, oxalic acid-sodium hydroxide mixture, oxalic acid-potassium oxalate mixture, etc.), lactate buffers {e.g., lactic acid-sodium lactate mixture, lactic acid-sodium hydroxide mixture, lactic acid-potassium lactate mixture, etc.) and acetate buffers {e.g., acetic acid-sodium acetate mixture, acetic acid-sodium hydroxide mixture, etc.). Additionally, phosphate buffers, histidine buffers and trimethylamine salts such as Tris can be used.

Preservatives

Preservatives can be added to a composition of the invention to retard microbial growth, and can be added in amounts ranging from 0.2%-1% (w/v). Suitable preservatives for use with antagonistic TNFR2 polypeptides (e.g., single-chain polypeptides, antibodies, or fragments thereof) of the invention include phenol, benzyl alcohol, meta-cresol, methyl paraben, propyl paraben, octadecyldimethylbenzyl ammonium chloride, benzalconium halides {e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the invention and include polhydric sugar alcohols, for example trihydric or higher sugar alcohols, such as glycerin, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Detergents

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

Other Pharmaceutical Carriers

Alternative pharmaceutically acceptable carriers that can be incorporated into a composition of the invention may include dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. A composition containing an antagonistic TNFR2 polypeptide of the invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

Compositions for Combination Therapy

Pharmaceutical compositions of the invention may optionally include more than one active agent. For instance, compositions of the invention may contain an antagonistic TNFR2 polypeptide, such as a single-chain polypeptide, antibody, or fragment thereof conjugated to, admixed with, or administered separately from another pharmaceutically active molecule, e.g., a cytotoxic agent, an antibiotic, or a T-lymphocyte (e.g., a gene-edited T-lymphocyte for use in CAR-T therapy). For instance, an antagonistic TNFR2 single-chain polypeptide, antibody, antibody fragment, or therapeutic conjugate thereof (e.g., a drug-antibody conjugate described herein), may be admixed with one or more additional active agents that can be used to treat cancer or another cell proliferation disorder (e.g., neoplasm). Alternatively, pharmaceutical compositions of the invention may be formulated for co-administration or sequential administration with one or more additional active agents that can be used to treat cancer or other cell proliferation disorders. Examples of additional active agents that can be used to treat cancer and other cell proliferation disorders and that can be conjugated to, admixed with, or administered separately from an antagonistic TNFR2 single-chain polypeptide, antibody, or antibody fragment of the invention include cytotoxic agents (e.g., those described herein), as well as antibodies that exhibit reactivity with a tumor antigen or a cell-surface protein that is overexpressed on the surface of a cancer cell. Exemplary antibodies that can be conjugated to, admixed with, or administered separately from antagonistic TNFR2 antibodies of the invention include, without limitation, Trastuzamb (HERCEPTIN®), Bevacizumab (AVASTIN®), Cetuximab (ERBITUX®), Panitumumab (VECTIBIX®), Ipilimumab (YERVOY®), Rituximab (RITUXAN® and MABTHERA®), Alemtuzumab (CAMPATH®), Ofatumumab (ARZERRA®), Gemtuzumab ozogamicin (MYLOTARG®), Brentuximab vedotin (ADCETRIS®), $^{90}$Y-Ibritumomab Tiuxetan (ZEVALIN®), and $^{131}$I-Tositumomab (BEXXAR®), which are described in detail in Scott et al. (Cancer Immun., 12:14-21, 2012); incorporated herein by reference.

Additional agents that can be conjugated to, admixed with, or administered separately from antagonistic TNFR2 polypeptides (e.g., single-chain polypeptides, antibodies, or fragments thereof) of the invention include T-lymphocytes that exhibit reactivity with a specific antigen associated with a particular pathology. For instance, antagonistic TNFR2 polypeptides (e.g., single-chain polypeptides, antibodies, or fragments thereof) of the invention can be formulated for administration with a T-cell that expresses a chimeric antigen receptor (CAR-T) in order to treat a cell proliferation disorder, such as a cancer described herein. Antagonistic TNFR2 polypeptides (e.g., single-chain polypeptides, antibodies, or fragments thereof) can synergize with CAR-T therapy by preventing T-reg cells from deactivating T-lymphocytes that have been genetically modified so as to express tumor-reactive antigen receptors. In this way, CAR-T cells can be administered to a patient prior to, concurrently with, or after administration of an antagonistic TNFR2 single-chain polypeptide, antibody, or antigen-binding fragment thereof in order to treat a mammalian subject (e.g., a human) suffering from a cell proliferation disorder, such as cancer.

CAR-T therapy is a particularly robust platform for targeting cancer cells in view of the ability to genetically engineer T-lymphocytes to express an antigen receptor specific to a tumor-associated antigen. For instance, identification of antigens overexpressed on the surfaces of tumors and other cancer cells can inform the design and discovery of chimeric T-cell receptors, which are often composed of cytoplasmic and transmembrane domains derived from a naturally-occurring T-cell receptor operatively linked to an extracellular scFv fragment that specifically binds to a particular antigenic peptide. T-cells can be genetically modified in order to express an antigen receptor that specifically binds to a particular tumor antigen by any of a variety of genome editing techniques described herein or known in the art. Exemplary techniques for modifying a T-cell genome so as to incorporate a gene encoding a chimeric antigen receptor include the CRISPER/Cas, zinc finger nuclease, TALEN, ARCUS™ platforms described herein. Methods for the genetic engineering of CAR-T lymphocytes have been described, e.g., in WO 2014/127261, WO 2014/039523, WO 2014/099671, and WO 20120790000; the disclosures of each of which are incorporated by reference herein.

CAR-T cells useful in the compositions and methods of the invention include those that have been genetically modified such that the cell does not express the endogenous T-cell receptor. For instance, a CAR-T cell may be modified by genome-editing techniques, such as those described herein, so as to suppress expression of the endogenous T-cell receptor in order to prevent graft-versus-host reactions in a patient receiving a CAR-T infusion. Additionally or alternatively, CAR-T cells can be genetically modified so as to reduce the expression of one or more endogenous MHC proteins. This is a particularly useful technique for the infusion of allogeneic T-lymphocytes, as recognition of foreign MHC proteins represents one mechanism that promotes allograft rejection. One of skill in the art can also modify a T-lymphocyte so as to suppress the expression of immune suppressor proteins, such as programmed cell death protein 1 (PD-1) and cytotoxic T-lymphocyte-associated protein 4 (CTLA-4). These proteins are cell surface receptors that, when activated, attenuate T-cell activation. Infusion of CAR-T cells that have been genetically modified so as to diminish the expression of one or more immunosuppressor proteins represents one strategy that can be used to prolong the T-lymphocyte-mediated cytotoxicity in vivo.

In addition to deleting specific genes, one can also modify CAR-T cells in order to express a T-cell receptor with a desired antigen specificity. For instance, one can genetically modify a T-lymphocyte in order to express a T-cell receptor that specifically binds to a tumor-associated antigen in order to target infused T-cells to cancerous cells. An exemplary T-cell receptor that may be expressed by a CAR-T cell is one that binds PD-L1, a cell surface protein that is often overexpressed on various tumor cells. As PD-L1 activates PD-1 on the surface of T-lymphocytes, targeting this tumor antigen with CAR-T therapy can synergize with antagonistic TNFR2 antibodies or antibody fragments of the invention in order to increase the duration of an immune response mediated by a T-lymphocyte in vivo. CAR-T cells can also be modified so as to express a T-cell receptor that specifically binds an antigen associated with one or more infectious disease, such as an antigen derived from a viral protein, a bacterial cell, a fungus, or other parasitic organism.

Other pharmaceutical compositions of the invention include those that contain an antagonistic TNFR2 antibody or antibody fragment, interferon alpha, and/or one or more antibiotics that can be administered to a patient (e.g., a human patient) suffering from an infectious disease. For instance, an antagonistic TNFR2 antibody or antibody fragment can be conjugated to, admixed with, or administered separately from an antibiotic useful for treating one or more infectious diseases, such as amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, meropenem, cefadroxil, cefazolin, cefazlexin, cefaclor, cefoxitin, cefprozil, cefuroxime, cefdinir, cefditoren, cefoperazone, clindamycin, lincomycin, daptomycin, erythromycin, linezolid, torezolid, amoxicillin, ampicillin, bacitracin, ciprofloxacin, doxycycline, and tetracycline, among others.

Blood-Brain Barrier Penetration

In certain embodiments, antagonistic TNFR2 polypeptides (e.g., single-chain polypeptides, antibodies, or fragments thereof) of the invention can be formulated to ensure proper distribution in vivo.

For example, the blood-brain barrier (BBB) excludes many highly hydrophilic compounds. To ensure that the therapeutic compositions of the invention cross the BBB (if desired), they can be formulated, for example, in liposomes. Methods of manufacturing liposomes have been described, e.g., U.S. Pat. Nos. 4,522,811; 5,374,548; and 5,399,331. The liposomes may comprise one or more moieties that are selectively transported into specific cells or organs, thereby enhancing targeted drug delivery (see, e.g., V. V. Ranade (*J. Clin. Pharmacol.* 29:685, 1989)). Exemplary targeting moieties include, e.g., folate or biotin (see, e.g., U.S. Pat. No. 5,416,016); mannosides (Umezawa et al. (Biochem. Biophys. Res. Commun. 153:1038, 1988)); antibodies (P. G. Bloeman et al. (FEBS Lett. 357:140, 1995); M. Owais et al. (Antimicrob. Agents Chemother. 39:180, 1995)); surfactant protein A receptor (Briscoe et al. (Am. J. Physiol. 1233:134, 1995)); the disclosures of each of which are incorporated herein by reference.

Routes of Administration and Dosing

Antagonistic TNFR2 polypeptides (e.g., single-chain polypeptides, antibodies, or fragments thereof) of the invention can be administered to a mammalian subject (e.g., a human) by a variety of routes such as orally, transdermally, subcutaneously, intranasally, intravenously, intramuscularly, intraocularly, intratumorally, parenterally, topically, intrathecally and intracerebroventricularly. The most suitable route for administration in any given case will depend on the particular antibody or antigen-binding fragment administered, the patient, pharmaceutical formulation methods, administration methods (e.g., administration time and administration route), the patient's age, body weight, sex, severity of the diseases being treated, the patient's diet, and the patient's excretion rate.

The effective dose of an anti-TNFR2 single-chain polypeptide, antibody, or antigen-binding fragment thereof of the invention can range from about 0.0001 to about 100 mg/kg of body weight per single (e.g., bolus) administration, multiple administrations or continuous administration, or to achieve a serum concentration of 0.0001-5000 µg/mL serum concentration per single (e.g., bolus) administration, multiple administrations or continuous administration, or any effective range or value therein depending on the condition being treated, the route of administration and the age, weight, and condition of the subject. In certain embodiments, e.g., for the treatment of cancer, each dose can range from about 0.0001 mg to about 500 mg/kg of body weight. For instance, a pharmaceutical composition of the invention may be administered in a daily dose in the range of 0.001-100 mg/kg (body weight). The dose may be administered one or more times (e.g., 2-10 times) per day, week, month, or year to a mammalian subject (e.g., a human) in need thereof.

Therapeutic compositions can be administered with medical devices known in the art. For example, in an embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the invention include: U.S. Pat. No. 4,487,603, which discloses an implantable micro-infusion pump for dispensing medication at a controlled rate; U.S. Pat. No.

4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Kits Containing Antagonistic Anti-TNFR2 Polypeptides

This invention also includes kits that contain antagonistic anti-TNFR2 polypeptides (e.g., single-chain polypeptides, antibodies, or fragments thereof). The kits provided herein may contain any of the antagonistic TNFR2 polypeptides described above, as well as any of the polynucleotides encoding these polypeptides, vectors containing these polypeptides, or cells engineered to express and secrete polypeptides of the invention (e.g., prokaryotic or eukaryotic cells). A kit of this invention may include reagents that can be used to produce the compositions of the invention (e.g., antagonistic anti-TNFR2 polypeptides, such as single-chain polypeptides, antibodies, or fragments thereof, conjugates containing antagonistic anti-TNFR2 polypeptides, polynucleotides encoding antagonistic anti-TNFR2 polypeptides, vectors containing these polypeptides). Optionally, kits of the invention may include reagents that can induce the expression of antagonistic TNFR2 antibodies within cells (e.g., mammalian cells), such as doxycycline or tetracycline. In other cases, a kit of the invention may contain a compound capable of binding and detecting a fusion protein that contains an antagonistic TNFR2 polypeptide and an epitope tag. For instance, in such cases a kit of the invention may contain maltose, glutathione, a nickel-containing complex, an anti-FLAG antibody, an anti-myc antibody, an anti-HA antibody, biotin, or streptavidin.

Kits of the invention may also include reagents that are capable of detecting an antagonistic TNFR2 single-chain polypeptide, antibody, or fragment thereof directly. Examples of such reagents include secondary antibodies that selectively recognize and bind particular structural features within the Fc region of an anti-TNFR2 antibody of the invention. Kits of the invention may contain secondary antibodies that recognize the Fc region of an antagonistic TNFR2 antibody and that are conjugated to a fluorescent molecule. These antibody-fluorophore conjugates provide a tool for analyzing the localization of antagonistic anti-TNFR2 antibodies, e.g., in a particular tissue or cultured mammalian cell using established immunofluorescence techniques. In some embodiments, kits of the invention may include additional fluorescent compounds that exhibit known sub-cellular localization patterns. These reagents can be used in combination with another antibody-fluorophore conjugate, e.g., one that specifically recognizes a different receptor on the cell surface in order to analyze the localization of an anti-TNFR2 antibody relative to other cell-surface proteins.

Kits of the invention may also contain a reagent that can be used for the analysis of a patient's response to treatment by administration of antagonistic TNFR2 polypeptides (e.g., single-chain polypeptides, antibodies, or fragments thereof) of the invention. For instance, kits of the invention may include an antagonistic TNFR2 polypeptide, such as a single-chain polypeptide, antibody, or antibody fragment, and one or more reagents that can be used to determine the quantity of T-reg cells in a blood sample withdrawn from a subject (e.g., a human) that is undergoing treatment with an antibody of the invention. Such a kit may contain, e.g., antibodies that selectively bind cell-surface antigens presented by T-reg cells, such as CD4 and CD25. Optionally, these antibodies may be labeled with a fluorescent dye, such as fluorescein or tetramethylrhodamine, in order to facilitate analysis of a population of T-reg cells by fluorescence-activated cell sorting (FACS) methods known in the art. Kits of the invention may optionally contain one or more reagents that can be used to quantify a population of tumor-reactive T-lymphocytes in order to determine the effectiveness of an antagonistic TNFR2 polypeptide of the invention in restoring tumor-infiltrating lymphocyte proliferation. For instance, kits of the invention may contain an antibody that selectively binds cell-surface markers on the surface of a cytotoxic T-cell, such as CD8 or CD3. Optionally, these antibodies may be labeled with fluorescent molecules so as to enable quantitation by FACS analysis.

A kit of the invention may also contain one or more reagents useful for determining the affinity and selectivity of an antagonistic TNFR2 single-chain polypeptide, antibody, or antigen-binding fragment thereof of the invention for one or more peptides derived from TNFR2 (e.g., a peptide containing the sequence of any one of SEQ ID NOs: 11, 19, 20, and 34-117, or a peptide containing between about 10 and about 30 continuous or discontinuous amino acids between positions 80 and 130 of SEQ ID NO: 7). For instance, a kit may contain an antagonistic TNFR2 antibody and one or more reagents that can be used in an ELISA assay to determine the $K_D$ of an antibody of the invention for one or more peptides that present a TNFR2 epitope in a conformation similar to that of the epitope in the native protein. A kit may contain, e.g., a microtiter plate containing wells that have been previously conjugated to avidin, and may contain a library of TNFR2-derived peptides, each of which conjugated to a biotin moiety. Such a kit may optionally contain a secondary antibody that specifically binds to the Fc region of an antagonistic TNFR2 antibody of the invention, and the secondary antibody may be conjugated to an enzyme (e.g., horseradish peroxidase) that catalyzes a chemical reaction that results in the emission of luminescent light.

Kits of the invention may also contain antagonistic TNFR2 polypeptides (e.g., single-chain polypeptides, antibodies, or fragments thereof) of the invention and reagents that can be conjugated to such a polypeptide, including those previously described (e.g., a cytotoxic agent, a fluorescent molecule, a bioluminescent molecule, a molecule containing a radioactive isotope, a molecule containing a chelating group bound to a paramagnetic ion, etc). These kits may additionally contain instructions for how the conjugation of an antagonistic TNFR2 polypeptide of the invention to a second molecule, such as those described above, can be achieved.

A kit of the invention may also contain a vector containing a polynucleotide that encodes an antagonistic anti-TNFR2 single-chain polypeptide, antibody, or fragment thereof, such as any of the vectors described herein. Alternatively, a kit may include mammalian cells (e.g., CHO cells) that have been genetically altered to express and secrete antagonistic TNFR2 polypeptides (e.g., single-chain polypeptides, antibodies, or fragments thereof) from the nuclear genome of the cell. Such a kit may also contain instructions describing how expression of the antagonistic TNFR2 single-chain polypeptide, antibody, or fragment thereof from a polynucleotide can be induced, and may additionally include reagents (such as, e.g., doxycycline or tetracycline) that can be used to promote the transcription of these polynucleotides. Such kits may be useful for the manufacture of antagonistic TNFR2 antibodies or antigen-binding fragments thereof of the invention.

Other kits of the invention may include tools for engineering a prokaryotic or eukaryotic cell (e.g., a CHO cell or a BL21(DE3) *E. coli* cell) so as to express and secrete an antagonistic TNFR2 single-chain polypeptide, antibody, or fragment thereof of the invention from the nuclear genome of the cell. For example, a kit may contain CHO cells stored in an appropriate media and optionally frozen according to methods known in the art. The kit may also provide a vector containing a polynucleotide that encodes a nuclease (e.g., such as the CRISPER/Cas, zinc finger nuclease, TALEN, ARCUS™ nucleases described herein) as well as reagents for expressing the nuclease in the cell. The kit can additionally provide tools for modifying the polynucleotide that encodes the nuclease so as to enable one to alter the DNA sequence of the nuclease in order to direct the cleavage of a specific target DNA sequence of interest. Examples of such tools include primers for the amplification and site-directed mutagenesis of the polynucleotide encoding the nuclease of interest. The kit may also include restriction enzymes that can be used to selectively excise the nuclease-encoding polynucleotide from the vector and subsequently re-introduce the modified polynucleotide back into the vector once the user has modified the gene. Such a kit may also include a DNA ligase that can be used to catalyze the formation of covalent phosphodiester linkages between the modified nuclease-encoding polynucleotide and the target vector. A kit of the invention may also provide a polynucleotide encoding an antagonistic anti-TNFR2 single-chain polypeptide, antibody, or fragment thereof, as well as a package insert describing the methods one can use to selectively cleave a particular DNA sequence in the genome of the cell in order to incorporate the polynucleotide encoding an antagonistic TNFR2 polypeptide into the genome at this site. Optionally, the kit may provide a polynucleotide encoding a fusion protein that contains an antagonistic TNFR2 single-chain polypeptide, antibody, or fragment thereof and an additional polypeptide, such as, e.g., those described herein.

Examples

The following examples are put forth so as to provide those of ordinary skill in the art with a description of how the compositions and methods claimed herein are performed, made, and evaluated, and are intended to be purely exemplary of the invention and are not intended to limit the scope of what the inventor regards as her invention.

Example 1. Mapping the Discrete Epitopes within TNFR2 that Interact with TNFRAB1 and TNFRAB2

Libraries of linear, cyclic, and bicyclic peptides derived from human TNFR2 were screened for distinct sequences within the protein that exhibit high affinity for TNFR2 antibody TNFRAB2. In order to screen conformational epitopes within TFNR2, peptides from distinct regions of the primary protein sequence were conjugated to one another to form chimeric peptides. These peptides contained cysteine residues at strategic positions within their primary sequences (see, e.g., FIG. 3, SEQ ID NOs: 34-117 and 134-252). This facilitated an intramolecular cross-linking strategy that was used to constrain individual peptides to a one of a wide array of three dimensional conformations. Unprotected thiols of cysteine residues were cross-linked via nucleophilic substitution reactions with divalent and trivalent electrophiles, such as 2,6-bis(bromomethyl)pyridine and 1,3,5-tris(bromomethyl)benzene, so as to form conformationally restricted cyclic and bicyclic peptides, respectively. In this way, peptides containing unique combinations of amino acids from disparate regions of the TNFR2 primary sequence were constrained so as to structurally pre-organize epitopes that may resemble those presented in the native TNFR2 tertiary structure. Libraries containing these peptides were screened by immobilizing peptides to distinct regions of a solid surface and treating the surface in turn with TNFRAB1 or TNFRAB2, secondary antibody conjugated to horseradish peroxidase (HRP), and HRP substrate (2,2'-azino-di-3-ethylbenzthiazoline sulfonate) in the presence of hydrogen peroxide. The solid surface was washed in between treatment with successive reagents so as to remove excess or non-specifically bound materials. The luminescence of each region of each surface was subsequently analyzed using a charge coupled device (CCD)—camera and an image processing system.

The "Constrained Libraries of Peptides on Surfaces" (CLIPS) platform starts with the conversion of the target protein, e.g., TNFR2, into a library of up to 10,000 overlapping peptide constructs, using a combinatorial matrix design (Timmerman et al., J. Mol. Recognit., 20: 283-29, 2007). On a solid carrier, a matrix of linear peptides is synthesized, which are subsequently shaped into spatially defined CLIPS constructs. Constructs representing multiple parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail. The raw luminescence data obtained from these ELISA experiments are reported in FIGS. 3A and 3B for TNFRAB1 and TNFRAB2, respectively. These results informed the analysis of epitopes present on the surface of TNFR2 that bind antagonistic TNFR2 antibodies. Structural models of TNFR2 illustrating epitopes that bind such antibodies are shown in FIGS. 4 and 15A-15C.

Peptide Synthesis

To reconstruct epitopes of the target molecule a library of peptides was synthesized. An amino functionalized polypropylene support was obtained by grafting a proprietary hydrophilic polymer formulation via reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS® liquid handling stations (Perkin Elmer). CLIPS technology allows one to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the CLIPS template (2,6-bis (bromomethyl)pyridine) is dissolved in ammonium bicarbonate (20 mM, pH 7.8)/acetonitrile (1:3(v/v)). This solution is added to a surface-bound peptide array. The CLIPS template will react with side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of H$_2$O and sonicated in disrupt-buffer containing 1% SDS/0.1% beta-mercaptoethanol in PBS (pH 7.2) at 70° C. for 30 minutes, followed by sonication in H$_2$O for another 45 minutes.

Analysis of Binding Affinities of Antagonistic TNFR2 Antibodies by Surface Plasmon Resonance The affinities of antagonistic TNFR2 antibodies for recombinant human TNFR2 were measured using BIA-CORE™ Analysis Services (Precision Antibody). Briefly, the antibody was biotinylated at a 5:1 stoichiometric ratio using biotinyl-LC-LC-NOSE (Thermo-Fisher) in PBS. Excess biotinylation reagent was removed by centrifugation chromatography and the biotinylated antibody was captured on 3000 RU of streptavidin surface to a level of 100 RU. Theoretical maximum of signal with TNFR2 with that level of antibody capture was 26 RU and that signal was reached with a preliminary experiment using 500 nM TNFR2 in the running buffer. Analysis of the kinetics of antigen binding was performed at a flow of 60 µL/min with 2 min injections. Antibodies were injected at a concentration of 1 mg/ml to the final capture of 100 RU. The instrument used was BIACORE™ 3000 with the BioCap chip (GE Healthcare). Double reference method was used for analysis. Reference channel contained the identical level of streptavidin. The thermodynamic and kinetic parameters of the binding of antagonistic TNFR2 antibodies TNFRAB1 and TNFRAB2 to TNFR2 as measured using this assay are shown in FIG. 13A.

ELISA Screening

The binding of antibody to each of the synthesized peptides was tested in an ELISA format. Surface-immobilized peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 2 µl/ml of 3 percent H$_2$O$_2$ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. The results are quantified and stored into the Peplab database. Occasionally a well contains an air-bubble resulting in a false-positive value, the cards are manually inspected and any values caused by an air-bubble are scored as 0.

To verify the quality of the synthesized peptides, a separate set of positive and negative control peptides was synthesized in parallel. These were screened with a negative control, antibody 57.9, an antibody that does not specifically bind TNFR2 (Posthumus et al. (J. Virology. 64:3304-3309, 1990)).

Peptides that bound TNFRAB1 and TNFRAB2 with high affinity are highlighted in FIGS. 3A and 3B, respectively. These peptides therefore contain residues within TNFR2 that are structurally configured into epitopes that are preferentially bound by TNFRAB1 and TNFRAB2.

Epitope Mapping

ELISA was also used to determine linear epitopes present on the extracellular surface of TNFR2. Linear peptides corresponding to various regions within the TNFR2 primary sequence were purchased from GenScript (Piscataway, N.J.), diluted in coating buffer and placed on Immulon 4HBX Flat Bottom Microtiter Plates (Thermo Scientific) at a concentration of 1 µg/well. Primary TNFR2 antagonistic antibodies (0.1 µg/well) were incubated with substrates. Secondary antibodies against rodent IgG were used to detect the primary antibodies. Absorbance was measured using the SPECTRAMAX® 190 Absorbance Plate Reader and analyzed with SoftMax Pro 6.3 (Molecular Devices). Results of these ELISA-based assays are shown in FIGS. 13B and 13C.

Example 2. Antagonistic TNFR2 Antibodies Inhibit T-Reg Cell Proliferation

Materials and Methods

Human T-reg Flow™ Kit (BioLegend, Cat. No. 320401)
  Cocktail Anti-human CD4 PE-Cy5/CD25 PE (BioLegend, Part No. 78930)
  Alexa Fluor® 488 Anti-human FOXP3, Clone 259D (BioLegend, Part No. 79467)
  Alexa Fluor® 488 Mouse IgG1, k Isotype Ctrl (ICFC), Clone MOPC-21 (BioLegend, Part No. 79486)
  FOXP3 Fix/Perm Buffer (4×) (BioLegend, Cat. No. 421401)
  FOXP3 Perm Buffer (10×) (BioLegend, Cat. No. 421402)
PE anti-human CD25, Clone: BC96 (BioLegend, Cat. No. 302606)
Alexa Fluor® 488 Anti-human FOXP3, Clone 259D (BioLegend, Cat. No. 320212)
PBS pH 7.4 (1×) (Gibco Cat. No. 10010-023)
HBSS (1×) (Gibco Cat. No. 14175-095)
FBS (heat inactivated)
15 ml tubes
Bench top centrifuge with swing bucket rotor for 15 ml tubes (set speed 1100 rpm or 200 g)

Antagonistic TNFR2 antibodies (TNFRAB1 and TNFRAB2) were tested for the ability to suppress the proliferation of T-reg cells. Cultured T-reg cells were treated with varying concentrations of the antagonistic TNFR2 antibodies in the presence and absence of stimulatory growth factors (e.g., TNFα) for set periods of time. T-reg cells were also cultured in the presence of TNFRAB1 at various concentrations ranging from 0.0008-25 µg/ml in the presence and absence of TNFα. As controls, T-reg cells were also incubated with TNFα alone at concentrations ranging from 0-40 ng/ml in order to select levels of TNFα that induce a high fractional increase in T-reg cell count. Additionally, T-reg cells were cultured in the presence of IL-2 alone and in the presence of TNFRAB2 alone.

Following the incubation of T-reg cells under the conditions described above, the cell counts were determined using flow cytometry analysis. T-reg cells at a density of 0.2-1×10$^6$ cells/100 µl were distributed into a 15-ml conical tube and centrifuged for 5 minutes in order to pellet the cells. The supernatant was discarded and cells were resuspended in 100 µl of wash buffer (1×HBSS containing 2% FBS). 5 µl of PE anti-human CD25 fluorophore-antibody conjugate were added to this mixture, and the cells were subsequently vortexed and incubated in the dark for 25 minutes. The cells were then washed by adding 1 ml of wash buffer and subsequently centrifuging for 5 minutes. The supernatant was then discarded and 1 ml of FoxP3 fixation/permeabilization buffer (1:4 dilution of 4×FOXP3 Fix/Perm buffer in PBS) was added to the cells. The cells were then vortexed and incubated in the dark for 20 minutes. Cells were subsequently centrifuged for 5 minutes and supernatant was discarded. Cells were then resuspended in 1 ml of fresh wash buffer, vortexed, and centrifuged for 5 minutes. Cells were subsequently resuspended in 1 ml of 1×FOXP3 Perm Buffer (1:10 dilution of 10×FOXP3 Perm Buffer in PBS), vortexed, and incubated in the dark for 15 minutes. Following incubation, cells were centrifuged for 5 minutes and supernatant was subsequently discarded. The cell pellet was then resuspended in 100 µl of 1×FOXP3 Perm Buffer. At this point, 5 µl of either Alexa Fluor® 488 anti-human FOXP3 or Alexa Fluor® 488 mouse IgG1, k isotype control were added to the cells. Cells were then vortexed and incubated in the dark for 35 minutes. Following incubation, cells were washed by adding 1 ml of fresh wash buffer to the cells, vortexing the cells and centrifuging for 5 minutes. The supernatant was then discarded and the cell pellet was resuspended in 0.2-0.5 ml of 1×HBSS free of FBS. Cell counts were then determined by flow cytometry analysis.

As seen in FIG. 5, incubation of antagonistic TNFR2 antibody TNFRAB1 suppressed T-reg cell proliferation in a dose dependent manner even when cells were co-incubated with 20 ng/ml TNFα. Strikingly, this concentration of TNFα was capable of inducing the largest fractional increase in T-reg cell count among the TNFα dosages analyzed in T-reg samples treated with TNFα alone. That TNFRAB1 is capable of diminishing T-reg cell proliferation even in the presence of activating levels of TNFα indicates that antagonistic TNFR2 antibodies are capable of not only competing with TNFα for receptor binding, but also exhibit the capacity to inhibit downstream signaling cascades that lead to T-reg cell growth and proliferation. For instance, when T-reg cells were incubated with TNFα alone at 20 ng/ml, the resulting T-reg population increased to 130% of untreated control cells. However, upon co-incubation of T-reg cells at 20 ng/ml with TNFRAB1, a steady dose-dependent suppression of cell proliferation is observed with concentrations ranging from 0.004-1.25 µg/ml of TNFRAB1.

Example 3. Generating Antagonistic TNFR2 Antibodies by Phage Display

An exemplary method for in vitro protein evolution of antagonistic TNFR2 antibodies of the invention is phage display, a technique which is well known in the art. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, e.g., a naive human germline sequence as described herein. These mutations can be performed using standard mutagenesis techniques described herein or known in the art. Each mutant sequence thus encodes an antibody corresponding in overall structure to the template except having one or more amino acid variations in the sequence of the template. Retroviral and phage display vectors can be engineered using standard vector construction techniques as described herein or known in the art. P3 phage display vectors along with compatible protein expression vectors, as is well known in the art, can be used to generate phage display vectors for antibody diversification as described herein.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its structure.

In a typical screen, a phage library is contacted with and allowed to bind a TNFR2-derived peptide (e.g., a peptide having the sequence of any one of SEQ ID NOs: 11, 19, 20, and 34-117, and particularly those that contain the KCRPG motif, as in SEQ ID NOs: 42, 50, 52-54, and 61-63), or a particular subcomponent thereof. To facilitate separation of binders and non-binders, it is convenient to immobilize the target on a solid support. Phage bearing a TNFR2-binding moiety can form a complex with the target on the solid support whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means. To isolate the binding phage exhibiting the polypeptides of the present invention, a protein elution is performed.

The recovered phage can then be amplified through infection of bacterial cells and the screening process can be repeated with the new pool that is now depleted in non-binding antibodies and enriched for antibodies that bind the target peptide. The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof, typically 10-50 out of about $10^9$ to $10^{10}$ original candidates from each library. An increase in the number of phage recovered at each round of selection is a good indication that convergence of the library has occurred in a screen. After a set of binding polypeptides is identified, the sequence information can be used to design other secondary phage libraries, biased for members having additional desired properties (See WO 2014/152660; incorporated herein by reference).

Example 4. Treatment of Cancer in a Human Patient by Administration of Antagonistic Anti-TNFR2 Antibodies The antagonistic TNFR2 antibodies of the invention can be administered to a human patient in order to treat a cell proliferation disorder, such as cancer. Administration of these antibodies suppresses the growth and proliferation of a population of T-reg cells. Antibodies of the invention can also be administered to a patient in order to suppress a T-reg-mediated immune response. For instance, a human patient suffering from cancer, e.g., a cancer described herein, can be treated by administering an antagonistic TNFR2 antibody of the invention by an appropriate route (e.g., intravenously) at a particular dosage (e.g., between 0.001 and 100 mg/kg/day) over a course of days, weeks, months, or years. If desired, the anti-TNFR2 antibody can be modified, e.g., by hyperglycosylation or by conjugation with PEG, so as to evade immune recognition and/or to improve the pharmacokinetic profile of the antibody.

The progression of the cancer that is treated with an antagonistic TNFR2 antibody of the invention can be monitored by any one or more of several established methods. A physician can monitor the patient by direct observation in order to evaluate how the symptoms exhibited by the patient have changed in response to treatment. A patient may also be subjected to MRI, CT scan, or PET analysis in order to determine if a tumor has metastasized or if the size of a tumor has changed, e.g., decreased in response to treatment with an anti-TNFR2 antibody of the invention. Optionally, cells can be extracted from the patient and a quantitative biochemical analysis can be conducted in order to determine the relative cell-surface concentrations of various growth factor receptors, such as the epidermal growth factor receptor. Based on the results of these analyses, a physician may prescribe higher/lower dosages or more/less frequent dosing of the antagonistic TNFR2 antibody in subsequent rounds of treatment.

Example 5. Producing a scFv TNFR2 Antagonist

Antibody fragments of the invention include scFv fragments, which consist of the antibody variable regions of the light and heavy chains combined in a single peptide chain. A TNFR2 antibody can be used as a framework for the development of a scFv antibody fragment by recombinantly expressing a polynucleotide encoding the variable region of a light chain of the TNFR2 antibody (e.g., TNFRAB1) operatively linked to the variable region of a heavy chain of that antibody. This can be accomplished using established mutagenesis protocols as described herein or known in the art. This polynucleotide can then be expressed in a cell (e.g., a CHO cell) and the scFv fragment can subsequently be isolated from the cell culture media.

Alternatively, scFv fragments derived from a TNFR2 antagonist can be produced by chemical synthetic methods (e.g., by Fmoc-based solid-phase peptide synthesis, as described herein). One of skill in the art can chemically synthesize a peptide chain consisting of the variable region of a light chain of the TNFR2 antibody (e.g., TNFRAB1) operatively linked to the variable region of a heavy chain of that antibody. Native chemical ligation can be used as a strategy for the synthesis of long peptides (e.g., greater than 50 amino acids). Native chemical ligation protocols are known in the art and have been described, e.g., by Dawson et al. (Science, 266:776-779, 1994); incorporated herein by reference.

Example 6. Producing a Humanized TNFR2 Antibody

One method for producing humanized TNFR2 antibodies of the invention is to import the CDRs of a TNFR2 antibody into a human antibody consensus sequence. Consensus human antibody heavy chain and light chain sequences are known in the art (see e.g., the "VBASE" human germline sequence database; Kabat et al. (Sequences of Proteins of Immunological Interest, Fifth Edition, U.S. Department of Health and Human Services, NIH Publication No. 91-3242, 1991); Tomlinson et al. (J. Mol. Biol. 227:776-798, 1992); and Cox et al. (Eur. J. Immunol. 24:827-836, 1994); incorporated herein by reference). Using established procedures, one can identify the variable domain framework residues and CDRs of a consensus antibody sequence (e.g., by sequence alignment (see Kabat, supra)). One can substitute one or more CDRs of the heavy chain and/or light chain variable domains of consensus human antibody with one or more corresponding CDRs of TNFRAB1, or another TNFR2 antagonist antibody described herein, in order to produce a humanized anti-TNFRAB1 variant using gene editing techniques described herein or known in the art. One example of a variable domain of a consensus human antibody includes the heavy chain variable domain EVQLVESGGGL-VQPGGSLRLSCAASGFTFSDYAMSWVRQAPGKGLE-WVAVISENGSDTYYADSVKGRFTISRDDSKNTLYLQ-MNSLRAEDTAVYYCARDRGGAVSYFDVWGQGTLV-TVSS (SEQ ID NO: 32) and the light chain variable domain DIQMTQSPSSLSASVGDRVTITCRASQDVSSYLAWY-QQKPGKAPKLLIYAASSLESGVPSRFSGSGSGTDFTL-TISSLQPEDFATYYCQQYNSLPYTFGQGTKVEIKRT (SEQ ID NO: 33), identified in U.S. Pat. No. 6,054,297; incorporated herein by reference (CDRs are shown in bold).

In order to produce humanized TNFR2 antibodies, one can recombinantly express a polynucleotide encoding the above consensus sequence in which one or more variable region CDRs have been replaced with one or more variable region CDR sequences of a TNFR2-specific antibody. For example, the CDRs 1-3 of the heavy chain variable domain of the consensus human antibody can be replaced with CDRs 1-3 having the sequence of SEQ ID NOs: 23-25, respectively, and the CDRs 1-3 of the light chain variable domains of the consensus human antibody can be replaced with CDRs 1-3 having the sequence of SEQ ID NOs: 26-28, respectively.

A polynucleotide encoding the above heavy chain and light chain variable domains operatively linked to one another can be incorporated into an expression vector (e.g., an expression vector optimized for protein expression in prokaryotic or eukaryotic cells as described herein or known in the art). The single-chain antibody fragment (scFv) can thus be expressed in a host cell and subsequently purified from the host cell medium using established techniques, such as size-exclusion chromatography and/or affinity chromatography as described herein.

Example 7. Treatment of HIV in a Human Patient by Administration of Antagonistic Anti-TNFR2 Antibodies The antagonistic TNFR2 antibodies of the invention can be administered to a human patient in order to treat a viral infection, such as HIV. Administration of these antibodies suppresses the growth and proliferation of a population of T-reg cells, which enhances the immune response of a patient by allowing the growth and proliferation of cytotoxic T-lymphocytes capable of mounting an attack on infected cells. For instance, a human patient suffering from HIV can be treated by administering an antagonistic TNFR2 antibody of the invention (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1) by an appropriate route (e.g., intravenously) at a particular dosage (e.g., between 0.001 and 100 mg/kg/day) over a course of days, weeks, months, or years. If desired, the anti-TNFR2 antibody can be modified, e.g., by hyperglycosylation or by conjugation with PEG, so as to evade immune recognition and/or to improve the pharmacokinetic profile of the antibody.

The progression of HIV that is treated with an antagonistic TNFR2 antibody of the invention can be monitored by any one or more of several established methods. A physician can monitor the patient by direct observation in order to evaluate how the symptoms exhibited by the patient have changed in response to treatment. A blood sample can also be withdrawn from the patient in order to analyze the cell count of one or more white blood cells in order to determine if the quantity of infected cells has changed (e.g., decreased) in response to treatment with an anti-TNFR2 antibody of the invention. Based on the results of these analyses, a physician may prescribe higher/lower dosages or more/less frequent dosing of the antagonistic TNFR2 antibody in subsequent rounds of treatment.

Example 8. Treatment of *Mycobacterium tuberculosis* in a Non-Human Mammal by Administration of Antagonistic Anti-TNFR2 Antibodies The antagonistic TNFR2 antibodies of the invention can be administered to a non-human mammal (e.g., a bovine mammal, pig, bison, horse, sheep, goat, cow, cat, dog, rabbit, hamster, guinea pig, or other non-human mammal) in order to treat a bacterial infection, such as *Mycobacterium tuberculosis*. Administration of these antibodies suppresses the growth and proliferation of a population of T-reg cells, which enhances the immune response of a patient by allowing the growth and proliferation of cytotoxic T-lymphocytes capable of mounting an attack on the pathogenic organism. For instance, a non-human mammal suffering from *Mycobacterium tuberculosis* can be treated by administering an antagonistic TNFR2 antibody of the invention (e.g., a TNFR2 antibody that specifically binds an epitope containing one or more residues of the KCRPG sequence of TNFR2 (residues 142-146 of SEQ ID NO: 7) and that does not exhibit specific binding to an epitope containing the KCSPG sequence of TNFR2 (residues 56-60 of SEQ ID NO: 7) and has a non-native constant region, such as a TNFR2 antibody that contains one or more CDRs or a variant thereof of TNFRAB1) by an appropriate route (e.g., intravenously) at a particular dosage (e.g., between 0.001 and 100 mg/kg/day) over a course of days, weeks, months, or years. If desired, the anti-TNFR2 antibody can be modified, e.g., by hyperglycosylation or by conjugation with PEG, so as to evade immune recognition and/or to improve the pharmacokinetic profile of the antibody.

The progression of the *Mycobacterium tuberculosis* infection that is treated with an antagonistic TNFR2 antibody of the invention can be monitored by any one or more of several established methods. A physician can monitor the patient by direct observation in order to evaluate how the symptoms exhibited by the patient have changed in response to treatment. A blood sample can also be withdrawn from the patient in order to analyze the cell count of one or more white blood cells in order to determine if the immune response has changed (e.g., increased) in response to treatment with an anti-TNFR2 antibody of the invention. Based on the results of these analyses, a physician may prescribe higher/lower dosages or more/less frequent dosing of the antagonistic TNFR2 antibody in subsequent rounds of treatment.

Figure 6D:
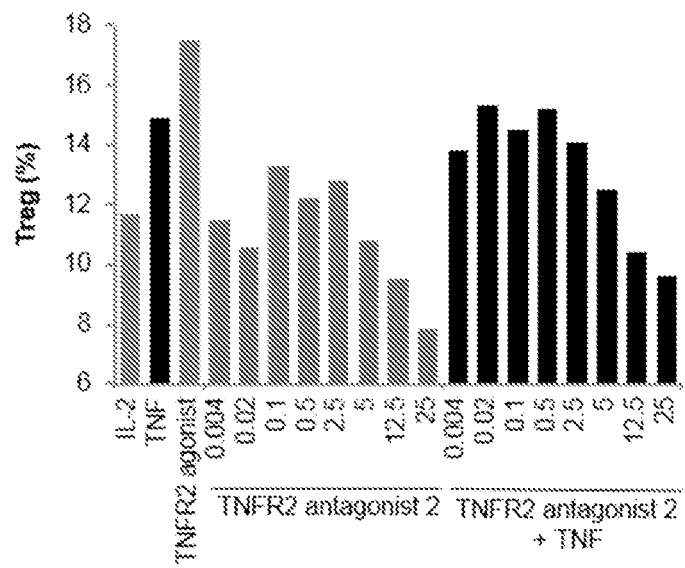
FIGS. 6D and 6E are graphs showing the results of duplicate experiments conducted in order to determine the effect of TNFRAB2 on T-reg cell proliferation.
Figure 6E:
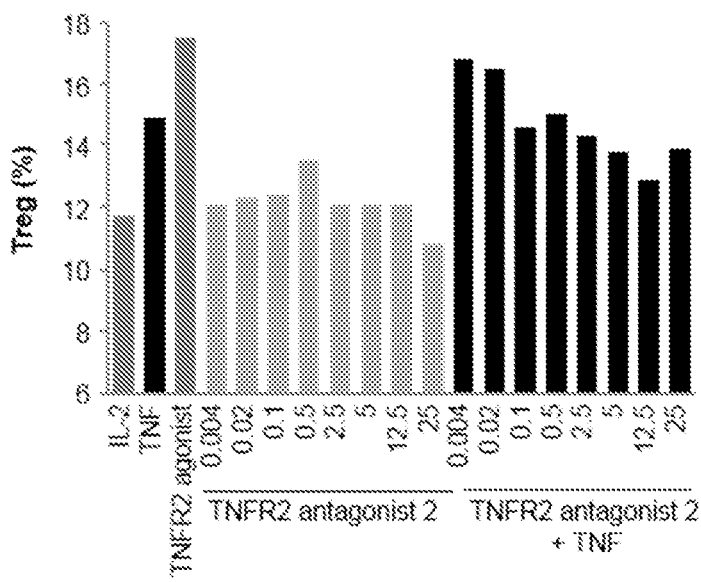
Figure 6F:
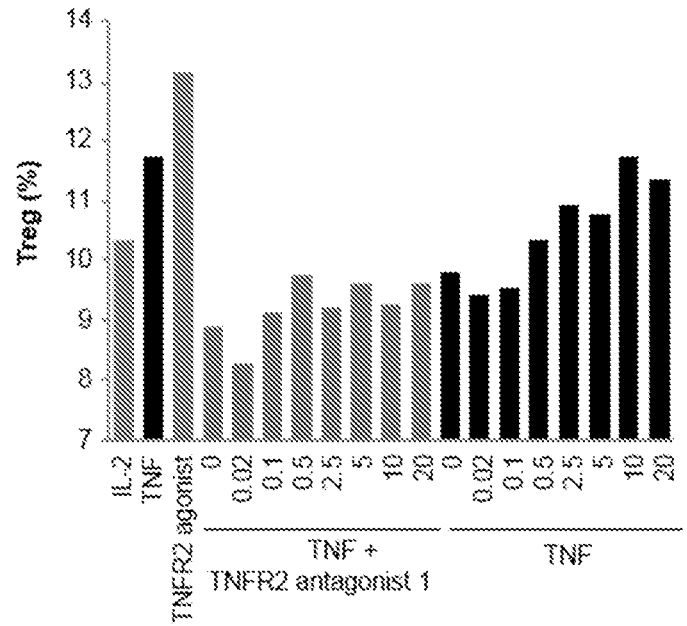
FIGS. 6F and 6G are graphs showing the results of duplicate experiments conducted in order to determine the effect of TNFRAB1 on T-reg cell proliferation.
Figure 6G:
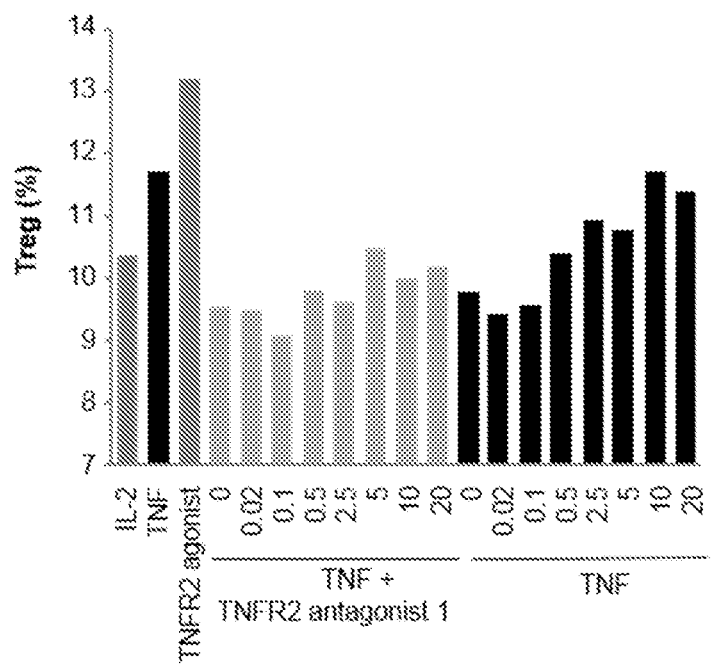
Figure 7A:
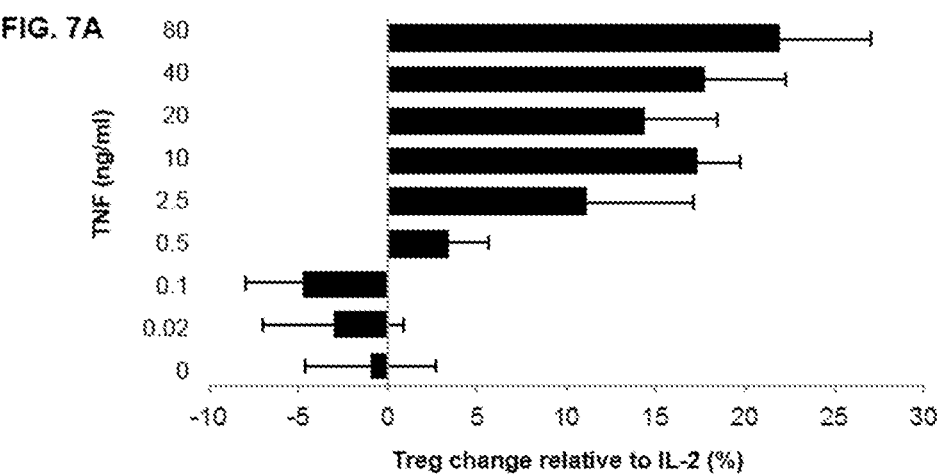
FIG. 7A is a graph showing the effect of TNFα on the proliferation of CD4+T-reg cells. Values on the x-axis indicate the percent change in the quantity of T-reg cells upon treatment with TNFα relative to treatment with IL-2.
Figure 7B:
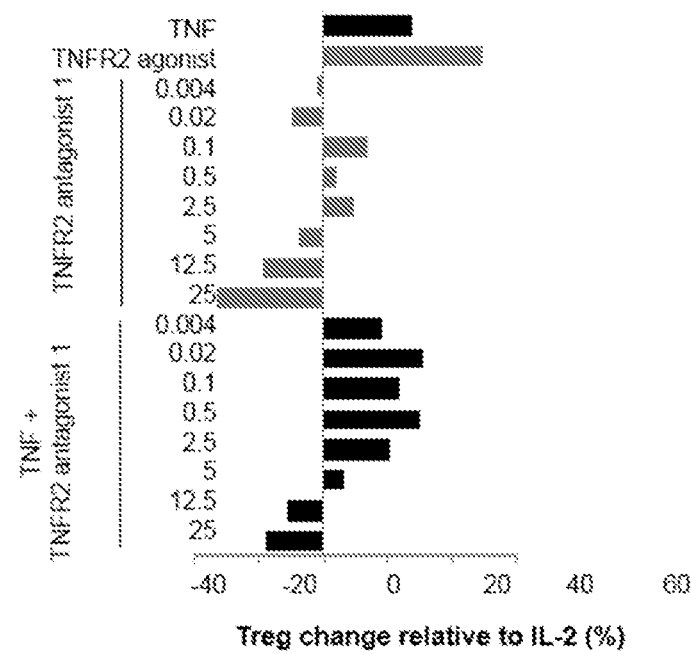
FIG. 7B is a graph showing the ability of TNFRAB1 to dominantly inhibit T-reg cell proliferation in the presence and absence of TNFα.
Figure 7C:
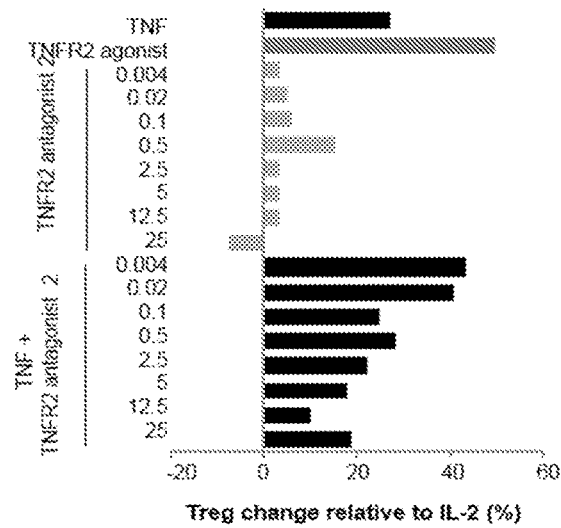
FIG. 7C is a graph showing the ability of TNFRAB2 to inhibit T-reg cell proliferation in the presence and absence of TNFα.
Figure 7D:
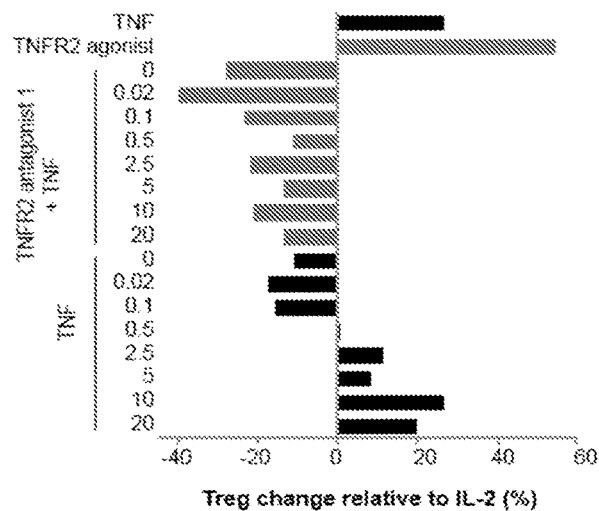
FIGS. 7D and 7E are graphs showing the effect of TNFR2 dominant antagonists on proliferation of T-reg cells in the presence and absence of TNFα.
Figure 7E:
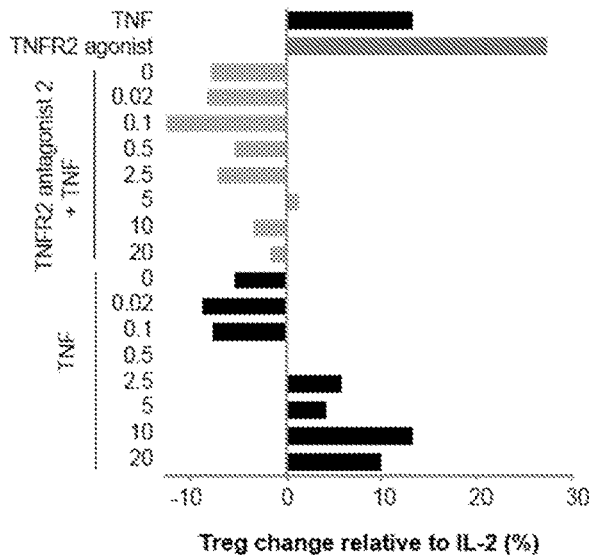
Figure 8A:
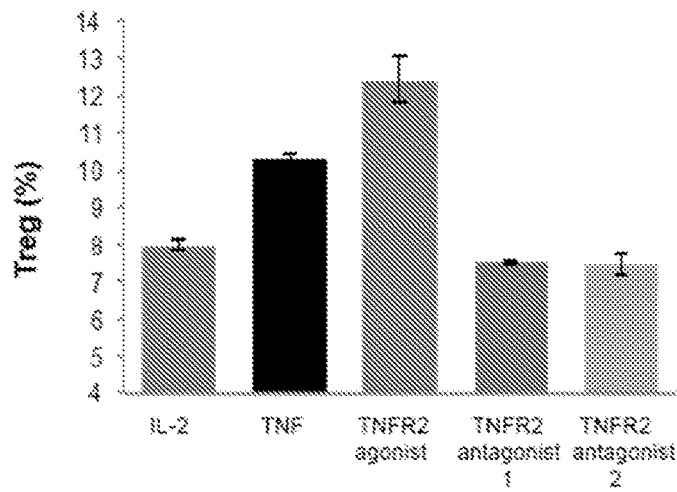
FIG. 8A is a graph showing the ability of TNFRAB1 and TNFRAB2 to inhibit the proliferation of T-reg cells generally.
Figure 8B:
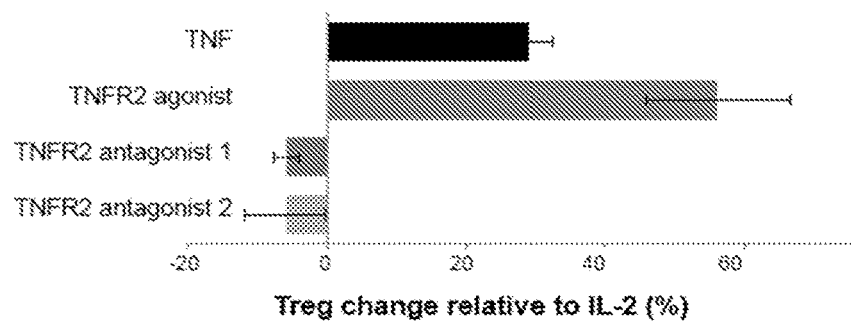
FIG. 8B is a graph showing the effect of TNFRAB1 and TNFRAB2 on T-reg cell proliferation relative to the effect induced by treatment with IL-2.
Figure 8C:
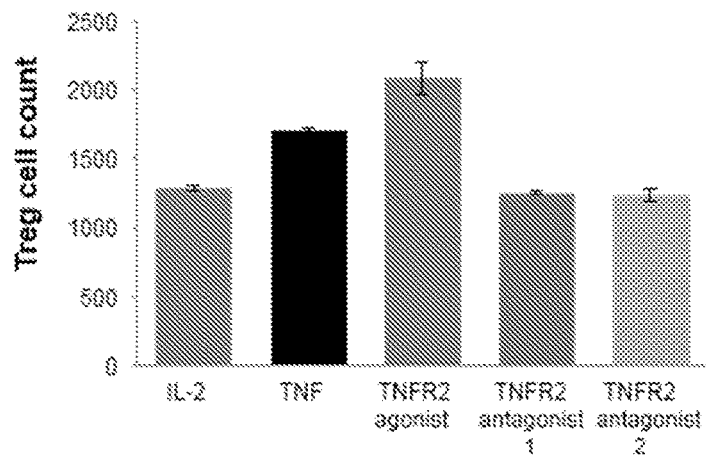
FIG. 8C is a graph showing the effect of TNFRAB1 and TNFRAB2 on total T-reg quantity.
Figure 8D:
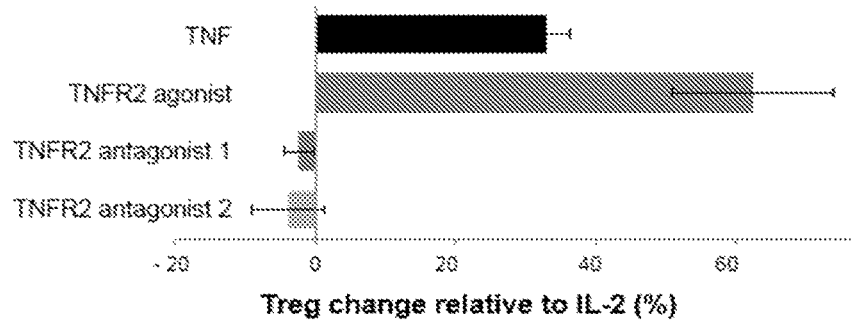
FIG. 8D is a graph showing the effect of TNFRAB1 and TNFRAB2 on total T-reg quantity relative to the effect induced by treatment with IL-2.
Figure 8E:
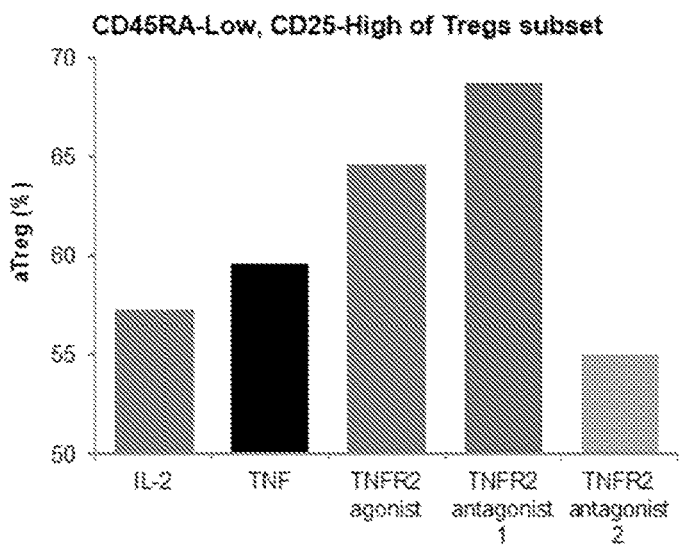
FIG. 8E is a graph demonstrating the effect of TNFRAB1 and TNFRAB2 on activated T-reg cells (aT-reg cells) that express CD25 in a high-affinity state ($CD25^{Hi}$) and CD45RA in a low-affinity state ($CD45RA^{Low}$).
Figure 8F:
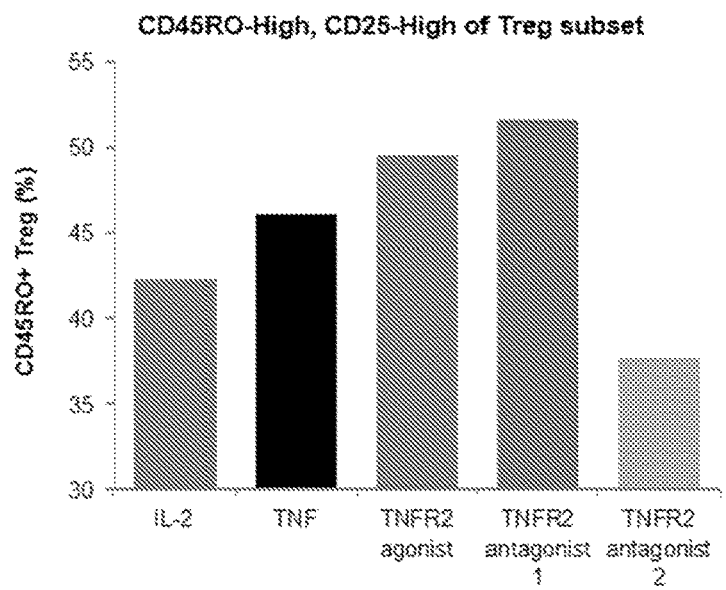
FIG. 8F is a graph showing the effect of TNFRAB1 and TNFRAB2 on a population of T-reg cells that express $CD45RO^{Hi}$ and $CD25^{Hi}$.
Figure 8G:
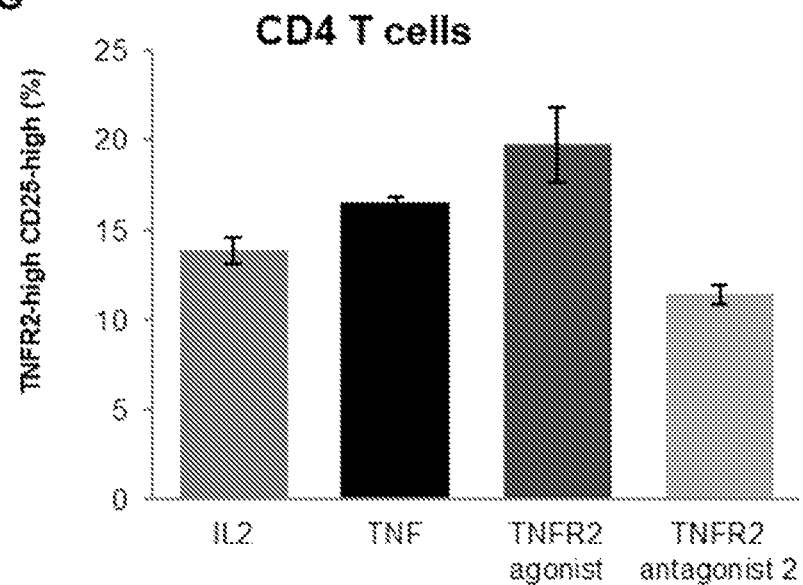
FIG. 8G is a graph showing the effect of TNFRAB2 on $CD25^{Hi}$-expressing CD4+ T cells.
Figure 8H:
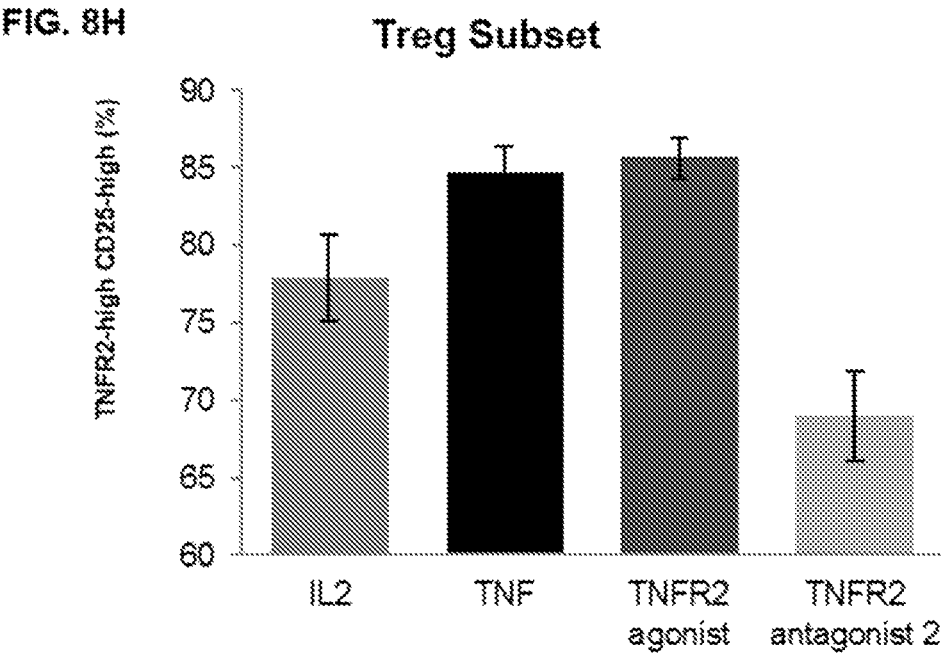
FIG. 8H is a graph demonstrating the effect of TNFRAB2 on $CD25^{Hi}$- expressing T-reg cells. These data demonstrate that, while the proliferation of both activated (aT-reg) and resting (rT-reg) cells is inhibited upon treatment with TNFRAB1 or TNFRAB2, antagonistic TNFR2 antibodies preferentially inhibit the proliferation of aT-reg cells.

Example 9. Antagonistic TNFR2 Antibodies Inhibit T-Reg Cell Proliferation in the Presence of IL-2 and TNF The presence of an elevated quantity of T-reg cells can hamper the ability of the immune system to combat cancer and infectious disease. TNFR2 represents an important checkpoint in T-reg proliferation and thus constitutes an ideal target for immunomodulation. To characterize the functional activity of two antagonistic TNFR2 monoclonal antibodies (mAbs), TNFRAB1 and TNFRAB2, a cell-based assay developed for homogeneous T-reg expansion was employed. It was first confirmed that normal human CD4+ cells incubated with increasing concentrations of TNFα resulted in a dose-dependent increase in T-reg cells (FIGS. 6A and 7A). We also confirmed that the presence of IL-2 is required for T-reg proliferation (FIG. 6B). As shown in FIGS. 6B-6G, relative to treatment with IL-2 alone, the effect on T-reg proliferation with TNF at 20 ng/ml is dramatic (>20% expansion) and enhanced further by co-incubation with the TNFR2 agonist (>60% expansion).

Antagonistic TNFR2 antibodies elicit an opposite effect on T-reg proliferation as measured using this assay. Both TNFR2 antagonistic antibodies induced suppressive effects on T-reg proliferation that resulted in a 4-15% decrease in the percentage of remaining T-reg cells in normal blood donors. Remarkably, the TNFR2 antagonistic effect is dominant and can even overcome the presence of a generous amount of TNFα (20 mg/ml) (FIGS. 6C-6G). The TNFR2 antagonistic effect on T-regs was dose dependent (FIGS. 6D-6G). More remarkable was the observation the when the two TNFR2 antagonistic antibodies were studied in the presence of TNFα, both TNFR2 antagonist antibodies were able to overcome TNFα agonism in a dose dependent fashion. Both antagonistic antibodies were capable of attenuating T-reg expansion and inverting the TNFα agonistic curve (FIGS. 6A and 6C-6G). This assay was also performed by incubating T-reg cells with a fixed amount of TNFR2 antagonistic antibody and escalating doses of TNFα (FIGS. 6D-6G). Again both TNFR2 antagonists in a dose-dependent fashion were capable of reversing TNFα agonism. It should be noted that this 48 hour T-reg expansion assay is performed with IL-2, an agonist, in the culture to prevent non-specific human CD4+ T-cell death. When the data obtained from these experiments were processed to determine the relative changes in T-reg proliferation in the presence of antagonistic TNFR2 antibodies as compared to the presence of IL-2 alone, the antagonistic properties of both antibodies persisted (FIGS. 7A-7E). Together these results demonstrate the functional ability of two TNFR2 antagonist antibodies to suppress T-reg proliferation in human CD4+ cells, and the effect is remarkably dominant over agonism driven by moderate to high doses of TNFα.

To conduct the T-reg suppression assays described above, peripheral blood mononuclear cells (PBMCs) were used as responders. PBMCs were isolated on the day of venipuncture using a Ficoll-Plaque Plus (GE Healthcare, Piscataway, N.J.) density gradient and were cryopreserved at −80'C. Cells were thawed one day prior to mixing with T-reg cells and were rested overnight in RPMI 1640 and IL-2 (10 U/ml). The next day, responder cells were stained with 1 μM carboxyfluorescein diacetate succinimidyl ester (CFSE). Responder cells ($5 \times 10^4$ cells) were then mixed with expanded T-reg cells at various ratios (0:1, 4:1, 2:1, 1:1), and stimulated with anti-CD3 mAb (HIT3a, BD Biosciences) and IL-2 (50 U/ml). Cells were collected after 4 days and analyzed by flow cytometry.

Human Subjects

Human blood samples from over 100 donors were collected according to a human studies protocol approved by the Massachusetts General Hospital Human Studies Committee (MGH-2001 P001379). All of the donors provided written informed consent. Blood was collected into BD Vacutainer EDTA tubes (BD Diagnostics) and processed within 2 hours of phlebotomy. T-reg samples isolated from ovarian cancer patients were obtained from women with newly diagnosed ovarian cancer prior to irradiation and prior to chemotherapy. These human studies were approved by the Massachusetts General Hospital Human Studies Committee (MGH-2015P002489; see Example 14 below).

Blood and Cell Culture

Fresh human blood was processed within 2 hours of venipuncture. Blood was washed twice with 1×HBSS (Invitrogen) plus 2% FBS (Sigma-Aldrich) and CD4+ cells were isolated using Dynabeads® CD4 Positive Isolation Kit (Invitrogen). Isolated CD4+ cells were resuspended in RPMI GlutaMAX™ (Life Technologies) plus 10% FBS (Sigma-Aldrich) and 1% penicillin-streptomycin (Life Technologies). Cells were seeded in 96-round-bottom well plates at a concentration of $0.2-1\times10^6$ cells/well, treated with either TNFR2 antagonist antibodies or TNFR2 agonists (as indicated in each example), and then incubated for up to 48 hours at 37° C. with 5% $CO_2$. Since isolated and cultured human T-cells die in the absence of IL-2 in the cell culture medium, all cell-based experiments described herein used a low level of IL-2 (100U/ml) in the culture media to prevent IL-2 withdrawal from influencing the data. T-reg cells isolated from sterile ovarian cancer ascites were obtained by first concentrating the cells in 50-ml conical tubes and then suspending the cell pellets to obtain CD4+ cell isolations (see Example 14 below).

Reagents and Flow Cytometry

Recombinant human TNF was purchased from Sigma-Aldrich and recombinant human IL-2 was purchased from Life Technologies. $F(ab')_2$ fragments of TNFRAB1 and TNFRAB2 were prepared using Pierce $F(ab')_2$ Preparation Kit (Life Technologies). Crosslinking antibodies against rodent IgG (ab9165 and ab99670) were purchased from Abcam (Cambridge, Mass.). Cells were prepared for flow cytometry using Human T-reg Flow™ Kit (BioLegend) according to the manufacturer instructions. Antibodies used for flow cytometry included Alexa Fluor® 488 Anti-human FOXP3, Clone 259D for intracellular staining of FOXP3, and PE Anti-human CD25 Clone BC96 for cell surface staining of CD25 (BioLegend). Fluorescently stained cells were resuspended in 1×HBSS (Invitrogen) and analyzed using a BD FACS Calibur flow cytometer machine (Becton Dickinson). FACS data was processed using FlowJo software (Version 10.0.8).

Statistical Analysis

Data analysis was performed by the paired Student t test using Excel (Microsoft) or GraphPad Prism-5 software (GraphPad Software, La Jolla, Calif.). Significance was determined by a two-sided p-value less than 0.05.

Example 10. Short Term Culture Effects on Activated T-Reg Cells by TNFR2 Antagonist Antibodies To investigate the ability of antagonistic TNFR2 antibodies to modulate TNFR2 secretion, soluble human TNFR2 was measured from cell culture supernatants using Quantikine® ELISA (R&D Systems). Briefly, supernatants were collected after 24-42 hour incubation of CD4+ cells with IL-2 (200 U/ml) alone or with TNF (20 ng/ml) or antagonistic TNFR2 antibodies (12.5 µg/ml) and either used immediately or frozen at −20° C. ELISA was performed according to the manufacturer's instructions. Absorbance was measured using the SpectraMax® 190 Absorbance Plate Reader and analyzed with SoftMax Pro 6.3 (Molecular Devices).

Figure 9A:
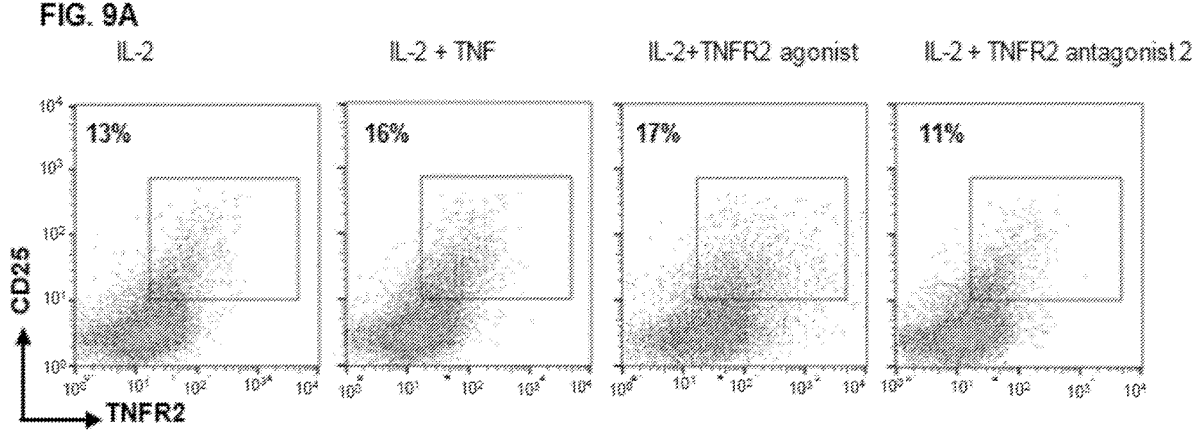
FIG. 9A is a series of 2-dimensional flow cytometry plots demonstrating the effect of agents that direct the growth of T-reg cells (e.g., TNFα, IL-2, and TNFR2 agonists) as well as a TNFR2 antagonist, TNFRAB2, on the proliferation of T-reg cells of various phenotypes. Treatment with a TNFR2 antagonist antibody preferentially inhibits the proliferation of $CD25^{Hi}$-expressing T-reg cells. The proportion of CD4+, $CD25^{Hi}$+ cells expressing TNFR2 after up to 48 hours of incubation with either IL-2 (200 U/ml) alone, with TNFα (20 ng/ml), or with TNFR2 antagonist antibodies (12.5 pg/ml) is shown.

T-reg cells exist in two states, activated (aT-reg) and resting (rT-reg); the two states can be distinguished on the basis of the expression of CD45RA. The phenotype of an aT-reg cell is $CD25^{Hi}CD45RA^{Low}$ while the phenotype of a rT-reg cell is $CD25^{Med}CD45RA^{Hi}$ aT-reg cells are more potent suppressors of immune function and therefore ideal targets for immunotherapy To investigate the efficacy of inhibiting aT-reg cells, it was first confirmed that the total number of T-reg cells, rather than simply the proportion of T-reg cells, was reduced when CD4+ cells were treated with the TNFR2 antagonists (FIGS. 8A-8H). Next, to determine which class of T-reg is inhibited by the TNFR2 antagonists, cells were stained by CD45RA. We found that while both classes of T-reg cells are inhibited, the aT-reg cells were suppressed to a greater extent than the rT-reg cells. These data suggest that the TNFR2 antagonist antibodies selectively inhibit the proliferation of aT-reg cells. High TNFR2 expression is another characteristic of suppressive T-reg cells. The level of TNFR2 expression was measured and it was found that TNFR2 antagonist treatment reduced the number of $TNFR2^{Hi}$-expressing cells. In contrast, mean fluorescent intensity (MFI) of TNFR2 expression remained similar among all treatments (FIG. 9A). Taken together, these data suggest that antagonistic TNFR2 antibodies, such as TNFRAB1 and TNFRAB2, are capable of selectively attenuating the proliferation of $CD25^{Hi}+$, $CD45RA^{Low}+$T-reg cells.

Figure 9B:
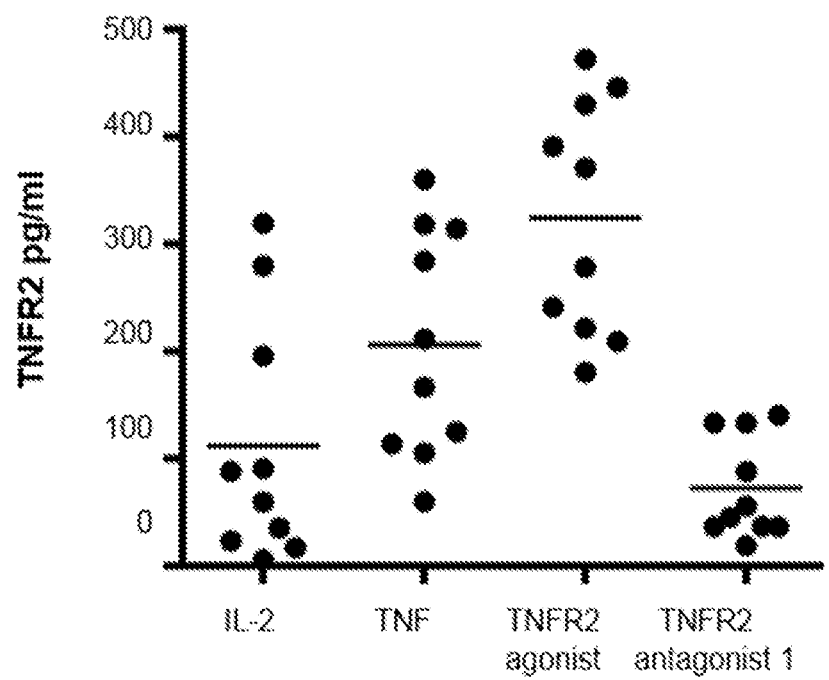
FIG. 9B is a graph showing the effect of TNFRAB1 on the secretion of TNFR2, shown in units of pg/ml.
Figure 9C:
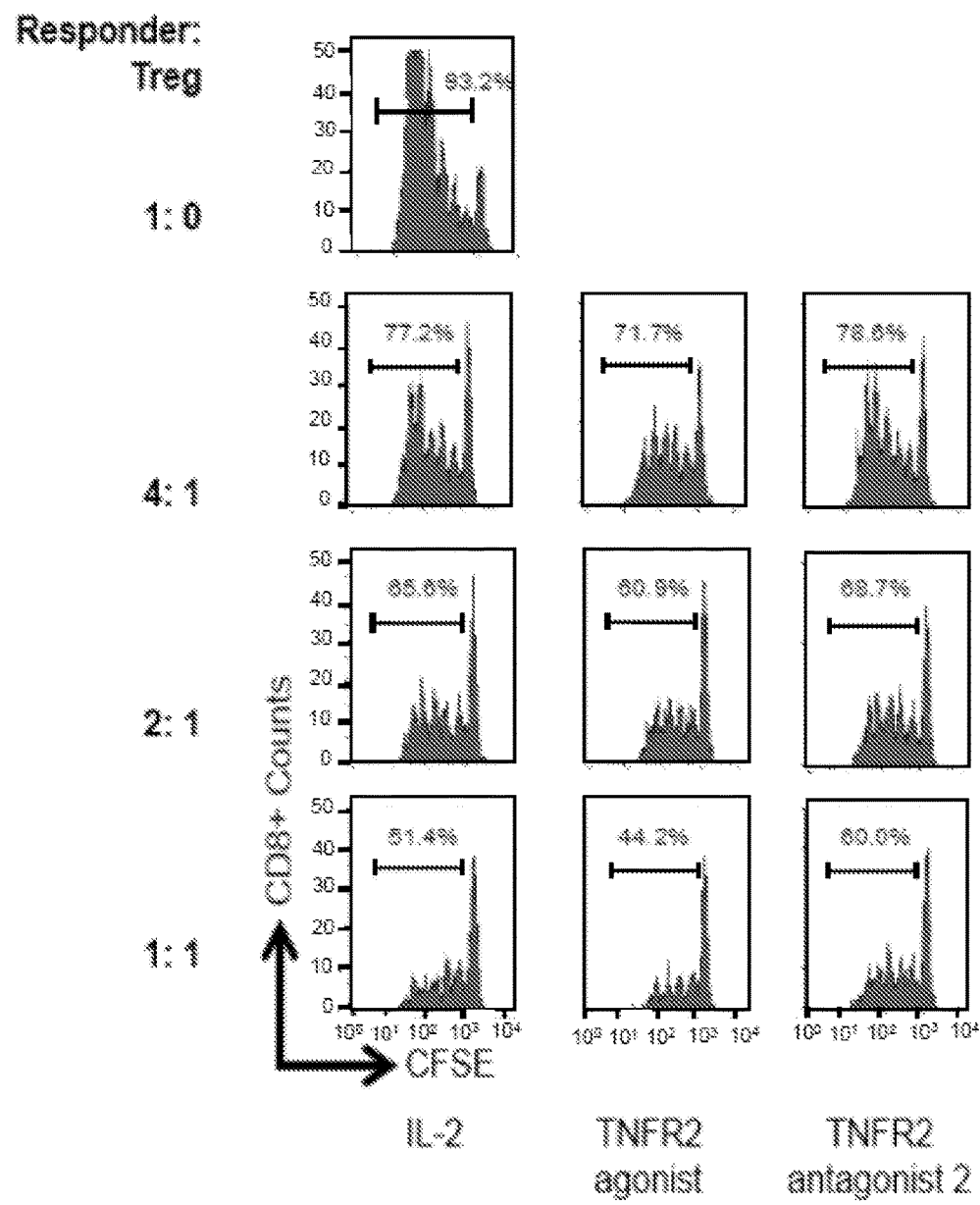
FIG. 9C is a series of 1-dimensional flow cytometry plots showing the effect of TNFRAB2 on CD8+ T-cell count as measured by carboxyfluorescein (CFSE) labeling.

The immune response is often characterized by an increase in soluble TNFR2 due to high protein turnover cells The level of soluble TNFR2 was therefore measured in culture supernatant after treatment with TNFR2-modulating agents in order to determine the effect of these molecules on immune activity. It was observed that TNF and the TNFR2 agonist increased the quantity of soluble TNFR2, whereas the TNFR2 antagonist reduced the level of soluble TNFR2 (FIG. 9B). Additionally, T-reg suppressor assays confirmed potent suppression of CD8+ cells by TNFR2 antagonism (FIGS. 9A and 9C). These data demonstrate that treatment of human CD4+ cells with a TNFR2 antagonist effectively reduces the number of activated and highly suppressive T-reg cells and had the additional benefit of inhibiting soluble decoy TNFR2 secretion.

To conduct T-reg suppression assays as described above, peripheral blood mononuclear cells (PBMCs) were used as responders. PBMCs were isolated on the day of venipuncture using a Ficoll-Plaque Plus (GE Healthcare, Piscataway, N.J.) density gradient and cryopreserved at −80° C. PBMCs were thawed the day before mixing with T-reg cells and were rested overnight in RPMI 1640 and IL-2 (10 U/ml). The next day, responder cells were stained with 1 pM carboxyfluorescein diacetate succinimidyl ester (CFSE). Responder cells ($5\times10^4$ cells) were then mixed with expanded T-reg cells at various ratios (0:1, 4:1, 2:1, 1:1), and stimulated with anti-CD3 mAb (HIT3a, BD Biosciences) and IL-2 (50 U/ml). Cells were collected after 4 days and analyzed by flow cytometry.

To measure the concentration of secreted TNFR2 as described above, the QUANTIKINE® ELISA assay kit was used (R&D Systems). Briefly, supernatants were collected after 24-42 hour incubation of CD4+ cells with IL-2 (200 U/ml) alone or with TNFα (20 ng/ml) or TNFR2 antagonist antibodies (12.5 µg/ml) and either used immediately or frozen at −20° C. ELISA assays were performed according to the manufacturer's instructions. Absorbance was measured using the SPECTRAMAX® 190 Absorbance Plate Reader and analyzed with SoftMax Pro 6.3 (Molecular Devices).

Example 11. TNFR2 Antagonist Activity is Independent of Non-Specific Fc Region Binding or Cross-Linking Non-specific binding by antibody Fc regions can result in arbitrary functional activity. Treatment of CD4+ cells with TNFR2 mAb F(ab')$_2$ fragments, with or without TNF, resulted in similar dose responses in T-reg cell quantities as observed with full monoclonal antibodies (FIGS. 10A-10D). This confirms that specific binding by the F(ab')$_2$ region of the antagonistic TNFR2 antibody to TNFR2, rather than non-specific binding mediated by the Fc region, is likely responsible for the suppressive activity. Purity of F(ab')$_2$ fragments and full antibodies were assessed by SDS-PAGE analysis (FIGS. 11A-11D).

Figure 10A:
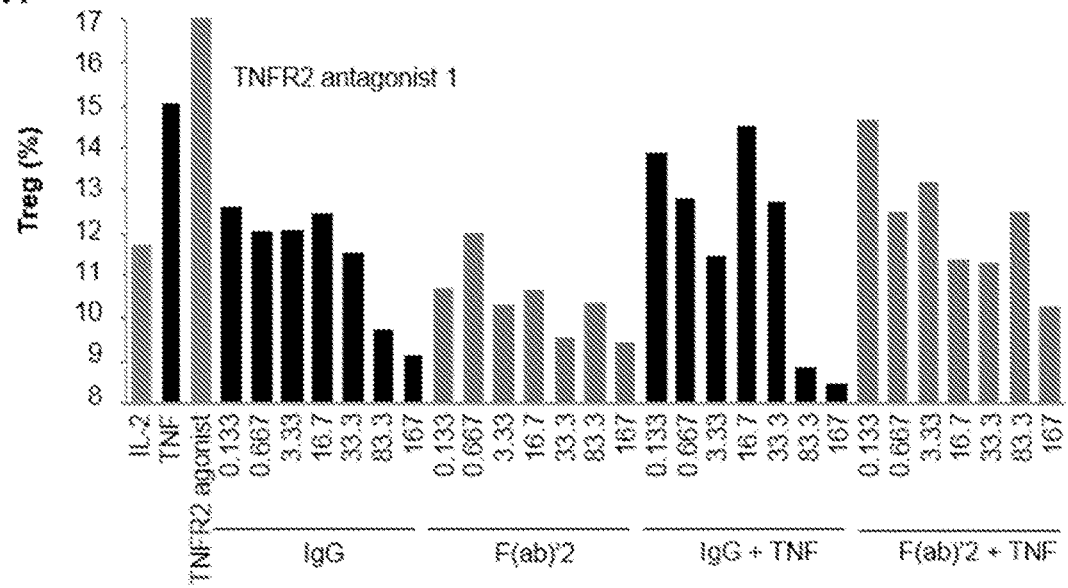
FIG. 10A is a graph showing the ability of full-length TNFRAB1 (IgG) as well as F(ab')$_2$ fragment of TNFRAB1 to inhibit the proliferation of T-reg cells.
Figure 10B:
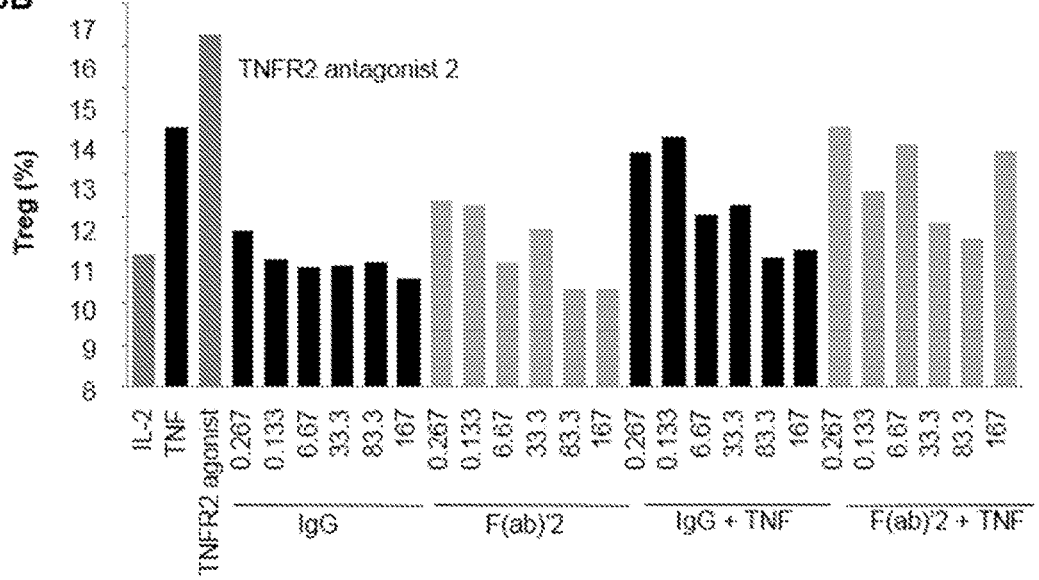
FIG. 10B is a graph showing the ability of full-length TNFRAB2 (IgG), as well as a F(ab')$_2$ fragment of TNFRAB2, to inhibit the proliferation of T-reg cells. These data demonstrate that specific binding of the Fab regions of these antagonistic TNFR2 antibodies to TNFR2 is likely responsible for modulating T-reg cell growth, rather than non-specific binding of the Fc regions of these antibodies. Incubation of freshly isolated CD4+ cells for up to 48 hrs with IL-2 (200 U/ml) plus either the full antibody or F(ab')2 fragment of TNFRAB1 or TNFRAB2 produces similar dose-dependent inhibition of T-reg cells in the presence or absence of TNFα (20 ng/ml).
Figure 10C:
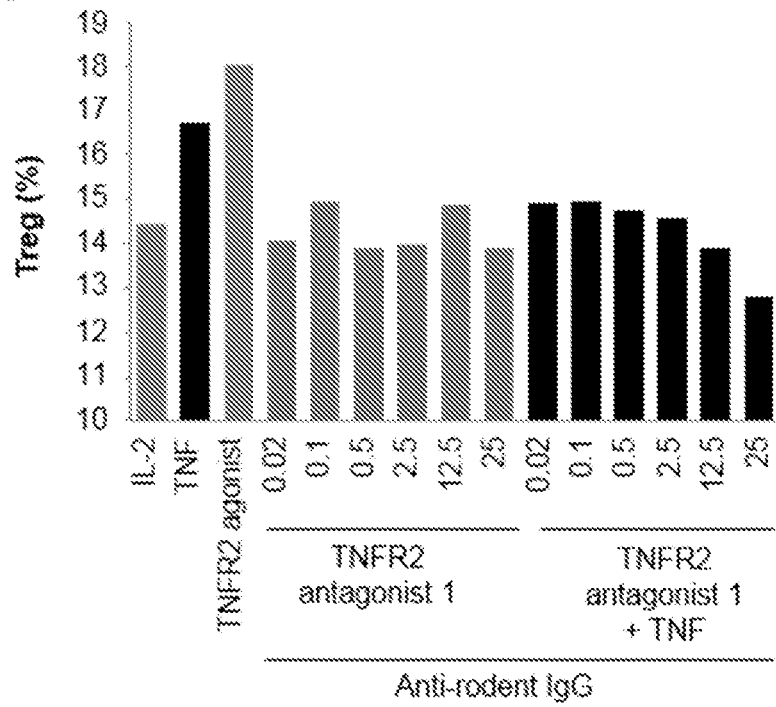
FIG. 10C is a graph showing the results of a dose-response assay in which T-reg cells were treated with TNFRAB1 in the presence of anti-IgG antibodies.
Figure 10D:
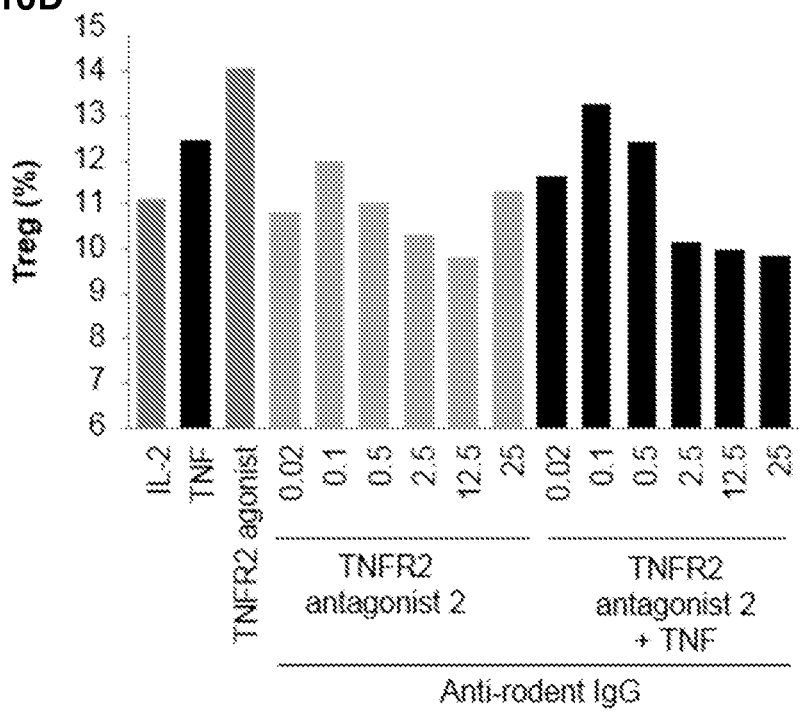
FIG. 10D is a graph showing the results of a dose-response assay in which T-reg cells were treated with TNFRAB2 in the presence of anti-IgG antibodies. The dose-dependent suppression of T-reg cell growth induced by TNFR2 antagonist antibodies was unaffected by the presence of anti-IgG molecules, indicating that non-specific cross-linking mediated by TNFRAB1 or TNFRAB2 is not responsible for the inhibitory effect of these antibodies on T-reg cell proliferation. Co-incubation of crosslinking antibody (2.5 µg/ml) with TNFR2 antagonist antibodies (0.02-25 µg/ml) does not affect the ability of the antibodies to inhibit T-reg proliferation in a dose-dependent manner. Data are presented as a single representative example.
Figure 11A:
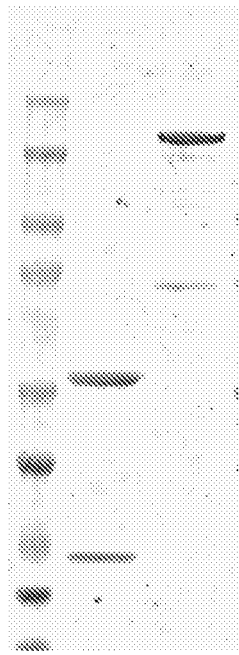
FIG. 11A is an image of a polyacrylamide gel showing the results of SDS-PAGE analysis conducted following the expression of TNFRAB1.
Figure 11B:
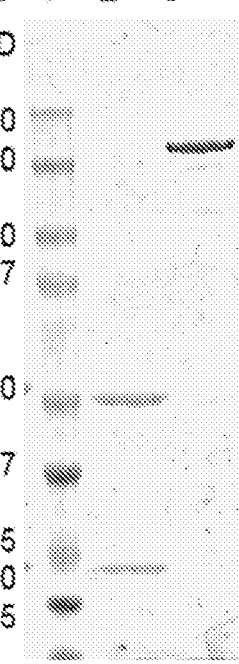
FIG. 11B is an image of a polyacrylamide gel showing the results of SDS-PAGE analysis conducted following the expression of TNFRAB2. Analysis of reduced and non-reduced TNFR2 antagonist antibodies (2.5 µg) is shown.
Figure 11C:
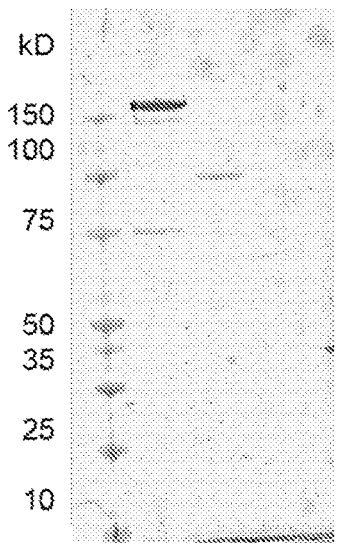
FIG. 11C is an image of a polyacrylamide gel showing the results of a SDS-PAGE analysis conducted following the expression of F(ab')$_2$ fragments of TNFRAB1.
Figure 11D:
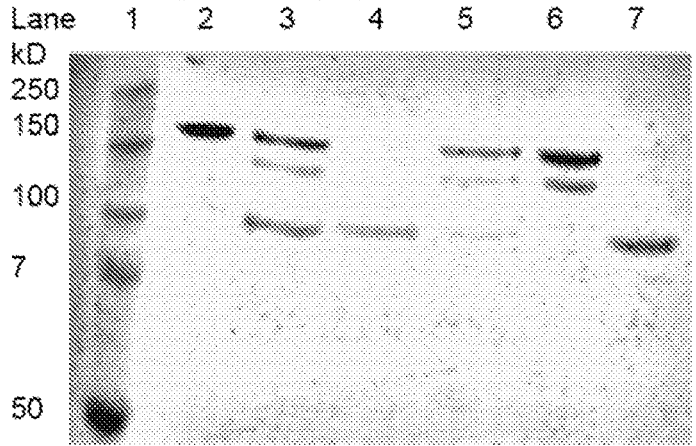
FIG. 11D is an image of a polyacrylamide gel showing the results of a SDS-PAGE analysis conducted following the expression of F(ab')$_2$ fragments of TNFRAB2. Analysis of TNFR2 antagonist antibodies before and after digestion in F(ab')2 fragment preparation is shown.

Crosslinking can also result in aberrant functional activity of antibodies. To rule out the possibility that non-specific crosslinking was a cause of the observed functional activity, a dose response assay was performed in which the TNFR2 antagonist antibodies were incubated with T-reg cells with and without anti-IgG antibodies. The dose-dependent suppression of T-reg cells by TNFR2 antagonist antibodies was unaffected by the presence of anti-IgG (FIGS. 10C and 10D). Taken together, these data confirm that the functional activity of TNFR2 antagonist antibodies is independent of non-specific Fc region activity or crosslinking.

To conduct the SDS-PAGE analysis described above, protein samples were run alongside PRECISION PLUS™ (BioRad) or PERFECT PROTEIN™ (EMD Millipore) markers on NuPAGE 4-12% Bis-Tris Gels with MOPS SDS Running Buffer (Life Technologies) at 100V for 1 hour. Gels were stained for 24 hours with SIMPLY BLUE™ Safe Stain (Invitrogen).

Figure 12A:
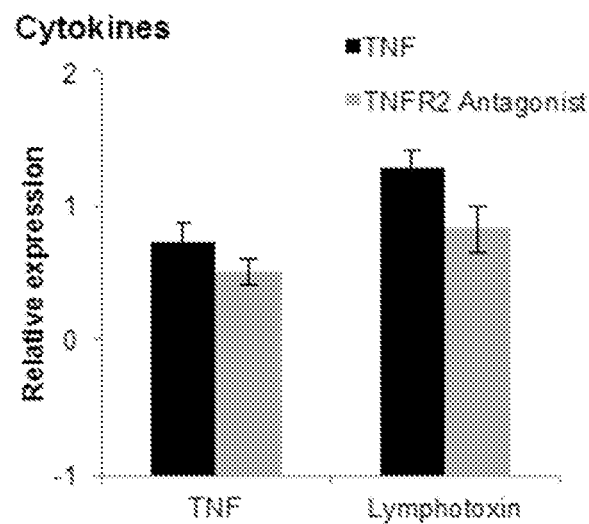
FIG. 12A is a graph showing the effect of TNFR2 antagonist antibodies on the expression of TNFα and lymphotoxin.
Figure 12B:
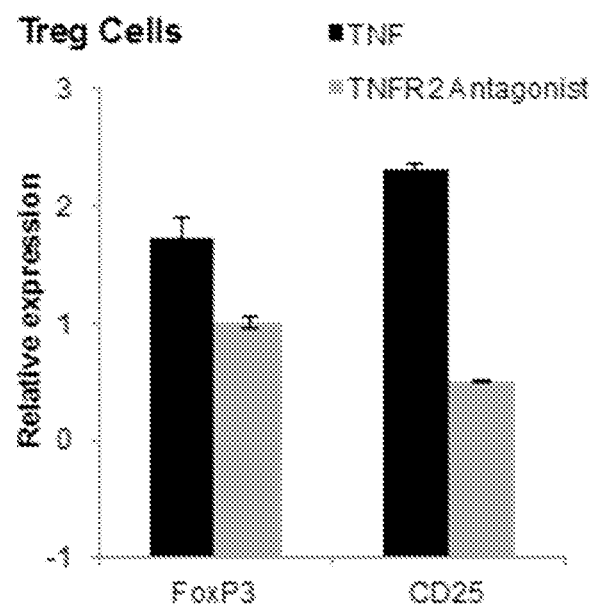
FIG. 12B is a graph showing the effect of TNFR2 antagonist antibodies on the expression of FoxP3 and CD25.
Figure 12C:
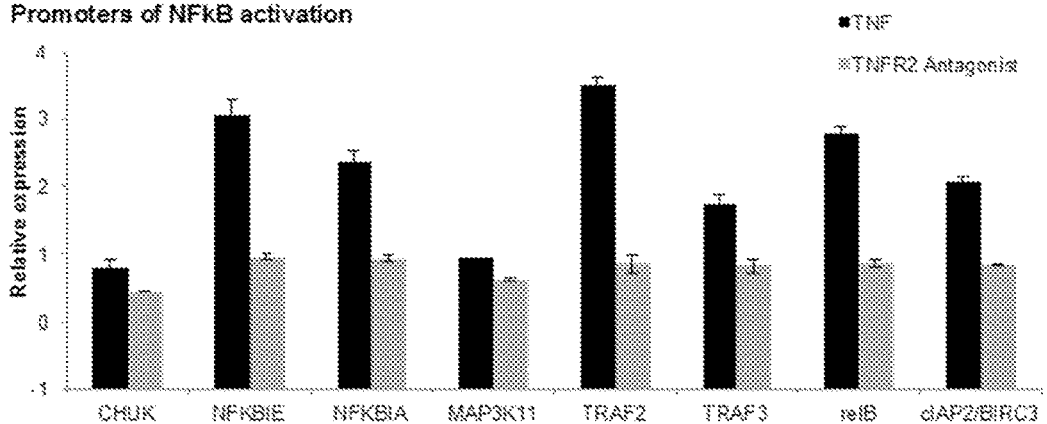
FIG. 12C is a graph showing the effect of TNFR2 antagonist antibodies on the expression of genes that promote NFκB activation: conserved helix-loop-helix ubiquitous kinase (CHUK), nuclear factor of kappa light polypeptide gene enhancer in B-cells inhibitor epsilon (NFKBIE), nuclear factor of kappa light polypeptide gene enhancer in B-cells inhibitor alpha (NFKBIA), mitogen-activated protein kinase 11 (MAP3K11), TNFα receptor-associated factor 2 (TRAF2), TNFα receptor-associated factor 3 (TRAF3), transcription factor relB, and baculoviral IAP repeat containing 3 protein (cIAP2/BIRC3). Real-time PCR analysis was used to detect RNA isolated from fresh CD4+ cells after incubation with IL-2 (50 U/ml) in combination with either TNFα (20 ng/ml) or the TNFR2 antagonist (2.5 µg/ml) for 3 hours.
Figure 12D:
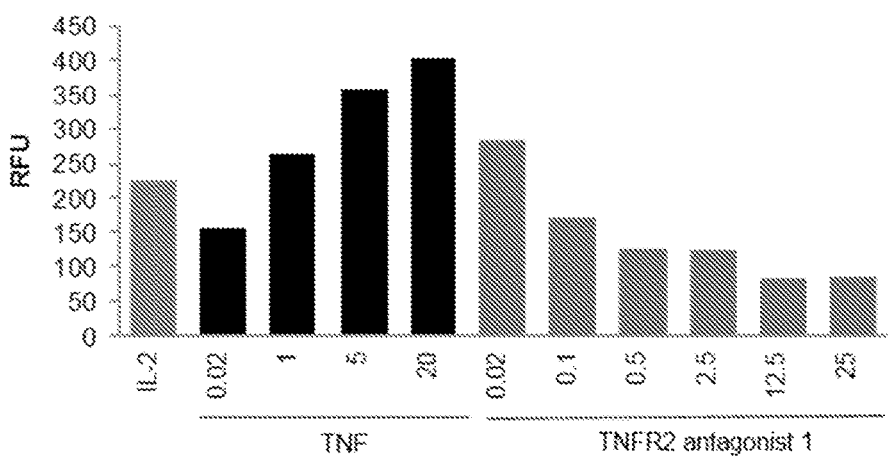
FIG. 12D is a graph showing the ability of TNFRAB1 to suppress NFκB activation as measured using a cell-based ELISA assay.
Figure 12E:
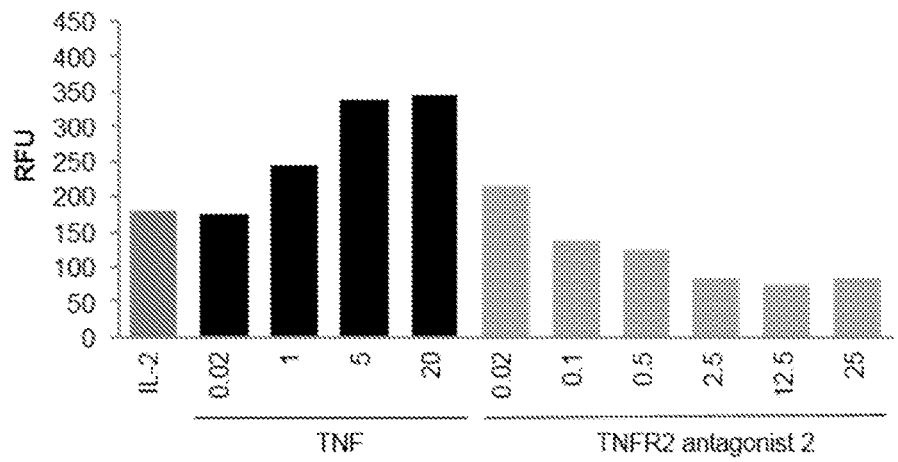
FIG. 12E is a graph showing the ability of TNFRAB2 to suppress NFκB activation as measured using a cell-based ELISA assay. Phosphorylated RelA/NFκB p65 was used as a marker of NFκB activity. Treatment of T-reg cells with antagonistic TNFR2 antibodies resulted in attenuated NFκB activation relative to treatment with TNFα. Using a cell-based ELISA, the phosphorylation RelA/NFκB p65 was measured after 10 minute incubation of fresh CD4+ cells with IL-2 (200 U/ml) and various concentrations of TNFα (0.2-20 ng/ml) or TNFR2 antagonist antibodies (0.02-25 µg/ml). Phosphorylation of RelA/NFκB p65 is induced by TNFα and inhibited by the TNFR2 antagonist mAbs in a dose-dependent manner.

Example 12. NFkB Activation and Gene Expression is Inhibited by Antagonistic TNFR2 Antibodies NFkB signaling is required for TNF-mediated cell response and has been proposed as a potential target for cancer therapy. Upon observing a decrease in T-reg cell proliferation following treatment with TNFR2 antagonist antibodies, it was hypothesized that the underlying signaling mechanism would involve a reduction in NFkB activation. To investigate the molecular response to TNFR2 antagonism, the expression of eight promoters of NFkB activation were measured by real-time PCR analysis. These proteins included: CHUK, NFKBIE, KNKBIA, MAP3K11, TRAF2, TRAF3, relB, cIAP2/BIRCH. The expression of TNF and lymphotoxin were additionally monitored, as well as two markers of T-reg cells, FoxP3 and CD25. In each case, treatment with TNFRAB2 resulted in down-regulation of gene expression compared to treatment with TNF (FIGS. 12A and 12B). Next, using phosphorylated RelA/NFkB p65 as a marker, it was demonstrated that treatment of CD4+ cells with either TNFR2 antagonist antibody reduced NFkB activation, whereas treatment with TNF increased NFkB activation (FIGS. 12C-12E). This suggests the effect of the two TNFR2 antagonist antibodies on TNFR2 signal transduction is highly similar. Additionally, analysis of the kinetic parameters of binding of antagonist TNFR2 antibodies to recombinant human TNFR2 revealed that there was no significant difference in association or dissociation rates between TNFRAB1 and TNFRAB2 (FIG. 13A).

To conduct gene expression assays, isolated CD4+ cells were incubated for 3 hours in the presence of IL-2 (50 U/ml) and TNFα (20 ng/ml) or TNFR2 antagonist antibody (2.5 µg/ml). Cells were collected and total RNA was isolated using RNAqueous-4PCR Kit (Ambion). The total RNA was reverse transcribed using High Capacity cDNA Reverse Transcription Kit (Applied-Biosystems). Real-time PCR was performed using the TaqMan® Array Human NFkB Pathway 96-well Plate with TaqMan® Gene Expression Master Mix and the ABI Prism 7000 Sequence Detection System (Applied-Biosystems).

NFkB activation was measured using the cell-based Human Phospho-RelA/NFkB p65 Immunoassay (R&D Systems). Briefly, fresh CD4+ cells were cultured in 96-well flat-bottom plates (0.2×10$^6$ cells/well) in the presence of IL-2 (200 U/ml) alone or in the presence of TNF or TNFR2 antagonists at the indicated concentrations for 10 minutes at 37° C. Cells were adhered to the plate by centrifugation and fixation and then stained according to the manufacturer's instructions. Fluorescence was read using the EnVision® Multilabel Plate Reader (Perkin Elmer) and normalized relative fluorescence units (RFU) were calculated.

Example 13. Binding of Antagonistic TNFR2 Antibodies to TNFR2 Maps to Overlapping Regions To further investigate the specific binding properties of the TNFR2 antagonist antibodies TNFRAB1 and TNFRAB2, epitope mapping analysis was performed and epitopes within human TNFR2 that bind these antibodies were correlated with a distinct location on the receptor surface. Linear peptide mapping of the two TNFR2 antagonists revealed that while both antagonistic antibodies exhibit a high affinity for the full-length target protein, these antibodies exhibited differential affinity for linear peptides. Specifically, TNFRAB1 exhibited moderate affinity to the epitope containing amino acids 112-139 of SEQ ID NO: 7 within human TNFR2, and exhibited strong affinity to the epitope containing amino acids 128-155 of SEQ ID NO: 7. TNFRAB2 did not bind to any linear peptide region (FIG. 13B). The affinity of TNFRAB1 for TNFR2 was not perturbed by the presence of TNFα, indicating that TNFα is not a competitor with this antibody for TNFR2 binding (FIG. 13C). To examine the conformational epitopes that bind the two antagonist antibodies, a three-dimensional binding analysis was conducted. For TNFRAB1, the 3D data was in agreement with the linear peptide mapping analysis and indicated that the region of amino acids 142-149 of SEQ ID NO: 7 within human TNFR2 were bound by TNFRAB1 with high affinity. Additionally, the 3D analysis revealed a new binding region at amino acids 161-169 of SEQ ID NO: 7 within human TNFR2 (FIGS. 13A-13C and 15A-15C). For TNFRAB2, even though there was no successful linear peptide binding, four binding regions were mapped by 3D analysis (FIGS. 15A-15C). Interestingly, there was partial overlap in the precise discontinuous epitopes of the two TNFR2 antagonist antibodies at amino acids 142-144 of SEQ ID NO: 7 within human TNFR2.

This later data was of interest since previous attempts to raise antagonistic TNFR2 antibodies against the TNFR2 binding site of the TNFR2 trimer signaling complex and/or to the exterior region of the trimer binding site to prevent TNFα entry and prevent stabilization of the TNF trimer had been unsuccessful. The solution structure of the TNFα and TNFR2 complexes had defined a central TNFα homotrimer surrounded by three TNFR2 receptors (Mukai et al. Science Signaling 3: ra83 (2010)). This arrangement had also been observed by many previous TNF superfamily members including TNFR1 with lymphotoxin, DR5 with TRAIL ligand, and Ox40 receptor with Ox40L (Banner et al. Cell 73: 431-445 (1993); Cha et al. J. Biol. Chem. 275: 31171-31177 (2000); Compaan et al. Structure 14:1321-1330 (2006); Hymowitz et al. Mol. Cell 4:563-571 (1999); Mongkolsapaya et al. Nat. Struct. Biol. 6:1048-1053 (1999)).

Figure 14A:
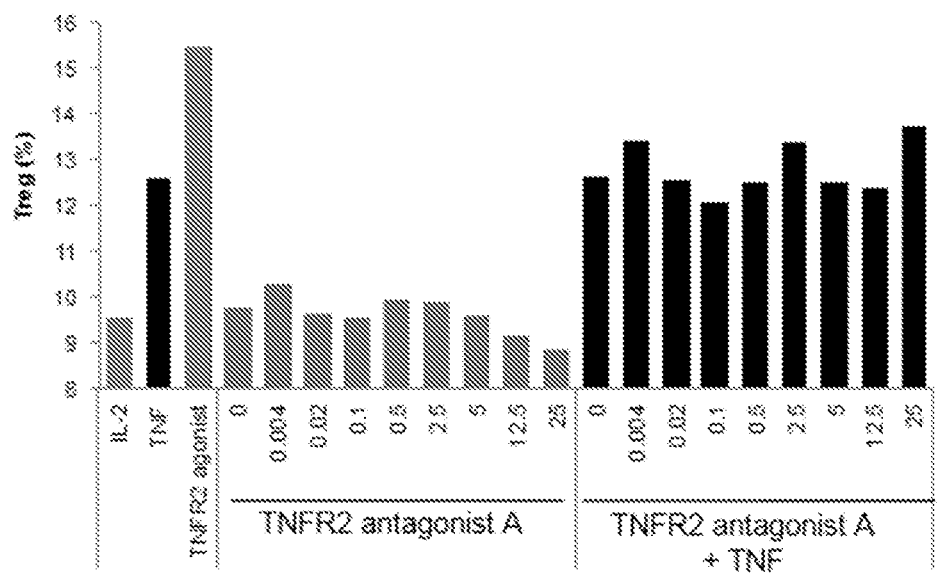
FIGS. 14A and 14B are graphs showing the results of duplicate experiments conducted in order to determine the effect of a recessive-TNFR2 antagonist antibody that mildly inhibits TNFR2 activity (recessive-antagonist TNFR2 antibody A) on the proliferation of T-reg cells.
Figure 14B:
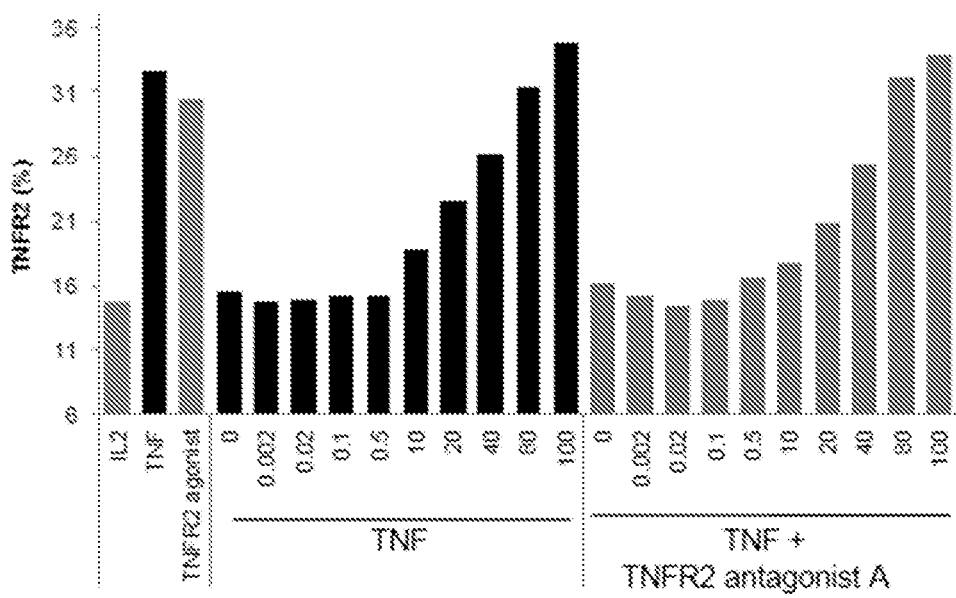
Figure 14C:
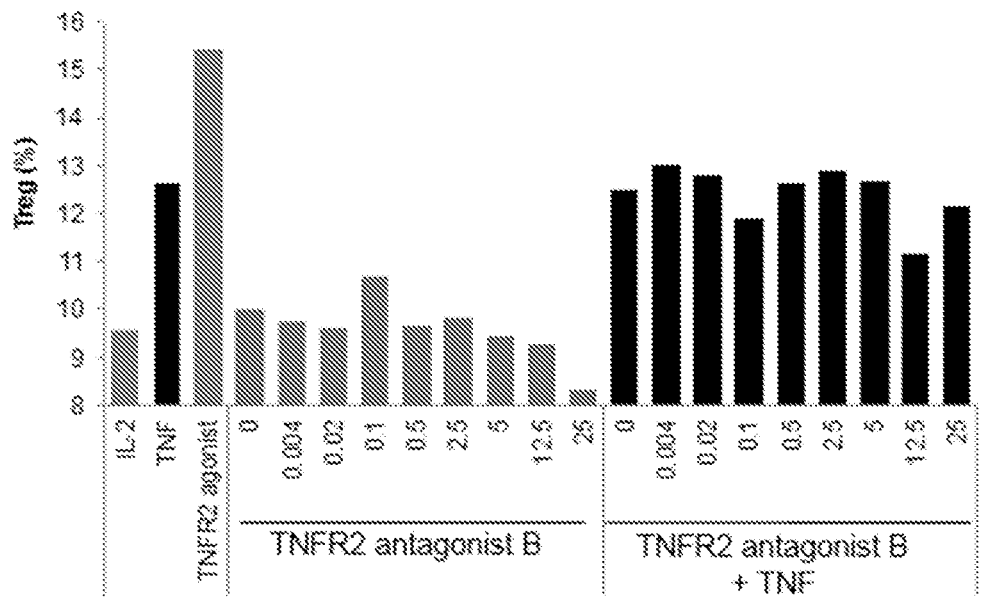
FIGS. 14C and 14D are graphs showing the results of duplicate experiments conducted in order to determine the effect of a second recessive-TNFR2 antagonist that mildly inhibits TNFR2 activity (recessive-antagonist TNFR2 antibody B) on the proliferation of T-reg cells. These recessive-antagonist antibodies were raised against the exterior region of TNFR2 in order to prevent TNFR2 trimerization that leads to NFκB activation.
Figure 14D:
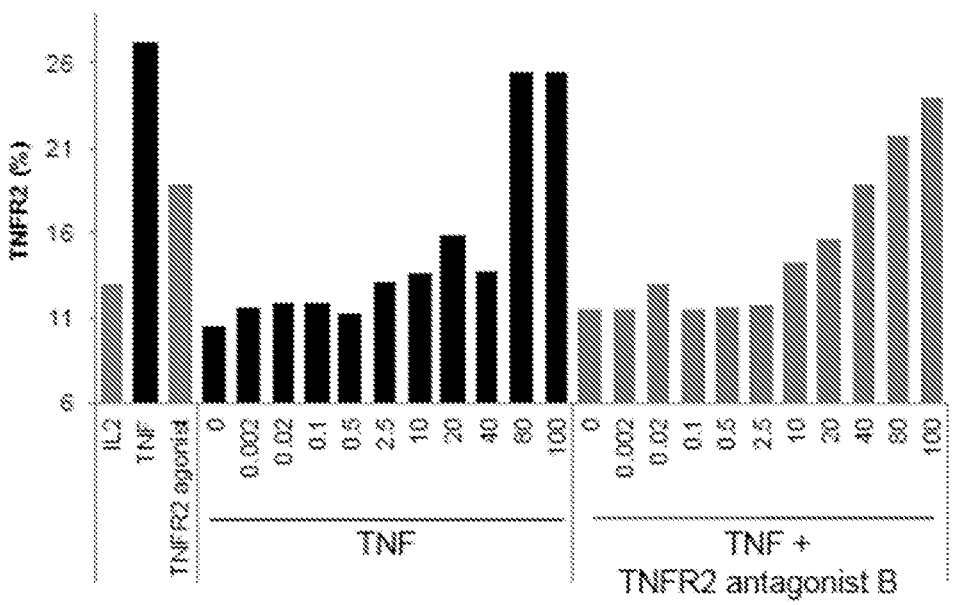
Figure 16A:
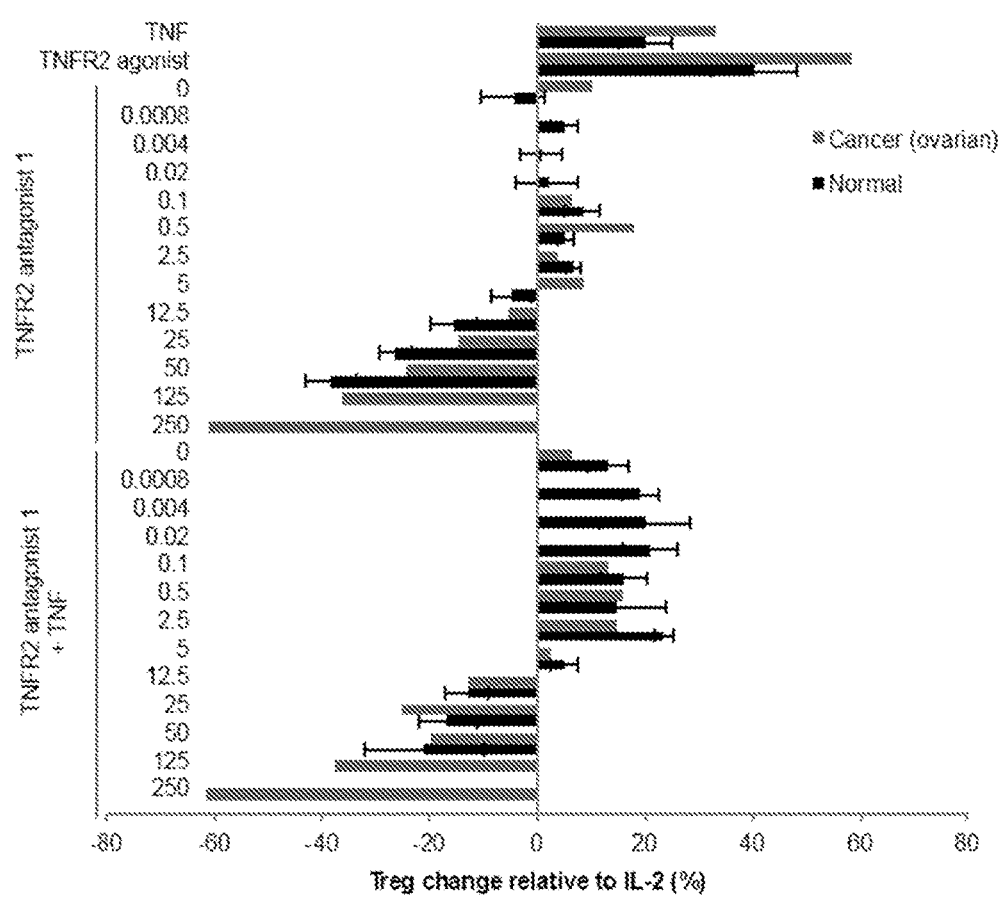
FIG. 16A is a graph showing the effect of TNFRAB1 on the proliferation of T-reg cells isolated from a patient presenting with ovarian cancer (grey shade) and of T-reg cells isolated from a subject not presenting with ovarian cancer (black shade).
Figure 16B:
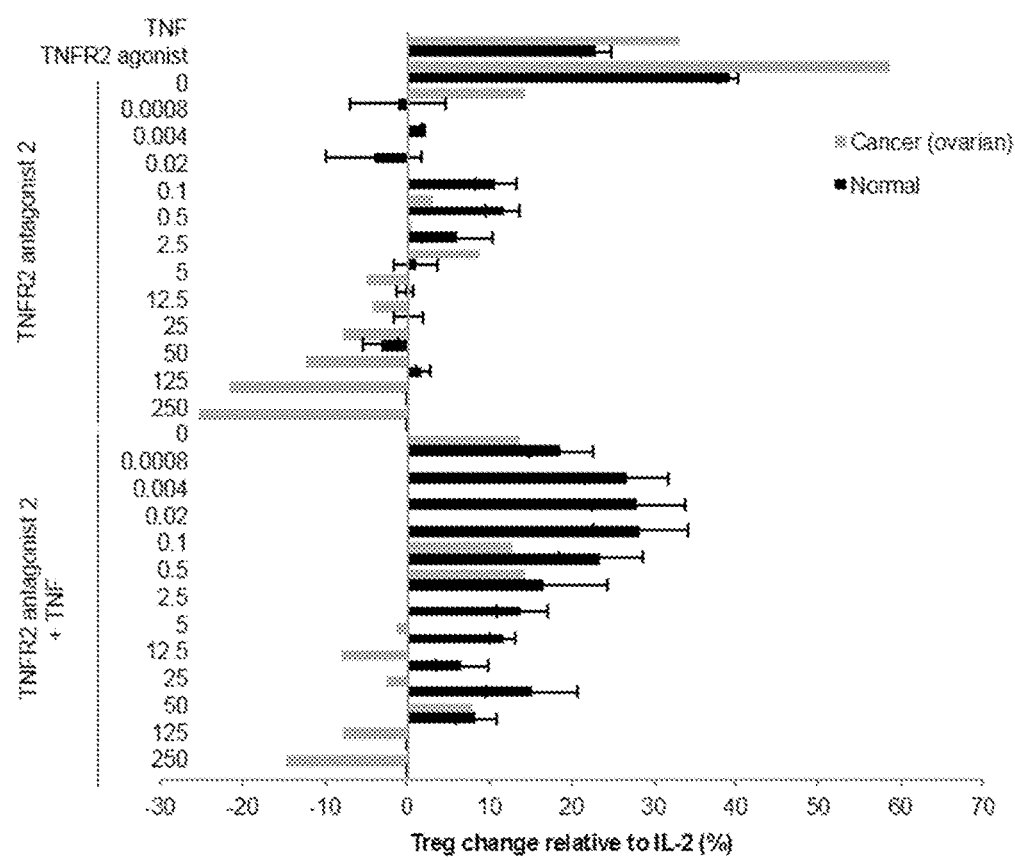
FIG. 16B is a graph showing the effect of TNFRAB2 on the proliferation of T-reg cells isolated from a patient presenting with ovarian cancer (grey shade) and of T-reg cells isolated from a subject not presenting with ovarian cancer (black shade).
Figure 17A:
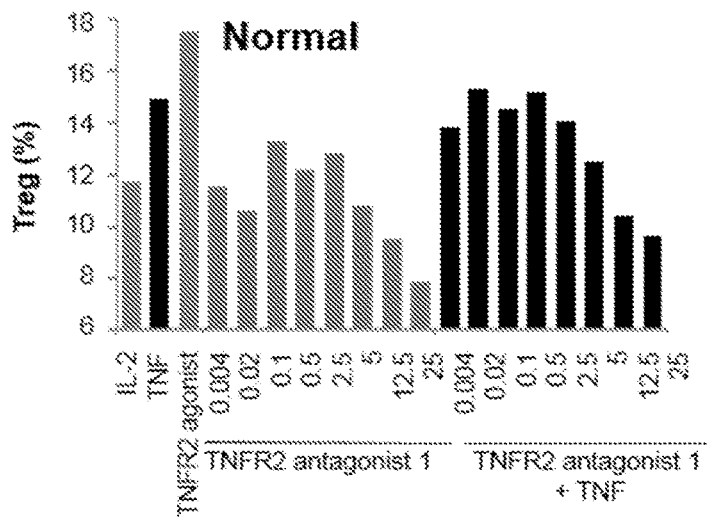
FIG. 17A is a graph showing the effect of TNFRAB1 on the proliferation of T-reg cells isolated from a subject not presenting with ovarian cancer.
Figure 17B:
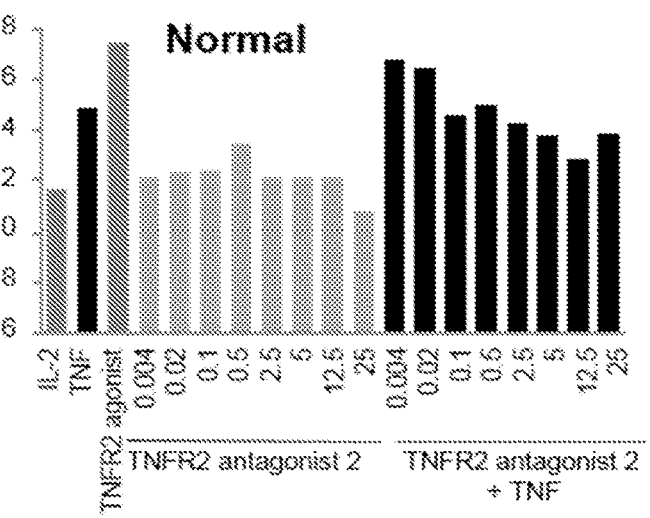
FIG. 17B is a graph showing the effect of TNFRAB2 on the proliferation of T-reg cells isolated from a subject not presenting with ovarian cancer.
Figure 17C:
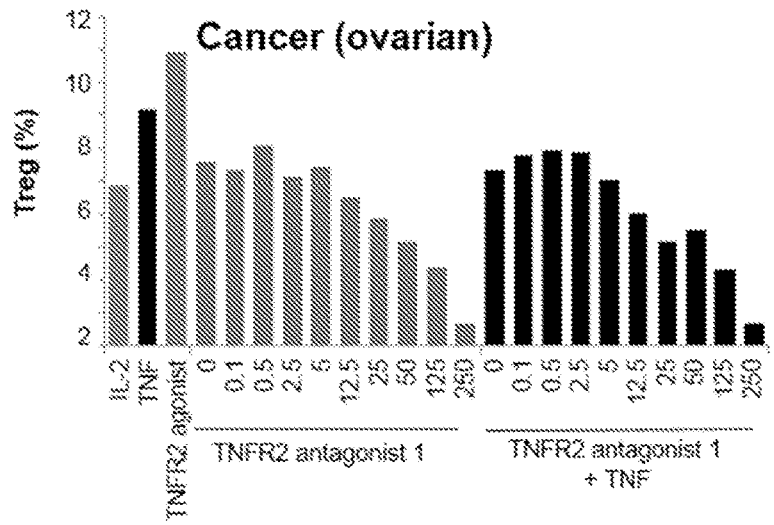
FIG. 17C is a graph showing the effect of TNFRAB1 on the proliferation of T-reg cells isolated from a subject presenting with ovarian cancer.
Figure 17D:
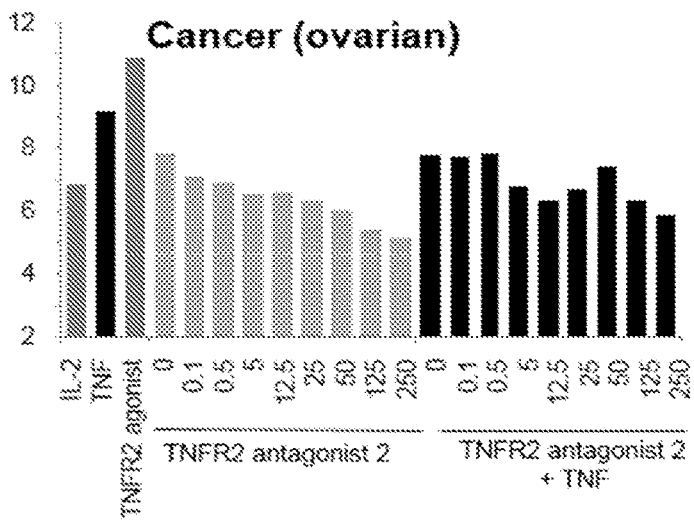
FIG. 17D is a graph showing the effect of TNFRAB2 on the proliferation of T-reg cells isolated from a subject presenting with ovarian cancer.
Figure 17E:
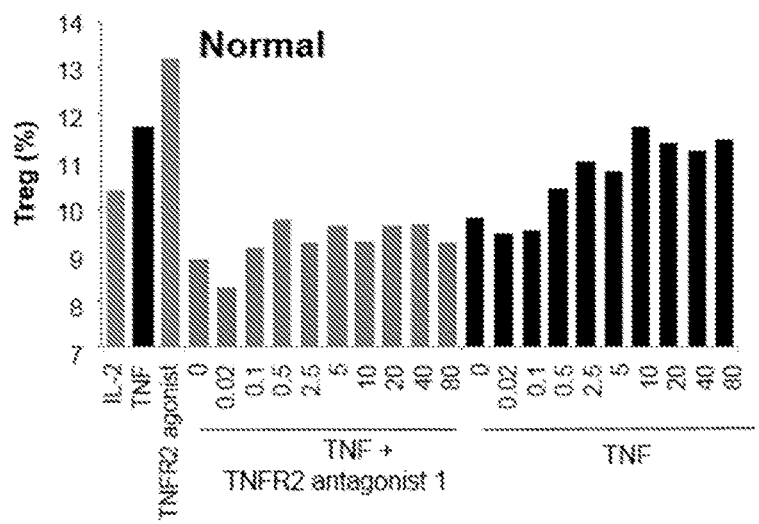
FIG. 17E is a graph showing the effect of TNFRAB1 on the proliferation of T-reg cells isolated from a subject not presenting with ovarian cancer (duplicate data set relative to FIG. 17A).
Figure 17F:
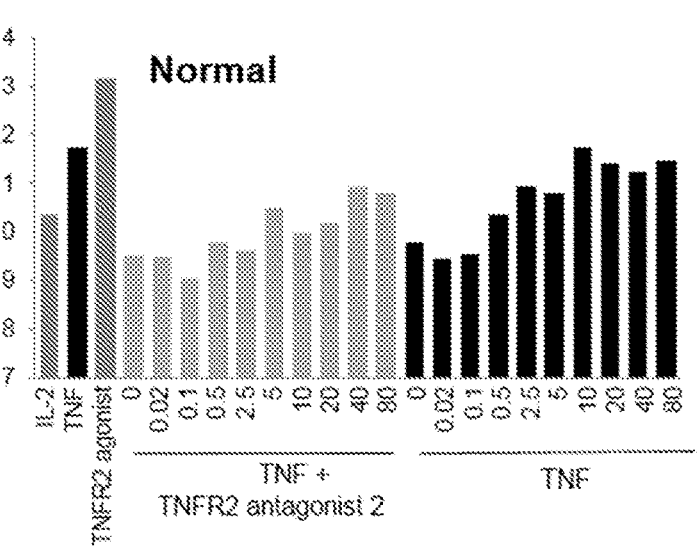
FIG. 17F is a graph showing the effect of TNFRAB2 on the proliferation of T-reg cells isolated from a subject not presenting with ovarian cancer (duplicate data set relative to FIG. 17B).
Figure 17G:
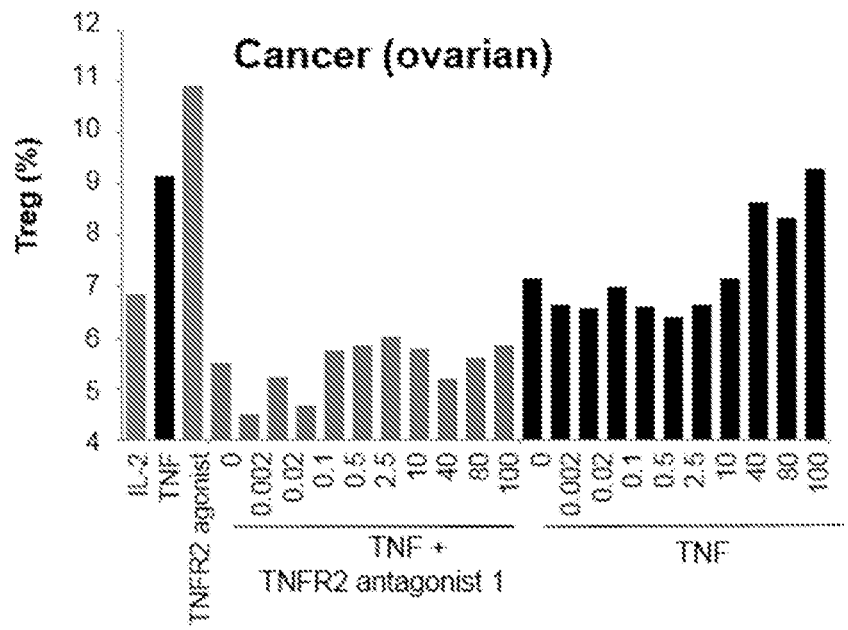
FIG. 17G is a graph showing the effect of TNFRAB1 on the proliferation of T-reg cells isolated from a subject presenting with ovarian cancer (duplicate data set relative to FIG. 17C).
Figure 17H:
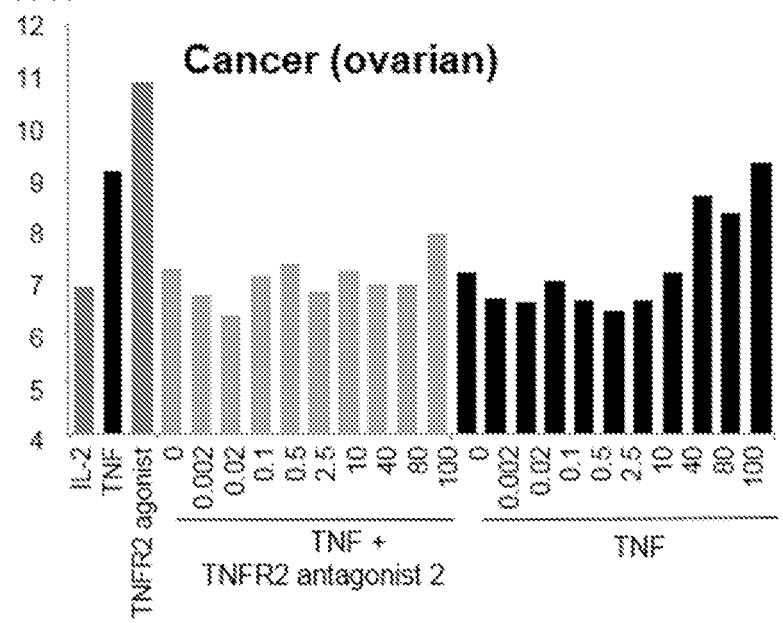
FIG. 17H is a graph showing the effect of TNFRAB2 on the proliferation of T-reg cells isolated from a subject presenting with ovarian cancer (duplicate data set relative to FIG. 17D).

Previous attempts to produce antagonistic antibodies to these regions to prevent TNFα binding and TNFR2 trimers yielded recessive-antagonistic antibodies with mild TNFR2 inhibitory activity having a common trait in T-reg proliferation assays. As FIGS. 14A-14D show, in the 48 hour T-reg assay these recessive-antagonistic antibodies performed as antagonists in the absence of a TNFR2-stimulating agent. Indeed, both recessive-antagonist TNFR2 antibodies A and B by themselves had a demonstration of dose response T-reg antagonism with a dose response from 0-25 µg/ml (FIGS. 14A and 14C). Importantly, when TNFα (20 mg/ml) was added to the cultures, these TNFR2-directed recessive-antagonistic antibodies A and B competed poorly with TNFα. In each case, TNFα driven agonism was dominant over this form of antagonism, at least the partial and weak antagonism with antibodies to prevent TNFα or TNFR2 trimer formations (FIG. 15C). This behavior is in contrast with the capacity of dominant antagonistic TNFR2 antibodies, such as TNFRAB1 and TNFRAB2 that bind the specific epitopes within TNFR2 identified and described herein, such as epitopes containing the KCRPG (SEQ ID NO: 19) motif of TNFR2 and other epitopes as identified in the descriptions of TNFRAB1 and TNFRAB2 provided herein. As opposed to recessive-antagonistic TNFR2 antibodies A and B, TNFR2 antagonistic antibodies TNFRAB1 and TNFRAB2 displayed the ability to attenuate TNFR2 signaling and T-reg proliferation even in the presence of a TNFR2 agonist, such as TNFα and IL-2. Importantly, the epitopes identified herein can be used to raise antagonistic TNFR2 antibodies that display an antagonistic effect that persists in the presence of TNFR2 stimulants.

Since linear peptide mapping only partially answered the question of why TNFRAB1 and TNFRAB2 were superior antagonists, we next explored identifying conformational epitopes of the two TNFR2 antagonists. We conducted three-dimensional (3D) binding analysis using the Pepscan technology (Pepscan, The Netherlands). For both TNFRAB1 and TNFRAB2, the 3D data showed overlapping regions from approximately aa138-aa150. What became apparent is that these binding regions did not appear to be able to bind to the classic TNFR2 trimer with trimeric TNFα since the site would have been on the interior of the trimer (FIG. 15B). Since other research groups had reported alternative forms of TNF independent forms of TNF superfamily members that were parallel or anti-parallel models, we mapped the epitopes on those sites (Naismith et al. J. Biol. Chem. 270:13303-13307 (1995); Naismith et al. Structure 4:1251-1262 (1996)). Surprisingly, only one model of TNFR2 antagonistic binding was optimal: a model in which the anti-parallel dimer (FIG. 15A) contains two TNFR2 antagonistic antibody binding regions that are spaced apart for the obligatory hinged TNFR2 antagonists and would appear to stabilize this TNFα-independent complex, another functional trait of these antibodies. With further modeling, it was apparent that the anti-parallel complex, but not the parallel dimer complex, would have intracellular regions that are distant from one another and would inhibit NFkB signaling as we had observed in our functional assays. Since all members of the TNF superfamily of receptors can display these less commonly studied anti-parallel conformations, antagonistic antibodies to any receptor of the TNFR superfamily can be made by designing or screening for antibodies or antigen-binding fragments thereof that bind surface-exposed epitopes within the anti-parallel TNFRS member protein (see, e.g., Example 15, below). These antibodies or antigen-binding fragments thereof can stabilize the anti-parallel forms of these proteins and thus prevent signaling, as well as the formation of active trimeric forms of these receptors that frequently also bind soluble cognate ligands. Known members of the TNF superfamily of receptors known to exhibit anti-parallel dimer structures include: TNFR1, TNFR2, Fas, DCR3, DR3, TRAIL-R1(DR4), TRAIL-R2 (DR5), TRAIL-R3, TRAIL-R4, DR6, EDAR, CD271, OPG, RANK, LTβR, TWEAK-R, HVEM, CD27, CD30, CD40, CD137, OX40, GITR, BCMA, TACI, BAFFR, EDAR2, TROY, and RELT, among others.

Example 14. TNFR2 Antagonist Activity on Cancer Cells

T-reg cells present in patients suffering from cancer are potent immune suppressors. This is particularly true for T-reg cells from tumor sites as compared to the T-reg cells of peripheral blood of the cancer patients or control subjects. To begin to understand the potency of TNFR2 antagonist antibody on ovarian cancer T-reg cells, fresh ovarian cancer T-reg cells were isolated and their proliferation characterized as described in Example 2. First with TNF and then with TNFR2 agonist, it was indeed the case that ovarian cancer residing T-reg cells expanded far greater than the T-reg cells from normal donors, a sign of hyper activation (FIGS. 16A-16B and 17A-17H). TNFR2 antagonistic antibodies inhibited T-reg cell proliferation in a dose-dependent fashion and with higher variability as compared to the tight dose response data obtained from analysis of proliferation of T-reg cells isolated from healthy donors. Additionally, both antagonistic antibodies more potently inhibited the proliferation of T-reg cells isolated from ovarian cancer patients as compared to healthy donors.

The experiments described above demonstrate that antagonistic TNFR2 antibodies are capable of inhibiting both normal and cancer-associated T-reg cell proliferation. Such antibodies can eliminate or inactivate potent suppressive T-reg cells, both in terms of the quantity of T-reg cells in culture as well as in terms of T-reg proliferation. The traits of these antibodies include the ability to attenuate intracellular early phosphoyrlation events that precede NFkB activation and the capacity to change the phenotype of the remaining T-reg cells such that these cells expressed reduced quantities of activation markers, such as CD45RO. Additionally, antagonistic TNFR2 antibodies may diminish the secretion of soluble TNFR2, a proinflammatory protein. Remarkably even in the presence of generous amounts of agonistic TNFα or agonistic TNFR2 antibodies added to cell culture media, antagonistic TNFR2 antibodies still act as dominant antagonists.

It is worthwhile contrasting antibody or ligand agonism of the TNFα receptors with antibody antagonism. The requirement for TNF and other TNF superfamily agonism with the natural ligands is well studied and requires aggregation and clustering for efficient signal transduction (Das et al. J. Mol. Endocrinol. 53:81-91 (2014); Siegel et al. J. Cell. Biol. 167:735-744 (2004); Takeda et al. Oncogene 26:3745-3757 (2007)). The most common confirmation for the tumor necrosis factor receptor superfamily is a trimeric receptor paired with trimers of the ligand (Gommerman et al. Nat. Rev. Immunol. 3:642-655 (2003); Loetscher et al. J. Biol. Chem. 266:18324-18329 (1991); Smith et al. Cell 76:959-962 (1994); Tartaglia J. Biol. Chem. 267:4304-4307 (1992);

Ware Annu. Rev. Immunol. 23:787-819 (2005)). Agonist antibodies seem to follow the same principles and also often require the Fc portions of their receptors for the associated cells through antibody-dependent cell-mediated cytotoxicity (ADCC) mechanisms, something that would stabilize the extracellular lattices. This exterior receptor oligomerization and clustering observed with TNFR2 agonism permits internal oligomerization of the reciprocal TRAF lattice network for brisk NFkB signaling (Cabal-Hierro et al. Cell Signal. 26:2658-2666 (2014); Yin et al. Nat. Struct. Mol. Biol. 16:658-666 (2009); Zheng et al. Mol. Cell. 38:101-113 (2010)). The stabilization of agonist is also promoted by the cooperation of the added ligand to the receptor. This appears important for many TNF receptor superfamily members for therapeutic effectiveness (Graves et al. Cancer Cell 26:177-189 (2014)).

The shared receptor binding regions of two TNFR2 antagonist antibodies studied herein leads us to a very different possible model of antibody binding to the TNFR2 receptor to cause stable and dominant antagonism. The commonly studied trimeric form of TNFR2 would not allow the newly identified antibody antagonists to bind to their amino acid sequences and explain how these antagonistic antibodies are dominant over TNFα or IL-2 (Mukai et al. Science Signal. 3:ra83 (2010)). Indeed, years of work generating TNFR2 antibodies to the binding region of TNFα in the trimer TNFR2 structure or to the exterior surface of the TNFα-binding region of the trimer did not generate potent antagonists that maintained dominant inhibition of receptor signaling in the presence of TNFR2 agonists. TNFR2 trimer-directed antibodies designed to compete with TNFα were not dominant, but exhibited neutralizing effects at times when challenged with the inflammatory environment of TNFα or IL-2.

The trimeric form of TNFR2 is the most commonly studied form of the TNFα receptor, as it relates to cell growth signals involving NFkB. Previous studies have proposed that TNFR2 and similar TNFα superfamily members like the lymphotoxin receptor can also exist as parallel and anti-parallel forms. These forms lack the TNF binding site (Naismith et al. J. Biol. Chem. 270:13303-13307 (1995); Naismith et al. Structure 4:1251-1262 (1996)). The data described herein show no added benefit of adding a cross-linking reagent to either augment antagonism or to convert antagonism to agonism. It would be hard to imagine that high-affinity TNFα binding of TNFα to trimeric TNFR2 could be competitively inhibited by an antibody, even with extremely high affinity. The anti-parallel dimeric form of TNFR2 fits best with the assessable binding site for antagonistic antibodies and the functional assay but there is also another feature to support this observation—the exterior interface is considerably more extensive and thus this would also cause the intracellular tails of TNFR2 to be a further distance apart as supported by others data (Naismith et al. Structure 4:1251-1262 (1996)). With TNFR2 trimerization the intracellular signaling regions of the TNFR2 are pulled close together, thus facilitating TRAF direct or indirect recruitment of the intracellular domains of these TNF superfamily receptors (Napetschnig et al. Annu. Rev. Biophys. 42:443-468 (2013); Yin et al. Nat. Struct. Mol. Biol. 16:658-666 (2009)). This agonist signal would subsequently engage other signaling proteins to activate the inhibitor of kB (IkB) kinase (IKK) and MAP kinases ultimately activating NFkB. The fact that the post-receptor signaling pathway is blocked to varying degrees with TNFR2 antagonistic antibodies suggests the recruitment of intracellular TRAFs are inhibited by the dominant stabilization of the exterior TNFR2 structure. It has been previously purposed by others that the anti-parallel dimers of TNFR1 could be an inhibitory complex and would not be able to bind TNF (Naismith et al. Structure 4:1251-1262 (1996)). The anti-parallel model more closely substantiates how antagonistic formation of this complex would explain dominance over TNF co-culture since new activation trimers could not be formed.

It is worth mentioning that as reported by others, the T-reg cells in the cancer environment are extremely potent compared to the T-reg cells of non-cancerous donors or even the T-reg cells isolated from the peripheral blood of cancerous donors (Govindaraj et al. Clin. Cancer Res. 20: 724-735 (2013)). As described herein, antagonistic TNFR2 antibodies are capable of inhibiting the proliferation of potent T-reg cells isolated from ovarian cancer patients. It has also been observed that accentuated inhibition of T-reg cells isolated from ovarian cancer patients is achieved with TNFR2 antagonist antibodies TNFRAB1 and TNFRAB2. This activity is beneficial in view of recent reports identifying the features of the TNFR2 gene sequence that imparts enhanced potency to TNFR2 signaling in cancer patients. In the setting of cutaneous T cell lymphoma, for instance, the gene for TNFR2 is a gene duplication and/or may be mutated in the intracellular region to confer constitutive agonism. This genetic pressure to constantly maintain TNFR2 growth signals is in line with exaggerated growth.

The antagonist antibodies described herein bind to the restricted regions of the TNFR2 receptor that modulate T-reg inhibition and even dominant inhibition in the presence of TNFα. These antagonists are very different from the recessive antagonists also described herein that can mildly inhibit T-reg cell proliferation but, when used in an inflammatory environment of TNF and IL-2, agonism dominates (FIGS. 14A-14D). Taken together, the data described above provides a new platform for the creation of additional antagonist TNFR2 antibodies beyond those described herein that would be capable of modulating T-reg cell growth in patients suffering from a cancer in which cancer cells express elevated quantities of TNFR2 (e.g., ovarian cancer) and may display antagonistic effects even in the presence of TNFR2 agonists. Remarkably, such antagonistic TNFR2 antibodies are more potent on the T-reg cells of ovarian cancer patients than on the T-reg cells of non-cancerous donors.

Example 15. Development and Activity of Antagonistic TNFRS Member Antibodies or Antigen-Binding Fragments Thereof Antagonistic antibodies and antigen-binding fragments thereof that bind other members of the TNFRS may bind these receptors in an anti-parallel dimer conformation, thereby rendering cognate ligand binding sites sterically inaccessible and thus precluding receptor activation. Such antibodies or antigen-binding fragments thereof can be developed using a variety of techniques. For instance, antagonistic antibodies or antigen-binding fragments that bind other TNFRS members can be produced that bind specific epitopes within TNFRS member proteins that are homologous in sequence and/or structure to those epitopes within TNFR2 that are bound by TNFRAB1 and TNFRAB2 as described herein, or that are within the same region of the TNFRS member as are those epitopes described herein with respect to TNFR2. Using conventional techniques, one of skill in the art can align the amino acid sequence of one or more TNFRS member proteins with that of human TNFR2 (SEQ ID NO: 7) in order to identify epitopes within the TNFRS member protein(s) that share sequence homology with, e.g., the KCRPGFGV (SEQ ID NO: 20), CKP-CAPGTF (SEQ ID NO: 21), CAPLRKCR (SEQ ID NO: 11), DSTYTQL (SEQ ID NO: 8), PECLSCGS (SEQ ID NO: 9), or RICTCRPG (SEQ ID NO: 10) motif within human TNFR2 (for instance, amino acid sequences within other TNFRS member proteins that have at least 85% sequence identity (e.g., 85%, 90%, 95%, 97%, 99%, or 100% sequence identity) to one or more of the aforementioned sequences within human TNFR2). Homologous epitopes isolated from other TNFRS member proteins can subsequently be used to produce antagonistic antibodies, e.g., using in vitro display techniques described herein, such as phage display (for instance, as described in Example 3, above), yeast display, ribosome display, or RNA display, among others. For instance, alignment of the amino acid sequences of TNFR2, DR3, and TNFR1 reveals that residues 138-150 of the DR3 amino acid sequence (GENBANK™ Accession No. AAQ88676.1) and residues 185-197 of the TNFR1 amino acid sequence (GENBANK™ Accession No. NP_001056) align with the region of TNFR2 containing the CAPLRKCR (SEQ ID NO: 11) and KCRPGFGV (SEQ ID NO: 20) motifs. Antagonistic DR3 antibodies or antigen-binding fragments thereof of the invention include those that bind an epitope within residues 138-150 of the DR3 amino acid sequence. Similarly, antagonistic TNFR1 antibodies or antigen-binding fragments thereof of the invention may bind an epitope within residues 185-197 of the TNFR1 amino acid sequence.

A peptide within a TNFRS member protein that aligns with one or more of the TNFR2 epitopes described above (such as a peptide that has at least 85% sequence identity (e.g., 85%, 90%, 95%, 97%, 99%, or 100% sequence identity) to the KCRPGFGV (SEQ ID NO: 20), CKP-CAPGTF (SEQ ID NO: 21), CAPLRKCR (SEQ ID NO: 11), DSTYTQL (SEQ ID NO: 8), PECLSCGS (SEQ ID NO: 9), or RICTCRPG (SEQ ID NO: 10) motif within human TNFR2 can be identified as described above and subsequently synthesized using conventional solid-phase peptide synthesis techniques known in the art or described herein or expressed recombinantly using cell-based protein expression techniques known in the art or described herein. The peptide can then be purified, e.g., using conventional HPLC techniques known in the art or described herein, and can subsequently be immobilized on a surface, such as a microtiter plate or a water-miscible resin. Libraries of antibodies or antigen-binding fragments can then be screened for molecules that bind the immobilized peptide using, e.g., phage display, yeast display, ribosome display, or RNA display techniques, among others, as described herein.

Antagonistic antibodies and antigen-binding fragments thereof of the invention that bind other members of the TNFRS and stabilize them in an anti-parallel dimer conformation may also be produced, e.g., using standard immunization techniques (e.g., in a non-human mammal). In particular, immunogenic polypeptides having an amino acid sequence that is the same or substantially similar to the amino acid sequences within TNFR2 that are bound by TNFRAB1 and TNFRAB2 as described herein, or that are within the same region of the TNFRS member as are those epitopes described herein with respect to TNFR2 can be used to produce antibodies or antigen fragments thereof according to the invention.

Antagonistic TNFRS member antibodies or antigen-binding fragments thereof generated as described above can bind and stabilize a TNFRS member protein in an anti-parallel dimer conformation, e.g., as shown in FIGS. 18A (DR3) and 18B (TNFR1). Such antibodies or antigen-binding fragments thereof can subsequently be used to inhibit TNFRS member signaling in a cell (e.g., a mammalian cell, such as a human cell or a bovine cell). For instance, one of skill in the art may use an antagonistic TNFRS member antibody or antigen-binding fragment thereof to suppress TNFR1, Fas, DCR3, DR3, TRAIL-R1 (DR4), TRAIL-R2 (DR5), TRAIL-R3, TRAIL-R4, DR6, EDAR, CD271, OPG, RANK, LTβR, TWEAK-R, HVEM, CD27, CD30, CD40, CD137, OX40, GITR, BCMA, TACI, BAFFR, EDAR2, TROY, or RELT-mediated signaling in a target cell. Inhibition of TNFRS member-mediated signaling in the target cell population can be measured using conventional techniques known in the art, such as immunoblot analysis in order to determine the extent of the expression of genes associated with the signal transduction cascades propagated by the above-described TNFRS member proteins.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A humanized, human, or chimeric antibody or antigen-binding fragment thereof capable of specifically binding human TNFR2, wherein the antibody or antigen-binding fragment thereof comprises the following complementarity-determining regions (CDRs):

(I)
(a) a CDR-H1 having the amino acid sequence GYTFTDYX (SEQ ID NO: 257);
(b) a CDR-H2 having the amino acid sequence VDPEYGST (SEQ ID NO: 258);
(c) a CDR-H3 having the amino acid sequence ARDDG-SYSPFDYWG (SEQ ID NO: 259);
(d) a CDR-L1 having the amino acid sequence QNINKY (SEQ ID NO: 260);
(e) a CDR-L2 having the amino acid sequence TYS or YTS; and
(f) a CDR-L3 having the amino acid sequence CLQYVNLXT (SEQ ID NO: 261);
or
(II)
(a) a CDR-H1 having the amino acid sequence GFTFSSY (SEQ ID NO: 23);
(b) a CDR-H2 having the amino acid sequence SSGGSY (SEQ ID NO: 24);
(c) a CDR-H3 having the amino acid sequence QRVDGYSSYWYFDV (SEQ ID NO: 25);
(d) a CDR-L1 having the amino acid sequence SASSSVYYMY (SEQ ID NO: 26);
(e) a CDR-L2 having the amino acid sequence STSNLAS (SEQ ID NO: 27); and
(f) a CDR-L3 having the amino acid sequence QQRRNY-PYT (SEQ ID NO: 28);
wherein
each X is independently leucine or isoleucine;
and wherein the antibody or antigen-binding fragment thereof inhibits T regulatory (Treg) cell proliferation in the presence of TNFα.

2. The antibody or antigen-binding fragment thereof of claim 1, wherein:
(a) said CDR-H1 has the amino acid sequence GYTFTDYX (SEQ ID NO: 257);
(b) said CDR-H2 has the amino acid sequence VDPEYGST (SEQ ID NO: 258);
(c) said CDR-H3 has the amino acid sequence ARDDG-SYSPFDYWG (SEQ ID NO: 259);
(d) said CDR-L1 has the amino acid sequence QNINKY (SEQ ID NO: 260);
(e) said CDR-L2 has the amino acid sequence TYS or YTS; and
(f) said CDR-L3 has the amino acid sequence CLQYVNLXT (SEQ ID NO: 261),
wherein each X is independently leucine or isoleucine.

3. The antibody or antigen-binding fragment thereof of claim 2, wherein said CDR-H1 has the amino acid sequence GYTFTDYL (SEQ ID NO: 274), said CDR-L2 has the amino acid sequence YTS, and said CDR-L3 has the amino acid sequence CLQYVNLIT (SEQ ID NO: 273).

4. The antibody or antigen-binding fragment thereof of claim 1, wherein:
(a) said CDR-H1 has the amino acid sequence GFTFSSY (SEQ ID NO: 23);
(b) said CDR-H2 has the amino acid sequence SSGGSY (SEQ ID NO: 24);
(c) said CDR-H3 has the amino acid sequence QRVDGYSSYWYFDV (SEQ ID NO: 25);
(d) said CDR-L1 has the amino acid sequence SASSSVYYMY (SEQ ID NO: 26);
(e) said CDR-L2 has the amino acid sequence STSNLAS (SEQ ID NO: 27); and
(f) said CDR-L3 has the amino acid sequence QQRRNY-PYT (SEQ ID NO: 28).

5. The antibody or antigen-binding fragment thereof of claim 1, wherein said antibody or antigen-binding fragment thereof comprises a heavy chain amino acid sequence having at least 85% sequence identity to the amino acid sequence of SEQ ID NO: 2 and/or a light chain amino acid sequence having at least 85% sequence identity to the amino acid sequence of SEQ ID NO: 4.

6. The antibody or antigen-binding fragment thereof of claim 5, wherein said light chain amino acid sequence is the amino acid sequence of SEQ ID NO: 4, and said heavy chain amino acid sequence is the amino acid sequence of SEQ ID NO: 2.

7. The antibody or antigen-binding fragment thereof of claim 1, wherein said antibody or antigen-binding fragment thereof:
(a) comprises a framework region comprising the amino acid sequence LLIR (SEQ ID NO: 262) bound to the N-terminus of said CDR-L2; and/or
(b) comprises a framework region comprising the amino acid sequence TLE bound to the C-terminus of said CDR-L2.

8. The antibody or antigen-binding fragment thereof of claim 1, wherein said antibody or antigen-binding fragment thereof is selected from the group consisting of a monoclonal antibody or antigen-binding fragment thereof, a polyclonal antibody or antigen-binding fragment thereof, a bispecific antibody or antigen-binding fragment thereof, a multi-specific antibody or antigen-binding fragment thereof, a dual-variable domain immunoglobulin, a monovalent antibody or antigen-binding fragment thereof, a single-chain Fv molecule (scFv), a diabody, a triabody, an antibody-like protein scaffold, a FY fragment, a Fab fragment, a F(ab')2 molecule, and a tandem scFv (taFv).

9. A construct comprising a first polypeptide domain and a second polypeptide domain, wherein said first polypeptide domain and said second polypeptide domain each independently comprise a single-chain polypeptide comprising the antibody or antigen-binding fragment thereof of claim 1, and wherein said construct lacks a murine Fc domain.

10. The construct of claim 9, wherein said first polypeptide domain and said second polypeptide domain are bound by a covalent linker selected from an amide bond and a disulfide bond.

11. The antibody or antigen-binding fragment thereof of claim 1, wherein said antibody or antigen-binding fragment thereof is conjugated to a therapeutic agent.

12. The antibody or antigen-binding fragment thereof of claim 11, wherein said therapeutic agent is a cytotoxic agent.

13. The antibody or antigen-binding fragment thereof of claim 1, wherein said antibody or antigen-binding fragment thereof is a single-chain polypeptide.

14. The antibody or antigen-binding fragment thereof of claim 1, wherein the antibody or antigen-binding fragment thereof has an isotype selected from the group consisting of IgG, IgA, IgM, IgD, and IgE.

15. The antibody or antigen-binding fragment thereof of claim 14, wherein the antibody or antigen-binding fragment thereof has an IgG isotype.

16. The antibody or antigen-binding fragment thereof of claim 15, wherein the antibody or antigen-binding fragment thereof has an IgG2 isotype.

* * * * *

UNITED STATES PATENT AND TRADEMARK OFFICE
CERTIFICATE OF CORRECTION

| | |
|---|---|
| PATENT NO. | : 10,906,982 B2 |
| APPLICATION NO. | : 15/573747 |
| DATED | : February 2, 2021 |
| INVENTOR(S) | : Denise L. Faustman |

It is certified that error appears in the above-identified patent and that said Letters Patent is hereby corrected as shown below:

In the Claims

Claim 1, Line 1, replace "A humanized, human, or" with -- A humanized or --.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*